(12) United States Patent
Berger et al.

(10) Patent No.: US 8,877,934 B2
(45) Date of Patent: Nov. 4, 2014

(54) N-HETEROARYL COMPOUNDS

(75) Inventors: Michael Berger, Schwabenheim (DE); Christopher Kern, Schwabenheim (DE); Marko Eck, Schwabenheim (DE); Jörg Schröder, Schwabenheim (DE)

(73) Assignee: Intervet Inc., Summit, NJ (US)

( * ) Notice: Subject to any disclaimer, the term of this patent is extended or adjusted under 35 U.S.C. 154(b) by 0 days.

(21) Appl. No.: 13/876,724

(22) PCT Filed: Sep. 28, 2011

(86) PCT No.: PCT/EP2011/066806
§ 371 (c)(1),
(2), (4) Date: Mar. 28, 2013

(87) PCT Pub. No.: WO2012/041873
PCT Pub. Date: Apr. 5, 2012

(65) Prior Publication Data
US 2013/0196993 A1    Aug. 1, 2013

Related U.S. Application Data

(60) Provisional application No. 61/388,466, filed on Sep. 30, 2010.

(30) Foreign Application Priority Data

Sep. 29, 2010 (EP) .................................... 10181553

(51) Int. Cl.
| | | |
|---|---|---|
| A61K 31/535 | (2006.01) |
| C07D 213/00 | (2006.01) |
| C07D 401/04 | (2006.01) |
| C07D 213/89 | (2006.01) |
| C07D 213/74 | (2006.01) |
| C07D 239/47 | (2006.01) |
| C07D 239/42 | (2006.01) |
| C07D 413/04 | (2006.01) |
| C07D 491/048 | (2006.01) |
| C07D 471/04 | (2006.01) |
| C07D 215/46 | (2006.01) |

(52) U.S. Cl.
CPC ............ *C07D 213/89* (2013.01); *C07D 401/04* (2013.01); *C07D 213/74* (2013.01); *C07D 239/47* (2013.01); *C07D 239/42* (2013.01); *C07D 413/04* (2013.01); *C07D 491/048* (2013.01); *C07D 471/04* (2013.01); *C07D 215/46* (2013.01)
USPC ....................................... 546/309; 514/235.8

(58) Field of Classification Search
None
See application file for complete search history.

(56) References Cited

FOREIGN PATENT DOCUMENTS

| | | |
|---|---|---|
| CN | 101284812 A | 10/2008 |
| EP | 1 900 772 A2 | 3/2008 |
| WO | 2004/035591 A1 | 4/2004 |
| WO | 2008/028689 A1 | 3/2008 |
| WO | 2008/028691 A1 | 3/2008 |

OTHER PUBLICATIONS

Silva, A., Mini-Reviews in Medicinal Chemistry, 2005, vol. 5, pp. 893-1014.*
Jabbar et al., "Anthelmintic resistance: the sate of play revisited", Life Sciences, 2006, pp. 2413-2431, vol. 79.
McKellar et al., "Veterinary anthelmintics: old and new", Trends in Parasitology, 2004, pp. 456-461, vol. 20(10).
International Search Report for corresponding PCT/EP2011/066806, mailed Dec. 14, 2011.
Golisade, et al., "Anti-Malarial Activity of N6- Substituted Adenosine Derivates. Part I", Bioorganic & Medical Chemistry, 2002, pp. 769-777, vol. 10.

\* cited by examiner

*Primary Examiner* — Heidi Reese

(57) ABSTRACT

This invention relates to certain N-heteroaryl compounds that are generally useful as medicaments, more specifically as medicaments for animals. The medicament can preferably be used for the treatment of helminth infections and the treatment of parasitosis, such as caused by helminth infections. This invention also relates to uses of the compounds to make medicaments and treatments comprising the administration of the compounds to animals in need of the treatments. This invention also relates to novel N-heteroaryl compounds and the preparation of said compounds. Moreover this invention relates to pharmaceutical compositions and kits comprising the compounds.

21 Claims, No Drawings

N-HETEROARYL COMPOUNDS

CROSS-REFERENCE TO RELATED APPLICATIONS

This application is a national stage entry under 35 U.S.C. §371 of PCT/EP2011/066806, filed on Sep. 28, 2011, which claims priority to U.S. Provisional Application No. 61/388,466, filed on Sep. 30, 2010, and EP Application No. 10181553.8, filed on Sep. 29, 2010. The content of PCT/EP2011/066806 is hereby incorporated by reference in its entirety.

FIELD OF THE INVENTION

This invention relates to novel N-heteroaryl compounds that are useful as medicaments, the preparation of such compounds and the use of such compounds. The medicament can preferably be used for the treatment of parasitic infections such as helminth infections and especially for the treatment of parasitoses, such as caused by helminth infections. This invention also relates to uses of the compounds to make medicaments and treatments comprising the administration of the compounds to animals in need of the treatments. Moreover this invention relates to pharmaceutical compositions and kits comprising the compounds.

BACKGROUND OF THE INVENTION

Parasitic diseases in animals cause substantial suffering and economic losses throughout the world. Thus, treatment of parasitic infections remains an important global endeavor. The causative organisms include helminths, such as nematodes, cestodes, and trematodes. These organisms can infect, for example, the stomach, intestinal tract, lymphatic system, muscle tissues, kidney, liver, lungs, heart, and brain of animals.

There are many known drugs (or "anthelmintic agents") available to treat various helminith parasite infections, see, e.g., McKellar, Q. A., et al., "Veterinary anthelmintics: old and new," *Review: Trends in Parasitology*, 20(10), 456-61 (October 2004). These anthelmintic agents treat specifically either nematode, cestode or trematode infections or have a broader anthelmintic spectrum. An example of an anthelmintic agent with sole effect on cestodes (tapeworms) is praziquantel. Some primary nematicidal compounds like fenbendazole, mebendazole, oxfendazole, albendazole have a broader spectrum than nematodes and treat cestode infections as well. Closantel, rafoxanide and triclabendazole are examples of specific compounds for the treatment of trematode infections (flukes).

While many parasitic infections can be treated with known drugs, evolutionary development of resistance by the parasites can render such drugs obsolete over time, see, e.g., Jabbar, A., et al., "Anthelmintic resistance: the state of play revisited," *Life Sciences*, 79, 2413-31 (2006). In addition, known drugs may have other deficiencies, such as limited spectrum of activity and the need for repeated treatments.

In WO 2008/028689 A1 certain N-(1-phtalazin-1-ylpiperidin-4-yl)-amides are described as EP2 receptor modulators. WO 2008/028691 A1 discloses as EP2 receptors certain N-(1-hetaryl-piperidin-4-yl)(het)arylamides.

There still exists a need for new medicaments, such as antiparasitic agents to ensure safe, effective, and convenient treatment of a wide range of parasitic helminth infections over a long period of time.

SUMMARY OF THE INVENTION

Briefly, this invention relates to compounds that can generally be used as a medicament for animals. The compounds correspond in structure to formula (I) or its pharmaceutically acceptable salts, solvates, N-oxides or prodrugs

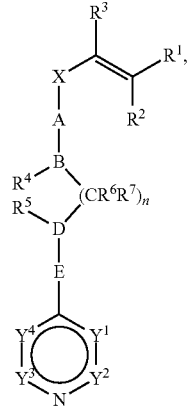

Formula (I)

wherein $R^1$ is halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_2$-$C_6$-alkenyl carbonyl, $SF_5$, $C_1$-$C_6$-alkyl sulfonyl, wherein each of the carbon-containing radicals optionally is substituted by one or more halogen atoms, preferably fluorine atoms, $R^2$ is hydrogen, halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_2$-$C_6$-alkenyl carbonyl, wherein each of the carbon-containing radicals optionally is substituted by one or more halogen atoms, preferably fluorine atoms, $R^3$ is hydrogen, $C_1$-$C_6$-alkyl or cycloalkyl, preferably hydrogen, $R^4$ is hydrogen, $C_1$-$C_6$-alkyl or cycloalkyl preferably hydrogen, $R^5$ is hydrogen, $C_1$-$C_6$-alkyl, cycloalkyl, acyl or $C_1$-$C_6$-alkyloxycarbonyl, $R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy, $C_1$-$C_6$-alkyloxy or cycloalkyloxy $R^7$ is hydrogen, $C_1$-$C_6$-alkyl or cycloalkyl or $R^6$ is joined together with $R^8$ to form a $C_1$-$C_3$-alkylene group and $R^7$ is joined together with $R^9$ to form a $C_1$-$C_3$-alkylene group, wherein one or both of said $C_1$-$C_3$-alkylene groups are optionally substituted by one or more $C_1$-$C_6$-alkyl or cycloalkyl radicals, n is an integer from 1 to 3, X is a carbonyl, thiocarbonyl or sulfonyl group, preferably a carbonyl group, A is a bond or $NR^8$, wherein $R^8$ is hydrogen or $C_1$-$C_6$-alkyl, preferably hydrogen, E is a bond or $NR^9$, wherein $R^9$ is hydrogen or $C_1$-$C_6$-alkyl, preferably hydrogen, B is N or $CR^{10}$, wherein $R^{10}$ is hydrogen or $C_1$-$C_6$-alkyl, preferably hydrogen, D is N or $CR^{11}$, wherein $R^{11}$ is hydrogen or $C_1$-$C_6$-alkyl, preferably hydrogen, $Y^1$ is C or N, wherein C is substituted by $R^{12}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^2$ is C or N, wherein C is substituted by $R^{13}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^3$ is C or N, wherein C is substituted by $R^{14}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio-$C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^4$ is C or N, wherein C is substituted by $R^{15}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, $C_1$-$C_6$-alkylthio, $C_1$-$C_6$-haloalkylthio $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl, or $Y^1$ and $Y^2$ and/or $Y^3$ and $Y^4$ are joined together to form a ring system, and wherein at least one of B and D is a nitrogen atom.

This invention also relates to compounds according to formula (I a) or its pharmaceutically acceptable salts, solvates or N-oxides

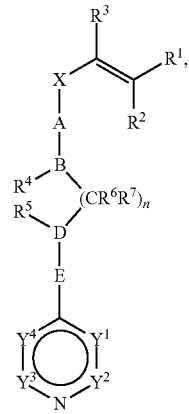

Formula (Ia)

wherein $R^1$ is hydrogen, halogen, $C_1$-$C_6$-alkyl, cycloalkyl, $C_1$-$C_6$-alkyloxy, cycloalkyloxy, $C_1$-$C_6$-alkylthio, cycloalkylthio, $C_2$-$C_6$-alkenyl, $C_2$-$C_6$-alkynyl, $C_1$-$C_6$-alkyloxy $C_1$-$C_6$-alkyl, cycloalkyloxy $C_1$-$C_6$-alkyl, $C_1$-$C_6$-alkyloxy cycloalkyl, cycloalkyloxy cycloalkyl, $C_1$-$C_6$-alkylthio $C_1$-$C_6$-alkyl, cycloalkylthio $C_1$-$C_6$-alkyl, $C_1$-$C_6$-alkylthio cycloalkyl, cycloalkylthio cycloalkyl, amino, $C_1$-$C_6$-alkylamino, cycloalkylamino, di-($C_1$-$C_6$-alkyl)amino, di-(cycloalkyl)amino, $C_1$-$C_6$-alkylamino-$C_1$-$C_6$-alkyl, cycloalkylamino-$C_1$-$C_6$-alkyl, $C_1$-$C_6$-alkylamino-cycloalkyl, cycloalkylamino-cycloalkyl, di-($C_1$-$C_6$-alkyl)amino-$C_1$-$C_6$-alkyl, di-($C_1$-$C_6$-alkyl)amino-cycloalkyl, di-(cycloalkyl)amino-$C_1$-$C_6$-alkyl, di-(cycloalkyl)amino-cycloalkyl, $C_1$-$C_6$-alkyl carbonyl, cycloalkylcarbonyl, $C_1$-$C_6$-alkyloxy carbonyl, cycloalkoxy carbonyl, $C_2$-$C_6$-alkenyl carbonyl, wherein each of the carbon-containing radicals optionally is substituted by one or more halogen atoms, preferably fluorine atoms, or $R^1$ is phenyl, furanyl, imidazolinyl, or thiophenyl, wherein each of the rings optionally is substituted by one or more radicals from the group of $C_1$-$C_6$-alkyl, cycloalkyl and halogen, preferably fluorine, $R^2$ is hydrogen, halogen, $C_1$-$C_6$-alkyl, cycloalkyl, $C_1$-$C_6$-alkyloxy, cycloalkyloxy, $C_1$-$C_6$-alkylthio, cycloalkylthio, $C_2$-$C_6$-alkenyl, $C_2$-$C_6$-alkynyl, $C_1$-$C_6$-alkyloxy $C_1$-$C_6$-alkyl, cycloalkyloxy $C_1$-$C_6$-alkyl, $C_1$-$C_6$-alkyloxy cycloalkyl, cycloalkyloxy cycloalkyl, $C_1$-$C_6$-alkylthio $C_1$-$C_6$-alkyl, cycloalkylthio $C_1$-$C_6$-alkyl, $C_1$-$C_6$-alkylthio cycloalkyl, cycloalkylthio cycloalkyl, amino, $C_1$-$C_6$-alkylamino, cycloalkylamino, di-($C_1$-$C_6$-alkyl)amino, di-(cycloalkyl)amino, $C_1$-$C_6$-alkylamino-$C_1$-$C_6$-alkyl, cycloalkylamino-$C_1$-$C_6$-alkyl, $C_1$-$C_6$-alkylamino-cycloalkyl, cycloalkylamino-cycloalkyl, di-($C_1$-$C_6$-alkyl)amino-$C_1$-$C_6$-alkyl, di-($C_1$-$C_6$-alkyl)amino-cycloalkyl, di-(cycloalkyl)amino-$C_1$-$C_6$-alkyl, di-(cycloalkyl)amino-cycloalkyl, $C_1$-$C_6$-alkyl carbonyl, cycloalkylcarbonyl, $C_1$-$C_6$-alkyloxy carbonyl, cycloalkoxy carbonyl, $C_2$-$C_6$-alkenyl carbonyl, wherein each of the carbon-containing radicals optionally is substituted by one or more halogen atoms, preferably fluorine atoms, or $R^1$ is phenyl, furanyl, imidazolinyl, or thiophenyl, wherein each of the rings optionally is substituted by one or more radicals from the group of $C_1$-$C_6$-alkyl, cycloalkyl and halogen, preferably fluorine, preferably $R^2$ is hydrogen, $R^3$ is hydrogen, $C_1$-$C_6$-alkyl or cycloalkyl, preferably hydrogen, $R^4$ is hydrogen, $C_1$-$C_6$-alkyl or cycloalkyl, preferably hydrogen, $R^5$ is hydrogen, $C_1$-$C_6$-alkyl, cycloalkyl or acyl, $R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxyl, $C_1$-$C_6$-alkyloxy or cycloalkoxy, $R^7$ is hydrogen, $C_1$-$C_6$-alkyl or cycyloalkyl, or $R^6$ and $R^7$ together represent an oxo-group or a thioxo-group, or $R^6$ is joined together with $R^8$ to form a $C_1$-$C_3$-alkylene group and $R^7$ is joined together with $R^9$ to form a $C_1$-$C_3$-alkylene group, wherein one or both of said $C_1$-$C_3$-alkylene groups are optionally substituted by one or more $C_1$-$C_6$-alkyl or cycloalkyl radicals, n is an integer from 1 to 3, X is a carbonyl or sulfonyl group, preferably a carbonyl group, A is a bond or $NR^8$, wherein $R^8$ is hydrogen or $C_1$-$C_6$-alkyl, preferably hydrogen, E is a bond or $NR^9$, wherein $R^9$ is hydrogen or $C_1$-$C_6$-alkyl, preferably hydrogen, B is N or $CR^{10}$, wherein $R^{10}$ is hydrogen or $C_1$-$C_6$-alkyl, preferably hydrogen, D is N or $CR^{11}$, wherein $R^{11}$ is hydrogen or $C_1$-$C_6$-alkyl, preferably hydrogen, $Y^1$ is C or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl) amino, cycloalkylthio, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl $Y^2$ is C or N, wherein C is substituted by $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, dioxolane such as 1,3-dioxolane, dioxane such as 1,3-dioxane, or dioxepane such as 1,3-dioxepane, each said ring being unsubstituted or substituted by $C_1$-$C_6$-alkyl or cycyloalkyl, $Y^3$ is C or N, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, $Y^4$ is C or N, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl) aminocarbonyl, $C_1$-$C_6$-alkoxycarbonyl, cycloalkyl, cycloalkyloxy, cycloalkylamino, ($C_1$-$C_6$-alkyl)-(cycloalkyl) amino, cycloalkylthio, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, or $Y^1$ and $Y^2$ and/or $Y^3$ and $Y^4$ are joined together to form a ring system, and wherein at least one of B and D is a nitrogen atom for treating a helminth infection.

The compounds of the formula (I) and pharmaceutically acceptable solvates, N-oxides, salts and prodrugs thereof are hereinafter together referred to as "compound(s) according to this invention".

The use of the compounds according to formula (I a) and pharmaceutically acceptable solvates, N-oxides and salts thereof is hereinafter referred to as "use according to the invention". The compounds according to formula (I a) are hereinafter referred to as "compound(s) corresponding to the use according to the invention".

This invention is directed, in part, to a novel compound of the formula (I) and pharmaceutically acceptable solvates, N-oxides and salts thereof, and its use as a medicament, preferably a medicament for animals, e.g. for treating parasitic infections such as helminth infections in animals. This invention also is directed, in part, to using at least one compound of the formula (I) and pharmaceutically acceptable solvates, N-oxides and salts thereof to prepare a medicament for treating an infection including diseases caused by such infections (e.g., parasitoses caused by a helminth infection) in animals.

This invention also is directed, in part, to methods of making the novel N-heteroaryl compounds, and intermediates thereof. The preferred embodiments specified in this description for the compounds represent likewise preferred embodiments for the intermediates.

This invention also is directed, in part, to pharmaceutical compositions. The pharmaceutical compositions comprise a) at least one N-heteroaryl compound according to this invention, and b) at least one excipient, and/or at least one active compound (preferably anthelmintic compound) which differs in structure from the component a).

This invention also is directed, in part, to methods for treating a parasitic infection in animals, particularly a treatment of parasitoses caused by a helminth infection. The methods comprise administering at least one compound according to this invention to the animal.

This invention also is directed, in part, to a kit. The kit comprises at least one N-heteroaryl compound according to this invention. In addition, the kit comprises at least one other component, such as another ingredient (e.g., an excipient or active ingredient), and/or an apparatus for combining the compound with another ingredient, and/or an apparatus for administering the compound, and/or a diagnostic tool.

Further benefits of Applicants' invention will be apparent to one skilled in the art from reading this specification.

DETAILED DESCRIPTION OF PREFERRED EMBODIMENTS

Compounds According to this Invention

The present invention also relates to compounds according to formula (I b) and pharmaceutically acceptable solvates, N-oxides, salts and prodrugs thereof and their use as a medicament.

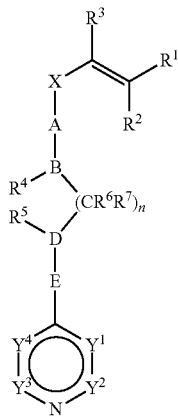

Formula (Ib)

In the compounds of the formula (I b) the radicals, indices and groups have the following meanings:

$R^1$ is halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl carbonyl, $C_2$-$C_6$-alkenyl carbonyl, wherein each of the carbon-containing radicals optionally is substituted by one or more halogen atoms, preferably fluorine atoms $R^2$ is hydrogen, halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_2$-$C_6$-alkenyl carbonyl, wherein each of the carbon-containing radicals optionally is substituted by one or more halogen atoms, preferably fluorine atom $R^3$ is hydrogen, $C_1$-$C_6$-alkyl or cycloalkyl, preferably hydrogen, $R^4$ is hydrogen, $C_1$-$C_6$-alkyl or cycloalkyl, preferably hydrogen, $R^5$ is hydrogen, $C_1$-$C_6$-alkyl, cycloalkyl or acyl $R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy, $C_1$-$C_6$-alkyloxy or cycloalkyloxy $R^7$ is hydrogen, $C_1$-$C_6$-alkyl or cycloalkyl, or $R^6$ is joined together with $R^8$ to form a $C_1$-$C_3$-alkylene group and $R^7$ is joined together with $R^9$ to form a $C_1$-$C_3$-alkylene group, wherein one or both of said $C_1$-$C_3$-alkylene groups are optionally substituted by one or more $C_1$-$C_6$-alkyl or cycloalkyl radicals, n is an integer from 1 to 3

X is a carbonyl or sulfonyl group, preferably a carbonyl group,

A is a bond or $NR^8$, wherein $R^8$ is hydrogen or $C_1$-$C_6$-alkyl, preferably hydrogen, E is a bond or $NR^9$, wherein $R^9$ is hydrogen or $C_1$-$C_6$-alkyl, preferably hydrogen, B is N or $CR^{10}$, wherein $R^{10}$ is hydrogen or $C_1$-$C_6$-alkyl, preferably hydrogen, D is N or $CR^{11}$, wherein $R^{11}$ is hydrogen or $C_1$-$C_6$-alkyl, preferably hydrogen, $Y^1$ is C or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, $Y^2$ is C or N, wherein C is substituted by $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, $Y^3$ is C or N, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, $Y^4$ is C or N, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl or cycloalkyl, or $Y^1$ and $Y^2$ and/or $Y^3$ and $Y^4$ are joined together to form a ring system, and wherein at least one of B and D is a nitrogen atom.

For a compound of formula (Ib), the radicals, indices and groups may have the following additional meaning (leading to compounds referred to here-beneath as "additional compound(s)"):

A first additional compound wherein $R^1$ is $SF_5$, a second additional compound wherein X is thiocarbonyl and a third additional compound wherein $R^1$ is $SF_5$ and X is thiocarbonyl.

For a next additional compound of any of the additional compounds mentioned here-above or beneath, $R^1$ may be a $C_1$-$C_6$-alkyl sulfonyl.

For a next additional compound of any of the additional compounds mentioned here-above or beneath, $R^5$ is $C_1$-$C_6$-alkyloxycarbonyl.

For next additional compounds of any of the additional compounds mentioned here-above or beneath, $Y^1$ is C wherein C is substituted by $R^{12}$ which is $C_1$-$C_6$-alkenyl, or Cycloalkyl, or Cycloalkyloxy, or Cycloalkylamino, or ($C_1$-$C_6$-alkyl)-(Cycloalkyl)amino, or Cycloalkylthio or $C_1$-$C_6$-haloalkylthio.

For next additional compounds of any of the additional compounds mentioned here-above or beneath, $Y^2$ is C wherein C is substituted by $R^{13}$ which is $C_1$-$C_6$-alkenyl, or Cycloalkyl, or Cycloalkyloxy, or Cycloalkylamino, or ($C_1$-$C_6$-alkyl)-(Cycloalkyl)amino, or Cycloalkylthio or $C_1$-$C_6$-haloalkylthio.

For next additional compounds of any of the additional compounds mentioned here-above or beneath, $Y^3$ is C wherein C is substituted by $R^{14}$ which is $C_1$-$C_6$-alkenyl, or Cycloalkyl, or Cycloalkyloxy, or Cycloalkylamino, or ($C_1$-$C_6$-alkyl)-(Cycloalkyl)amino, or Cycloalkylthio or $C_1$-$C_6$-haloalkylthio.

For next additional compounds of any of the additional compounds mentioned here-above, $Y^4$ is C wherein C is substituted by $R^{15}$ which is $C_1$-$C_6$-alkenyl, or Cycloalkyl, or Cycloalkyloxy, or Cycloalkylamino, or ($C_1$-$C_6$-alkyl)-(Cycloalkyl)amino, or Cycloalkylthio or $C_1$-$C_6$-haloalkylthio.

The compounds according to formula (Ib) and the additional compounds are also included in the terms "compounds according to this invention".

The present invention also relates to compounds of formula (I) and pharmaceutically acceptable solvates, N-oxides, salts and prodrugs thereof and their use as a medicament. In the compounds of the formula (I) the radicals, indices and groups have the following meanings:

$R^1$ is halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_2$-$C_6$-alkenyl carbonyl, $SF_5$, $C_1$-$C_6$-alkyl sulfonyl, wherein each of the carbon-containing radicals optionally is substituted by one or more halogen atoms, preferably fluorine atoms, $R^2$ is hydrogen, halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_2$-$C_6$-alkenyl carbonyl, wherein each of the carbon-containing radicals optionally is substituted by one or more halogen atoms, preferably fluorine atoms $R^3$ is hydrogen, $C_1$-$C_6$-alkyl or cycloalkyl, preferably hydrogen.

X is a carbonyl, thiocarbonyl or sulfonyl group, preferably a carbonyl group.

$R^4$ is hydrogen, $C_1$-$C_6$-alkyl or cycloalkyl, preferably hydrogen.

$R^5$ is hydrogen, $C_1$-$C_6$-alkyl, cycloalkyl, acyl or $C_1$-$C_6$-alkyloxycarbonyl.

$R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy, $C_1$-$C_6$-alkyloxy or cycloalkyloxy. Preferably $R^6$ is hydrogen, $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), phenyl, phenyl $C_1$-$C_6$-alkyl, more preferably $R^6$ is hydrogen or $C_1$-$C_6$-alkyl.

$R^7$ is hydrogen, $C_1$-$C_6$-alkyl or cycicoalkyl, preferably hydrogen.

Alternatively $R^6$ is joined together with $R^8$ to form a $C_1$-$C_3$-alkylene group and $R^7$ is joined together with $R^9$ to form a $C_1$-$C_3$-alkylene group, wherein one or both of said $C_1$-$C_3$-alkylene groups are optionally substituted by one or more $C_1$-$C_6$-alkyl or cycloalkyl radicals.

If $R^6$ is joined together with $R^8$ to form a $C_1$-$C_3$-alkylene group and $R^7$ is joined together with $R^9$ to form a $C_1$-$C_3$-alkylene group a spiro compound is formed, wherein said $C_1$-$C_3$-alkylene groups are preferably ethylene groups. One or both of said $C_1$-$C_3$-alkylene groups are optionally substituted by one or more $C_1$-$C_6$-alkyl or cycloalkyl radicals.

The group $(CR^6R^7)_n$ represents a $C_1$-$C_3$-alkylene group, preferably an ethylene group, which is unsubstituted or is substituted by $R^7$=$C_1$-$C_6$-alkyl and/or by $R^6$=$C_1$-$C_6$-alkyl, Cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl) amino $C_1$-$C_6$-alkyl, or phenyl, phenyl $C_1$-$C_6$-alkyl, wherein each phenyl group is optionally substituted by hydroxy or $C_1$-$C_6$-alkyloxy, preferably the group $(CR^6R^7)_n$ represents a $C_1$-$C_3$-alkylene group, preferably an ethylene group, which is unsubstituted or substituted by $C_1$-$C_6$-alkyl.

The substructure A-B($R^4$)—$(CR^6R^7)_n$-D($R^5$)-E represents a chain of 3 to 7 chain atoms, preferably of 4 to 6 chain atoms. In a preferred embodiment A-B($R^4$)—$(CR^6R^7)_n$-D($R^5$)-E represents an ethylenediamine, propylenediamine or butylenediamine chain, which is unsubstituted or substituted as defined in formula (I) above.

In another preferred embodiment A-B($R^4$)—$(CR^6R^7)_n$-D($R^5$)-E represents a semicarbazide chain with B($R^4$), D($R^5$) and E being NH, A being a bond, n=1, and W and $R^7$ forming an oxo-group.

In another preferred embodiment A-B($R^4$)—$(CR^6R^7)_n$-D($R^5$)-E represents a semicarbazide chain with B($R^4$), D($R^5$) and A being NH, E being a bond, n=1, and $R^6$ and $R^7$ forming an oxo-group.

In another preferred embodiment A-B(R$^4$)—(CR$^6$R$^7$)$_n$-D(R$^5$)-E represents a thiosemicarbazide chain with B(R$^4$), D(R$^5$) and E being NH, A being a bond, n=1, and R$^6$ and R$^7$ forming a thioxo-group.

In another preferred embodiment A-B(R$^4$)—(CR$^6$R$^7$)$_n$-D(R$^5$)-E represents a thiosemicarbazide chain with B(R$^4$), D(R$^5$) and A being NH, E being a bond, n=1, and R$^6$ and R$^7$ forming a thioxo-group.

In another preferred embodiment A-B(R$^4$)—(CR$^6$R$^7$)$_n$-D(R$^5$)-E represents an ethylamine or propylamine chain with A and E being a bond, B being N, D(R$^5$) being CH$_2$, CH(C$_1$-C$_6$-alkyl) or C(C$_1$-C$_6$-alkyl)$_2$, and n=1 or 2.

The integer n is from 1 to 3, and is preferably 2. If n is larger than 1 the CR$^6$R$^7$-groups can be identical or different.

The group of the formula (A) in formula (I) and formula (II)

Formula (A)

represents a mono- or polycyclic heterocyclic ring system. A monocyclic ring system is obtained if the carbon/nitrogen atoms Y$^1$, Y$^2$, Y$^3$ and Y$^4$ are unsubstituted or substituted but not joined together. A polycyclic ring system is obtained if either Y$^1$ and Y$^2$ are joined together or Y$^3$ and Y$^4$ are joined together or both Y$^1$ and Y$^2$ as well as Y$^3$ and Y$^4$ are joined together.

A ring system formed by joining together Y$^1$ and Y$^2$ is a saturated or non-saturated ring system (e.g. an aromatic ring system). The ring system itself is a monocyclic or polycyclic ring system, preferably a monocyclic, bicyclic or tricyclic, preferably a monocyclic or bicyclic ring system. The ring system contains from 4 to 10 ring atoms, preferably from 5 to 8 ring atoms, more preferably from 5 to 6 ring atoms, wherein the number of ring atoms includes Y$^1$ and Y$^2$. The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of C$_1$-C$_6$-alkyl, C$_1$-C$_6$-alkyloxy, C$_1$-C$_6$-alkoxycarbonyl and C$_1$-C$_6$-alkylthio.

A ring system formed by joining together Y$^3$ and Y$^4$ is a saturated or non-saturated ring system (e.g. an aromatic ring system). The ring system itself is a monocyclic or polycyclic ring system, preferably a monocyclic, bicyclic or tricyclic, preferably a monocyclic or bicyclic ring system. The ring system contains from 4 to 10 ring atoms, preferably from 5 to 8 ring atoms, more preferably from 5 to 6 ring atoms, wherein the number of ring atoms includes Y$^3$ and Y$^4$. The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of C$_1$-C$_6$-alkyl, C$_1$-C$_6$-alkyloxy, C$_1$-C$_6$-alkoxycarbonyl and C$_1$-C$_6$-alkylthio.

The mentioning of the preferred embodiments of the ring system formed by joining together Y$^1$ and Y$^2$ and/or Y$^3$ and Y$^4$ is intended to disclose all combinations of the preferred embodiments, including but not limited to a saturated, monocyclic, bicyclic or tricyclic ring system with 4 to 10 ring atoms, one, two or three ring heteroatoms from the group of nitrogen, sulphur and oxygen, which is unsubstituted or substituted by one or two radicals from the group of C$_1$-C$_6$-alkyl, C$_1$-C$_6$-alkyloxy and C$_1$-C$_6$-alkylthio, or an unsaturated, monocyclic or bicyclic ring system with 5 to 6 ring atoms, one or two ring heteroatoms, which is unsubstituted, etc.

The group of the formula (A) preferably represents a pyridine (Y$^1$, Y$^2$, Y$^3$ and Y$^4$ are C), pyrimidine, quinoline, quinazoline, thienopyrimidine, thienopyridine, triazolopyrimidine, pyridopyridine, pyrrolopyridine, pyrazolopyrimidine, pyrazolopyridine, furopyridine, 2,3-dihydrofuropyridine, 2,3-dihydro-1,4-dioxinopyridine, furopyrimidine, pyridazine or cinnoline group, wherein each group is optionally substituted by one or more radicals, preferably by one or two radicals, selected from the group of C$_1$-C$_6$-alkyl, C$_1$-C$_6$-alkenyl, Cycloalkyl, Cycloalkyloxy, C$_1$-C$_6$-haloalkyl, C$_1$-C$_6$-alkoxy, C$_1$-C$_6$-haloalkoxy, halogen, nitrilo, nitro, amino, C$_1$-C$_6$-alkylamino, Cycloalkylamino, di(C$_1$-C$_6$-alkyl)amino, (C$_1$-C$_6$-alkyl)-(Cycloalkyl)amino, N-pyrrolidinyl, N-piperidinyl, N-morpholinyl, thiol, hydroxy, C$_1$-C$_6$-alkylthio, Cycloalkylthio, C$_1$-C$_6$-haloalkylthio, C$_1$-C$_6$-alkyl carbonyl, C$_1$-C$_6$-alkylcarbonylamino, aminocarbonyl, C$_1$-C$_6$-alkylaminocarbonyl, di(C$_1$-C$_6$-alkyl)aminocarbonyl, C$_1$-C$_6$-alkoxycarbonyl, dioxolane such as 1,3-dioxolane, dioxane such as 1,3-dioxane, or dioxepane such as 1,3-dioxepane, wherein each ring is unsubstituted or substituted by C$_1$-C$_6$-alkyl.

In another preferred embodiment the group of formula (A) is a pyridine, pyrimidine, quinoline, quinazoline, thienopyrimidine or thienopyridine group, wherein each group is optionally substituted by one or more radicals, preferably by one or two radicals, selected from the group of C$_1$-C$_6$-alkyl, C$_1$-C$_6$-haloalkyl, C$_1$-C$_6$-alkoxy, C$_1$-C$_6$-haloalkoxy, nitrilo, nitro, amino, C$_1$-C$_6$-alkylamino, di(C$_1$-C$_6$-alkyl)amino, N-pyrrolidinyl, N-piperidinyl, N-morpholinyl, thiol, hydroxy, C$_1$-C$_6$-alkylthio, C$_1$-C$_6$-alkyl carbonyl, aminocarbonyl, C$_1$-C$_6$-alkylaminocarbonyl, di(C$_1$-C$_6$-alkyl)aminocarbonyl, dioxolane such as 1,3-dioxolane, dioxane such as 1,3-dioxane, or dioxepane such as 1,3-dioxepane, wherein each ring is unsubstituted or substituted by C$_1$-C$_6$-alkyl.

In another preferred embodiment the group of formula (A) is a pyridine, pyrimidine, quinoline, quinazoline, thienopyrimidine or thienopyridine group (preferably a pyridine, pyrimidine or quinoline group), wherein each group is optionally substituted by one or more radicals, preferably by one or two radicals, selected from the group of C$_1$-C$_6$-haloalkyl, C$_1$-C$_6$-alkoxy, C$_1$-C$_6$-haloalkoxy, amino, C$_1$-C$_6$-alkylamino, di(C$_1$-C$_6$-alkyl)amino, N-pyrrolidinyl, N-piperidinyl, N-morpholinyl, C$_1$-C$_6$-alkylthio, C$_1$-C$_6$-alkoxycarbonyl, dioxolane such as 1,3-dioxolane, dioxane such as 1,3-dioxane, or dioxepane such as 1,3-dioxepane, each ring is unsubstituted or substituted by C$_1$-C$_6$-alkyl.

In another preferred embodiment the group of formula (A) is a pyridine, pyrimidine or quinoline group, preferably a pyridine or pyrimidine group, wherein each group is optionally substituted by one or more radicals, preferably by one or two radicals, selected from the group of C$_1$-C$_6$-alkyl, C$_1$-C$_6$-haloalkyl, C$_1$-C$_6$-alkoxy, C$_1$-C$_6$-haloalkoxy, nitrilo, nitro, amino, C$_1$-C$_6$-alkylamino, di(C$_1$-C$_6$-alkyl)amino, N-pyrrolidinyl, N-piperidinyl, N-morpholinyl, thio, C$_1$-C$_6$-alkylthio, C$_1$-C$_6$-alkyl carbonyl, aminocarbonyl, C$_1$-C$_6$-alkylaminocarbonyl, di(C$_1$-C$_6$-alkyl)aminocarbonyl, C$_1$-C$_6$-alkoxycarbonyl, dioxolane such as 1,3-dioxolane, dioxane such as 1,3-dioxane, or dioxepane such as 1,3-dioxepane, wherein each ring is unsubstituted or substituted by C$_1$-C$_6$-alkyl.

In another preferred embodiment the group of formula (A) is a pyridine or quinoline group, preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyrimidine group, which is optionally substituted by one or more radicals, preferably by one or two radicals, selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio.

In another preferred embodiment of all of the embodiments of compounds according to the invention as described herein, in the group of formula (A) no more than one of $R^{12}$, $R^{13}$, $R^{14}$ and $R^{15}$ represents a halogen atom, more preferably the group of formula (A) contains no more than one halogen atom in total.

Preferably at least two of A, B, D and E contain a nitrogen atom. More preferably at least one of A and B and at least one of D and E contains a nitrogen atom, even more preferred one of A and B and one of D and E contains a nitrogen atom.

In some embodiments each of A, B, D and E contains a nitrogen atom. In other embodiments each of A, B and D, or each of A, B and E, or each of A, D and E, or each of B, D and E contains a nitrogen atom. In still other embodiments each of A and D, or each of B and E, or each of B and D contains a nitrogen atom.

In some embodiments B is N, D is N and each of A and E is a bond. In other embodiments A is $NR^8$, B is $CR^{10}$, D is N, and E is a bond, or A is $NR^8$, B is N, D is N and E is a bond, or A is a bond, B is N, D is N and E is $NR^9$, or A is a bond, B is N, D is $CR^{11}$ and E is $NR^9$, wherein $R^8$ to $R^{11}$ are as defined above.

In a preferred compound of formula (I)

$R^1$ is halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_2$-$C_6$-alkenyl carbonyl, $SF_5$, $C_1$-$C_6$-alkyl sulfonyl, wherein each of the carbon-containing radicals optionally is substituted by one or more halogen atoms, preferably fluorine atoms, $R^2$ is hydrogen, $R^3$ is hydrogen, $R^4$ is hydrogen or $C_1$-$C_6$-alkyl, preferably hydrogen, $R^5$ is hydrogen, $C_1$-$C_6$-alkyl, acyl or $C_1$-$C_6$-alkyloxycarbonyl, $(CR^6R^7)_n$ is a $C_1$-$C_3$-alkylene group, preferably an ethylene group, which is optionally substituted by one or more $C_1$-$C_6$-alkyl radicals, A is a bond or $NR^B$, wherein $R^8$ is H or $C_1$-$C_6$-alkyl, E is a bond or $NR^9$, wherein $R^9$ is H or $C_1$-$C_6$-alkyl, B is N or $CR^{10}$, wherein $R^{19}$ is H or $C_1$-$C_6$-alkyl, D is N or $CR^{11}$, wherein $R^{11}$ is H or $C_1$-$C_6$-alkyl, X is a carbonyl, thiocarbonyl or sulfonyl group, preferably a carbonyl group, $Y^1$ is C or N, wherein C is substituted by $R^{12}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^2$ is C or N, wherein C is substituted by $R^{13}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^3$ is C or N, wherein C is substituted by $R^{14}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^4$ is C or N, wherein C is substituted by $R^{15}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, $C_1$-$C_6$-alkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl, or $Y^1$ and $Y^2$ and/or $Y^3$ and $Y^4$ are joined together to form a ring system, and wherein at least one of B and D is a nitrogen atom.

A preferred compound has the formula (II),

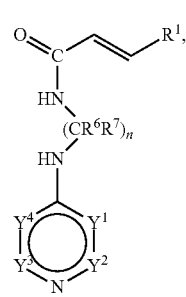

Formula (II)

wherein $R^1$ is $C_1$-$C_6$-alkyl, $C_1$-$C_6$-alkyloxy $C_1$-$C_6$-alkyl, or $C_1$-$C_6$-alkylthio $C_1$-$C_6$-alkyl, wherein each of the carbon-containing radicals is unsubstituted or substituted by one or more halogen atoms, preferably by one or more fluorine atoms, e.g. by 1 to 10, preferably by 1 to 5, fluorine atoms, $R^6$ is hydrogen, $C_1$-$C_6$-alkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy or $C_1$-$C_6$-alkyloxy, preferably $R^6$ is hydrogen, $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), phenyl, phenyl $C_1$-$C_6$-alkyl, more preferably $R^6$ is hydrogen or $C_1$-$C_6$-alkyl, even more preferably hydrogen, $R^7$ is hydrogen or $C_1$-$C_6$-alkyl, preferably hydrogen, n is 2 or 3, preferably 2, $Y^1$ is C or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, Cycloalkyl, Cycloalkyloxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $Y^2$ is C or N, preferably C, wherein C is substituted by $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, Cycloalkyl, Cycloalkyloxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^3$ is C or N, preferably C, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, Cycloalkyl, Cycloalkyloxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^4$ is C or N, preferably C, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, or $Y^1$ and $Y^2$ and/or $Y^3$ and $Y^4$ are joined together to form a 5- or 6-membered ring system.

In a preferred compound of the formula (II)

$R^1$ is $C_1$-$C_6$-alkyl, $C_1$-$C_6$-alkyloxy $C_1$-$C_6$-alkyl, or $C_1$-$C_6$-alkylthio $C_1$-$C_6$-alkyl, di-($C_1$-$C_6$-alkyl)amino-$C_1$-$C_6$-alkyl, wherein each of the carbon-containing radicals unsubstituted or substituted by one or more halogen atoms, preferably by one or more fluorine atoms, e.g. by 1 to 10, preferably by 1 to 5, fluorine atoms, $Y^1$ is C or N, wherein C is substituted by $R^{12}$ which is H, or $C_1$-$C_6$-alkyl, $Y^2$ is C, wherein C is substituted by $R^{13}$ is H, $C_1$-$C_6$-alkoxy, $C_1$-$C_6$-alkyl carbonyl, Cycloalkyl, Cycloalkyloxy, $C_1$-$C_6$-alkylthio, $Y^3$ is C, wherein C is substituted by $R^{14}$ is H, $C_1$-$C_6$-alkoxy, $C_1$-$C_6$-alkyl carbonyl, Cycloalkyl, Cycloalkyloxy, $C_1$-$C_6$-alkylthio, $Y^4$ is C, wherein C is substituted by $R^{15}$ is H, $C_1$-$C_6$-alkoxy, $C_1$-$C_6$-alkylthio, or $Y^1$ and $Y^2$ or $Y^3$ and $Y^4$ are joined together to form a 5- or 6-membered ring system.

In a preferred compound of the formula (I) or (II)

$R^2$ is hydrogen, $R^3$ is hydrogen, $R^4$ is hydrogen or $C_1$-$C_6$-alkyl, preferably hydrogen, $R^5$ is hydrogen or $C_1$-$C_6$-alkyl, preferably hydrogen, $R^6$ is hydrogen or $C_1$-$C_6$-alkyl, preferably hydrogen, $R^7$ is hydrogen, X is a carbonyl group, n is 2, the group of formula (A) represents a pyridine, pyrimidine or quinoline group, preferably a pyridine or pyrimidine group, more preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, Cycloalkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl, and one of A and B and one of D and E contains a nitrogen atom.

In another preferred compound of the formula (I) or (II)

$R^1$ is $C_1$-$C_6$-alkyl which is unsubstituted or substituted by one or more halogen atoms, preferably by one or more fluorine atoms, e.g. by 1 to 10, preferably by 1 to 5, fluorine atoms.

In another preferred compound of the formula (II) the group of the formula (A)

Formula (A)

represents a pyridine, pyrimidine, quinoline, quinazoline, thienopyrimidine, thienopyridine, triazolopyrimidine, pyridopyridine, pyrrolopyridine, pyrazolopyrimidine, pyrazolopyridine, furopyridine, 2,3-dihydrofuropyridine, 2,3-dihydro-1,4-dioxinopyridine, furopyrimidine, pyridazine or cinnoline group, wherein each group is optionally substituted by one or more radicals, preferably by one or two radicals, selected from the group of $C_1$-$C_6$-alkyl, Cycloalkyl, Cycloalkoxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group (preferably a pyridine, pyrimidine or quinoline group), wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyridine, pyrimidine or quinoline group, preferably a pyridine or pyrimidine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl, and preferably selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio.

In another preferred embodiment the group of formula (A) is a pyridine or quinoline group, preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyrimidine group, which is optionally substituted by one or more radicals, preferably by one or two radicals, selected from the group of $C_1$-$C_6$-alkyl, $C_1$-$C_6$-alkoxy, $C_1$-$C_6$-haloalkoxy, amino, $C_1$-$C_6$-alkylamino, N-pyrrolidinyl, N-piperidinyl, N-morpholinyl, di($C_1$-$C_6$-alkyl)amino, $C_1$-$C_6$-alkylthio.

Use According to this Invention

The present invention also relates to compounds of formula (I a) and pharmaceutically acceptable solvates, N-oxides and salts thereof and their use for treating a helminth infection In the compounds of the formula (I a) the radicals, indices and groups have the following meanings:

$R^1$ is hydrogen, halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals optionally is substituted by one or more halogen atoms, preferably fluorine atoms, or $R^1$ is phenyl, furanyl, imidazolinyl, or thiophenyl, wherein each of the rings optionally is substituted by one or more radicals from the group of $C_1$-$C_6$-alkyl and halogen, preferably fluorine, $R^2$ is hydrogen, halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, amino, $C_1$-$C_6$-alkylamino, di-($C_1$-$C_6$-alkyl)amino, $C_1$-$C_6$-alkylamino-$C_1$-$C_6$-alkyl, di-($C_1$-$C_6$-alkyl)amino-$C_1$-$C_6$-alkyl, $C_1$-$C_6$-alkyl carbonyl, $C_1$-$C_6$-alkyloxy carbonyl, $C_2$-$C_6$-alkenyl carbonyl, wherein each of the carbon-containing radicals optionally is substituted by one or more halogen atoms, preferably fluorine atoms, or $R^2$ is phenyl, furanyl, imidazolinyl, or thiophenyl, wherein each of the rings optionally is substituted by one or more radicals from the group of $C_1$-$C_6$-alkyl and halogen, preferably fluorine, preferably $R^2$ is hydrogen, $R^3$ is hydrogen or $C_1$-$C_6$-alkyl, preferably hydrogen.

X is a carbonyl or sulfonyl group, preferably a carbonyl group.

$R^4$ is hydrogen or $C_1$-$C_6$-alkyl, preferably hydrogen.

$R^5$ is hydrogen, $C_1$-$C_6$-alkyl or acyl, preferably hydrogen.

$R^6$ is hydrogen, $C_1$-$C_6$-alkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy or $C_1$-$C_6$-alkyloxy. Preferably $R^6$ is hydrogen, $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), phenyl, phenyl $C_1$-$C_6$-alkyl, more preferably $R^6$ is hydrogen or $C_1$-$C_6$-alkyl.

$R^7$ is hydrogen or $C_1$-$C_6$-alkyl, preferably hydrogen.

Alternatively $R^6$ and $R^7$ together represent an oxo-group or a thioxo-group or $R^6$ is joined together with $R^8$ to form a $C_1$-$C_3$-alkylene group and $R^7$ is joined together with $R^9$ to form a $C_1$-$C_3$-alkylene group, wherein one or both of said $C_1$-$C_3$-alkylene groups are optionally substituted by one or more $C_1$-$C_6$-alkyl radicals.

If $R^6$ is joined together with $R^8$ to form a $C_1$-$C_3$-alkylene group and $R^7$ is joined together with $R^9$ to form a $C_1$-$C_3$-alkylene group a spiro compound is formed, wherein said $C_1$-$C_3$-alkylene groups are preferably ethylene groups. One or both of said $C_1$-$C_3$-alkylene groups are optionally substituted by one or more $C_1$-$C_6$-alkyl radicals.

The group $(CR^6R^7)_n$ represents a $C_1$-$C_3$-alkylene group, preferably an ethylene group, which is unsubstituted or is substituted by R⁷=$C_1$-$C_6$-alkyl and/or by R⁶=$C_1$-$C_6$-alkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, or phenyl, phenyl $C_1$-$C_6$-alkyl, wherein each phenyl group is optionally substituted by hydroxy or $C_1$-$C_6$-alkyloxy, preferably the group ($CR^6R^7$)$_n$ represents a $C_1$-$C_3$-alkylene group, preferably an ethylene group, which is unsubstituted or substituted by $C_1$-$C_6$-alkyl.

The substructure A-B(R⁴)—($CR^6R^7$)$_n$-D(R⁵)-E represents a chain of 3 to 7 chain atoms, preferably of 4 to 6 chain atoms. In a preferred embodiment A-B(R⁴)—($CR^6R^7$)$_n$-D(R⁵)-E represents an ethylenediamine, propylenediamine or butylenediamine chain, which is unsubstituted or substituted as defined in formula (I) above.

In another preferred embodiment A-B(R⁴)—($CR^6R^7$)$_n$-D(R⁵)-E represents a semicarbazide chain with B(R⁴), D(R⁵) and E being NH, A being a bond, n=1, and R⁶ and R⁷ forming an oxo-group.

In another preferred embodiment A-B(R⁴)—($CR^6R^7$)$_n$-D(R⁵)-E represents a semicarbazide chain with B(R⁴), D(R⁵) and A being NH, E being a bond, n=1, and W and R⁷ forming an oxo-group.

In another preferred embodiment A-B(R⁴)—($CR^6R^7$)$_n$-D(R⁵)-E represents a thiosemicarbazide chain with B(R⁴), D(R⁵) and E being NH, A being a bond, n=1, and R⁶ and R⁷ forming a thioxo-group.

In another preferred embodiment A-B(R⁴)—($CR^6R^7$)$_n$-D(R⁵)-E represents a thiosemicarbazide chain with B(R⁴), D(R⁵) and A being NH, E being a bond, n=1, and R⁶ and R⁷ forming a thioxo-group.

In another preferred embodiment A-B(R⁴)—($CR^6R^7$)$_n$-D(R⁵)-E represents an ethylamine or propylamine chain with A and E being a bond, B being N, D(R⁵) being $CH_2$, CH($C_1$-$C_6$-alkyl) or C($C_1$-$C_6$-alkyl)$_2$, and n=1 or 2.

The integer n is from 1 to 3, and is preferably 2. If n is larger than 1 the $CR^6R^7$-groups can be identical or different.

The group of the formula (A) in formula (Ia)

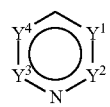

Formula (A)

represents a mono- or polycyclic heterocyclic ring system. A monocyclic ring system is obtained if the carbon/nitrogen atoms Y¹, Y², Y³ and Y⁴ are unsubstituted or substituted but not joined together. A polycyclic ring system is obtained if either Y¹ and Y² are joined together or Y³ and Y⁴ are joined together or both Y¹ and Y² as well as Y³ and Y⁴ are joined together.

A ring system formed by joining together Y¹ and Y² is a saturated or non-saturated ring system (e.g. an aromatic ring system). The ring system itself is a monocyclic or polycyclic ring system, preferably a monocyclic, bicyclic or tricyclic, preferably a monocyclic or bicyclic ring system. The ring system contains from 4 to 10 ring atoms, preferably from 5 to 8 ring atoms, more preferably from 5 to 6 ring atoms, wherein the number of ring atoms includes Y¹ and Y². The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of $C_1$-$C_6$-alkyl, $C_1$-$C_6$-alkyloxy, $C_1$-$C_6$-alkoxycarbonyl and $C_1$-$C_6$-alkylthio.

A ring system formed by joining together Y³ and Y⁴ is a saturated or non-saturated ring system (e.g. an aromatic ring system). The ring system itself is a monocyclic or polycyclic ring system, preferably a monocyclic, bicyclic or tricyclic, preferably a monocyclic or bicyclic ring system. The ring system contains from 4 to 10 ring atoms, preferably from 5 to 8 ring atoms, more preferably from 5 to 6 ring atoms, wherein the number of ring atoms includes Y³ and Y⁴. The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of $C_1$-$C_6$-alkyl, $C_1$-$C_6$-alkyloxy, $C_1$-$C_6$-alkoxycarbonyl and $C_1$-$C_6$-alkylthio.

The mentioning of the preferred embodiments of the ring system formed by joining together Y¹ and Y² and/or Y³ and Y⁴ is intended to disclose all combinations of the preferred embodiments, including but not limited to a saturated, monocyclic, bicyclic or tricyclic ring system with 4 to 10 ring atoms, one, two or three ring heteroatoms from the group of nitrogen, sulphur and oxygen, which is unsubstituted or substituted by one or two radicals from the group of $C_1$-$C_6$-alkyl, $C_1$-$C_6$-alkyloxy and $C_1$-$C_6$-alkylthio, or an unsaturated, monocyclic or bicyclic ring system with 5 to 6 ring atoms, one or two ring heteroatoms, which is unsubstituted, etc.

The group of the formula (A) preferably represents a pyridine (Y¹, Y², Y³ and Y⁴ are C), pyrimidine, quinoline, quinazoline, thienopyrimidine, thienopyridine, triazolopyrimidine, pyridopyridine, pyrrolopyridine, pyrazolopyrimidine, pyrazolopyridine, furopyridine, 2,3-dihydrofuropyridine, 2,3-dihydro-1,4-dioxinopyridine, furopyrimidine, pyridazine or cinnoline group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, halogen, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group (preferably a pyridine, pyrimidine or quinoline group), wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkoxycarbonyl, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyridine, pyrimidine or quinoline group, preferably a pyridine or pyrimidine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine or quinoline group, preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyrimidine group, which is optionally substituted by one or more radicals, preferably by one or two radicals, selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio.

In another preferred embodiment of all embodiments of the use according to the invention, in the group of formula (A) no more than one of $R^{12}$, $R^{13}$, $R^{14}$ and $R^{15}$ represents a halogen atom, more preferably the group of formula (A) contains no more than one halogen atom in total.

Preferably at least two of A, B, D and E contain a nitrogen atom. More preferably at least one of A and B and at least one of D and E contains a nitrogen atom, even more preferred one of A and B and one of D and E contains a nitrogen atom.

In some embodiments each of A, B, D and E contains a nitrogen atom. In other embodiments each of A, B and D, or each of A, B and E, or each of A, D and E, or each of B, D and E contains a nitrogen atom. In still other embodiments each of A and D, or each of B and E, or each of B and D contains a nitrogen atom.

In some embodiments B is N, D is N and each of A and E is a bond. In other embodiments A is $NR^8$, B is $CR^{10}$, D is N, and E is a bond, or A is $NR^8$, B is N, D is N and E is a bond, or A is a bond, B is N, D is N and E is $NR^9$, or A is a bond, B is N, D is $CR^{11}$ and E is $NR^9$, wherein $R^8$ to $R^{11}$ are as defined above.

In a preferred compound of formula (Ia)

$R^1$ is hydrogen, halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkyloxy $C_1$-$C_6$-alkyl, $C_1$-$C_6$-alkylthio $C_1$-$C_6$-alkyl, $C_1$-$C_6$-alkylamino, di-($C_1$-$C_6$-alkyl) amino, $C_1$-$C_6$-alkylamino-$C_1$-$C_6$-alkyl, di-($C_1$-$C_6$-alkyl) amino-$C_1$-$C_6$-alkyl, $C_1$-$C_6$-alkyl carbonyl, $C_1$-$C_6$-alkyloxy carbonyl, or $C_2$-$C_6$-alkenyl carbonyl, wherein each of the carbon-containing radicals optionally is substituted by one or more halogen atoms, preferably fluorine atoms, $R^2$ is hydrogen, $R^3$ is hydrogen, $R^4$ is hydrogen or $C_1$-$C_6$-alkyl, preferably hydrogen, $R^5$ is hydrogen, $C_1$-$C_6$-alkyl or acyl, $(CR^6R^7)_n$ is a $C_1$-$C_3$-alkylene group, preferably an ethylene group, which is optionally substituted by one or more $C_1$-$C_6$-alkyl radicals, A is a bond or $NR^8$, wherein $R^8$ is H or $C_1$-$C_6$-alkyl, E is a bond or $NR^9$, wherein $R^9$ is H or $C_1$-$C_6$-alkyl, B is N or $CR^{10}$, wherein $R^{10}$ is H or $C_1$-$C_6$-alkyl, D is N or $CR^{11}$, wherein $R^{11}$ is H or $C_1$-$C_6$-alkyl, $Y^1$ is C or N, wherein C is substituted by $R^{12}$ which is hydrogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each ring being unsubstituted or substituted by $C_1$-$C_6$-alkyl, $Y^2$ is C or N, wherein C is substituted by $R^{13}$ which is hydrogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^3$ is C or N, wherein C is substituted by $R^{14}$ which is hydrogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^4$ is C or N, wherein C is substituted by $R^{15}$ which is hydrogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane such as 1,3-dioxolane, dioxane such as 1,3-dioxane, or dioxepane such as 1,3-dioxepane, each said ring being unsubstituted or substituted by $C_1$-$C_6$-alkyl, or $Y^1$ and $Y^2$ and/or $Y^3$ and $Y^4$ are joined together to form a ring system, and wherein two of A, B, D and E contain a nitrogen atom and at least one of B and D is a nitrogen atom, preferably B and D represent a nitrogen atom and A and E are a bond.

A preferred compound for use according to the invention has the formula (II) as depicted immediately here-beneath,

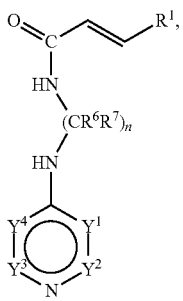

Formula (II)

wherein $R^1$ is $C_1$-$C_6$-alkyl, $C_1$-$C_6$-alkyloxy $C_1$-$C_6$-alkyl, or $C_1$-$C_6$-alkylthio $C_1$-$C_6$-alkyl, $C_1$-$C_6$-alkylamino-$C_1$-$C_6$-alkyl, di-($C_1$-$C_6$-alkyl)amino-$C_1$-$C_6$-alkyl, wherein each of the carbon-containing radicals is unsubstituted or substituted by one or more halogen atoms, preferably by one or more fluorine atoms, e.g. by 1 to 10, preferably by 1 to 5, fluorine atoms, $R^6$ is hydrogen, $C_1$-$C_6$-alkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy or $C_1$-$C_6$-alkyloxy, preferably $R^6$ is hydrogen, $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), phenyl, phenyl $C_1$-$C_6$ alkyl, more preferably $R^6$ is hydrogen or $C_1$-$C_6$-alkyl, even more preferably hydrogen, $R^7$ is hydrogen or $C_1$-$C_6$-alkyl, preferably hydrogen, n is 2 or 3, preferably 2, $Y^1$ is C or N, wherein C is substituted by $R^{12}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, phenyl, $Y^2$ is C or N, preferably C, wherein C is substituted by $R^{13}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^3$ is C or N, wherein C is substituted by $R^{14}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, each said ring being unsubstituted or substituted by $C_1$-$C_6$-alkyl, $Y^4$ is C or N, preferably C, wherein C is substituted by $R^{15}$ which is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, phenyl, or $Y^1$ and $Y^2$ and/or $Y^3$ and $Y^4$ are joined together to form a 5- or 6-membered ring system.

In a preferred compound of the formula (IIa)

$R^1$ is $C_1$-$C_6$-alkyl, $C_1$-$C_6$-alkyloxy $C_1$-$C_6$-alkyl, or $C_1$-$C_6$-alkylthio $C_1$-$C_6$-alkyl, di-($C_1$-$C_6$-alkyl)amino-$C_1$-$C_6$-alkyl, wherein each of the carbon-containing radicals unsubstituted or substituted by one or more halogen atoms, preferably by one or more fluorine atoms, e.g. by 1 to 10, preferably by 1 to 5, fluorine atoms, $Y^1$ is C or N, wherein C is substituted by $R^{12}$ which is H, or $C_1$-$C_6$-alkyl, $Y^2$ is C, wherein C is substituted by $R^{13}$ is H, $C_1$-$C_6$-alkoxy, $C_1$-$C_6$-alkyl carbonyl, $Y^3$ is C, wherein C is substituted by $R^{14}$ is H, $C_1$-$C_6$-alkoxy, $C_1$-$C_6$-alkyl carbonyl, $Y^4$ is C, wherein C is substituted by $R^{15}$ is H, $C_1$-$C_6$-alkoxy, or $Y^1$ and $Y^2$ or $Y^3$ and $Y^4$ are joined together to form a 5- or 6-membered ring system.

In a preferred compound of the formula (I a) or (IIa)

$R^2$ is hydrogen or $C_1$-$C_6$-alkyl, preferably hydrogen, $R^3$ is hydrogen or $C_1$-$C_6$-alkyl, preferably hydrogen, $R^4$ is hydrogen or $C_1$-$C_6$-alkyl, preferably hydrogen, $R^5$ is hydrogen or $C_1$-$C_6$-alkyl, preferably hydrogen, $R^6$ is hydrogen or $C_1$-$C_6$-alkyl, preferably hydrogen, $R^7$ is hydrogen, X is a carbonyl group, n is 2, the group of formula (A) represents a pyridine, pyrimidine or quinoline group, preferably a pyridine or pyrimidine group, more preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl, and one of A and B and one of D and E contains a nitrogen atom.

In another preferred compound of the formula (Ia) or (IIa)

$R^1$ is $C_1$-$C_6$-alkyl which is unsubstituted or substituted by one or more halogen atoms, preferably by one or more fluorine atoms, e.g. by 1 to 10, preferably by 1 to 5, fluorine atoms.

In another preferred compound of the formula (IIa) the group of the formula (A)

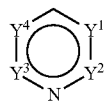
Formula (A)

represents a pyridine, pyrimidine, quinoline, quinazoline, thienopyrimidine, thienopyridine, triazolopyrimidine, pyridopyridine, pyrrolopyridine, pyrazolopyrimidine, pyrazolopyridine, furopyridine, 2,3-dihydrofuropyridine, 2,3-dihydro-1,4-dioxinopyridine, furopyrimidine, pyridazine or cinnoline group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, $C_1$-$C_6$-alkoxycarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl.

In another preferred embodiment the group of formula (A) is a pyridine, pyrimidine, quinoline, quinazoline, thienopyrimidine or thienopyridine group (preferably a pyridine, pyrimidine or quinoline group), wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyridine, pyrimidine or quinoline group, preferably a pyridine or pyrimidine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane such as 1,3-dioxolane, dioxane such as 1,3-dioxane, or dioxepane such as 1,3-dioxepane, wherein each ring is unsubstituted or substituted by $C_1$-$C_6$-alkyl, and preferably selected from the group of $C_1$-$C_6$-alkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio.

In another preferred embodiment the group of formula (A) is a pyridine or quinoline group, preferably a pyridine group, wherein each group is optionally substituted by one or more radicals, preferably by one or two radicals, selected from the group of $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, dioxolane such as 1,3-dioxolane, dioxane such as 1,3-dioxane, or dioxepane such as 1,3-dioxepane, each ring is unsubstituted or substituted by $C_1$-$C_6$-alkyl.

In another preferred embodiment the group of formula (A) is a pyrimidine group, which is optionally substituted by one or more radicals, preferably by one or two radicals, selected from the group of $C_1$-$C_6$-alkyl, $C_1$-$C_6$-alkoxy, $C_1$-$C_6$-haloalkoxy, amino, $C_1$-$C_6$-alkylamino, N-pyrrolidinyl, N-piperidinyl, N-morpholinyl, di($C_1$-$C_6$-alkyl)amino, $C_1$-$C_6$-alkylthio.

Salts, Solvates, N-Oxides and Prodrugs

A salt of the compounds of the formula (I), (Ia) or (Ib), or another compound may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e. to an animal) for a therapeutic benefit, the salt is pharmaceutically acceptable.

Salts may also be of advantage in the synthesis of the compounds according to this invention. For instance certain intermediates may advantagously be used in form of their salts in the preparation process of the compounds according to this invention.

In general, an acid addition salt can be prepared by reacting a free base compound with an approximately stoichiometric amount of an inorganic or organic acid. Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

A solvate of a compound of the formula (I), (Ia) or (Ib), or another compound may be formed by aggregation of said compound of the formula (I) with solvent molecules such as water, alcohols, for example ethanol, aromatic solvents such as toluene, ethers, halogenated organic solvents such as dichloromethane, preferably in a definite proportion by weight.

An N-oxide of a compound of the formula (I), (Ia) or (Ib), or another compound may be formed by oxidation of an N-atom in an amine or N-heterocycle such as pyridine by oxidation agents such as hydrogen peroxide, peracids or inorganic oxidation agents such as potassium peroxymonosulfate (oxone). In preferred N-oxides a nitrogen atom in the group of formula (A) is oxidized, more preferred are N-oxides wherein the nitrogen atom in the para-position is oxidized:

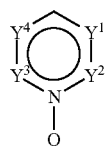

This invention also encompasses prodrug derivatives of the compounds of formula (I) and (Ib). The term prodrug refers to compounds that are transformed in vivo to yield the parent compound of formula (I) or (Ib). In vivo means that in the case of, for example, treatment of a parasitic infection this transformation can occur in the host organism and/or the parasite. Various forms of prodrugs are well known in the art. For example, if the group of formula (A) represents a pyridine, it is possible to form pyridinium salts such as, for example, acyloxyalkylpyridinium salts, which can offer advantages in terms of higher solubility for parenteral dosage forms, which are described in S. K. Davidsen et al., *J. of Med. Chem.* 37 4423-4429 (1994). Other examples of possible prodrugs are compounds that form the double bond present in formula (I) and (Ib) by elimination from a saturated precursor compound:

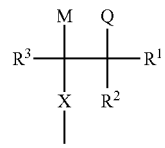

Elimination of MQ will generate compounds of formula (I) or (Ib). If M is hydrogen, this type of elimination is also known in the art as retro-Michael reaction or retro-Michael addition. Examples of such retro-Michael reactions that occur in vivo to generate unsaturated compounds are described in, for example, S. C. Alley, *Bioconjugate Chem.* 19, 759-765 (2008); D. Lopez, *Abstracts of Papers*, 231$^{st}$ National Meeting, Atlanta, Ga., United States, Mar. 26-30, 2006, MEDI-292.

Isomers

The compounds according to this invention, their intermediates and compounds corresponding to the use according to the invention, may exist in various isomeric forms. A reference to a compound according to this invention, an intermediate thereof or a compound corresponding to the use according to the invention always includes all possible isomeric forms of such compound.

In some embodiments, such compounds may have two or more isomers, such as optical isomers or conformational isomers. For example, the compounds can have a cis or trans configuration at the —$CXR^3$=$CR^1R^2$ double bond. In some preferred embodiments, such compound has the (E) configuration, in other embodiments, the compound has the (Z) configuration. In a preferred embodiment the compounds have (E) configuration. For instance the compounds of the formula (II), the compounds of Table A wherein $R^2$=$R^3$=H and the compounds of Table B exhibit (E) configuration.

Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound.

Treatment Methods

This section pertains to compounds according to the invention and compounds corresponding to the use according to the invention. The compounds and were applicable pharmaceutically acceptable solvates, N-oxides, salts and prodrugs thereof may generally be used as a medicament for animals. In some embodiments of this invention, one or more, preferably one compound according to this invention is administered to treat infections such as parasitic infections (e.g. helminth infections) of an animal (or make a medicament to treat infections such as parasitic infections of an animal). In one embodiment one or more, preferably one compound according to this invention is administered to treat parasitoses of an animal (or make a medicament to treat parasitoses of an animal). The use according to the invention is directed to treat helminth infections.

The term "(parasitic) infection" includes conditions associated with or caused by one or more (parasitic) pathogens; said conditions include clinical conditions (parasitoses) and sub-clinical conditions. The term "treatment of parasitic infection" thus includes both the treatment of parasitoses and the treatment of sub-clinical conditions. The treatment of a parasite infection generally implies the suppression of parasite (e.g. helminth) burdens in the animal below that level at which economic loss occurs.

Sub-clinical conditions are typically conditions not directly leading to clinical symptoms in the parasite infected animal but leading to economic losses. Such economic losses can be e.g. by depression of growth in young animals, lower feed efficiency, lower weight gain in meat producing animals, lower milk production in ruminants, lower egg production in laying hens, or lower wool-production in sheep.

The term "parasitoses" relates to clinically manifest pathologic conditions and diseases associated with or caused by an infection by one or more parasites, such as, for example parasitic gastroenteritis or anemia in ruminants e.g. sheep and goats or colic in horses.

In general, the prevention or treatment of parasitic infection including parasitoses is achieved by administering one or more, preferably one compound according to this invention to treat a parasitic infection such as a helminth infection, the latter treatment being the sole treatment of the use according to the invention.

Thus the invention provides a method of treating a (parasitic) infection such as a helminth infection, including parasitoses, which comprises administering to the animal an antiparasitically, preferably an anthelmintically, effective amount of one or more compounds according to this invention, or where applicable, a compound corresponding to the use according to the invention. Preferably nematode, cestode or trematode infections are treated, more preferably nematode infections.

"Treating (parasitic) infections" includes treating parasitoses and means to partially or completely inhibit the development of (parasitic) infections of an animal susceptible to (parasitic) infection, reduce or completely eliminate the symptoms of infections of an animal having infections, and/or partially or completely cure infections of an animal having infections. This can be achieved by alleviating or reducing pathogen numbers such as parasite numbers in an animal.

The effect of the compounds according to this invention or the use according to the invention can be e.g. ovicidal, larvicidal, and/or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate. Alternatively the parasite is not killed but paralyzed and is then dislodged and excreted by the host animal.

In another aspect the present invention thus provides a pharmaceutical composition comprising an anthelmintically effective amount of one or more, preferably one compound according to this invention or a compound corresponding to the use according to the invention and one or more pharmaceutically acceptable excipients.

The compounds and pharmaceutical compositions according to this invention are useful in treating parasitic infections such as helminth infections of animals. An "effective amount," is the amount or quantity of a compound that is required to alleviate or reduce parasite numbers in an animal, and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound e.g. the parasite count is reduced, after a first administration, by an amount ranging from 5% to about 100%.

This can be evaluated by counting parasites (especially helminthes) directly after necroscopy of the host animal.

The reduction of parasite numbers, especially gastrointestinal helminth parasites can be alternatively measured indirectly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount".

A single administration of a compound according to this invention or a compound corresponding to the use according to the invention is typically sufficient to treat a parasitic infection such as a helminth infection, preferably a nematode, cestode or trematode infection, more preferably a nematode infection. Although such a single dose is typically preferred, it is contemplated that multiple doses can be used. When the compound is orally administered, the total dose to treat a disease such as a helminth infection is generally greater than about 0.01 mg/kg (i.e., milligram of compound per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 0.5 to about 15 mg/kg, from about 1 to about 10 mg/kg. The same dose range may be suitable for other dosage routes. For example, in some embodiments, the same dose range is used for subcutaneous administration. The desired dose, however, may be less in some instances where the compound according to this invention is administered intravenously.

If the compound according to this invention or a compound corresponding to the use according to the invention is administered parenterally via an injection, the concentration of the compound in the dosage form preferably is sufficient to provide the desired therapeutically effective amount of the compound in a volume that is acceptable for parenteral administration.

Factors affecting the preferred dosage may include, for example, the parasite species infection to be treated and the development stages of the parasites, the type (e.g., species and breed), age, size, sex, diet, activity, and condition of the of the infected animal; the dosage route; pharmacological considerations, such as the activity, efficacy, pharmacokinetic, and toxicology profiles of the particular composition administered; and whether the compound being administered as part of a combination of active ingredients. Thus, the preferred amount of the compound can vary, and, therefore, can deviate from the typical dosages set forth above. Determining such dosage adjustments is generally within the skill of those in the art.

In a preferred embodiment the compounds according to this invention are used to treat a helminth infection, such as an infection caused by one or more helminths selected from the group consisting of a) cestodes: e.g. *Anaplocephala* spp.; *Dipylidium* spp.; *Diphyllobothrium* spp.; *Echinococcus* spp.; *Moniezia* spp.; *Taenia* spp.; b) trematodes e.g. *Dicrocoelium* spp.; *Fasciola* spp.; *Paramphistomum* spp.; *Schistosoma* spp.; or c) nematodes, e.g.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.;

*Nippostrongylus* spp.; *Oesophagostomum* spp.; *Onchocerca* spp.; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; Teladorsagia spp.; *Toxascaris* spp.; *Trichinella* spp.; *Trichuris* spp.; *Trichostrongylus* spp.; *Triodontophorous* spp.; *Uncinaria* spp., and/or *Wuchereria* spp.;

It is contemplated that the compounds according to this invention and compounds corresponding to the use according to the invention may be used to treat animals, including humans and non-human animals, especially non-human mammals. Such non-human mammals include, for example, livestock mammals (e.g., swine, livestock ruminats like bovines, sheep, goats, etc.), laboratory mammals (e.g., mice, rats, jirds, etc.), companion mammals (e.g., dogs, cats, equines, etc.), and wild and zoo mammals (e.g., buffalo, deer, etc.). It is contemplated that the compounds also are suitable to treat non-mammals, such as poultry (e.g., turkeys, chickens, ducks, etc.) and fish (e.g., salmon, trout, koi, etc.).

In some embodiments, one or more, preferably one compound according to this invention or a compound corresponding to the use according to the invention is used to treat an infection by a helminth, such as a nematode, cestode or trematode, preferably a nematode (such as *Haemonchus contortus*), that is resistant to one or more other anthelmintic agents. In some embodiments, the compound according to this invention is active against a helminth, such as a nematode, cestode or trematode, preferably a nematode such as *Haemonchus contortus*, that is resistant to one or more of the following anthelmintics: an avermectin (e.g., ivermectin, selamectin, doramectin, abamectin, and eprinomectin); a milbemycin (moxidectin and milbemycin oxime); a pro-benzimidazole (e.g., febantel, netobimin, and thiophanate); a benzimidazole derivative, such as a thiazole benzimidazole derivative (e.g., thiabendazole and cambendazole) or a carbamate benzimidazole derivative (e.g., fenbendazole, albendazole (oxide), mebendazole, oxfendazole, parbendazole, oxibendazole, flubendazole, and triclabendazole); an imidazothiazole (e.g., levamisole and tetramisole); a tetrahydropyrimidine (morantel and pyrantel), an organophosphate (e.g., trichlorphon, haloxon, dichlorvos, and naphthalophos); a salicylanilide (e.g., closantel, oxyclozanide, rafoxanide, and niclosamide); a nitrophenolic compound (e.g., nitroxynil and nitroscanate); benzoenedisulphonamide (e.g., clorsulon); a pyrazinaisoquinoline (e.g., praziquantel and epsiprantel); a heterocyclic compound (e.g., piperazine, diethylcarbamazine, dichlorophen, and phenothiazine); an arsenical (e.g., thiacetarsamide, melorsamine, and arsenamide); cyclooctadepsipeptide (e.g., emodepside); and a paraherquamide.

In some such embodiments, for example, the compound according to this invention or a compound corresponding to the use according to the invention is active against a helminth (for example, *Haemonchus contortus*) resistant to an avermectin, such as ivermectin. In other embodiments, the compound according to this invention is alternatively or additionally active against a helminth (for example, *Haemonchus contortus*) resistant to a benzimidazole derivative, such as fenbendazole. In other embodiments, the compound according to this invention is alternatively or additionally active against a helminth (for example, *Haemonchus contortus*) resistant to levamisole. And, in other embodiments, the compound according to this invention is alternatively or additionally active against a helminth (for example, *Haemonchus contortus*) resistant to pyrantel.

The compounds according to this invention or the compounds corresponding to the use according to the invention may be administered in various dosage forms. The term "dosage form" means that the compounds are formulated into a product suitable for administering to the animal via the envisaged dosage route. Such dosage forms are sometimes referred to herein as formulations or pharmaceutical composition.

The formulation type chosen for a dosage form in any instance will depend upon the particular purpose envisaged and the physical, chemical and biological properties of the compound according to this invention.

Dosage forms useful in the current invention can be liquid, semi-solid or solid dosage forms.

Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability. A dry powder (or granule) for reconstitution is reconstituted as a solution or as a suspension immediately prior to injection. The principal advantage of this dosage form is that it overcomes the problem of instability in solution or suspension.

One possible dosage route is the oral dosage route, wherein the compound is administered via the mouth. Oral dosage forms suitable for oral administration comprise liquids (e.g. drench or drinking water formulations), semi-solids (e.g. pastes, gels), and solids (e.g. tablets, capsules, powders, granules, chewable treats, premixes and medicated blocks).

A drench is a liquid oral formulation that is administered directly into the mouth/throat of an animal, especially a livestock animal, by means of a "drench gun" or syringe or another suitable device. When the composition is administered in the animal recipient's drinking water or as a drench, it may be convenient to use a solution or suspension formulation. This formulation can be, for example, a concentrated suspension that is mixed with water or a dry preparation that is mixed and suspended in the water.

Semi-solid oral formulations (pastes or gels) are generally administered via an applicator directly into the mouth of an animal or mixed with the feed.

Solid oral formulations are either administered directly to an animal (tablet, capsule) or mixed with the feed or via medicated feed blocks.

When the oral formulation is administered via a non-human animal's feed, it may, for example, be fed as a discrete feed or as a chewable treat. Alternatively (or additionally), it may, for example, be intimately dispersed in the animal recipient's regular feed, used as a top dressing, or in the form of solid pellets, paste or liquid that is added to the finished feed. When the oral formulation is administered as a feed additive, it may be convenient to prepare a "premix" in which the oral formulation is dispersed in a liquid or solid carrier. This "premix" is, in turn, dispersed in the animal's feed using, for example, a conventional mixer.

Several modified-release delivery systems have been developed, that take advantage of the unique anatomy of the ruminant forestomach, i.e. for intra-ruminal administration. An intraruminal bolus is a specific formulation for ruminants (cattle, sheep, goats, buffalos, camelids, deer etc). It is a veterinary delayed release delivery system which remains in the rumeno-reticular sac of a ruminant animal over an extended period of time and in which the therapeutically active substance has a predictable and delayed release pattern. Such intraruminal boluses are usually administered using a balling gun or another suitable device.

It is contemplated that the compounds according to this invention or compounds corresponding to the use according to the invention may alternatively be administered via non-oral dosage routes, such as topically (e.g., via a spot-on, pour-on or transdermal patch), or parenterally (e.g., subcutaneous injection, intravenous injection, intramuscular injection, etc.).

For instance the compounds may be administered topically using a transdermal formulation (i.e. a formulation that passes through the skin). Alternatively the compounds may be administered topically via the mucosa.

Topical dosage forms suitable for topical administration comprise liquids (e.g. bath, spray, spot-on), semi-solids (e.g. creams, gels), and solids (e.g. patches, powders, collars). Typical topical formulations for animals are liquid or semi-liquid dosage forms. Typical formulations for transdermal and mucosal administration include, for example, pour-ons, spot-ons, dips, sprays, mousses, shampoos, powders, gels, hydrogels, lotions, solutions, creams, ointments, dusting powders, dressings, foams, films, skin patches, limb bands, collars, ear tags, wafers, sponges, fibers, bandages, and microemulsions. When a liquid formulation is used topically on skin, it can be administered by, for example, pouring on (pour-on or spot-on), spreading, rubbing, atomizing, spraying, dipping, bathing, or washing.

The pour-on or spot-on methods, for example, comprise applying the formulation to a specific location of the skin or coat, such as on the neck or backbone of the animal. This may be achieved by, for example, applying a swab or drop of the pour-on or spot-on formulation to a relatively small area of the recipient animal's skin or coat (i.e., generally no greater than about 10% of the animal recipient's skin or coat). In some embodiments, the compound is dispersed from the application site to wide areas of the fur due to the spreading nature of the components in the formulation and the animal's movements while, in parallel, being absorbed through the skin and distributed via the animal recipient's fluids and/or tissues.

Parenteral formulations and delivery systems for non-oral routes comprise liquids (e.g. solutions, suspensions, emulsions, and dry powders for reconstitution), semi-solids and solids (e.g. implants). The majority of implants that are used in veterinary medicine are compressed tablets or dispersed matrix systems in which the drug is uniformly dispersed within a nondegradable polymer or alternatively extrusion products.

Pharmaceutical Compositions

This invention also is directed to pharmaceutical compositions (or medicaments) comprising one or more, preferably one compound according to this invention. The compositions also may (and preferably will) comprise one or more pharmaceutically acceptable excipients. The following subject matter about pharmaceutical compositions is also applicable to pharmaceutical compositions comprising compounds corresponding to the use according to this invention.

Pharmaceutical compositions of the present invention may be manufactured by, for example, processes known in the art. These processes include, for example, a variety of known mixing, dissolving, granulating, emulsifying, encapsulating, entrapping, and lyophilizing processes. Optimal formulation depends on, for example, the dosage route (e.g. oral, injection, topical).

Solid dosage forms, for example, may be prepared by, for example, intimately and uniformly mixing the compounds with fillers, binders, lubricants, glidants, disintegrants, flavoring agents (e.g., sweeteners), buffers, preservatives, pharmaceutical-grade dyes or pigments, and controlled release agents.

Oral dosage forms other than solids may be prepared by mixing the compounds with, for example, one or more solvents, viscosity-enhancing agents, surfactants, preservatives, stabilizers, resins, fillers, binders, lubricants, glidants, disintegrants, co-solvents, sweeteners, flavorings, perfuming agents, buffers, suspending agents, and pharmaceutical-grade dyes or pigments.

Contemplated binders include, for example, gelatin, acacia, and carboxymethyl cellulose.

Contemplated lubricants include, for example, magnesium stearate, stearic acid, and talc.

Contemplated disintegrants include, for example, corn starch, alginic acid, sodium carboxymethylcellulose, and sodium croscarmellose.

Contemplated buffers include, for example, sodium citrate, and magnesium and calcium carbonate and bicarbonate.

Contemplated solvents include, for example, water, petroleum, animal oils, vegetable oils, mineral oil, and synthetic oil. Physiological saline solution or glycols (e.g., ethylene glycol, propylene glycol, or polyethylene glycol) also may be included. The solvent preferably has sufficient chemical properties and quantity to keep the compounds solubilized at temperatures in which the composition is stored and used.

Contemplated viscosity-enhancing agents include, for example, polyethylene, methylcellulose, sodium carboxymethylcellulose, hydroxypropyl-methylcellulose, hydroxypropylcellulose, sodium alginate, carbomer, povidone, acacia, guar gum, xanthan gum, tragacanth, methylcellulose, carbomer, xanthan gum, guar gum, povidone, sodium carboxymethylcellulose, magnesium aluminum silicate, carboxyvinyl polymers, carrageenan, hydroxyethyl cellulose, laponite, water-soluble salts of cellulose ethers, natural gums, colloidal magnesium aluminum silicateor finely divided silica, homopolymers of acrylic acid crosslinked with an alkyl ether of pentaerythritol or an alkyl ether of sucrose, and carbomers.

Contemplated surfactants include, for example, polyoxyethylene sorbitan fatty acid esters; polyoxyethylene monoalkyl ethers; sucrose monoesters; lanolin esters and ethers; alkyl sulfate salts; and sodium, potassium, and ammonium salts of fatty acids.

Contemplated preservatives include, for example, phenol, alkyl esters of parahydroxybenzoic acid (e.g., methyl p-hydroxybenzoate (or "methylparaben") and propyl p-hydroxybenzoate (or "propylparaben")), sorbic acid, o-phenylphenol benzoic acid and the salts thereof, chlorobutanol, benzyl alcohol, thimerosal, phenylmercuric acetate and nitrate, nitromersol, benzalkonium chloride, and cetylpyridinium chloride.

Contemplated stabilizers include, for example, chelating agents and antioxidants.

Solid dosage forms also may comprise, for example, one or more excipients to control the release of the compounds. For example, it is contemplated that the compounds may be dispersed in, for example, hydroxypropylmethyl cellulose. Some oral dosage forms (e.g., tablets and pills) also may be prepared with enteric coatings.

Topical dosage route uses, for example, a concentrated liquid or semi-liquid solution, suspension (aqueous or non-aqueous), emulsion (water-in-oil or oil-in-water), or microemulsion comprising a compounds dissolved, suspended, or emulgated in a pharmaceutically-acceptable liquid vehicle. In such embodiments, a crystallization inhibitor optionally may generally be present.

Such a pour-on or spot-on formulation can be prepared by dissolving, suspending, or emulsifying the compounds in a suitable skin-fitted solvent or solvent mixture. Other excipients may be included as well, such as, for example, a surfactant, colorant, antioxidant, stabilizer, adhesive, etc. Contemplated solvents include, for example, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oil, DMF, liquid paraffin, silicone, dimethylacetamide, N-methylpyrrolidone, or 2,2-dimethyl-4-oxy-methylene-1,3-dioxolane.

In some embodiments, a topical formulation (particularly a pour-on or spot-on formulation) comprises a carrier that promotes the absorption or penetration of the compounds through the skin into the blood stream, other bodily fluids (lymph), and/or body tissue (fat tissue). Contemplated examples of dermal penetration enhancers include, for example, dimethylsulfoxide, isopropyl myristate, dipropylene glycol pelargonate, silicone oil, aliphatic esters, triglycerides, and fatty alcohols.

Topical formulations also (or alternatively) may comprise, for example, one or more spreading agents. These substances act as carriers that assist in distributing an active ingredient over the animal recipient's coat or skin. They may include, for example, isopropyl myristate, dipropylene glycol pelargonate, silicone oils, fatty acid esters, triglycerides, and/or fatty alcohols. Various spreading oil/solvent combinations also may be suitable, such as, for example, oily solutions, alcoholic and isopropanolic solutions (e.g., solutions of 2-octyl dodecanol or oleyl alcohol), solutions of esters of monocarboxylic acids (e.g., isopropyl myristate, isopropyl palmitate, lauric acid oxalic ester, oleic acid oleyl ester, oleic acid decyl ester, hexyl laurate, oleyl oleate, decyl oleate, and caproic acid esters of saturated fatty alcohols having a carbon chain of 12 to 18 carbons), solutions of esters of dicarboxylic acids (e.g., dibutyl phthalate, diisopropyl isophthalate, adipic acid diisopropyl ester, and di-n-butyl adipate), or solutions of esters of aliphatic acids (e.g., glycols). When the formulation comprises a spreading agent, it also may be advantageous to include a dispersant, such as, for example, pyrrolidin-2-one, N-alkylpyrrolidin-2-one, acetone, polyethylene glycol or ether or ester thereof, propylene glycol, or synthetic triglycerides.

When formulated in, for example, an ointment, it is contemplated that the compounds may be mixed with, for example, either a paraffinic or a water-miscible ointment base. When formulated in a cream, it is contemplated that the compounds may be formulated with, for example, an oil-in-water cream base. In some instances, the aqueous phase of the cream base includes, for example at least about 30% (w/w) of a polyhydric alcohol, such as propylene glycol, butane-1,3-diol, mannitol, sorbitol, glycerol, polyethylene glycol, or a mixture thereof.

Injectable formulations may be prepared according to, for example, the known art using suitable solvents, solubilizing agents, protecting agents, dispersing agents, wetting agents, and/or suspending agents. Contemplated carrier materials include, for example, water, ethanol, butanol, benzyl alcohol, glycerin, 1,3-butanediol, Ringer's solution, isotonic sodium chloride solution, bland fixed oils (e.g., synthetic mono- or diglycerides), vegetable oil (e.g., corn oil), dextrose, mannitol, fatty acids (e.g., oleic acid), dimethyl acetamide, surfactants (e.g., ionic and non-ionic detergents), N-methylpyrrolidone, propylene glycol, and/or polyethylene glycols (e.g., PEG 400). Contemplated solubilizing agents include, for example, polyvinyl pyrrolidone, polyoxyethylated castor oil, polyoxyethylated sorbitan ester, and the like. Contemplated protecting agents include, for example, benzyl alcohol, trichlorobutanol, p-hydroxybenzoic acid ester, n-butanol, and the like.

In some embodiments, a parenteral formulation is, for example, prepared from sterile powders or granules having one or more of the carriers materials discussed above for other formulations. The compound is, for example, dissolved or suspended in a liquid comprising water, polyethylene glycol, propylene glycol, ethanol, corn oil, cottonseed oil, peanut oil, sesame oil, benzyl alcohol, sodium chloride, and/or various buffers. The pH generally may be adjusted, if necessary, with a suitable acid, base, or buffer.

Other inert ingredients may generally be added to the composition as desired. To illustrate, it is contemplated that these may include, for example, lactose, mannitol, sorbitol, calcium carbonate, sodium carbonate, tribasic calcium phosphate, dibasic calcium phosphate, sodium phosphate, kaolin, compressible sugar, starch, calcium sulfate, dextro or microcrystalline cellulose, colloidal silicon dioxide, starch, sodium starch glycolate, crospovidone, microcrystalline cellulose, tragacanth, hydroxypropylcellulose, pregelatinized starch, povidone, ethylcellulose, hydroxypropylcellulose, hydroxypropylmethylcellulose, and methylcellulose.

Further aspects regarding formulation of drugs and various excipients are found in, for example, Gennaro, A. R., et al., eds., *Remington: The Science and Practice of Pharmacy* (Lippincott Williams & Wilkins, 20th Ed., 2000). Another source regarding formulation of drugs and various excipients is found in, for example, Liberman, H. A., et al., eds., *Pharmaceutical Dosage Forms* (Marcel Decker, New York, N.Y., 1980).

The concentration of the compounds according to this invention in the applied dosage form may vary widely depending on, for example, the dosage route. In general, the concentration is from about 1 to about 70% (by weight). In some such embodiments, for example, the concentration is from about 1 to about 50% (by weight), or from about 10 to about 50% (by weight). In other embodiments, the concentration is from about 35 to about 65% (by weight), from about 40 to about 60% (by weight), from about 45 to about 55% (by weight), or about 50% (by weight).

In another aspect the present invention thus provides a pharmaceutical composition comprising an anthelmintically effective amount of one or more, preferably one compound according to this invention and one or more pharmaceutically acceptable excipients.

The formulation type chosen for a dosage form in any instance will depend upon the particular purpose envisaged and the physical, chemical and biological properties of the compound according to this invention.

The compounds and pharmaceutical compositions according to this invention are useful in treating parasitic infections such as helminth infections of animals. An "effective amount," is the amount or quantity of a compound that is required to alleviate or reduce parasite numbers in an animal, and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound.

This can be evaluated by counting parasites (especially helminthes) directly after necroscopy of the host animal.

The reduction of parasite numbers, especially gastrointestinal helminth parasites can be alternatively measured indirectly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount".

Examples of Contemplated Combination Therapies

The methods and pharmaceutical compositions of this invention encompass methods wherein a compound according to this invention or a compound corresponding to the use according to the invention is the sole active ingredient administered to the recipient animal. It is contemplated, however, that the methods and pharmaceutical compositions also encompass combination therapies wherein a compound is administered in combination with one or more other pharmaceutically acceptable active ingredients. The other active ingredient(s) may be, for example, one or more other compounds according to this invention or one or more other compounds corresponding to the use according to the invention. Alternatively (or additionally), the other active ingredient(s) may be one or more pharmaceutically acceptable compounds that are not compounds according to this invention or compounds corresponding to the use according to the invention. The other active ingredient(s) may target the same and/or different parasites and conditions.

Contemplated active ingredient(s) that may be administered in combination with the compounds include, for example, pharmaceutically acceptable anthelmintics, insecticides and acaricides, insect growth regulators, anti-inflammatories, anti-infectives, anti-protozoals, hormones, dermatological preparations (e.g., antiseptics and disinfectants), and immunobiologicals (e.g., vaccines and antisera) for disease prevention.

Therefore this invention is also directed to the use as a medicament of combinations comprising a) one or more compounds according to this invention or one or more compounds corresponding to the use according to this invention with b) one or more pharmaceutically acceptable active compounds which differ in structure from component a). The active compounds b) are preferably anthelmintic compounds, more preferably selected from the group consisting of avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); benzimidazole derivatives, such as a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole, flubendazole, and triclabendazole); an imidazothiazoles (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazineisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); and amino-acetonitrile compounds (e.g. monepantel, AAD 1566); tribendimidine (amidine compound); amidine compounds (e.g., amidantel and tribendimidin), including all pharmaceutically acceptable forms, such as salts, solvates or N-oxides.

Preferred combinations are comprising a) one compound selected from the group compounds A-1 to A-697, Aa-1 to Aa-5, and B-1 to B-204 of Tables A and B below and variants as mentioned at the bottom of these tables (or salts, solvates, N-oxides or prodrugs thereof) and b) one compound selected from the group consisting of anthelmintic avermectins (e.g., ivermectin, selamectin, doramectin, abamectin, emamectin and eprinomectin); milbemycins (moxidectin and milbemycin oxime); pro-benzimidazoles (e.g., febantel, netobimin, and thiophanate); benzimidazole derivatives, such as triclabendazole, thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole, flubendazole); imidazothiazoles (e.g., levamisole and tetramisole); tetrahydropyrimidines (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazineisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); amino-acetonitrile compounds (e.g. monepantel, AAD 1566); tribendimidine (amidine compound); and amidantel (amidine compound); including all pharmaceutically acceptable forms, such as salts.

Preferred combinations comprise at least one compound selected from the group of compounds A-1 to A-697, Aa-1 to Aa-5, and B-1 to B-204 of Tables A and B below and variants as mentioned at the bottom of these tables (or salts, solvates or N-oxides thereof) and abamectin, ivermectin, emamectin, eprinomectin, doramectin, moxidectin, milbemycin oxime; or closantel, oxyclozanide, rafoxanide, niclosamide; or nitroxynil, nitroscanate, clorsulon; or praziquantel and epsiprantel; or emodepside, derquantel, monepantel.

Examples of such combinations are combinations of one of the compounds A-1 to A-697, Aa-1 to Aa-5, and B-1 to B-204 of Tables A and B below and variants as mentioned at the bottom of these tables with abamectin.

Other examples are combinations of one of the compounds A-1 to A-697, Aa-1 to Aa-5, and B-1 to B-204 of Tables A and B below and variants as mentioned at the bottom of these tables with ivermectin.

Other examples are combinations of one of the compounds A-1 to A-697, Aa-1 to Aa-5, and B-1 to B-204 of Tables A and B below and variants as mentioned at the bottom of these tables with emamectin.

Other examples are combinations of one of the compounds A-1 to A-697, Aa-1 to Aa-5, and B-1 to B-204 of Tables A and B below and variants as mentioned at the bottom of these tables with eprinomectin.

Other examples are combinations of one of the compounds A-1 to A-697, Aa-1 to Aa-5, and B-1 to B-204 of Tables A and B below and variants as mentioned at the bottom of these tables with doramectin.

Other examples are combinations of one of the compounds A-1 to A-697, Aa-1 to Aa-5, and B-1 to B-204 of Tables A and B below and variants as mentioned at the bottom of these tables with moxidectin.

Other examples are combinations of one of the compounds A-1 to A-697, Aa-1 to Aa-5, and B-1 to B-204 of Tables A and B below and variants as mentioned at the bottom of these tables with milbemycin oxime.

Other examples are combinations of one of the compounds A-1 to A-697, Aa-1 to Aa-5, and B-1 to B-204 of Tables A and B below and variants as mentioned at the bottom of these tables with closantel.

Other examples are combinations of one of the compounds A-1 to A-697, Aa-1 to Aa-5, and B-1 to B-204 of Tables A and B below and variants as mentioned at the bottom of these tables with oxyclozanide.

Other examples are combinations of one of the compounds A-1 to A-697, Aa-1 to Aa-5, and B-1 to B-204 of Tables A and B below and variants as mentioned at the bottom of these tables with rafoxanide.

Other examples are combinations of one of the compounds A-1 to A-697, Aa-1 to Aa-5, and B-1 to B-204 of Tables A and B below and variants as mentioned at the bottom of these tables with niclosamide.

Other examples are combinations of one of the compounds A-1 to A-697, Aa-1 to Aa-5, and B-1 to B-204 of Tables A and B below and variants as mentioned at the bottom of these tables with nitroxynil.

Other examples are combinations of one of the compounds A-1 to A-697, Aa-1 to Aa-5, and B-1 to B-204 of Tables A and B below and variants as mentioned at the bottom of these tables with nitroscanate.

Other examples are combinations of one of the compounds A-1 to A-697, Aa-1 to Aa-5, and B-1 to B-204 of Tables A and B below and variants as mentioned at the bottom of these tables with clorsulon.

Other examples are combinations of one of the compounds A-1 to A-697, Aa-1 to Aa-5, and B-1 to B-204 of Tables A and B below and variants as mentioned at the bottom of these tables with praziquantel.

Other examples are combinations of one of the compounds A-1 to A-697, Aa-1 to Aa-5, and B-1 to B-204 of Tables A and B below and variants as mentioned at the bottom of these tables with epsiprantel.

Other examples are combinations of one of the compounds A-1 to A-697, Aa-1 to Aa-5, and B-1 to B-204 of Tables A and B below and variants as mentioned at the bottom of these tables with emodepside.

Other examples are combinations of one of the compounds A-1 to A-697, Aa-1 to Aa-5, and B-1 to B-204 of Tables A and B below and variants as mentioned at the bottom of these tables with derquantel.

Other examples are combinations of one of the compounds A-1 to A-697, Aa-1 to Aa-5, and B-1 to B-204 of Tables A and B below and variants as mentioned at the bottom of these tables with monepantel.

Examples of such combinations are combinations of a salt of one of the compounds A-1 to A-697, Aa-1 to Aa-5, and B-1 to B-204 of Tables A and B below and variants as mentioned at the bottom of these tables with abamectin.

Other examples are combinations of a salt of one of the compounds A-1 to A-697, Aa-1 to Aa-5, and B-1 to B-204 of Tables A and B below and variants as mentioned at the bottom of these tables with ivermectin.

Other examples are combinations of a salt of one of the compounds A-1 to A-697, Aa-1 to Aa-5, and B-1 to B-204 of Tables A and B below and variants as mentioned at the bottom of these tables with emamectin.

Other examples are combinations of a salt of one of the compounds A-1 to A-697, Aa-1 to Aa-5, and B-1 to B-204 of Tables A and B below and variants as mentioned at the bottom of these tables with eprinomectin.

Other examples are combinations of a salt of one of the compounds A-1 to A-697, Aa-1 to Aa-5, and B-1 to B-204 of Tables A and B below and variants as mentioned at the bottom of these tables with doramectin.

Other examples are combinations of a salt of one of the compounds A-1 to A-697, Aa-1 to Aa-5, and B-1 to B-204 of Tables A and B below and variants as mentioned at the bottom of these tables with moxidectin.

Other examples are combinations of a salt of one of the compounds A-1 to A-697, Aa-1 to Aa-5, and B-1 to B-204 of Tables A and B below and variants as mentioned at the bottom of these tables with milbemycin oxime.

Other examples are combinations of a salt of one of the compounds A-1 to A-697, Aa-1 to Aa-5, and B-1 to B-204 of Tables A and B below and variants as mentioned at the bottom of these tables with closantel.

Other examples are combinations of a salt of one of the compounds A-1 to A-697, Aa-1 to Aa-5, and B-1 to B-204 of Tables A and B below and variants as mentioned at the bottom of these tables with oxyclozanide.

Other examples are combinations of a salt of one of the compounds A-1 to A-697, Aa-1 to Aa-5, and B-1 to B-204 of Tables A and B below and variants as mentioned at the bottom of these tables with rafoxanide.

Other examples are combinations of a salt of one of the compounds A-1 to A-697, Aa-1 to Aa-5, and B-1 to B-204 of Tables A and B below and variants as mentioned at the bottom of these tables with niclosamide.

Other examples are combinations of a salt of one of the compounds A-1 to A-697, Aa-1 to Aa-5, and B-1 to B-204 of Tables A and B below and variants as mentioned at the bottom of these tables with nitroxynil.

Other examples are combinations of a salt of one of the compounds A-1 to A-697, Aa-1 to Aa-5, and B-1 to B-204 of Tables A and B below and variants as mentioned at the bottom of these tables with nitroscanate.

Other examples are combinations of a salt of one of the compounds A-1 to A-697, Aa-1 to Aa-5, and B-1 to B-204 of Tables A and B below and variants as mentioned at the bottom of these tables with clorsulon.

Other examples are combinations of a salt of one of the compounds A-1 to A-697, Aa-1 to Aa-5, and B-1 to B-204 of Tables A and B below and variants as mentioned at the bottom of these tables with praziquantel.

Other examples are combinations of a salt of one of the compounds A-1 to A-697, Aa-1 to Aa-5, and B-1 to B-204 of Tables A and B below and variants as mentioned at the bottom of these tables with epsiprantel.

Other examples are combinations of a salt of one of the compounds A-1 to A-697, Aa-1 to Aa-5, and B-1 to B-204 of Tables A and B below and variants as mentioned at the bottom of these tables with emodepside.

Other examples are combinations of a salt of one of the compounds A-1 to A-697, Aa-1 to Aa-5, and B-1 to B-204 of Tables A and B below and variants as mentioned at the bottom of these tables with derquantel.

Other examples are combinations of a salt of one of the compounds A-1 to A-697, Aa-1 to Aa-5, and B-1 to B-204 of Tables A and B below and variants as mentioned at the bottom of these tables with monepantel.

Examples of such combinations are combinations of a solvate of one of the compounds A-1 to A-697, Aa-1 to Aa-5, and B-1 to B-204 of Tables A and B below and variants as mentioned at the bottom of these tables with abamectin.

Other examples are combinations of a solvate of one of the compounds A-1 to A-697, Aa-1 to Aa-5, and B-1 to B-204 of Tables A and B below and variants as mentioned at the bottom of these tables with ivermectin.

Other examples are combinations of a solvate of one of the compounds A-1 to A-697, Aa-1 to Aa-5, and B-1 to B-204 of Tables A and B below and variants as mentioned at the bottom of these tables with emamectin.

Other examples are combinations of a solvate of one of the compounds A-1 to A-697, Aa-1 to Aa-5, and B-1 to B-204 of Tables A and B below and variants as mentioned at the bottom of these tables with eprinomectin.

Other examples are combinations of a solvate of one of the compounds A-1 to A-697, Aa-1 to Aa-5, and B-1 to B-204 of Tables A and B below and variants as mentioned at the bottom of these tables with doramectin.

Other examples are combinations of a solvate of one of the compounds A-1 to A-697, Aa-1 to Aa-5, and B-1 to B-204 of Tables A and B below and variants as mentioned at the bottom of these tables with moxidectin.

Other examples are combinations of a solvate of one of the compounds A-1 to A-697, Aa-1 to Aa-5, and B-1 to B-204 of Tables A and B below and variants as mentioned at the bottom of these tables with milbemycin oxime.

Other examples are combinations of a solvate of one of the compounds A-1 to A-697, Aa-1 to Aa-5, and B-1 to B-204 of Tables A and B below and variants as mentioned at the bottom of these tables with closantel.

Other examples are combinations of a solvate of one of the compounds A-1 to A-697, Aa-1 to Aa-5, and B-1 to B-204 of Tables A and B below and variants as mentioned at the bottom of these tables with oxyclozanide.

Other examples are combinations of a solvate of one of the compounds A-1 to A-697, Aa-1 to Aa-5, and B-1 to B-204 of Tables A and B below and variants as mentioned at the bottom of these tables with rafoxanide.

Other examples are combinations of a solvate of one of the compounds A-1 to A-697, Aa-1 to Aa-5, and B-1 to B-204 of Tables A and B below and variants as mentioned at the bottom of these tables with niclosamide.

Other examples are combinations of a solvate of one of the compounds A-1 to A-697, Aa-1 to Aa-5, and B-1 to B-204 of Tables A and B below and variants as mentioned at the bottom of these tables with nitroxynil.

Other examples are combinations of a solvate of one of the compounds A-1 to A-697, Aa-1 to Aa-5, and B-1 to B-204 of Tables A and B below and variants as mentioned at the bottom of these tables with nitroscanate.

Other examples are combinations of a solvate of one of the compounds A-1 to A-697, Aa-1 to Aa-5, and B-1 to B-204 of Tables A and B below and variants as mentioned at the bottom of these tables with clorsulon.

Other examples are combinations of a solvate of one of the compounds A-1 to A-697, Aa-1 to Aa-5, and B-1 to B-204 of Tables A and B below and variants as mentioned at the bottom of these tables with praziquantel.

Other examples are combinations of a solvate of one of the compounds A-1 to A-697, Aa-1 to Aa-5, and B-1 to B-204 of Tables A and B below and variants as mentioned at the bottom of these tables with epsiprantel.

Other examples are combinations of a solvate of one of the compounds A-1 to A-697, Aa-1 to Aa-5, and B-1 to B-204 of Tables A and B below and variants as mentioned at the bottom of these tables with emodepside.

Other examples are combinations of a solvate of one of the compounds A-1 to A-697, Aa-1 to Aa-5, and B-1 to B-204 of Tables A and B below and variants as mentioned at the bottom of these tables with derquantel.

Other examples are combinations of a solvate of one of the compounds A-1 to A-697, Aa-1 to Aa-5, and B-1 to B-204 of Tables A and B below and variants as mentioned at the bottom of these tables with monepantel.

Examples of such combinations are combinations of an N-oxide of one of the compounds A-1 to A-697, and B-1 to B-204 of Tables A and B below and variants as mentioned at the bottom of these tables with abamectin.

Other examples are combinations of an N-oxide of one of the compounds A-1 to A-697, and B-1 to B-204 of Tables A and B below and variants as mentioned at the bottom of these tables with ivermectin.

Other examples are combinations of an N-oxide of one of the compounds A-1 to A-697, and B-1 to B-204 of Tables A and B below and variants as mentioned at the bottom of these tables with emamectin.

Other examples are combinations of an N-oxide of one of the compounds A-1 to A-697, and B-1 to B-204 of Tables A and B below and variants as mentioned at the bottom of these tables with eprinomectin.

Other examples are combinations of an N-oxide of one of the compounds A-1 to A-697, and B-1 to B-204 of Tables A and B below and variants as mentioned at the bottom of these tables with doramectin.

Other examples are combinations of an N-oxide of one of the compounds A-1 to A-697, and B-1 to B-204 of Tables A and B below and variants as mentioned at the bottom of these tables with moxidectin.

Other examples are combinations of an N-oxide of one of the compounds A-1 to A-697, and B-1 to B-204 of Tables A and B below and variants as mentioned at the bottom of these tables with milbemycin oxime.

Other examples are combinations of an N-oxide of one of the compounds A-1 to A-697, and B-1 to B-204 of Tables A and B below and variants as mentioned at the bottom of these tables with closantel.

Other examples are combinations of an N-oxide of one of the compounds A-1 to A-697, and B-1 to B-204 of Tables A and B below and variants as mentioned at the bottom of these tables with oxyclozanide.

Other examples are combinations of an N-oxide of one of the compounds A-1 to A-697, and B-1 to B-204 of Tables A and B below and variants as mentioned at the bottom of these tables with rafoxanide.

Other examples are combinations of an N-oxide of one of the compounds A-1 to A-697, and B-1 to B-204 of Tables A and B below and variants as mentioned at the bottom of these tables with niclosamide.

Other examples are combinations of an N-oxide of one of the compounds A-1 to A-697, and B-1 to B-204 of Tables A and B below and variants as mentioned at the bottom of these tables with nitroxynil.

Other examples are combinations of an N-oxide of one of the compounds A-1 to A-697, and B-1 to B-204 of Tables A and B below and variants as mentioned at the bottom of these tables with nitroscanate.

Other examples are combinations of an N-oxide of one of the compounds A-1 to A-697, and B-1 to B-204 of Tables A and B below and variants as mentioned at the bottom of these tables with clorsulon.

Other examples are combinations of an N-oxide of one of the compounds A-1 to A-697, and B-1 to B-204 of Tables A and B below and variants as mentioned at the bottom of these tables with praziquantel.

Other examples are combinations of an N-oxide of one of the compounds A-1 to A-697, and B-1 to B-204 of Tables A and B below and variants as mentioned at the bottom of these tables with epsiprantel.

Other examples are combinations of an N-oxide of one of the compounds A-1 to A-697, and B-1 to B-204 of Tables A and B below and variants as mentioned at the bottom of these tables with emodepside.

Other examples are combinations of an N-oxide of one of the compounds A-1 to A-697, and B-1 to B-204 of Tables A and B below and variants as mentioned at the bottom of these tables with derquantel.

Other examples are combinations of an N-oxide of one of the compounds A-1 to A-697, and B-1 to B-204 of Tables A and B below and variants as mentioned at the bottom of these tables with monepantel.

The compounds as described in this specification can be combined with pharmaceutically acceptable insecticides or acaricides. Such pharmaceutically acceptable insecticides and acaricides include, for example, acetamiprid, acetoprole, amitraz, amidoflumet, avermectin, azadirachtin, bifenthrin, bifenazate, buprofezin, bistrifluoron, chlorfenapyr, chlorfluazuron, chlorantraniliprole, chlorpyrifos, chromafenozide, clothianidin, cyantraniliprole, cyflumetofen, β-cyfluthrin, cyhalothrin, λ-cyhalothrin, cymiazole cypermethrin, cyromazine, deltamethrin, demiditraz, diafenthiuron, diazinon, diflubenzuron, dimefluthrin, dinotefuran, emamectin, esfenvalerate, ethiprole, fenoxycarb, fenpropathrin, fenvalerate, fipronil, flonicamid, flubendiamide, flucythrinate, tau-fluvalinate, flufenoxuron, halofenozide, hexaflumuron, imidacloprid, indoxacarb, lufenuron, metaflumizone, methoprene, metofluthrin, methoxyfenozide, nitenpyram, novaluron, noviflumuron, permethrin, phosmet, profluthrin, protrifenbute, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen, spirotetramat, sulfoxaflor, tebufenozide, tebufenpyrad, teflubenzuron, tefluthrin, tetrachlorvinphos, tetramethylfluthrin, thiacloprid, thiamethoxam, tolfenpyrad, tralomethrin, and triflumuron. General references discussing antiparasitic agents, such as insecticides and acaricides, include, for example, *The Pesticide Manual*, 13th Edition, C. D. S. Tomlin, Ed., British Crop Protection Council, Farnham, Surrey, U.K. (2003).

The compounds as described in tis specification can be combined with pharmaceutically acceptable insect growth regulators. Such pharmaceutically acceptable insect growth regulators include, for example, methoprene, pyriproxyfen, tetrahydroazadirachtin, chlorfluazuron, cyromazine, diflubenzuron, fluazuron, flucycloxuron, flufenoxuron, hexaflumuron, lufenuron, ifenuron, tebufenozide, and triflumuron. These compounds tend to provide both initial and sustained treatment of parasite infections at all stages of insect development, including eggs, on the animal subject, as well as within the environment of the animal subject.

The compounds as described in this specification can be combined with pharmaceutically acceptable anti-protozoals. Such pharmaceutically acceptable anti-protozoals include, for example, triazintriones like, for example, toltrazuril and ponazuril and triazindiones such as clazuril, diclazuril and letrazuril.

In some contemplated embodiments, the compounds are administered with dihydroazole compounds, such as, for example, compounds discussed in WO 2010/75591.

In some contemplated embodiments, the compounds are administered with anthelminic proteins, such as, for example *Bacillus thuringensis* crystal proteins e.g. described in WO 2010/053517.

In some contemplated embodiments, the compounds are administered with pyridylmethylamine derivatives, such as, for example, pyridylmethylamine derivatives discussed in European Patent Appl. EP0539588 or Intl Patent Appl. Publ. WO2007/115643.

In some contemplated embodiments, the compounds is administered with nodulisporic acids and derivatives thereof, such as, for example, compounds discussed in U.S. Pat. Nos. 5,399,582; 5,945,317; 5,962,499; 5,834,260; 6,221,894; or 5,595,991; or Intl Patent Appl. Publ. 1996/29073.

Other antiparasitic compounds contemplated to be useful in combination therapies with the compounds include, for example, imidazo[1,2-b]pyridazine compounds discussed in US Patent Appl. Publ. No. 2005-0182059; 1-(4-Mono and di-halomethylsulphonylphenyl)-2-acylamino-3-fluoropropanol compounds discussed U.S. Pat. No. 7,361,689; trifluoromethanesulfonanilide oxime ether compounds discussed in U.S. Pat. No. 7,312,248; n-[(phenyloxy)phenyl]-1,1,1-trifluoromethanesulfonamide and n-[(phenylsulfanyl)phenyl]-1,1,1-trifluoromethanesulfonamide compounds discussed in US Patent Appl. Publ. 2006-0281695; and 2-phenyl-3-(1H-pyrrol-2-yl)acrylonitrile compounds discussed in US Appl. Publ. 2006/0128779; isoxazoline compounds discussed in WO Patent Appl, Publ. 2005-085216, WO 2007-026965, WO 2007-070606, WO 2007-075459, WO 2007-079162, WO 2007-105814, WO 2007-125984, WO 2008-019760, WO 2008-122375, WO 2008-150393, WO 2009-002809, WO 2009-003075, WO 2009-022746, WO 2009-035004, WO 2009-045999, WO 2009-051956, WO 2009-035004.

In the contemplated combination therapies, the compounds according to this invention may be administered before, simultaneously, and/or after the other active ingredient(s). In addition, the compounds according to this invention may be administered in the same composition as the other active ingredient(s) and/or in separate compositions from the other active ingredient(s). Further, the compounds according to this invention and other active ingredient(s) may be administered via the same and/or different dosage route.

When the compounds according to this invention are administered in a combination therapy, the weight ratio of the active ingredients may vary widely. Factors influencing this ratio include, for example, the particular compounds; the identity of the other active ingredient(s) be administered in the combination therapy; the dosage route of the compounds and other active ingredient(s); the target condition and pathogen; the type (e.g., species and breed), age, size, sex, diet, activity, and condition of the animal; and pharmacological considerations, such as the activity, efficacy, pharmacokinetic, and toxicology profiles of the compounds and other active ingredient(s). In some contemplated embodiments, for example, the weight ratio of the compounds to the other active ingredient(s) is, for example, is from about 1:3000 to about 3000:1. In some such instances, the weight ratio is from about 1:300 to about 300:1. In other such instances, the weight ratio is from about 1:30 and about 30:1.

In addition to other active ingredients, it is contemplated that the compounds may be administered with one or more other compounds that beneficially affects (e.g. enhances or prolongs) the activity (or other characteristic, such as safety) of the compounds. For example, it is contemplated that the compounds may be administered with one or more synergists, such as, for example, piperonyl butoxide (PBO) and triphenyl phosphate (TPP). Other synergists include, for example, N-(2-ethylhexyl)-8,9,10-trinorbom-5-ene-2,3-dicarboxamide (also known as "ENT 8184" or "MGK 264") and Verbutin (also known as "MB-599").

This invention also is directed to kits that are, for example, suitable for use in performing the methods of treatment described above. The kit comprises a therapeutically effective amount of one or more compounds of this invention, and an additional component. The additional component(s) may be, for example, one or more of the following: another ingredient (e.g., an excipient or active ingredient), an apparatus for combining the compound of this invention with another ingredient and/or for administering the compound of this invention, or a diagnostic tool.

The compounds used according to this invention show an excellent activity in treating parasite infections and in addition are acceptable for the animals treated.

Compounds of the current invention are useful agronomically for protecting field crops from phytophagous invertebrate pests and also nonagronomically for protecting other horticultural crops and plants from phytophagous invertebrate pests.

Invertebrate pests are insects, acarids, mollusks, fungi and nematodes that cause damage to field crops or other horticultural crops and plants.

Nonagronomic uses of the compounds of this invention and compositions include control of invertebrate pests in stored grains, beans and other foodstuffs and in textiles such as clothing and carpets. Nonagronomic uses of the compounds of formula (I) and compositions also include invertebrate pest control in ornamental plants, forests, in yards, along roadsides and railroad rights of way, and on turf such as lawns, golf courses and pastures.

Compounds of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Invertebrate pests are controlled in agronomic and nonagronomic applications by applying one or more compounds of formula (I), typically in the form of a composition, in a biologically effective amount, to the environment of the pests, including the agronomic and/or nonagronomic locus of infestation, to the area to be protected, or directly on the pests to be controlled.

Examples of suitable compositions comprising a compound of the invention include granular compositions wherein the additional active compound is present on the same granule as the compound of the invention or on granules separate from those of the compound of the invention.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention.

EXAMPLES

The following examples are merely illustrative, and not limiting to the remainder of the disclosure in any way.

A. General Description of Synthesis of Compounds According to this Specification The compounds as described in this specification can be obtained by various synthesis routes. A person skilled in the art will choose the synthetic route to obtain compounds as described in this specification depending on the nature of its radicals as defined in Formula (I). This is illustrated in the following schemes, which are merely illustrative but not limiting the disclosure in any way.

Scheme 1:

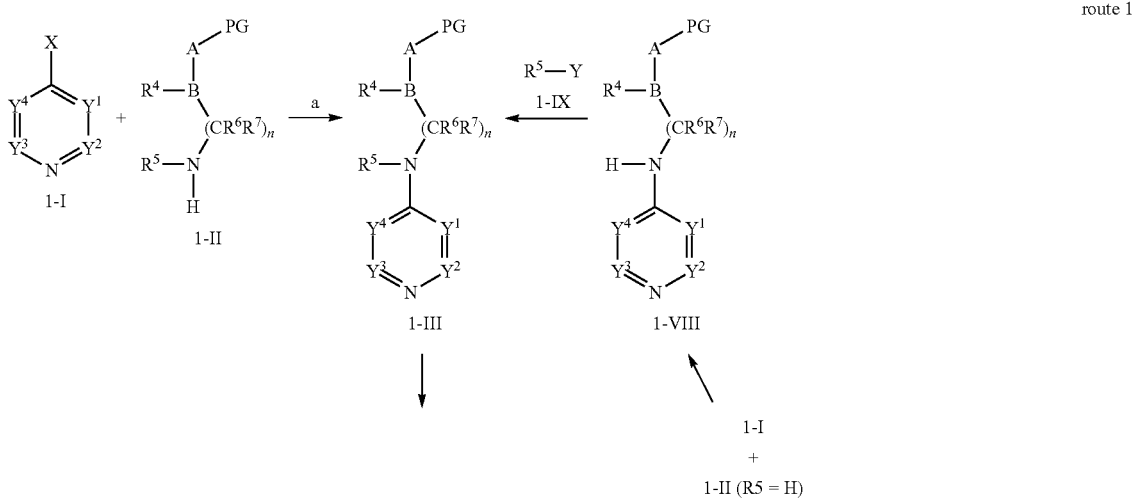

-continued route 2

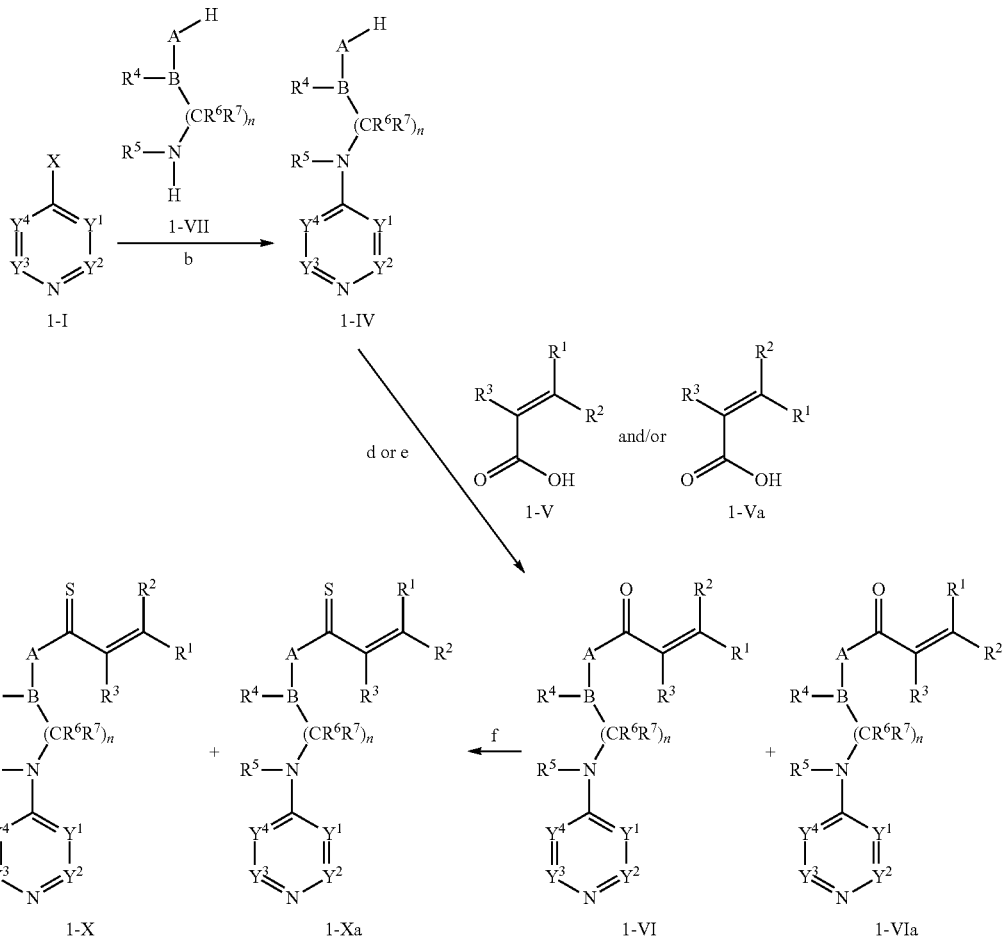

Exemplary conditions: a: palladium acetate, 2,2'-Bis(diphenylphosphino)-1,1'-binaphthyl (BINAP), caesium carbonate, dioxane;
b: 1-methoxy-2-propanol, 110° C. d: oxalyl chloride, dichloromethane (DCM), dimethylformamide (DMF) then DCM, triethylamine (TEA);
e: 2-(1H-Benzotriazole-1-yl)-1,1,3,3-tetramethylaminium hexafluorophosphate (HBTU), diisopropylethylamine, DMF, room temperature;
f: Lawesson's reagent, tetrahydrofuran (THF), 130° C.

A compound of general formula 1-VI can be synthesized as shown in scheme 1: in route 2 a heteroaryl compound 1-I is reacted with a diamine 1-VII to give 1-IV. 1-I contains a suitable leaving group X, which is preferably a halogen like chloro or bromo or a nitro group. The reaction with 1-VII takes place in an inert solvent like DMF or dimethylacetamide, preferably in a diol-derived solvent like ethyleneglycolmonomethylether or propyleneglycolmonomethylether or 1-methoxy-2-propanol and preferably at elevated temperatures. The reaction might also be done without any solvent with neat reactants. 1-VII is employed preferably in excess. An additional base might be added. Alternatively, the reaction can be done in pyridine as solvent. The diamine can be protected with a suitable protecting group as in 1-II of route 1. Suitable protecting groups (PG) for the nitrogen in 1-II include, but are not limited to, preferably tert-butyl carbamate (Boc), benzyl carbamate (Cbz) and the like. A protected diamine 1-II can be reacted under the same conditions as 1-VII, alternatively Pd-catalysis can be used employing a Pd-containing molecule like palladium acetate, a phosphorus-containing ligand like BINAP, a base like caesium carbonate or sodium tert-butoxide in a solvent like an ether-containing solvent like diethylether, dioxane or tetrahydrofuran, preferably dioxane or an inert solvent like toluene. The protecting group in the intermediate 1-III can be removed by suitable methods known to a person skilled in the art; if PG is a Boc-group, for example, the protecting group can be removed by an acid like trifluoroacetic acid or hydrochloric acid to give the amine 1-IV. Other suitable methods for protection and deprotection are described in, for example, Green and Wuts, *Protective Groups in Organic Synthesis*, 3$^{rd}$ edition, John Wiley & Sons, New York, 1999. If 1-I and 1-II are reacted and $R^5$ is H, the resulting 1-VIII can be reacted with 1-IX to give the intermediate 1-III. 1-IX contains a suitable leaving group Y, e.g. a chloro and is, depending on the nature of the radical $R^5$ an alkylating or acylating agent that is reacted under conditions known to a person skilled in the art. 1-IV is acylated with an unsaturated acid derivative 1-V to give the final product 1-VI. 1-V can be accompanied by the isomeric 1-Va, so that a mixture of 1-V and 1-Va is used in the acylation step. In this case a mixture of 1-VI and 1-VIa is formed that can be separated by methods known to a person skilled in the art, e.g. by chromatography. Or 1-Va can be used in a pure form in the acylation step to give 1-VIa. Thus, if in the following descriptions and schemes the acid 1-V is mentioned, the same applies for the isomeric acid 1-Va, either in its pure form or in form of a mixture of 1-V and 1-Va. The same applies for reaction products derived from 1-V: these can be obtained in pure form if the isomerically pure 1-V or 1-Va are used in the acylation step, or they can be obtained as a mixture if a mixture of 1-V and 1-Va is used and might be separated then by methods known to a person skilled in the art, e.g. by chromatography. There are many acylation methods known to a person skilled in the art: 1-V can be converted to an acid chloride with oxalyl chloride, thionyl chloride or the like which can be isolated or used directly to react with 1-IV in the presence of a base like triethylamine or diisopropylethylamine to give 1-VI. The base might also be polymer-supported to ease work-up. The base might be used in excess, the excess might be removed using aqueous work-up or polymer-supported reagents like polymer-supported acid chloride. The acid 1-V can also be reacted directly with the amine 1-IV using coupling reagents like N,N,N',N'-tetramethyl-O-(7-azabenzotriazol-1-yl)-uronium hexafluorophosphate (HATU), N,N,N',N'-tetramethyl-O-(1H-benzotriazol-1-yl)-uronium hexafluorophosphate (HBTU), 1-hydroxy-7-azabenzotriazole (HOAt), N,N'-dicyclohexylcarbodiimide (DCC) or the like. Other suitable amide coupling procedures are described in Goodman, M.; Felix, A.; Moroder, L.; Toniolo, C. in volume E22a of *Methods of Organic Chemistry* (Houben-Weyl), *Synthesis of Peptides and Peptidomimetics*, 4th edition, Georg Thieme Verlag, Stuttgart N.Y., 2002. 1-VI and 1-VIa can be converted into their thiocarbonyl analogue 1-X and 1-Xa by treatment with, for example, Lawesson's reagent under microwave heating. Other methods are described in, for example, Smith, M. B.; March, J.; *March's Advanced Organic Chemistry*, John Wiley & Sons, Hoboken; N.J., 2007, 1277-1280. A compound of general formula 1-VI can be substituted at $Y^1$-$Y^4$. This substituent can already be present in the heteroaryl compound 1-I. A person skilled in the art will appreciate that it can also be introduced in a compound 1-III, 1-IV or 1-VI. For example, $Y^1$-$Y^4$ in 1-I might be substituted by a potential leaving group like, for example, halogen, which can be replaced by another group, for example a nucleophilic group in, for example, a nucleophilic substitution reaction. Or, for example, $Y^1$-$Y^4$ in 1-III might be substituted by a potential leaving group like, for example, halogen, which can be replaced by another group, for example a nucleophilic group in, for example, a nucleophilic substitution reaction. Or, for example, $Y^1$-$Y^4$ in 1-IV might be substituted by a potential leaving group like, for example, halogen, which can be replaced by another group, for example a nucleophilic group in, for example, a nucleophilic substitution reaction. 1-I might also be substituted at $Y^1$-$Y^4$ with a group that can react with a group present in the reaction partner 1-II or 1-VII like, for example, the amino group in 1-II or 1-VII. In this case the reacting group in 1-I can be protected by a protecting group by methods known to a person skilled in the art. For example, 1-I can be substituted by an acyl group. This acyl group can be protected as, for example, an oxolan prior to the reaction with 1-II or 1-VII and deprotected by, for example, aqueous acid after the reaction with 1-II or 1-VII as described in, for example, Green and Wuts, *Protective Groups in Organic Synthesis*, 3rd edition, John Wiley & Sons, New York, 1999. The same applies to the following schemes in an analogous way.

The heteroaryl compound 1-I can be substituted at the N-Atom with oxygen, thus being a heteroaryl-N-oxid, for example a quinoline-N-oxid or a pyridine-N-oxid. Methods for the synthesis of such heteroaryl-N-oxides are described in, for example, R. Kreher (editor), volume E7a of *Methods of Organic Chemistry (Houben-Weyl), Hetarenes II part 1*, 4th edition, Georg Thieme Verlag, Stuttgart-N.Y., 1991. A person skilled in the art will appreciate that the synthetic transformations described in scheme 1 result in this case in the corresponding heteroaryl-N-oxides of heteroaryl compounds of general formula 1-VI and 1-VIa, for example.

Intermediates of formula 1-IV in which $Y^1$-$Y^4$ are C, substituted by $R^{12}$, $R^{13}$, $R^{14}$ and $R^{15}$=halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl or phenyl, and wherein at least one of $R^{12}$ and $R^{13}$=$C_1$-$C_6$-alkoxy or $C_1$-$C_6$-haloalkoxy, B is N, A is N or a bond, n is 2, $R^6$ and $R^7$=H, and $R^4$ and $R^5$ are defined as in formula (I) or (II) above, are new and a subject of this invention. In one preferred embodiment $R^{12}$=$C_1$-$C_6$-alkoxy or $C_1$-$C_6$-haloalkoxy, in another preferred embodiment $R^{13}$=$C_1$-$C_6$-alkoxy or $C_1$-$C_6$-haloalkoxy.

Scheme 2:

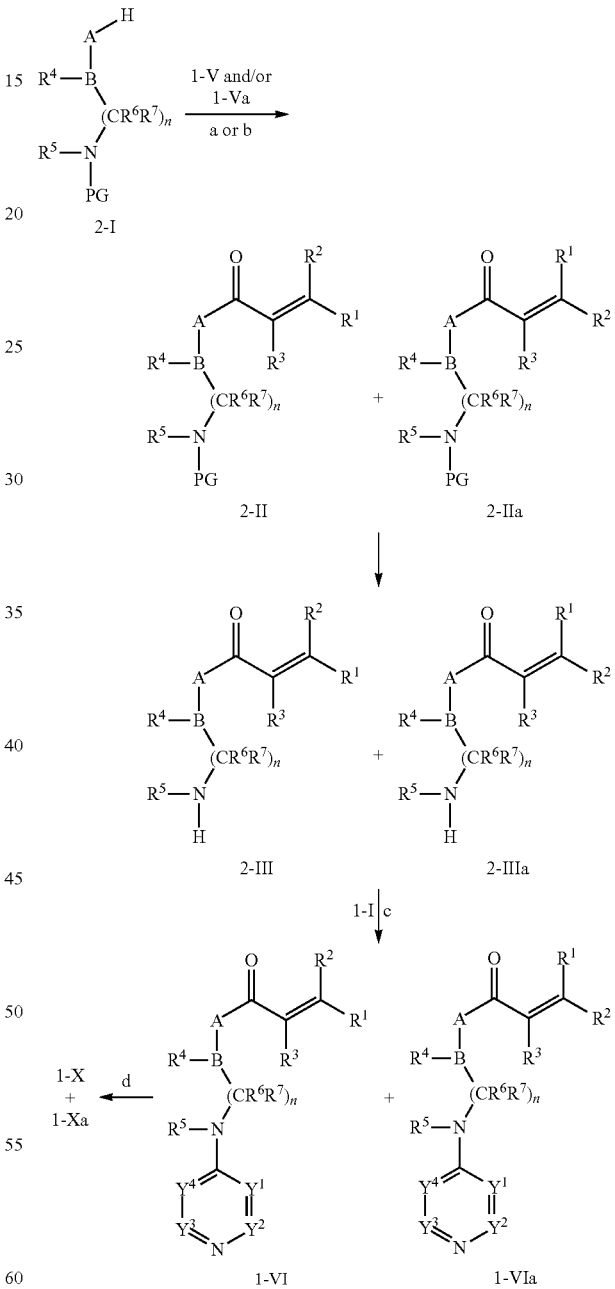

Exemplary conditions: a: oxalyl chloride, DCM, DMF then DCM, triethylamine; b: HBTU, N-ethyl-diisopropylamine (EDIPA), DMF, room temperature; c: palladium acetate, BINAP, caesium carbonate, dioxane; d: Lawesson's reagent, THF, 130° C.

An alternative synthetic route is shown in scheme 2: the diamine 2-I is coupled with 1-V as described for 1-IV followed by deprotection as described for 1-III yielding 2-III which is reacted with 1-I as described for the reaction of 1-I with 1-II.

in scheme 1. The protecting group (PG) is removed and the amine 3-IV is acylated with an unsaturated acid 1-V to give the final product 3-V by methods that have been described in Scheme 3:

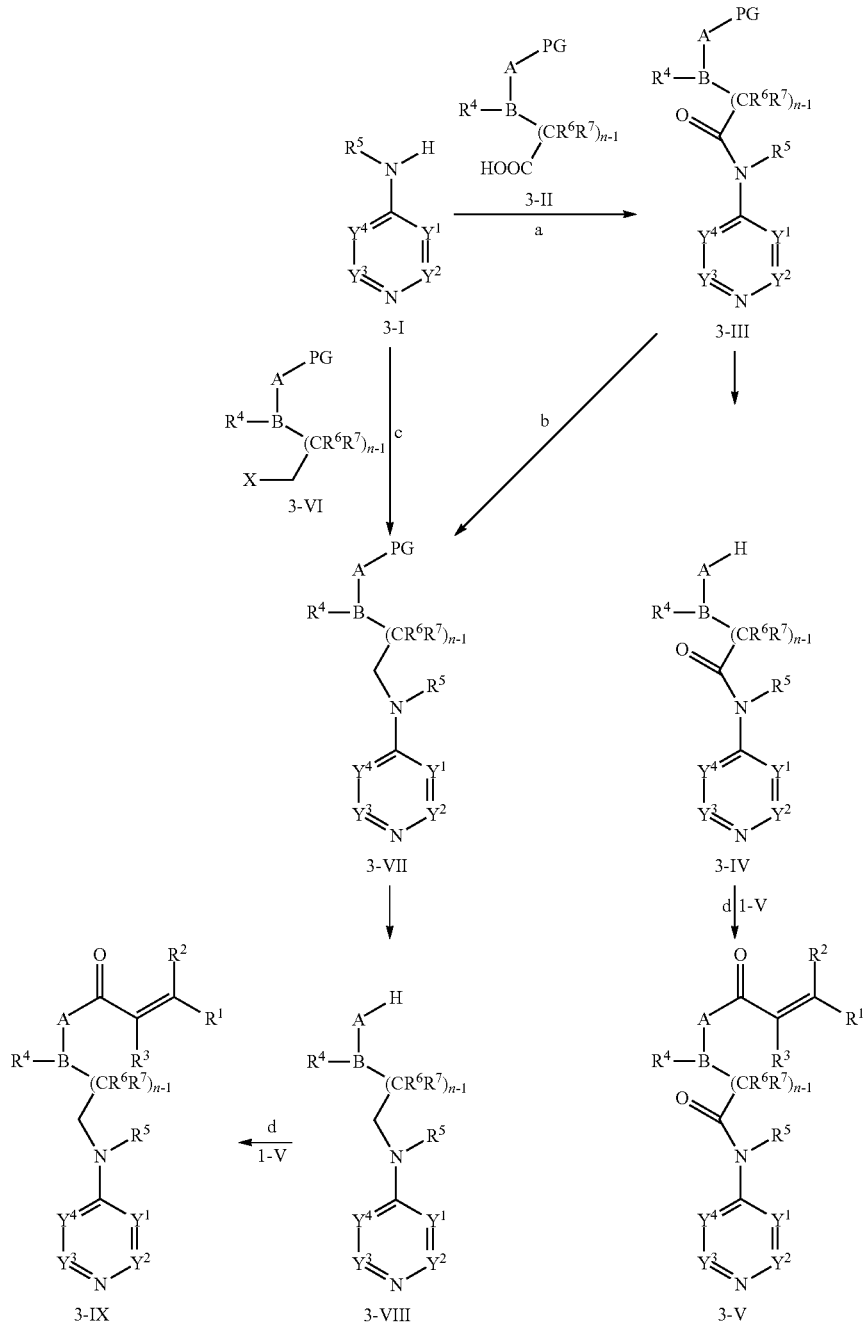

Exemplary conditions:
a: oxalyl chloride, DCM, DMF then DCM, triethylamine
b: LiAlH$_4$, THF;
c: DCM, triethylamine;
d: HBTU, EDIPA, DMF, room temperature A compound of general formula 3-V can be synthesized as shown in scheme 3: A heteroarylaminocompound 3-I is acylated with an amino acid derivative 3-II by methods known to a person skilled in the art, some of which have been described scheme 1. The oxo-group in 3-III can be reduced to give 3-VII employing reducing agents like, for example, lithium aluminium hydride. Other methods are described in, for example, Smith, M. B.; March, J.; *March's Advanced*

*Organic Chemistry,* John Wiley & Sons, Hoboken; N.J., 2007, 1841-1842. The sequence of deprotection and acylation with an unsaturated acid gives the final product 3-IX. 3-VII can also be obtained by reacting heteroarylaminocompound 3-I with 3-VI instead of 3-II. 3-VI contains a suitable leaving group X, like, for example, chloride or methanesulfonyl under conditions that are described in, for example, WO2006/60461 (example 303-304.4) or EP1574504 (example 2). Aminoacid derivatives 3-II are commercially available and can be transformed by methods known to a person skilled in the art to compounds 3-VI.

Intermediates of formula 3-IV in which $Y^1$-$Y^4$ are C, substituted by $R^{12}$, $R^{13}R^{14}$ and $R^{15}$=halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl or phenyl, and wherein at least one of $R^{12}$ and $R^{13}$=$C_1$-$C_6$-alkoxy or $C_1$-$C_6$-haloalkoxy, B is N, A is N or a bond, n is 2 or 3, $R^6$ and $R^7$=H, and $R^4$ and $R^5$ are defined as in formula (I) or (II) above, are new and a subject of this invention. In one preferred embodiment $R^{12}$=$C_1$-$C_6$-alkoxy or $C_1$-$C_6$-haloalkoxy, in another preferred embodiment $R^{13}$=$C_1$-$C_6$-alkoxy or $C_1$-$C_6$-haloalkoxy.

Scheme 4:

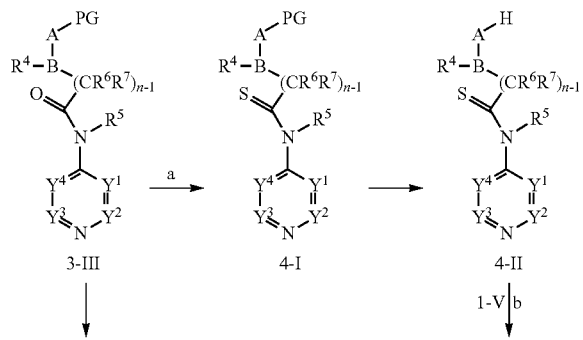

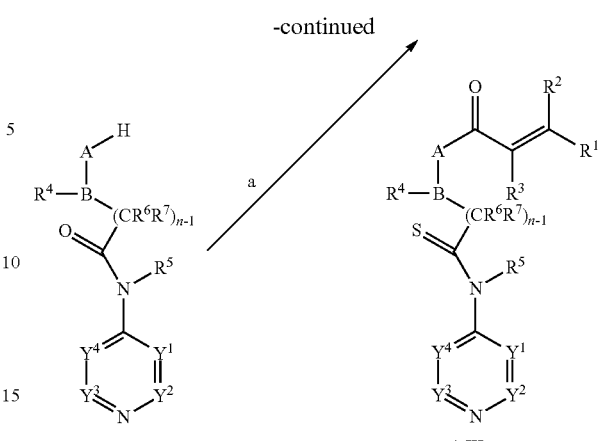

3-IV    4-III

Exemplary conditions:
a: Lawesson's reagent;
b: HBTU, diisopropylethylamine, DMF, room temperature A compound of general formula 4-III can be synthesized as shown in scheme 4: The oxo-group in 3-III can converted to a thioxo-group by methods known to a person skilled in the art, for example, the Laweson's reagent can be used. This and other methods is described in, for example, Smith, M. B.; March, J.; *March's Advanced Organic Chemistry*, John Wiley & Sons, Hoboken; N.J., 2007, 1277-1280. The sequence of deprotection and acylation with an unsaturated acid that has been described in scheme 1 gives the final product 4-111. Alternativly, the conversion of the oxo- into the thioxo-group can be done after deprotection of 3-III to 3-IV to give the thioxo compound 4-II which is then acylated to the final product 4-111.

Intermediates of formula 4-II in which $Y^1$-$Y^4$ is substituted by $R^{12}$, $R^{13}$, $R^{14}$ and $R^{15}$=halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl or phenyl, and wherein at least one of $R^{12}$ and $R^{13}$=$C_1$-$C_6$-alkoxy or $C_1$-$C_6$-haloalkoxy, B is N, A is N or a bond, n is 2 or 3, $R^6$ and $R^7$=H, and $R^4$ and $R^5$ are defined as in formula (I) or (II) above, are new and a subject of this invention. In one preferred embodiment $R^{12}$=$C_1$-$C_6$-alkoxy or $C_1$-$C_6$-haloalkoxy, in another preferred embodiment $R^{13}$=$C_1$-$C_6$-alkoxy or $C_1$-$C_6$-haloalkoxy.

Scheme 5:

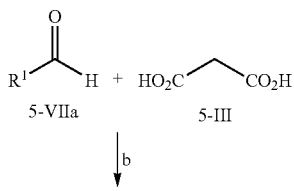

-continued

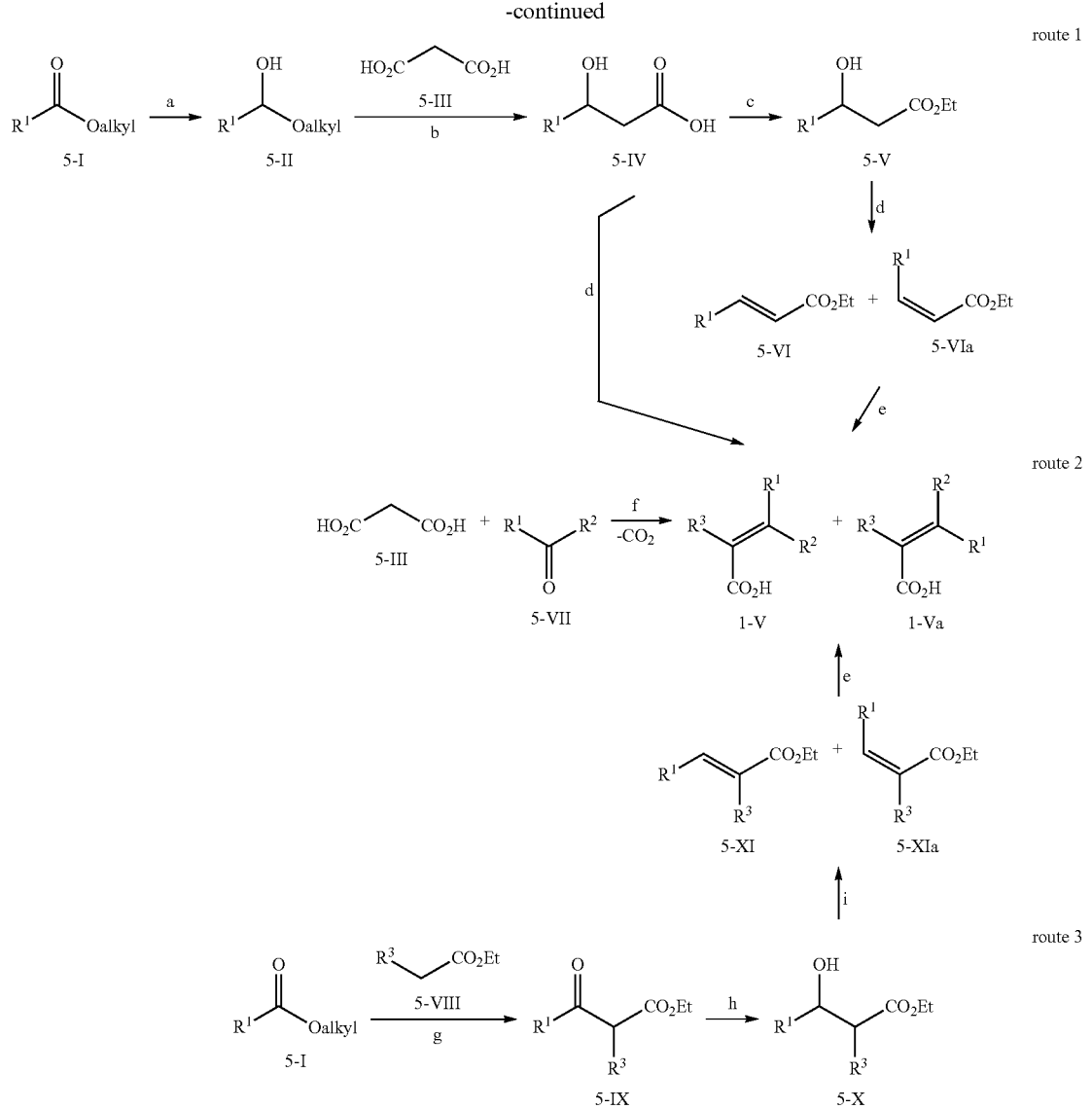

Exemplary conditions: a: sodium borohydride, methanol; b: pyridine, piperidine; c: ethanol, HCl; d: phosphorpentoxide; e: NaOH; f: pyridine, piperidine, reflux; g: LiN(Si(CH$_3$)$_3$)$_2$, THF; h: sodium borohydride, toluene; i: phosphorpentoxide (R$^3$ = H)

The unsaturated acids used for acylation (1-V in scheme 1) can be synthesized in several ways, many of which are described in: J. Falbe in volume E5, part 1 of *Methods of Organic Chemistry (Houben-Weyl), Carboxylic acids*, 4$^{th}$ edition, Georg Thieme Verlag, Stuttgart-N.Y., 1985. The preferred route will be chosen by a person skilled in the art according to the nature of the radicals R$^1$, R$^2$ and R$^3$. For example, in scheme 5, if R$^2$ is H and R$^1$ is alkyl preferably route 2 will be chosen. If R$^2$ is H and R$^1$ is alkyl substituted by halogen like F and/or Cl, route 1 or 3 will preferably be chosen. According to route 2 in scheme 5 malonic acid 5-III is condensed with an aldehyde or ketone 5-VII to yield directly the crotonic acid 1-V, which can be accompanied by the isomeric 1-Va. Suitable reaction conditions include heating the reactants in a solvent, preferably pyridine with the addition of piperidine. According to route 1, a carboxylic ester 5-I is reduced to the hemiacetal 5-11, which is condensed with malonic acid in a manner analogous to route 1. Alternatively, the aldehyde 5-VIIa can be condensed with malonic acid to give the hydroxyacid 5-IV. The hydroxyacid 5-IV might be isolated or used directly in a dehydration step to yield I-V. Preferably, the hydroxyacid is esterified to 5-V which is dehydrated to 5-VI and hydrolysed to the acid 1-V. Methods for the dehydration of 5-IV and 5-V are described in, for example, M. Jagodzinska et al.; *Tetrahedron* 63 (2007), 2042-2046; P. F. Bevilaqua, *J. Org. Chem.* 94 (1984), 1430-1434 and include treatment of a hydroxyacid or -ester like 5-IV or 5-V with P$_2$O$_5$ at preferably elevated temperatures or treatment with diethylazodicarboxylate and triphenylphosphine.

According to route 3 an ester 5-I is condensed with a CH-acidic ester 5-VIII to give a beta-keto ester 5-IX which is reduced to the hydroxyester 5-X. Methods for the condensation of an ester with another CH-acidic ester are known to a person skilled in the art, as well as methods for the reduction of a keto group to a hydroxygroup and are described in, for example, M. Jagodzinska et al.; *Tetrahedron* 63 (2007), 2042-2046; T. Kitazume; *J. Fluorine Chemistry* 42 (1989), 17-29. 5-X is then converted to the crotonic acid 1-V in a manner analogous to the one described above for 5-V.

In all of the described routes, 1-V might be accompanied by the isomeric 1-Va. Depending on the nature of the radicals $R^1$ and $R^2$ the isomers 1-V and 1-Va can be formed in varying proportions. For example if $R^2$ is H, the E-isomer 1-V is predominantly formed. The isomeric 1-V and 1-Va can be separated by methods known to a person skilled in the art, e.g. by chromatography and can be used as pure isomers in subsequent reactions. Or 1-V and 1-Va can be used as a mixture in subsequent reactions and the resulting isomeric products can be separated in a later step. Unsaturated acids with $R^1$=alkyl substituted by alkylamino or dialkylamino and $R^2$=H and $R^3$=H can also be obtained as described in, for example, WO2006/127203 or US2003/50222, respectively. Unsaturated acids with $R^1$=$SF_5$ and $R^2$=H and $R^3$=H can also be obtained as described in, for example, V. K. Brel, *Synthesis* 2006, 339-343. Unsaturated acids with $R^1$=alkylthio and alkylsulfonyl and $R^2$=H and $R^3$=H can also be obtained as described in, for example, J. T. Moon, *Bioorg. Med. Chem. Letters* 20 (2010) 52-55. Many unsaturated acids 1-V used as starting materials are also commercially available by a large number of vendors as listed in, for example, the Symyx Available Chemicals Directory (ACD).

Scheme 6:

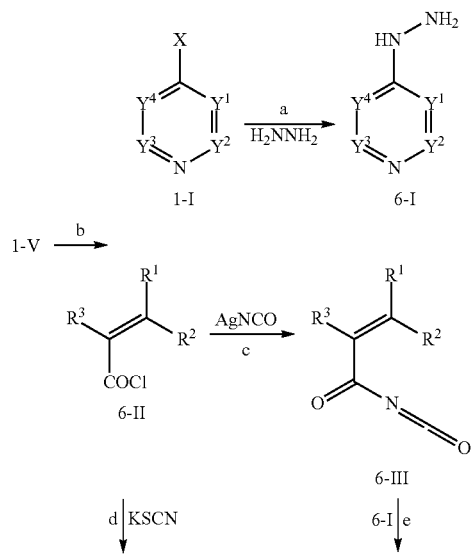

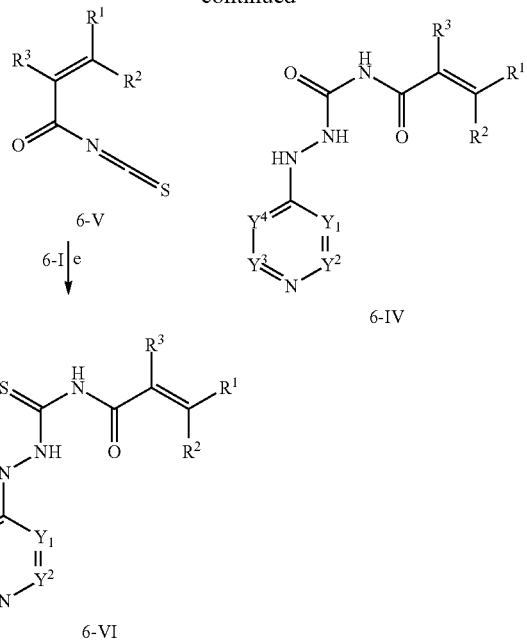

Exemplary conditions: a: hydrazine hydrate, 150° C.; b: DCM, oxalyl chloride, DMF, room temperature; c: benzene, room temperature; d: acetonitrile, room temperature; e: DMF, $K_2CO_3$, room temperature Compounds of the general formula 6-IV can be synthesized as shown in scheme 6: A heteroaryl compound 1-I containing a suitable leaving group X is reacted with hydrazine to give the hydrazino compound 6-I. Suitable leaving groups comprise, for example, a halogen like chloro. The reaction is performed preferably at elevated temperatures. An unsaturated carboxylic acid 1-V is converted into its acid chloride 6-II by methods known to a person skilled in the art, which is converted to the acyl isocyanate 6-III by reaction with an isocyanate salt like, for example, silver isocyanate. 6-III is then reacted with the hydrazino compound 6-I to give the final product 6-IV, for example by reaction in a solvent like DMF in the presence of a base like potassium carbonate. The thioxo analogue 6-VI is synthesized analogously by employing the acyl isothiocyanate 6-V, that is obtained from the carboxylic acid chloride 6-II by reaction with an isothiocyanate salt like, for example, potassium isothiocyanate in a solvent like, for example, acetonitrile. Similar reactions are described in, for example, WO2004/48347; O. Tsuge, T. Hatta, R. Mizuguchi, *Heterocycles* 38, (1994), 235-241; G. Shaw, R. N. Warrener, *J. Chem. Soc.* (1958) 157-161; G. Shaw, R. N. Warrener, *J. Chem. Soc.* (1958) 153-156.

Scheme 7:

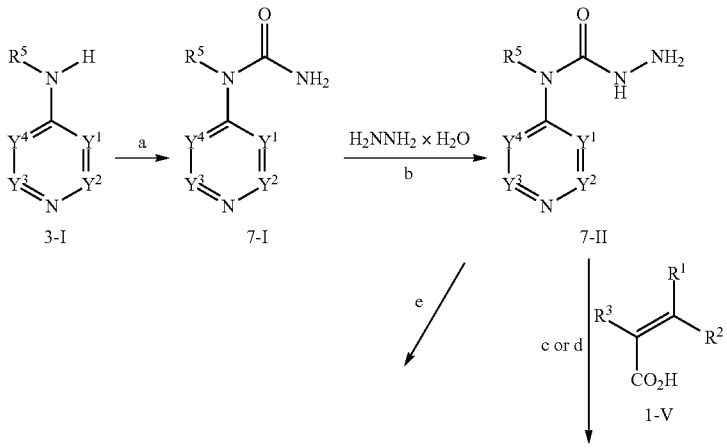

-continued

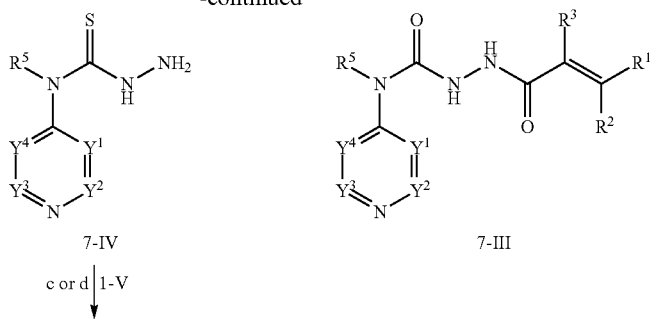
7-IV      7-III c or d | 1-V

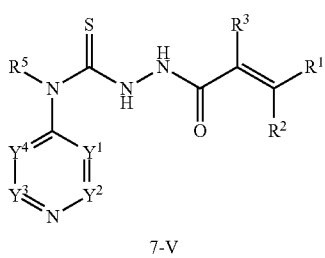
7-V

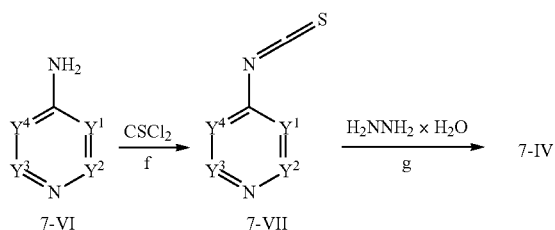
7-VI      7-VII

Exemplary conditions: a: sodium cyanate, acetic acid; b: water, ethanol, reflux; c: oxalyl chloride, DCM, DMF then DCM, triethylamine; d: HBTU, diisopropylethylamine, DMF, room temperature; e: Lawesson's reagent; f: benzene, triethylamine, reflux; g: THF.
($R^5$ = H)

A compound of general formula 7-III can be synthesized as shown in scheme 7: a heteroarylamine 3-I is converted to the corresponding urea 7-I by treatment with sodium cyanate. Reaction with hydrazine according to U.S. Pat. No. 5,098,462 yields the carbazine 7-II which is acylated with an unsaturated acid 1-V as described in scheme 1 to give the final product 7-III. The thioxo-analogue 7-V is obtained by converting the carbazine 7-II to the thiocarbazine 7-IV with, for example, Lawesson's reagent, followed by acylation with 1-V as described above. The thiocarbazine 7-IV can also be obtained by conversion of the heteroarylamine 7-VI into the isothiocyanate 7-VII by reaction with thiophosgen followed by addition of hydrazine.

Scheme 8:

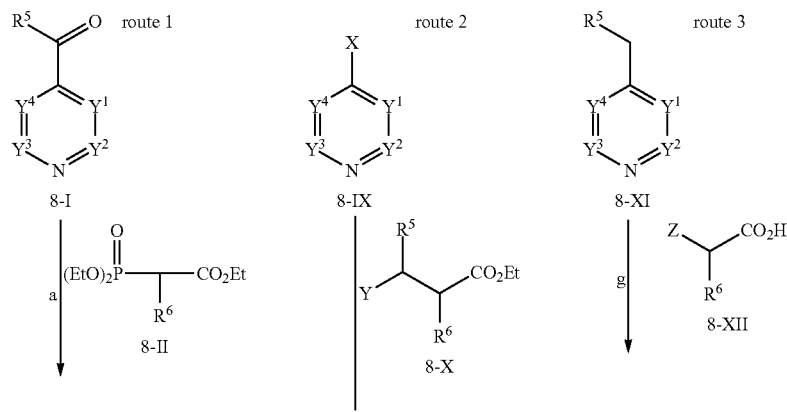

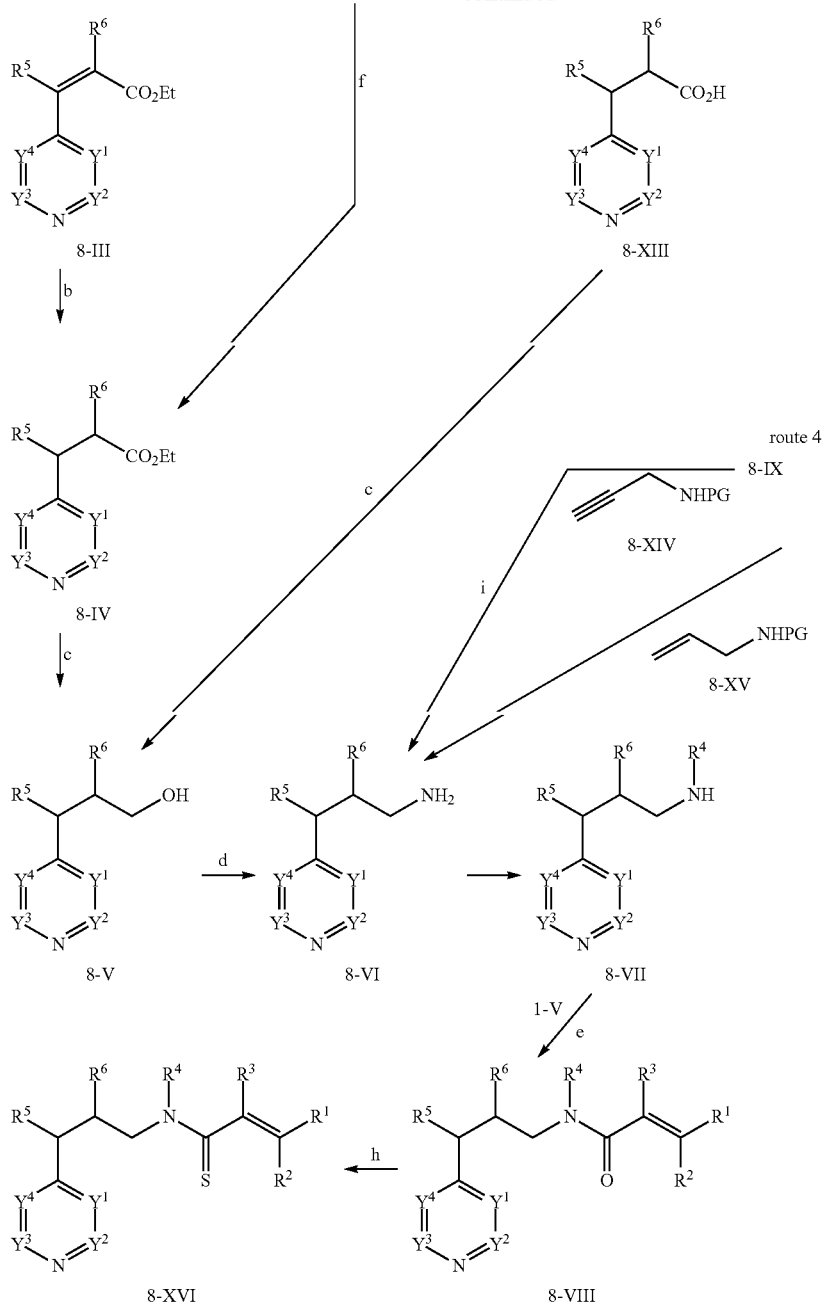

Exemplary conditions: a: THF, LiOH; b: hydrogen, ethanol, Pd/C; c: LiAlH$_4$; d: 1. phthalimide, PPh$_3$, N$_2$(COOEt)$_2$, THF, 2. N$_2$H$_4$, methanol; e: HBTU, diisopropylethylamine, DMF; f: Zn/Cu, Pd(PPh$_3$)$_2$, dimethylacetamide; g: NaNH$_2$, NH$_{3(l)}$; h: Lawesson's reagent, THF, 130° C.; i: Pd(PPh$_3$)$_2$Cl$_2$, 1,4-diazabicyclo[2,2,2]octane, THF.

A compound of general formula 8-VIII can be synthesized as shown in scheme 8: in route 1 a heteroarylcarbonyl compound 8-I is reacted with a phosphonic acid derivative 8-II in a Horner-Wadsworth-Emmons reaction to form the unsaturated ester 8-III which is reduced to the saturated ester 8-IV by methods known to a person skilled in the art, e.g. hydrogenation with a suitable catalyst like, for example, palladium on charcoal. Reduction of the ester to the alcohol 8-V by, for example, a hydride transfering reagent like lithium aluminium hydride is followed by transformation to the amine 8-VI. The latter transformation can be archived by, for example, the known Gabriel synthesis via formation of an intermediate phthalimide. Substitution of the nitrogen in 8-VI to give 8-VII can be done by methods known to a person skilled in the art using, for example, alkylation agents like alkylhalogens or using reductive alkylation procedures as described in, for example, Smith, M. B.; March, J.; *March's Advanced Organic Chemistry*, John Wiley & Sons, Hoboken; N.J., 2007, 1288-1292. Acylation with the unsaturated acid 1-V under conditions that have been described in scheme 1 gives the final product 8-VIII. A person skilled in the art can choose an alternative route depending on the availability, for example commercial availability of starting materials. In route 2 a heteroaryl compound 8-IX containing a suitable leaving group X like a halogen, preferably a iodine, is reacted with a zincorganic reagent that is synthesized, for example in situ, from the ester 8-X containing a halogen atom Y, preferably an iodine, by methods known to a person skilled in the art, for example as described in Sakamoto, T., *Synthesis*, (1988), 485-486 to give the intermediate ester 8-IV. In route 3 a heteroarylalkyl compound 8-IX is reacted with a carboxylic acid 8-XII containing a halogen atom z to give the substituted acid 8-XIII as described in, for example, Adger, B. M., et. Al. *J. Chem. Soc. Perkin Trans. I* (1988), 2791-2796, that is reduced to the hydroxy intermediate 8-V by methods known to a person skilled in the art. In route 4, a heteroaryl compound 8-IX containing a suitable leaving group X like a halogen, preferably an iodine or bromine, is reacted with a protected amine 8-XIV containing a terminal triple bond in a Sonogashira-type coupling. Reduction of the triple bond and removal of the protecting group yields the amine 8-VI. Alternatively, 8-IV can be obtained by coupling of the protected amine 8-XV containing a terminal double bond with 8-IX in a Heck-type reaction followed by reduction and deprotection. Conversion into the thiocarbonyl analogue 8-XVI can be achieved by treatment with, for example, Lawesson's reagent under microwave heating. Other methods are described in, for example, Smith, M. B.; March, J.; *March's Advanced Organic Chemistry*, John Wiley & Sons, Hoboken; N.J., 2007, 1277-1280.

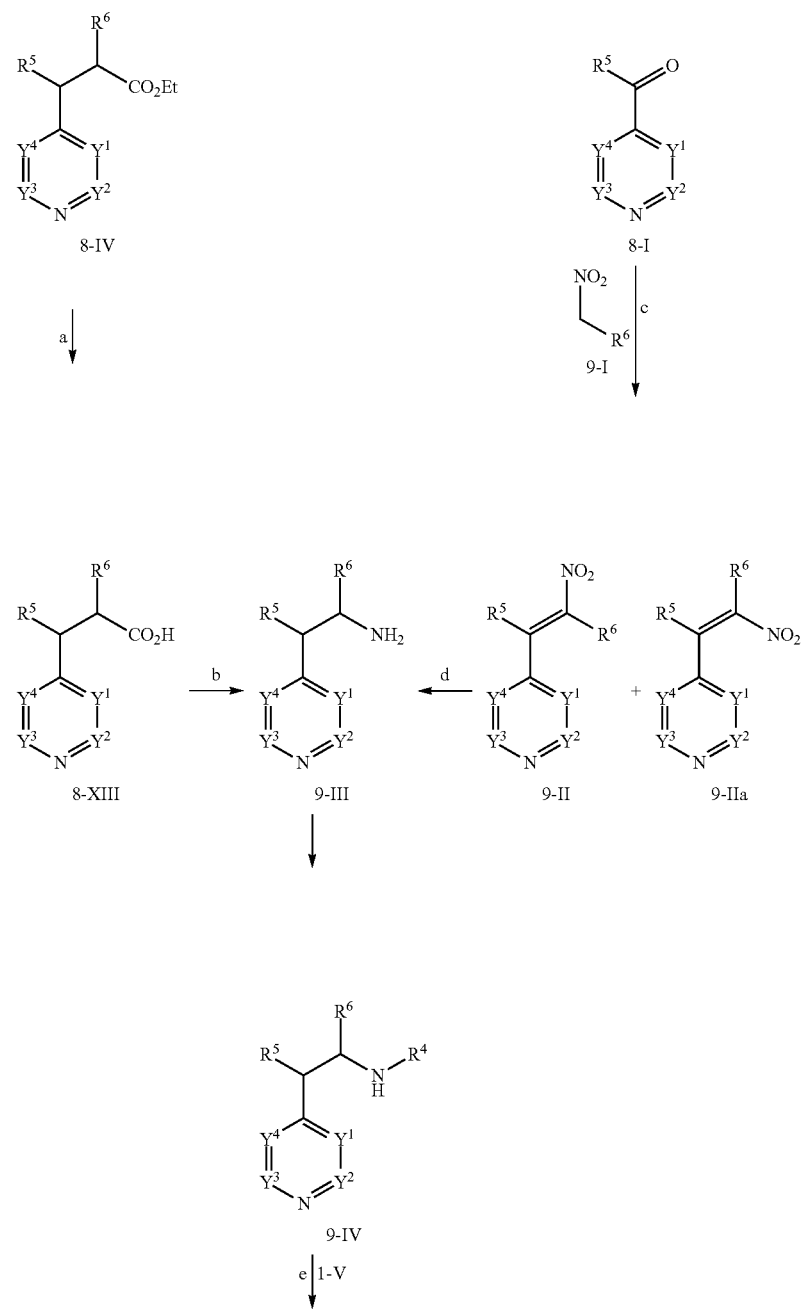

Scheme 9:

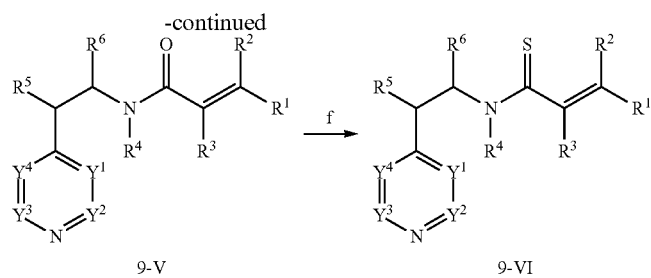

Exemplary conditions: a: NaOH, H₂O; b: NaN₃, H₂SO₄; c: 1. DCM, TEA 2. DCM, methanesulfonyl chloride, TEA; d: hydrogen, Raney nickel, methanol; e: HBTU, diisopropylethylamine, DMF; f: Lawesson's reagent, THF, 130° C.

Compounds of the general formula 9-V can be synthesized as shown in scheme 9: a heteroarylcarboxylic acid 8-XIII that has been described in scheme 8 is transformed into the amine 9-III with a Schmidt reaction as described in, for example, Claudi, F. et al. *Eur. J. Med. Chem.* 30(5), (1995), 415-421. 8-XIII can also be obtained by hydrolysis of the ester 8-IV that has been described in scheme 8. Alternatively, a heteroarylcarbonyl compound 8-I can be transformed to a mixture of 9-II and the isomeric 9-IIa as described in, for example, WO2008/125839 (example 36) followed by reduction to 9-III as described in, for example, Monti, D. et al. *Farmaco*, 36(6), (1981), 412-418. The primary amine in 9-III is then substituted as has been described in scheme 8 and acylation with a unsaturated acid as has been described in scheme 1 gives the final product 9-V. Conversion into the thiocarbonyl analogue 9-VI can be achieved by treatment with, for example, Lawesson's reagent under microwave heating.

Scheme 10:

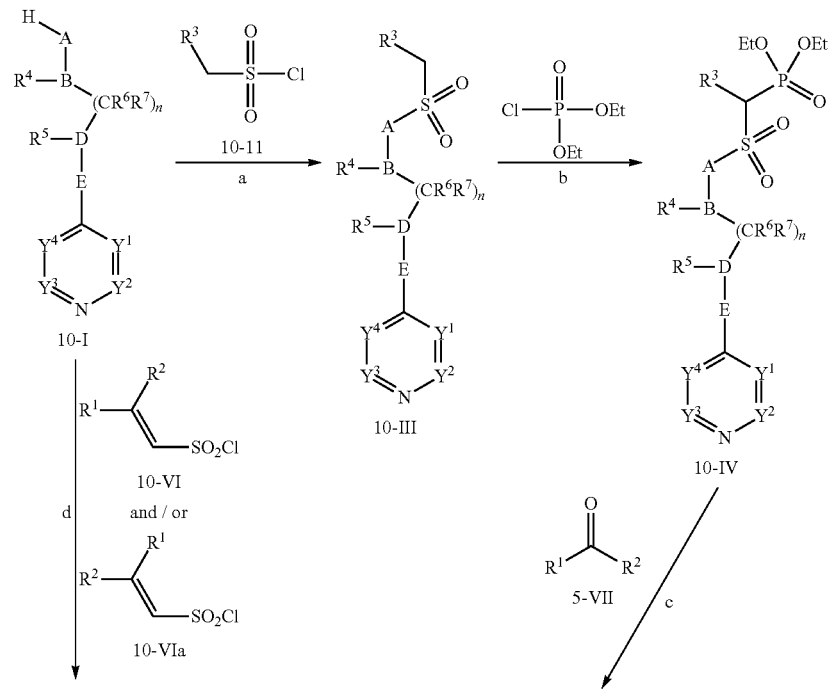

10-V and/or 10-Va

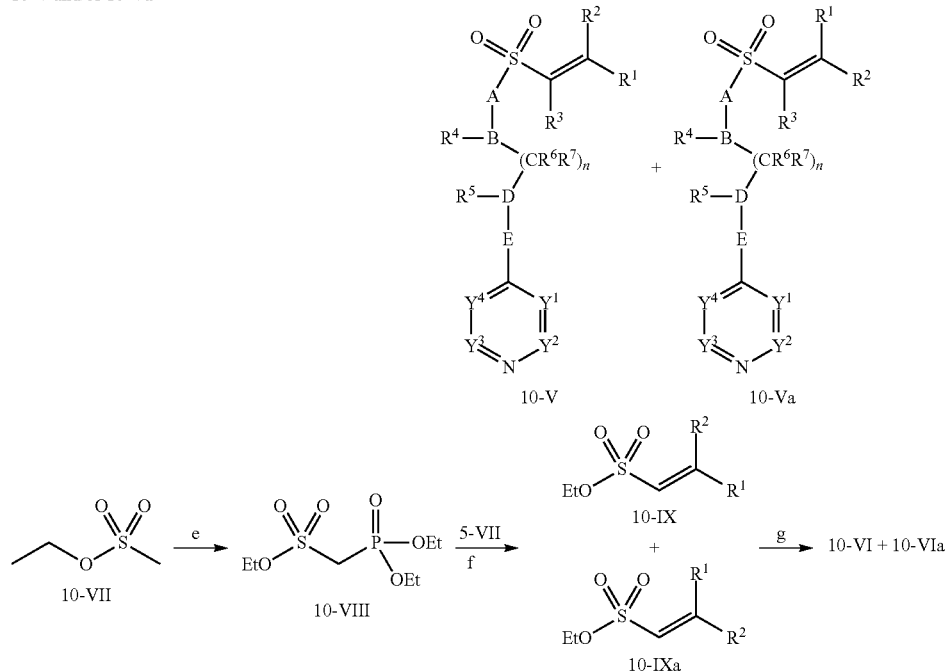

Exemplary conditions: a: DCM, TEA, 0° C.; b: LiN(Si(CH₃)₃)₂, THF, -78° C.; c: LiBr, DBU, THF, -10° C. to room temperature; d: TEA, DCM,; e: (EtO)₂POCl, n-butyllithium (n-BuLi), THF, -80° C.; f: tetrabutylammonium iodide, acetone, reflux, then sulfuryl chloride, triphenylphospine, DCM.

A compound of the general formula 10-V can be synthesized as shown in scheme 10: A compound 10-I which contains an NH-group is reacted with an alkylsulfonic acid chloride 10-II in the presence of a suitable base like triethylamine in a solvent like dichloromethane. 10-I can be synthesized, for example, according to schemes 1, 2, 3, 4, 8 or 9. The sulfonamide 10-III is deprotonated with a strong base like lithium diisopropylamide, lithium hexamethyldisilazide or n-butyl-lithium at low temperature like −78° C. and reacted with diethylchlorophosphate to give 10-IV. 10-IV is then reacted with a carbonyl compound 5-VII to give the final product 10-V. The last step is carried out in the presence of lithium bromide and a strong base like 1,8-diaza-7-bicyclo[5.4.0] undecene (DBU). Similar reactions are described in, for example, Z. Wrobel, *Tetrahedron* 57 (2001), 7899-7907. Depending on the nature of the radicals R¹, R² and R³ the isomeric final products 10-V and 10-Va can be formed in differing proportions. For example, if R² is H and R³ is H, then the E-isomer 10-V is formed predominantly. If a mixture of 10-V and 10-Va is formed, this can be separated by methods known to a person skilled in the art, e.g. by chromatography. Alternatively, the vinylsulfonyl chloride 10-VI can be synthesized first starting from the methanesulfonate 10-VII by deprotonation and reaction with diethylchlorophosphate, followed by deprotonation and reaction with a carbonylcompound 5-VII leading to the unsaturated sulfonate 10-IX which is converted to 10-VI. This sulfonyl chloride is then coupled to the amino compound 10-I to give the final product 10-VI.

Scheme 11:

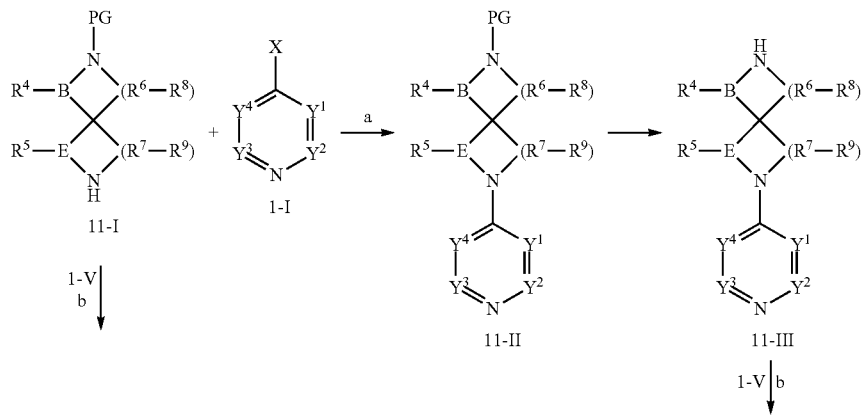

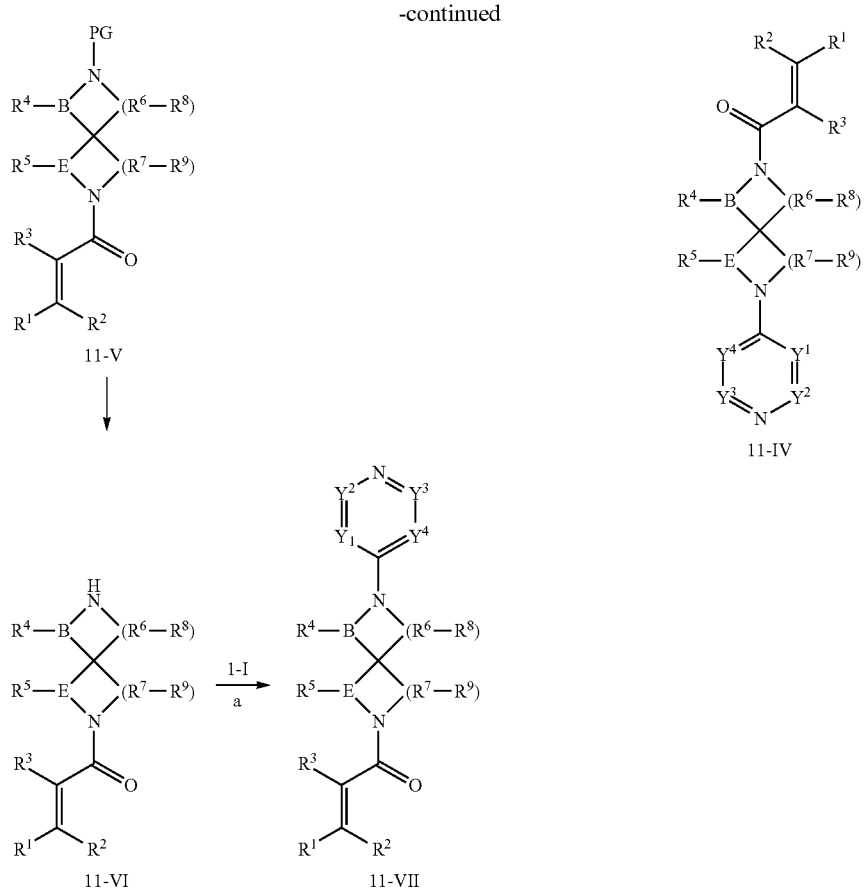

Exemplary conditions: a: Pd₂(dba)₃, BINAP, potassium tert.butylat, TEA, toluene, b: HBTU, diisopropylethylamine, DMF A spiro-compound that is formed when $R^6$ is joined together with $R^8$ to form a $C_1$-$C_3$ alkylene group and $R^7$ is joined together with $R^9$ to form a $C_1$-$C_3$ alkylene group can be synthesized as shown in scheme 11: A spirocyclic diamine 11-I is coupled to a heteroaryl compound 1-I to give 11-II. 11-I can be monoprotected by a suitable protecting group like the ones that have been described in scheme 1. The synthesis of compounds like 11-I has been described in, for example, Burckhard, J., Carreira, E. M., *Organic Lett.* 10 (2008), 3525-3526 and Burckhard, J., Guerot, C., Knust, H., Rogers-Evans, M., Carreira, E. M., *Organic Lett.* 12 (2010), 1944-1947. Pd-catalysis can be used employing a Pd-containing molecule like palladium acetate or Pd₂(dba)₃, a phosphorus-containing ligand like BINAP, a base like caesium carbonate or sodium tert-butoxide in a solvent like an ether-containing solvent like diethylether, dioxane or tetrahydrofuran, or an inert solvent like toluene as described in, for example, Burckhard, J., Carreira, E. M., *Organic Lett.* 10 (2008), 3525-3526. Deprotection and acylation with an unsaturated acid 1-V gives the final product 11-IV. The sequence might be altered so that the spirocyclic diamine 11-I is first acylated to give 11-V. Deprotection and coupling with the heteroaryl compound 1-I gives 11-IV.

Heteroaryl compounds 1-I and 8-IX can be synthesized by several methods known to those skilled in the art. Quinoline derivatives are described in, for example, R. Kreher (editor), volume E7a of *Methods of Organic Chemistry (Houben-Weyl), Hetarenes II, part 1, 4th edition*, Georg Thieme Verlag, Stuttgart-N.Y., 1991; pyridine derivatives are described in, for example, R. Kreher (editor), volume E7b of *Methods of Organic Chemistry (Houben-Weyl), Hetarenes II, part 2, 4th edition*, Georg Thieme Verlag, Stuttgart-N.Y., 1992; pyrimidines are described in, for example, E. Schaumann (editor), volume E9b of *Methods of Organic Chemistry (Houben-Weyl), Hetarenes IV, part 2a, 4th edition*, Georg Thieme Verlag, Stuttgart-N.Y., 1998; quinazoline derivatives are described in E. Schaumann (editor), in volume E9b of *Methods of Organic Chemistry (Houben-Weyl), Hetarenes IV, part 2b, 4th edition*, Georg Thieme Verlag, Stuttgart-N.Y., 1997; pyridazines and cinnolines in, for example, E. Schaumann (editor), volume E9a of *Methods of Organic Chemistry (Houben-Weyl), Hetarenes IV, part I, 4th edition*, Georg Thieme Verlag, Stuttgart-N.Y., 1997; pyridopyridines in *The Chemistry of Heterocyclic Compounds*, Volume 63, The Naphthyridines, D. J. Brown, P. Wipf, E. C. Taylor (Eds), John Wiley & Sons, New York, 2007; thienopyridines, furopyridines, thienopyrimidines, furopyrimidines, pyrrolopyridines, pyrazolopyrimidines, pyrazolopyridines, pyridopyridines and triazolopyrimidines are described in, for example, A. R. Katritzky, C. W. Rees, E. F. V. Scriven (Editors), volume 7 of *Comprehensive Heterocyclic Chemistry II*, Elsevier Science Ltd., Oxford—N.Y., 1996. The synthesis of furopyridines is also described in, for example, S. Shiotani, K. Tanaguchi, *J. Heterocyclic Chem.*, 33, (1996), 1051-1056; S. Shiotani, K. Tanaguchi, *J. Heterocyclic Chem.*, 34, (1997), 925-929. 2-3-Dihydrofuropyridines are described in, for example, F. Suzenet, M. Khouili, S. Lazar, G. Guillaument, *Synlett*, (2009), 92-96. 2,3-Dihydro-1,4-dioxinopyridines are described in, for example, B. Joseph, A. Benarab, G. Guillaument, *Heterocycles* 38, (1994), 1355-1360. Many heteroaryl compounds 1-I used materials are also commercially available by a large number of vendors as listed in, for example, the Symyx Available Chemicals Directory (ACD).

Amines 1-II, 1-VII, 2-I, 3-I, 7-VI, amino acid derivatives 3-II, used as starting materials are commercially available by a large number of vendors as well as carboxylic esters 5-I and 5-VIII, aldehydes 5-VIIa, ketones 8-I, halocarboxylic esters 8-X, halocarboxylic acids 8-XII, phosphonic acid derivatives 8-II and carbonyl compounds 5-VII as listed in, for example, the Symyx Available Chemicals Directory (ACD).). In addition, carboxylic esters can be obtained by methods known to a person skilled in the art and described in, for example, J. Falbe (editor), volume E5 of *Methods of Organic Chemistry (Houben-Weyl), Carboxylic acids and Derivatives, part I*, $4^{th}$ edition, Georg Thieme Verlag, Stuttgart-N.Y., 1985. Likewise, aldehydes can be obtained by methods described in, for example, J. Falbe (editor), volume E3 of *Methods of Organic Chemistry (Houben-Weyl), Aldehydes*, $4^{th}$ edition, Georg Thieme Verlag, Stuttgart-N.Y., 1983 and ketones as described in, for example, volume VII, part 2 a-c of *Methods of Organic Chemistry (Houben-Weyl), Ketones I-III*, $4^{th}$ edition, Georg Thieme Verlag, Stuttgart-N.Y., 1973-1977.

B. Synthesis Examples

The following examples are for illustrative purposes only and are not intended to limit the scope of the invention. The compounds were named using Symyx® draw version 3.1.Net software (Symyx Technologies, Inc.).

The methods described in the examples can be easily adapted by a person skilled in the art to make other compounds, and intermediates thereof. For instance, a person skilled in the art could replace in the examples the exemplified starting compounds by other compounds of the formulae I-I, 1-II, 1-V, I-VII, 1-IX, 2-I, 3-I, 3-II, 3-VI, 5-I, 5-VII, 5-VIII, 5-XI, 7-VI, 8-I, 8-II, 8-IX, 8-X, 8-XI, 8-XII, 10-I, 10-II, 10-V (e.g. commercially available compounds), perform routine adaptions of the reaction conditions, if any, and use them for the synthesis of further compounds according to this invention.

Example 1

Synthesis of (E)-3-cyclopropyl-N-methyl-N-[2-[methyl-(2-methyl-4-quinolyl)amino]ethyl]prop-2-enamide (A-197)

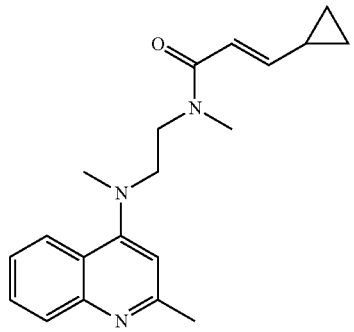 [SMILES: Cc1cc(N(C)CCN(C)C(=O)/C=C/C2CC2)c2ccccc2n1]

Step A: N,N'-Dimethyl-N-(2-methyl-4-quinolyl)ethane-1,2-diamine

4-Chloroquinaldine (1.5 g, 5 mmol) was mixed with N,N'-dimethylethylenediamine (2.45 ml, 25 mmol) and 1-methoxy-2-propanol (8 ml) and stirred at 110° C. overnight. The mixture was purified by column chromatography (pre-packed silica column, gradient of heptane/ethyl acetate each containing 1% triethylamine). 0.4 g were obtained (1.75 mmol; 35%). MS (APCI) m/z=230.0 [M+H]$^+$.

Step B: (E)-3-Cyclopropylprop-2-enoic acid

Malonic acid (18.9 g, 180 mmol), cyclopropanecarbaldehyde (4.5 g, 60 mmol) and piperidine (0.7 ml) were mixed with pyridine (37 ml) and stirred under reflux for 2 hours, stirring was continued overnight at room temperature. The mixture was poured into 2M hydrochloric acid (200 ml), the phases were separated and the aqueous phase was extracted with dichloromethane (60 ml). The organic phases were combined, the solvent was removed under reduced pressure and the residue was purified by column chromatography (pre-packed silica column, gradient of petrolether/ethyl acetate). 6.2 g of an off-white crystalline solid was obtained (51.6 mmol, 86%). MS (APCI) m/z=112.9 [M+H]$^+$.

Step C: (E)-3-Cyclopropyl-N-methyl-N-[2-[methyl-(2-methyl-4-quinolyl)amino]ethyl]prop-2-enamide (E)-3-Cyclopropylprop-2-enoic acid (22 mg, 0.2 mmol) and HBTU (76 mg, 0.2 mmol) were dissolved in a 1:1 mixture of anhydrous THF and anhydrous DMF (2 ml). After 5 minutes N,N'-dimethyl-N-(2-methyl-4-quinolyl)ethane-1,2-diamine (52 mg, 0.23 mmol) and triethylamine (62 μl, 0.45 mmol) were added and the mixture was stirred at room temperature for 2 hours. The mixture was diluted with ethyl acetate, washed with water, saturated sodium bicarbonate solution, brine and dried over magnesium sulfate. The solvent was removed under reduced pressure and purified by preparative HPLC (gradient of water containing 0.1% NH$_3$ and acetonitrile) to yield 28.3 mg (0.087 mmol, 43.5%).

Example 2

Synthesis of (E)-4,4,5,5,5-pentafluoro-N-[3-methyl-2-(4-quinolylamino)butyl]pent-2-enamide (B-4)

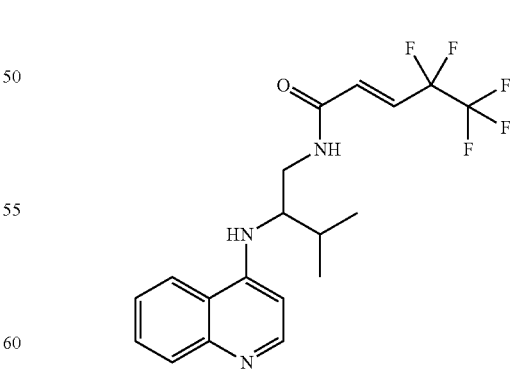

Step A: 1-Ethoxy-2,2,3,3,3-pentafluoro-propan-1-ol

Ethyl 2,2,3,3,3-pentafluoropropionate (10.99 grams, 57.2 mmol) was dissolved in anhydrous methanol (57 ml) and cooled under argon to −60° C. Sodium borohydride (2.16 grams, 57.2 mmol) was added in four portions. After the addition was complete, stirring was continued for one hour and the temperature was held below −45° C. The mixture was cooled to −60° C. and 1M hydrochloric acid (172 ml) was added dropwise so that the temperature remained below −45° C. The mixture was slowly warmed to room temperature and extracted with diethylether (3×100 ml). The combined organic phases were washed with water (two times), dried over magnesium sulfate, the solvent was removed under reduced pressure. 9.76 g (50.3 mmol, 88%) were obtained and used directly in the next step.

Step B: 6,6,7,7,7-Pentafluoro-3-hydroxy-pentanoic acid

1-Ethoxy-2,2,3,3,3-pentafluoro-propan-1-ol (9.76 g, 50.3 mmol) was mixed with malonic acid (15.73 g, 0.15 mole), piperidine (0.611 ml) and pyridine (30 ml) and heated at 120° C. until gas evolution ceased (4 hours). The solvent was removed under reduced pressure, the residue treated with 1M hydrochloric acid and extracted with diethylether (3×). The combined organic phases were washed with water (2×), dried over magnesium sulfate, the solvent was removed under reduced pressure. 9.81 g (47.2 mmol, 94%) were obtained and used directly in the next step.

Step C: Ethyl 4,4,5,5,5-pentafluoro-3-hydroxy-pentanoate 6,6,7,7,7-Pentafluoro-3-hydroxy- (9.81 g, 47.2 mmol) was dissolved in anhydrous ethanol (47 ml), concentrated sulfuric acid was added (0.534 ml) and the mixture was heated under reflux. A solution of hydrochloric acid in anhydrous methanol was added (1M, 8 ml) and heating was continued for 3 hours. The solvent was removed under reduced pressure and 11.9 g were obtained which were used directly in the next step.

Step D: Ethyl (E)-4,4,5,5,5-pentafluoropent-2-enoate

Ethyl 4,4,5,5,5-pentafluoro-3-hydroxy-pentanoate (11.9 g from step C) was placed in a 25 ml round-bottom flask and phosphorpentoxid was added in small portions until the educt was almost completely absorbed. The temperature was raised slowly to 140° C. until a brown syrup was obtained. The flask was connected to a distilling apparatus and the product isolated by distillation at reduced pressure (50 mbar, 50° C.). 5.5 g (25.2 mmol, 50% over 2 steps) were obtained.

Step E: (E)-4,4,5,5,5-Pentafluoropent-2-enoic acid

Ethyl (E)-4,4,5,5,5-pentafluoropent-2-enoate (5.5 g, 25.2 mmol) was suspended in 10% NaOH (14.5 ml) and heated at reflux until a homogenous solution was obtained (40 min). After cooling to room temperature the mixture was washed with diethylether (2×) and acidified under ice-cooling with concentrated sulfuric acid. The mixture was extracted with diethylether (3×), the combined organic phases were washed with water, dried over magnesium sulfate and the solvent removed under reduced pressure. 2.64 g (13.9 mmol, 55%) were obtained. MS (ES) M/z=189.0 [M−H]⁻.

Step F: 3-Methyl-2-(4-quinolylamino)butanamide

4-Chloroquinoline (0.82 g, 5 mmol), valinamide (0.64 g, 5.5 mmol) and diisopropylamine (1.9 ml, 11 mmol) were mixed with 1-methoxy-2-propanol (8 ml) and heated with stirring at reflux for 48 hours. The solvent was removed under reduced pressure, the residue was partitioned between water and ethyl acetate, the phases were separated, the aqueous phase was washed 3 times with ethyl acetate and basified with 50% NaOH. A precipitate formed that was filtered off and dried in air to give 0.2 g of a solid (0.78 mmol, 14%). MS (APCI) M/z=243.6 [M+H]⁺.

Step G:
3-Methyl-N2-(4-quinolyl)butane-1,2-diamine

3-Methyl-2-(4-quinolylamino)butanamide (460 mg, 1.9 mmol) was dissolved in anhydrous THF (30 ml) under argon, the mixture was cooled to 0° C. and a 1M solution of borane in anhydrous THF (8 ml, 8 mmol) was added with stirring. Stirring was continued for 1 hour at 0° C., the cooling bath was removed and the mixture was allowed to warm to room temperature overnight with stirring. The mixture was quenched with 1M NaOH and extracted with ethyl acetate. The organic phase was evaporated to dryness under reduced pressure and the residue was purified by column chromatography (pre-packed silica column, gradient of ethyl acetate/methanol containing 1% ammonia). 220 mg was obtained (0.96 mmol, 51%). MS (APCI) m/z=229.8 [M+H]⁺.

Step H: (E)-4,4,5,5,5-Pentafluoro-N-[3-methyl-2-(4-quinolylamino)butyl]pent-2-enamide (E)-4,4,5,5,5-Pentafluoropent-2-enoic acid (29 mg, 0.15 mmol) was dissolved in anhydrous DMF (1 ml), HBTU (60 mg, 0.15 mmol) and diisopropylamine (26 μl, 0.15 mmol) were added and the mixture was stirred at room temperature for 15 minutes. 3-Methyl-N2-(4-quinolyl)butane-1,2-diamine (34.4 mg, 0.15 mmol) dissolved in 1 ml anhydrous DMF together with diisopropylethylamine (26 μl, 0.15 mmol) was added and the resulting mixture was stirred at room temperature for 3 hours. The mixture was evaporated to dryness under reduced pressure and the resulting residue was purified by preparative HPLC (gradient of water containing 0.1% NH₃ and acetonitrile) to yield 7.3 mg (0.018 mmol, 12%).

Example 3

Synthesis of (E)-N-[2-[(2-methoxy-4-quinoly)amino]ethyl]hex-2-enamide (A-177)

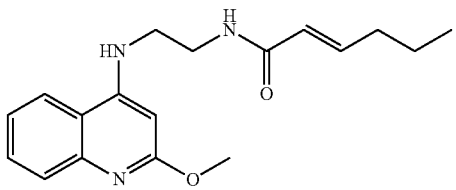 [SMILES: CCC/C=C/C(=O)NCCNc1cc(OC)nc2ccccc12]

Step A: 4-Chloro-2-methoxy-quinoline

To a solution of (2.5 g, 12.6 mmol) 2,4-dichloro-quinoline in anhydrous toluene (20 ml) was added a suspension of solid sodium methoxide (2.5 g, 46.3 mmol) in anhydrous toluene (20 ml). The mixture was stirred under reflux for 16 hours and then allowed to cool to room temperature. The solid that had formed was filtered off and washed with 50 ml toluene. The filtrate was evaporated to dryness under reduced pressure to yield a red solid (2.1 g, 10.8 mmol, 86%). MS (ES) m/z=193.1 [M+H]⁺.

Step B: N-(2-Methoxy-4-quinolyl)ethane-1,2-diamine

4-Chloro-2-methoxy-quinoline (484 mg, 2.5 mmol) and 1,2-diaminoethan (751 mg, 12.5 mmol) were mixed with 1-methoxy-2-propanol and stirred at 110° C. for 24 hours. The mixture was evaporated to dryness and the residue was purified by column chromatography (pre-packed silica column, gradient of ethyl acetate/methanol each containing 1% triethylamine). 0.324 g were obtained (1.49 mmol; 60%). MS (APCI) m/z=218.0 [M+H]⁺.

Step C: (E)-N-[2-[(2-Methoxy-4-quinolyl-amino]ethyl]hex-2-enamide

N-(2-Methoxy-4-quinolyl)ethane-1,2-diamine (21.7 mg, 0.1 mmol) was dissolved in anhydrous dichloromethane (1 ml) together with triethylamine (17.4 µl, 0.125 mmol). (E)-hex-2-enoyl chloride (16.6 mg, 0.125 mmol) was added and the mixture was shaken for 10 minutes, diluted with dichloromethane and washed with 10% sodium bicarbonate solution (2 times), water and evaporated to dryness under reduced pressure. The resulting residue was purified by preparative HPLC (gradient of water containing 0.1% NH₃ and acetonitrile) to yield 3.4 mg (0.0109 mmol, 11%).

Example 4

Synthesis of (E)-N-[2-[(5-ethyl-6-methyl-pyrimidin-4-yl)-amino]ethyl]-4-methyl-pent-2-enamide (A-20)

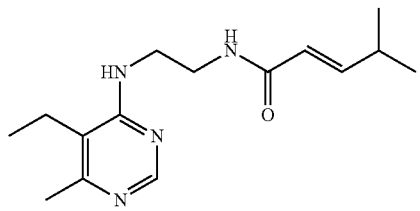 [SMILES: CCc1c(C)ncnc1NCCNC(=O)/C=C/C(C)C]

Step A: N-(5-Ethyl-6-methyl-pyrimidin-4-yl)ethane-1,2-diamine hydrochloride

4-Chloro-5-ethyl-6-methylpyrimidin (570 mg, 4 mmol) was mixed with 1,2-diaminoethane (2 ml, 30 mmol) and stirred at 150° C. in a closed vessel under microwave heating. The mixture was evaporated to dryness under reduced pressure to yield 1.255 g of a solid. MS (APCI) m/z=181.1 [M+H]⁺.

Step B: (E)-N-[2-[(5-Ethyl-6-methyl-pyrimidin-4-yl)amino]ethyl]-4-methyl-pent-2-enamide (E)-4-Methylpent-2-enoic acid (46 mg, 0.4 mmol), HBTU (152 mg, 0.4 mmol) and triethylamine (82 µl, 0.6 mmol) were dissolved in a 1:1 mixture of anhydrous DMF and anhydrous acetonitrile (2 ml), after 20 minutes N-(5-ethyl-6-methyl-pyrimidin-4-yl)ethane-1,2-diamine hydrochloride (40 mg, 0.185 mmol) was added. The mixture was stirred at room temperature for 2 hours and left to stand at room temperature overnight. The reaction mixture was diluted with ethyl acetate, washed with water, saturated sodium bicarbonate solution and brine, dried over magnesium sulfate and evaporated to dryness under reduced pressure. The residue was purified by preparative HPLC (gradient of water containing 0.1% NH₃ and acetonitrile) to yield 9 mg (0.033 mmol, 18%).

Example 5

Synthesis of (E)-N-[3-[(2-methyl-4-pyridyl)amino]propyl]hex-2-enamide (A-89)

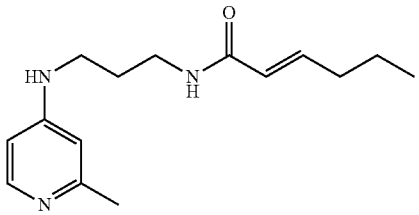 [SMILES: CCC/C=C/C(=O)NCCCNc1ccnc(C)c1]

Step A: N-(2-Methyl-4-pyridyl)propane-1,3-diamine hydrochloride

4-Chloro-2-picoline (441 µl, 4 mmol) was mixed with 1,3-diaminopropane (1.67 ml, 20 mmol) and stirred in a closed vessel at 180° C. under microwave heating for one hour. The solvent was removed under reduced pressure, toluene was added to the residue and the mixture was evaporated to dryness under reduced pressure to yield 1.076 of a solid. MS (APCI) m/z=165.8 [M+H]⁺.

Step B: (E)-N-[3-[(2-Methyl-4-pyridyl)amino]propyl]hex-2-enamide (E)-4-Hex-2-enoic acid (23 mg, 0.2 mmol) and HBTU (76 mg, 0.2 mmol) were dissolved in a 1:1 mixture of anhydrous DMF and anhydrous acetonitrile (2 ml), after 5 minutes triethylamine (82 µl, 0.6 mmol) and N-(2-Methyl-4-pyridyl)propane-1,3-diamine hydrochloride (40 mg, 0.2 mmol) was added. To the mixture basic aluminium oxide was added, stirring was continued for one hour, the mixture was filtered and the filtrate was evaporated to dryness under reduced pressure. The residue was purified by preparative HPLC (gradient of water containing 0.1% NH₃ and acetonitrile) to yield 20.2 mg (0.077 mmol, 39%).

Example 6

Synthesis of (E)-4,4,5,5,5-pentafluoro-N-[2-[[2-(2-methyl-1,3-dioxolan-2-yl)-4-pyridyl]amino]ethyl]pent-2-enamide (A-133)

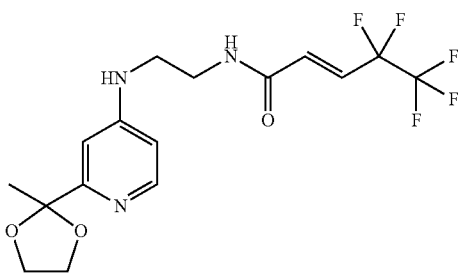 [SMILES: CC1(c2cc(NCCNC(=O)/C=C/C(F)(F)C(F)(F)F)ccn2)OCCO1]

Step A:
4-Chloro-2-(2-methyl-1,3-dioxolan-2-yl)pyridine 1-(4-Chloro-2-pyridyl)ethanone (440 mg, 2.83 mmol) and ethyleneglycol (480 mg, 3 mmol) were mixed with toluene (10 ml), a catalytic amount of p-toluenesulfonic acid was added and the mixture was heated at reflux overnight. The mixture was evaporated to dryness to yield 523 mg of a solid (2.6 mmol, 93%). MS (APCI) m/z=200.0 [M+H]$^+$.

Step B: N-[2-(2-Methyl-1,3-dioxolan-2-yl)-4-pyridyl]ethane-1,2-diamine

4-Chloro-2-(2-methyl-1,3-dioxolan-2-yl)pyridine (500 mg, 2.5 mmol) was mixed with 1,2-diaminoethane (1.09 ml, 26.2 mmol) and stirred in a closed vessel at 180° C. with microwave heating for 30 minutes in two batches. The mixture was evaporated to dryness, the solid residue was washed with acetone. The washing solution was evaporated to dryness and this solid residue was washed with acetonitrile. The solid residues were combined and dried under reduced pressure to yield 531 mg of a solid (2.38 mmol, 95%). MS (APCI) m/z=224.1 [M+H]$^+$.

Step C: (E)-4,4,5,5,5-Pentafluoro-N-[2-[[2-(2-methyl-1,3-dioxolan-2-yl)-4-pyridyl]amino]-ethyl]pent-2-enamide (E)-4,4,5,5,5-Pentafluoropent-2-enoic acid (133 mg, 0.7 mmol) and HBTU (265 mg, 0.7 mmol) were dissolved in a 2:1 mixture of anhydrous DMF and anhydrous THF (3 ml) and stirred at room temperature for 15 minutes. N-[2-(2-Methyl-1,3-dioxolan-2-yl)-4-pyridyl]ethane-1,2-diamine (100 mg, 0.45 mmol) was added and stirring was continued for 3 hours. The reaction mixture was diluted with ethyl acetate, washed with water, saturated sodium bicarbonate solution and brine, dried over magnesium sulfate and evaporated to dryness under reduced pressure. The residue was purified by preparative HPLC (gradient of water containing 0.1% NH$_3$ and acetonitrile) to yield 47 mg (0.12 mmol, 26%).

Example 7

Synthesis of (E)-N-[2-[(2-acetyl-4-pyridyl)amino]ethyl]-4,4,5,5,5-pentafluoro-pent-2-enamide (A-134)

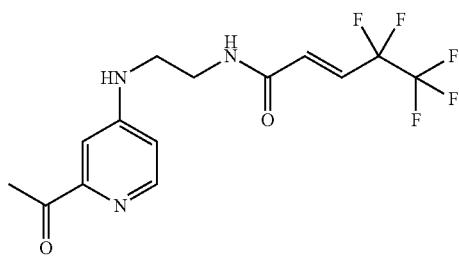 [SMILES: CC(=O)c1cc(NCCNC(=O)/C=C/C(F)(F)C(F)(F)F)ccn1]

(E)-4,4,5,5,5-Pentafluoro-N-[2-[[2-(2-methyl-1,3-dioxolan-2-yl)-4-pyridyl]amino]ethyl]pent-2-enamide (35 mg, 0.09 mmol) was dissolved in aceton (1 ml), 4M hydrochloric acid (0.5 ml) was added and the mixture was stirred in a closed vessel at 100° C. for 15 minutes with microwave heating. The mixture was diluted with water, extracted with ethyl acetate and the organic phase was washed with brine, dried over magnesium sulfate and evaporated to dryness. The resulting residue was purified by preparative HPLC (gradient of water containing 0.1% NH$_3$ and acetonitrile) to yield 2.5 mg (0.0071 mmol, 7.9%).

Example 8

Synthesis of (E)-4,4,5,5,5-pentafluoro-N-[3-[(2-methyl-4-quinolyl)amino]propyl]pent-2-enamide (A-217)

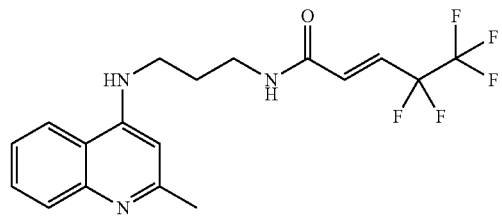 [SMILES: Cc1cc(NCCCNC(=O)/C=C/C(F)(F)C(F)(F)F)c2ccccc2n1]

Step A: tert-Butyl N-[2-[(2-methyl-4-quinolyl)amino]propyl]carbamate

Palladium(II)acetate (126 mg, 0.56 mmol), caesium carbonate (2.6 g, 8 mmol) and BINAP (498 mg, 0.8 mmol) were suspended in anhydrous dioxane under an atmosphere of argon and sonicated for 40 minutes. To this mixture was added 4-chloroquinaldine (711 mg, 4 mmol) and tert-butyl N-(3-aminopropyl)carbamate (697 mg, 4 mmol) and the mixture was stirred at 110° C. overnight. After cooling to room temperature, the mixture was diluted with ethyl acetate and filtered, the filtrate was evaporated to dryness, the resulting residue was dissolved in dichloromethane and filtered through a column packed with basic alumina. The product was eluted with ethyl acetate, the solution evaporated to dryness and 771 mg (2.44 mmol, 61%) were obtained. MS (APCI) m/z=315.8 [M+H]$^+$.

Step B: N-(2-Methyl-4-quinolyl)propane-1,3-diamine hydrochloride tert-Butyl N-[2-[(2-methyl-4-quinolyl)amino]propyl]carbamate (771 mg, 2.44 mmol) was dissolved in dichloromethane (20 ml), trifluoroacetic acid (1.5 ml) was added and the mixture was stirred at room temperature for 3 hours. The mixture is evaporated to dryness under reduced pressure, the residue dissolved in dioxane and evaporated again.

The residue is again dissolved in dioxane and a 4M solution of HCl in dioxane is added to precipitate the hydrochloride salt of the product which is filtered off and dried under reduced pressure. MS (APCI) m/z=216.1 [M+H]$^+$.

Step C: (E)-4,4,5,5,5-Pentafluoro-N-[3-[(2-methyl-4-quinolyl)amino]propyl]pent-2-enamide (E)-4,4,5,5,5-Pentafluoropent-2-enoic acid (38 mg, 0.2 mmol) and HBTU (76 mg, 0.2 mmol) were dissolved in a 1:1 mixture of anhydrous DMF and anhydrous acetonitrile (2 ml), after 5 minutes triethylamine (82 µl, 0.6 mmol) and N-(2-methyl-4-quinolyl)propane-1,3-diamine hydrochloride (48 mg, 0.24 mmol) was added and stirring was continued for 3 hours. To the mixture basic aluminium oxide was added, stirring was continued for one hour, the mixture was filtered and the filtrate was evaporated to dryness under reduced pressure. The residue was purified by preparative HPLC (gradient of water containing 0.1% NH₃ and acetonitrile) to yield 28.4 mg (0.076 mmol, 38%).

Example 9

Synthesis of (E)-3-cyclopropyl-N-[2-[(2-methoxy-6-methyl-pyrimidin-4-yl)-methyl-amino]ethyl]prop-2-enamide (A-77)

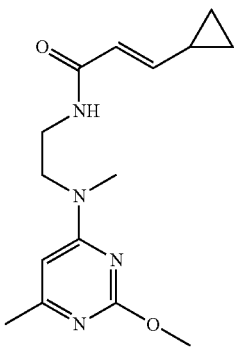 [SMILES: COc1nc(C)cc(N(C)CCNC(=O)/C=C/C2CC2)n1]

Step A: 4-Chloro-2-methoxy-6-methyl-pyrimidine

To anhydrous methanol (10 ml) was added sodium (230 mg, 10 mmol) and the mixture was stirred under an argon atmosphere until a clear solution had formed. This solution was added dropwise over two hours with stirring to a solution of 2,4-dichloro-6-methylpyrimidine (1.79 g, 11 mmol) in anhydrous methanol (10 ml) under cooling so that the temperature remained below 10° C. Stirring was continued for 30 minutes, then water was added (2 ml), the mixture was filtered and the filtrate was evaporated to dryness under reduced pressure. The residue was purified by column chromatography (pre-packed silica column, gradient of heptane/ethyl acetate). 750 mg was obtained (4.75 mmol, 47%). MS (APCI) m/z=159.2 [M+H]⁺.

Step B: N-(2-Methoxy-6-methyl-pyrimidin-4-yl)-N-methyl-ethane-1,2-diamine

4-Chloro-2-methoxy-6-methyl-pyrimidine (320 mg, 2 mmol) was mixed with N-Boc-N'-methyl-2,3-diaminoethan (464 mg, 2.2 mmol), diisopropylethylamine (285 mg, 2.2 mmol) and dipropyleneglycolmomomethylether (4 ml) and stirred overnight at 120° C. The mixture was evaporated to dryness. The residue was dissolved in a 1:1 mixture of dichloromethane and trifluoroacetic acid and stirred at room temperature for 3 hours. The volatiles were removed under reduced pressure, the residue taken up in dichloromethane and evaporated again. Dissolving in dichloromethane and evaporation was repeated two times. The residue was dissolved in water, basified with 5N NaOH and extracted with ethyl acetate. Evaporation of the organic phase yielded 450 mg of light brown, viscous oil (quantitative). MS (APCI) m/z=197.1 [M+H]⁺.

Step C: (E)-3-Cyclopropyl-N-[2-[(2-m ethoxy-6-methyl-pyrimidin-4-yl)-methyl-amino]ethyl]prop-2-enamide (E)-3-Cyclopropylprop-2-enoic acid (11.2 mg, 0.1 mmol) and diisopropylethylamine (17.4 µl, 1 mmol) were dissolved in anhydrous DMF (0.5 ml), HBTU (39 mg, 0.1 mmol) was added and the mixture was stirred for 15 minutes at room temperature. N-(2-methoxy-6-methyl-pyrimidin-4-yl)-N-methyl-ethane-1,2-diamine (19.6 mg, 0.1 mmol) and diisopropylethylamine (17.4 µl, 0.1 mmol), dissolved in anhydrous DMF (0.5 ml) were added and the mixture was stirred at room temperature overnight. The mixture was purified directly by preparative HPLC (gradient of water containing 0.1% NH₃ and acetonitrile) to yield 13.7 mg (0.047 mmol, 47.2%).

Example 10

Synthesis of (E)-4,4,5,5-tetrafluoro-N-[2-[[2-methyl-6-(2-methylbutoxy)-4-pyridyl]amino]ethyl]pent-2-enamide (A-323)

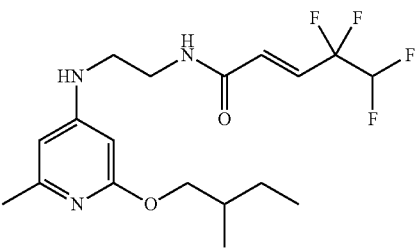 [SMILES: CCC(C)COc1cc(NCCNC(=O)/C=C/C(F)(F)C(F)F)cc(C)n1]

Step A: 2-Chloro-6-methyl-pyridine 1-oxide

2-Chloro-6-methylpyridine (12.76 g, 0.1 mol) was dissolved together with m-chloroperbenzoic acid (17.56 g, 0.15 mol) in DCM (100 ml) and stirred at 40° C. for 90 minutes. The heating bath was removed and stirring was continued overnight at room temperature. The reaction mixture was quenched with saturated sodium thiosulfate solution and the pH was adjusted to 8 with 1M NaOH. The phases were separated, the aqueous phase extracted with DCM and the combined organic phases were dried over magnesium sulfate. The solvent was removed under reduced pressure and unreacted 2-chloro-6-methylpyridine was removed by distillation (2 mbar, 65° C.). 2-Chloro-6-methyl-pyridine 1-oxide was obtained as residue (6.0 g of a yellow oil, 0.042 mol, 42%). MS (ESI) m/z=144.0 [M+1]⁺.

Step B: 2-Chloro-4-nitro-6-methyl-pyridine 1-oxide

2-Chloro-6-methyl-pyridine 1-oxide (5.0 g, 0.035 mol) was dissolved in concentrated sulfuric acid (20 ml) at 0° C. An ice-cooled mixture of concentrated nitric acid (12 ml) in concentrated sulfuric acid (20 ml) was added dropwise with stirring at 0° C. The cooling bath was removed, stirring was continued for 3 hours at 90° C. The mixture was poured into a mixture of icewater and ethyl acetate and the resulting precipitate was removed by filtration. The phases of the filtrate were separated, the aqueous phase was extracted several times with ethyl acetate, basified with NaOH and extracted again with ethyl acetate. The combined organic phases were dried over magnesium sulfate and the solvent removed under reduced pressure. The residue was combined with the filtered residue above to yield 6.21 g of a yellow solid (0.033 mol, 94%). MS (ESI) m/z=189.0 [M+1]⁺.

Step C: 2-Chloro-4-nitro-6-methyl-pyridine

2-Chloro-4-nitro-6-methyl-pyridine 1-oxide (6.2 g, 0.033 mol) was dissolved in chloroform (100 ml), phosphorus trichloride was added (22.6 g, 0.165 mol) and the mixture was heated under reflux for 2 days. The mixture was cooled to room temperature, poured into icewater and the mixture was neutralized with solid potassium carbonate. The phases were separated, the aqueous phase was extracted three times with chloroform, the combined organic phases were dried over magnesium sulfate. The solvent was removed under reduced pressure after which 5.326 g of a brown oil was obtained (0.031 mol, 94%) which was used directly in the next step.

Step D:
N-(2-Chloro-6-methyl-4-pyridyl)ethane-1,2-diamine

2-Chloro-4-nitro-6-methyl-pyridine (5.29 g, 0.031 mol) was dissolved in ethanol (100 ml) and added dropwise with stirring to a solution of ethylenediamine (18.4 g, 0.31 mol) in ethanol (200 ml). The mixture was stirred at 60° C. for 2 days. The solvent was removed under reduced pressure and excess of ethylenediamine was removed by repeated azeotropic evaporation with toluene under reduced pressure. The raw product was dissolved in chloroform, extracted three times with 1M HCl, the combined aqueous extracts were basified with NaOH and extracted with DCM and ethyl acetate. The combined organic extracts were dried over magnesium sulfate, the solvent was removed under reduced pressure to yield 3.92 g of a solid residue (0.021 mol, 68%). MS (APCI) m/z=186.0 [M+1]⁺.

Step E: N-[2-Methyl-6-(2-methylbutoxy)-4-pyridyl]ethane-1,2-diamine

N-(2-Chloro-6-methyl-4-pyridyl)ethane-1,2-diamine (0.205 g, 1.2 mmol) was combined with the sodium salt of 2-methylbutan-1-ol (0.66 g, 6 mmol, that had been obtained by treating 2-methylbutan-1-ol with sodium hydride dispersion in THF), diphenylether (2.2 g) and DMSO (0.75 ml). The mixture was heated at 160° C. for 16 hours and purified by column chromatography (silica, ethyl acetate/methanol, 1% concentrated NH₃) to yield 200 mg of a brown oil (0.84 mmol, 70%). MS (APCI) m/z=237.9 [M+1]⁺.

Step F: Ethyl 4,4,5,5-tetrafluoro-3-oxo-pentanoate

Lithium hexamethyldisilazide (250 ml of a 1M solution in THF, 0.25 mol) was cooled in an argon atmosphere to −78° C. and ethyl acetate (23 ml, 0.26 mol) was added dropwise with stirring. Stirring was continued for one hour at −78° C., then methyl 2,2,3,3-tetrafluoropropionate (22 g, 0.137 mol) was added dropwise with stirring. Stirring was continued for three hours at −78° C., then a saturated solution of ammonium chloride (175 ml) was added dropwise. The mixture was allowed to reach room temperature overnight. The mixture was acidified with 1M HCl, the phases were separated. The aqueous phase was extracted with ethyl acetate, the combined organic phases were washed two times with 1M HCl, brine, dried over sodium sulfate. The solvent was removed under reduced pressure and the residue was purified by vacuum distillation to yield 25.7 g (0.119 mmol, 87%) of a colourless liquid that was used directly in the next step.

Step G: Ethyl 4,4,5,5-tetrafluoro-3-hydroxy-pentanoate

Ethyl 4,4,5,5-tetrafluoro-3-oxo-pentanoate (25.7 g, 0.119 mol) was dissolved in toluene (260 ml) and cooled to 0° C. Sodium borohydride (5.4 g, 0.143 mol) was added portionwise, and the mixture was allowed to reach room temperature overnight with stirring. The mixture was then cooled to 0° C. and acidified with 1M HCl. The phases were separated, the aqueous phase was extracted two times with ethyl acetate, the combined organic phases were dried over magnesium sulfate and the solvent was reduced under reduced pressure. The residue was dissolved in a minimum amount of methanol and evaporated to dryness under reduced pressure to yield 22.9 g (0.105 mol, 88%) that were used directly in the next step.

Step H: Ethyl (E)-4,4,5,5-tetrafluoropent-2-enoate

Ethyl 4,4,5,5-tetrafluoro-3-hydroxy-pentanoate (22.9 g, 0.105 mol) was mixed with phosphorus pentoxide (7.5 g, 0.053 mol) and the resulting mixture was stirred at 80° C. for two hours. The product was isolated by vacuum distillation (53 mbar, 92° C.) to yield 15.9 g of a liquid (0.08 mol, 76%) that was used directly in the next step.

Step I: (E)-4,4,5,5-tetrafluoropent-2-enoic acid

Ethyl (E)-4,4,5,5-tetrafluoropent-2-enoate (15.9 g, 0.08 mol) was dissolved in ethanol (30 ml), 4M NaOH was added (15 ml) and the mixture was stirred at room temperature overnight. The mixture was diluted with water, washed with ethylacetate, acidified with 1M HCl and extracted with ethyl acetate. The organic extract was dried over magnesium sulfate, the solvent was removed under reduced pressure. 12.8 g of a colourless oil was obtained (0.074 mmol, 93%). MS (ESI, negative detection) m/z=170.9 [M−1]⁻.

Step J: (E)-4,4,5,5-tetrafluoro-N-[2-[[2-methyl-6-(2-methylbutoxy)-4-pyridyl]amino]ethyl]-pent-2-enamide (E)-4,4,5,5-tetrafluoropent-2-enoic acid (21 mg, 0.12 mmol) was dissolved in DCM (1 ml), oxalyl chloride was added (10 µl, 0.12 mmol) followed by a drop of DMF. The mixture was stirred for 10 minutes at room temperature. N-[2-methyl-6-(2-methylbutoxy)-4-pyridyl]-ethane-1,2-diamine (18 mg, 0.1 mmol) was dissolved in DMF (0.5 ml), the mixtures were combined, TEA (42 µl, 0.3 mmol) was added and the resulting mixture was stirred at room temperature for 1 hour. The mixture was diluted with ethyl acetate, washed with water and saturated sodium bicarbonate solution, dried over magnesium sulfate, the solvent was removed under reduced pressure. The residue was purified by preparative HPLC (gradient of water containing 0.1% NH₃ and acetonitrile) to yield 13 mg of a white solid (0.039 mmol, 39%).

Example 11

Synthesis of (E)-3-methyl-N-[2-[(2-methyl-4-quinolyl)amino]ethyl]but-1-ene-1-sulfonamide (A-447)

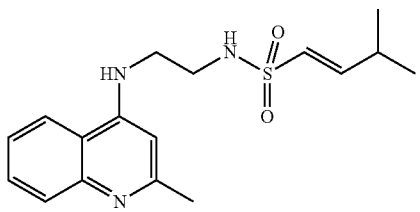 [SMILES: Cc1cc(NCCNS(=O)(=O)/C=C/C(C)C)c2ccccc2n1]

Step A: Ethyl diethoxyphosphorylmethanesulfonate

A solution of ethyl methanesulfonate (4.14 mL, 40.2 mmol) in anhydrous tetrahydrofuran (100 ml) was cooled to −78° C. under a nitrogen atmosphere. N-Butyllithium (20 ml, 50.0 mmol) was added slowly in 7 minutes after which stirring was continued for 15 minutes. Diethyl phosphorochloridate (4.36 mL, 30.2 mmol) was added, the reaction mixture was stirred for 2.5 h, the cooling bath was removed and the mixture was allowed to reach room temperature. The reaction mixture was quenched with aqueous saturated ammonium chloride (150 ml) and the resulting mixture was extracted with EtOAc (2×100 ml). The combined extracts were dried over sodium sulfate and concentrated under reduced pressure to yield 9.20 g of a yellow oil. The oil was purified over silicagel (600 g) using a gradient of ethyl acetate (0-100%) in heptane to yield 1.75 g of the product (6.7 mol, 17%).

Step B: Ethyl (E)-3-methylbut-1-ene-1-sulfonate

Mineral oil was removed from sodium hydride (84.4 mg, 2.110 mmol) with heptane (2×4 ml) under a nitrogen atmosphere after which anhydrous tetrahydrofuran (10 ml) was added. To this suspension was added dropwise a solution of ethyl (diethoxyphosphoryl)methanesulfonate (500 mg, 1.921 mmol) in anhydrous tetrahydrofuran (10 ml) upon which hydrogen gas evolved from the mixture. After 5 minutes a clear slightly yellow solution was obtained. Isobutyraldehyde (200 µl, 2.191 mmol) was added and the resulting mixture was stirred at room temperature over night. The reaction mixture was quenched with a mixture of brine (50 ml) and aqueous saturated ammonium chloride solution (150 ml). The aqeuous mixture was extracted with dichloromethane (3×70 ml), the combined organic layers were dried over sodium sulfate and concentrated under reduced pressure to yield 550 mg of a slightly yellow oil that was used directly in the next step.

Step C: Tetrabutylammonium (E)-3-methylbut-1-ene-1-sulfonate

A solution of (E)-ethyl 3-methylbut-1-ene-1-sulfonate (550 mg of step B) and tetrabutylammonium iodide (1128 mg, 3.05 mmol) in acetone (40 ml) was refluxed over night after which volatiles were removed under reduced pressure. 1.26 g of a white solid was obtained and used as such in the next reaction step.

Step D: (E)-3-Methylbut-1-ene-1-sulfonyl chloride

To a solution of triphenylphosphine (1.055 g, 4.02 mmol) in dichloromethane (50 ml) under a nitrogen atmosphere was added at 0° C. sulfuryl dichloride (0.359 ml, 4.42 mmol). The mixture was stirred at 0° C. for 15 minutes after which a solution of tetrabutylammonium (E)-3-methylbut-1-ene-1-sulfonate (1.25 g of Step C) in dichloromethane (10 ml) was added dropwise. The reaction mixture was stirred at room temperature for 5 h after which the mixture was concentrated under reduced pressure. The residue was taken up in diethylether and filtered over a glass filter to remove triphenylphosphinoxide. The filtrate was concentrated under reduced pressure to yield 102 mg of a brown oil which was used directly in the next step.

Step E: (E)-3-methyl-N-[2-[(2-methyl-4-quinolyl)amino]ethyl]but-1-ene-1-sulfonamide To a solution of N1-(2-methylquinolin-4-yl)ethane-1,2-diamine (161 mg, 0.800 mmol) and triethylamine (0.350 ml, 2.51 mmol) in acetonitrile (5 ml) was added a solution of (E)-3-methylbut-1-ene-1-sulfonyl chloride (102 mg of step D) in dichloromethane (1 ml). The mixture was stirred 30 minutes at room temperature, concentrated under reduced pressure and the residue was purified by column chromatography over aluminum oxide using a gradient of methanol (2-10%) in dichloromethane to yield 83 mg of an off-white foam (0.25 mmol; 13% over 4 steps).

Example 12

Synthesis of (E)-N-[2-[(2,6-dimethyl-4-pyridyl)amino]propyl]-4,4,4-trifluoro-but-2-enamide (B-13)

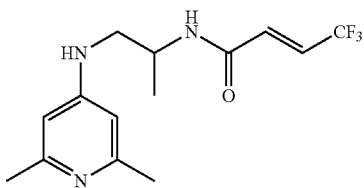 [SMILES: Cc1cc(NCC(C)NC(=O)/C=C/C(F)(F)F)cc(C)n1]

Step A: tert-Butyl N-[2-[(2,6-dimethyl-4-pyridyl)amino]propyl]carbamate

A mixture of 4-Chloro-2,6-dimethylpyridine (131 mg, 0.925 mmol), tert-butyl 2-aminopropylcarbamate hydrochloride (151 mg, 0.717 mmol), cesium carbonate (750 mg, 2.302 mmol), and anhydrous 1,4-dioxane (3 ml) was treated with tris(dibenzylideneacetone)dipalladium(0) (39 mg, 0.043 mmol) and 9,9-dimethyl-4,5-bis(diphenylphosphino)xanthene (74 mg, 0.128 mmol) under an atmosphere of argon. The mixture was heated at 110° C. for 8 hours, allowed to reach room temperature and filtered. The filter residue was washed with DCM, the combined filtrates were evaporated. The residue was purified by column chromatography using a gradient of methanol (1-10%) in dichloromethane to yield 241 mg of a yellow oil. MS (ESI) m/z=280.2.

Step B: N2-(2,6-Dimethyl-4-pyridyl)propane-1,2-diamine hydrochloride

To tert-butyl 2-(2,6-dimethylpyridin-4-ylamino)propyl-carbamate (147 mg, 0.526 mmol) dissolved in 1,4-dioxane (1 ml) a 4N solution of HCl in dioxane (2 ml, 8.00 mmol) was added. Within a few minutes a precipitate started to form. The solvent was removed in a stream of nitrogen, to the residue was added diethylether and the mixture was allowed to stand at room temperature overnight. The solvent was filtered off, the residue was dried under reduced pressure to yield 135 mg of an off-white solid MS (ESI) m/z=180.0.

Step C: (E)-N-[2-[(2,6-Dimethyl-4-pyridyl)amino]propyl]-4,4,4-trifluoro-but-2-enamide (E)-4,4,4-Trifluorobut-2-enoic acid (15.4 mg, 0.11 mmol) was dissolved in DCM (0.75 ml containing one drop of dimethyl formamide), oxalyl chloride was added (14 mg, 0.11 mmol) and the solution was stirred at room temperature for 15 minutes. This solution was added to a solution of N2-(2,6-dimethyl-4-pyridyl)propane-1,2-diamine (21.6 mg, 0.1 mmol) and diisopropylethylamine (44 µl, 0.25 mmol) dissolved in dimethylformamide (1 ml) and the resulting mixture was stirred at room temperature overnight. The volatiles were removed under reduced pressure and the residue was purified by preparative HPLC (gradient of water containing 0.1% NH₃ and acetonitrile) to yield 10.7 mg (0.035 mmol, 35%).

Example 13

Synthesis of (E)-N-[2-[(2,6-dimethyl-1-oxo-4-pyridyl)amino]ethyl]-4-methyl-pent-2-enamide (Aa-4)

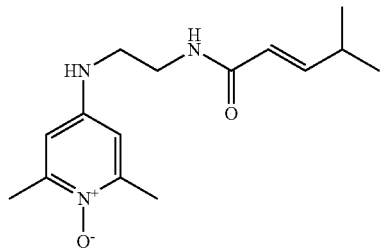 [SMILES: Cc1cc(NCCNC(=O)/C=C/C(C)C)cc(C)[n+]1[O-]]

Step A: 4-Bromo-2,6-dimethyl-pyridine 1-oxide

4-Bromo-2,6-dimethylpyridine (0.5 g, 2.69 mmol) was dissolved in DCM (10 ml), cooled to 0° C. and combined with a solution of m-chloroperbenzoic acid in DCM (75%, 0.928 g, 4.03 mmol in 5 ml). The resulting mixture was stirred at 0° C. for 15 minutes and for 5 hours at room temperature. The mixture was washed with saturated sodium bicarbonate solution, the phases were separated with a phase separator, the organic phase was evaporated under reduced pressure. The residue was purified by column chromatography (silica, gradient of 0.5 to 10% methanol in DCM). 475 of a yellow solid was obtained (2.35 mmol, 88%). MS (ESI) m/z=204.0 [M+1]⁺.

Step B: tert-Butyl N-[2-[(2,6-dimethyl-1-oxo-4-pyridyl)amino]ethyl]carbamate

4-Bromo-2,6-dimethyl-pyridine 1-oxide (475 mg, 2.35 mmol), tert-butyl N-(2-aminoethyl)carbamate (452 mg, 2.82 mmol), cesium carbonate (1.68 g, 5.17 mmol) and BI NAP (racemic, 73.2 mg, 0.118 mmol) were mixed with anhydrous dioxane (10 ml) under an argon atmosphere. Tris(dibenzylideneacetone)dipalladium(0) was added (108 mg, 0.118 mmol) and the mixture was stirred at 100° C. overnight. The mixture was diluted with dioxane, filtered through Celite, the filter residue was washed three times with dioxane, the combined filtrates were evaporated under reduced pressure. The residue was purified by column chromatography (silica, gradient of DCM to DCM containing 10% 7N ammonia in methanol) to yield 482 mg (1.71 mmol, 73%). MS (ESI) m/z=282.2 [M+1]⁺.

Step C: N-(2,6-Dimethyl-1-oxo-4-pyridyl)ethane-1,2-diamine hydrochloride tert-Butyl N-[2-[(2,6-dimethyl-1-oxo-4-pyridyl)amino]ethyl]carbamate (482 mg, 1.71 mmol) was dissolved in DCM (50 ml) and a 4N solution of HCl in dioxane was added (2.15 ml, 8.6 mmol). The mixture was stirred at room temperature overnight. The solvent was removed under reduced pressure and 397 mg of a beige solid was obtained that was used directly in the next step. MS (ESI) m/z=182.2 [M+1]⁺.

Step D: (E)-N-[2-[(2,6-Dimethyl-1-oxo-4-pyridyl)amino]ethyl]-4-methyl-pent-2-enamide (E)-4-Methylpent-2-enoic acid (118 mg, 1.034 mmol), HATU (327 mg, 0.861 mg) and N,N-diisopropylethylamine (0.236 ml, 1.378 mmol) were mixed with DCM (2 ml) and stirred at room temperature for 30 minutes. The resulting solution was added with stirring to a suspension of N-(2,6-dimethyl-1-oxo-4-pyridyl)ethane-1,2-diamine hydrochloride (125 mg, 0.574 mmol) and N,N-diisopropylethylamine (0.098 ml, 0.574 mmol) in DCM (2 ml). The resulting mixture was stirred overnight at room temperature. The solvent was removed in a stream of nitrogen and the residue was purified by column chromatography (silica, gradient of 2.5% of 7N ammonia in methanol in DCM to 10% of 7N ammonia in methanol in DCM) to yield 53.1 mg of a yellow solid (0.191 mmol, 33%).

Example 14

Synthesis of (E)-4,4,4-trifluoro-N-[2-(furo[3,2-b]pyridin-7-ylamino)-2-oxo-ethyl]but-2-enamide (B-44)

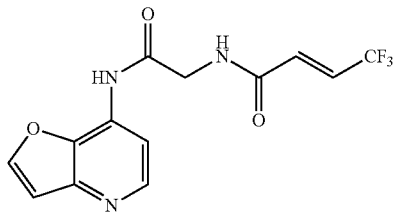 [SMILES: O=C(/C=C/C(F)(F)F)NCC(=O)Nc1ccnc2ccoc12]

Step A: tert-Butyl N-[2-(furo[3,2-b]pyridin-7-ylamino)-2-oxo-ethyl]carbamate

To a solution of 2-(tert-butoxycarbonylamino)acetic acid (660 mg, 3.77 mmol) in acetonitrile (20 ml) was added HBTU (1.491 g, 3.93 mmol) and the resulting solution was stirred 40 minutes at room temperature. Then triethylamine (0.785 ml, 5.63 mmol) was added and the mixture was stirred another five minutes at room temperature. Next furo[2,3-b]pyridin-4-amine (253 mg, 1.886 mmol) was added and the reaction mixture was stirred at 60° C. over night. The acetonitrile was removed under reduced pressure and the residue was redissolved in dichloromethane (50 ml). The solution in dichloromethane was washed with aqueous 1N NaOH (40 ml). The aqueous phase was extracted with dichloromethane (2×15 ml), the combined organic phases were dried over sodium sulfate and concentrated under reduced pressure to yield 1.03 g of a slightly brown oil. The crude product was purified by column chromatography (silica gel using a gradient of 2 to 6% MeOH in DCM to yield 350 mg of a white foam (1.2 mmol, 64%). MS (ESI) m/z=292.2 [M+1]⁺.

Step B: 2-Amino-N-furo[3,2-b]pyridin-7-yl-acetamide hydrochloride

Tert-Butyl 2-(furo[2,3-b]pyridin-4-ylamino)-2-oxoethylcarbamate (350 mg, 1.2 mmol) was placed in ethanol (96%)

(3.0 ml) and hydrogen chloride in dioxane (5.0 ml, 20.00 mmol) was added after which the resulting mixture was stirred at room temperature over night. The solids were filtered off, washed subsequently with EtOH and diethylether and dried in a stream of air. 230 mg of a white powder was obtained (1.01 mmol, 84%). MS (ESI) m/z=191.9 [M+1]+.

Step C: (E)-4,4,4-Trifluoro-N-[2-(furo[3,2-b]pyridin-7-ylamino)-2-oxo-ethyl]but-2-enamide (E)-4,4,4-Trifluorobut-2-enoic acid (15.4 mg, 0.11 mmol) was dissolved in DCM (0.75 ml containing one drop of dimethyl formamide), oxalyl chloride was added (14 mg, 0.11 mmol) and the solution was stirred at room temperature for 15 minutes. This solution was added to a solution of 2-amino-N-furo[3,2-b]pyridin-7-yl-acetamide hydrochloride (25.3 mg, 0.11 mmol) and diisopropylethylamine (44 µl, 0.25 mmol) dissolved in dimethylformamide (1 ml) and the resulting mixture was stirred at room temperature overnight. The volatiles were removed under reduced pressure and the residue was purified by preparative HPLC (gradient of water containing 0.1% NH3 and acetonitrile) to yield 6.9 mg (0.022 mmol, 20%).

Example 15

Synthesis of 1,3-dimethyl-4-[2-[[(E)-4,4,4-trifluorobut-2-enoyl]amino]-ethylamino]pyrazolo-[3,4-b]-pyridine-5-carboxamide (A-381)

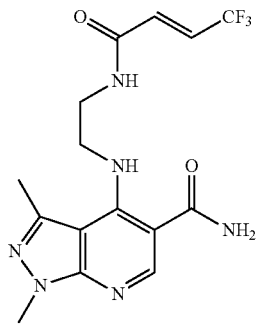 [SMILES: Cc1nn(C)c2ncc(C(N)=O)c(NCCNC(=O)/C=C/C(F)(F)F)c12]

Step A: Ethyl 4-[2-(tert-butoxycarbonylamino)ethylamino]-1,3-dimethyl-pyrazolo[3,4-b]pyridine-5-carboxylate To a mixture of ethyl 4-chloro-1,3-dimethyl-1H-pyrazolo[3,4-b]pyridine-5-carboxylate (500 mg, 1.971 mmol) and potassium carbonate (817 mg, 5.91 mmol) in acetonitrile (15 ml) was slowly added tert-butyl N-(2-aminoethyl)carbamate (1.248 ml, 7.88 mmol) via a syringe. The reaction mixture was stirred at room temperature for 3 hours. The solids were filtered off over a glass filter and washed with a 1:1 mixture of EtOH and DCM. The combined filtrates were concentrated under reduced pressure to give a white semisolid, which was purified by column chromatography (silica gel using a gradient of ethanol (0-5%) in DCM) to yield 658 mg of a white solid (1.743 mmol, 88%). MS (ESI) m/z=378.2 [M+1]+.

Step B: 4-[2-(tert-Butoxycarbonylamino)ethylamino]-1,3-dimethyl-pyrazolo[3,4-b]pyridine-5-carboxylic acid To a solution of ethyl 4-[2-(tert-butoxycarbonylamino) ethylamino]-1,3-dimethyl-pyrazolo[3,4-b]pyridine-5-carboxylate (303 mg, 0.803 mmol) in methanol (30 ml) was added sodium hydroxide (4.02 g, 101 mmol) in water (10 ml) and the resulting mixture was heated at reflux for 1.5 hours. The mixture was allowed to cool to −50° C. after which ammonium chloride (6.07 g, 113 mmol) was added. The mixture was stirred at reflux for 15 minutes after which the solids were filtered off. The solids were washed with ethanol (150 ml) and the combined filtrates were concentrated under reduced pressure to yield 2.32 g of a white solid that was purified by filtration over a pad of silicagel in a glassfilter using 10% (1% AcOH in MeOH) in DCM. The filtrate was concentrated under reduced pressure to yield 240 mg (0.687 mmol, 86%). MS (ESI) m/z=350.2 [M+1]+.

Step C: tert-Butyl N-[2-[[5-[(4-methoxyphenyl)methylcarbamoyl]-1,3-dimethyl-pyrazolo[3,4-b]pyridin-4-yl]amino]ethyl]carbamate To a solution of 4-[2-(tert-butoxycarbonylamino)ethylamino]-1,3-dimethyl-pyrazolo[3,4-b]pyridine-5-carboxylic acid (96.1 mg, 0.275 mmol) in N,N-dimethylformamide (2.5 ml) was subsequently added N1-((ethylimino)methylene)-N3,N3-dimethylpropane-1,3-diamine hydrochloride (91.8 mg, 0.479 mmol), 3-hydroxytriazolo[4,5-b]pyridine (39.7 mg, 0.292 mmol) and triethylamine (0.115 ml, 0.825 mmol). The reaction mixture was stirred for five minutes after which (4-methoxyphenyl)methanamine (0.072 ml, 0.550 mmol) was added. The reaction mixture was stirred at room temperature over night. The reaction mixture was partitioned between water (40 ml) and EtOAc (50 ml). The organic layer was separated and the aqueous phase was further extracted with EtOAc (3×40 ml) and dichloromethane (1×50 ml). The combined organic layers were dried over sodium sulfate and concentrated under reduced pressure to yield 360 mg of a yellow liquid which was purified by column chromatography (silicagel using a gradient of MeOH (1-7%) in dichloromethane) to give 43 mg of a colorless sticky oil (0.092 mmol, 33%) MS (ESI) m/z=469.3 [M+1]+.

Step D: 4-(2-Aminoethylamino)-1,3-dimethyl-pyrazolo[3,4-b]pyridine-5-carboxamide trifluoromethanesulfonate To a solution of tert-Butyl N-[2-[[5-[(4-methoxyphenyl)methylcarbamoyl]-1,3-dimethyl-pyrazolo[3,4-b]pyridin-4-yl]amino]ethyl]carbamate (43 mg, 0.092 mmol) in dichloromethane (2.0 ml) was added trifluoromethanesulfonic acid (2.0 mL, 22.60 mmol) and the resulting orange-red mixture was stirred at room temperature over night. The reaction mixture was diluted with dichloromethane (40 ml) and diethylether (100 ml) subsequently upon which a white precipitate was formed. The mixture was stirred for 15 minutes after which the white solids were filtered off, washed with diethylether and dried in a stream of air. 43 mg of an off-white solid was obtained and used directly in the next step. MS (ESI) m/z=249.2.

Step E: 1,3-Dimethyl-4-[2-[[(E)-4,4,4-trifluorobut-2-enoyl]amino]ethylamino]pyrazolo-[3,4-b]-pyridine-5-carboxamide (E)-4,4,4-Trifluorobut-2-enoic acid (21 mg, 0.15 mmol) was dissolved in DCM (2 ml containing one drop of dimethyl formamide), oxalyl chloride was added (19 mg, 0.15 mmol) and the solution was stirred at room temperature for 15 minutes. This solution was added to a solution of 4-(2-aminoethylamino)-1,3-dimethyl-pyrazolo[3,4-b]pyridine-5-carboxamide trifluoromethanesulfonate (40 mg, 0.1 mmol) and diisopropylethylamine (60 μl, 0.35 mmol) dissolved in dimethylformamide (1 ml) and the resulting mixture was stirred at room temperature overnight. The volatiles were removed under reduced pressure and the residue was purified by preparative HPLC (gradient of water containing 0.1% NH$_3$ and acetonitrile) to yield 2.1 mg (0.005 mmol, 5.7%).

Example 16

Synthesis of (E)-N-[2-[(6-amino-2-methylsulfanyl-pyrimidin-4-yl)amino]-ethyl]-4,4,4-trifluoro-but-2-enamide (A-374)

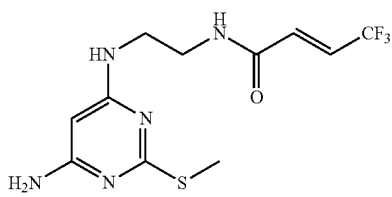 [SMILES: CSc1nc(N)cc(NCCNC(=O)/C=C/C(F)(F)F)n1]

Step A: tert-Butyl N-[2-[(6-amino-2-methylsulfanyl-pyrimidin-4-yl)amino]ethyl]carbamate 6-Chloro-2-methylsulfanyl-pyrimidin-4-amine (176 mg, 1 mmol) was dissolved together with tert-butyl N-(2-aminoethyl)carbamate (200 mg, 1.25 mmol) and triethylamine (174 μl, 1.25 mmol) in THF (2 ml). The mixture was stirred at 180° C. under microwave heating for 8 hours. The mixture was diluted with ethyl acetate and the resulting solution was washed with a solution of sodium bicarbonate (5%) and brine, dried over magnesium sulfate, the volatiles were removed under reduced pressure. The residue dissolved in DCM and purified by filtration over silica to yield 105 mg (0.35 mmol, 35%) MS (ESI) m/z=300.2 [M+1]$^+$.

Step B: N6-(2-Aminoethyl)-2-methylsulfanyl-pyrimidine-4,6-diamine trifluoromethane-sulfonate Tert-Butyl N-[2-[(6-amino-2-methylsulfanyl-pyrimidin-4-yl)amino]ethyl]carbamate (105 mg, 0.35 mmol) was dissolved in a mixture of DCM (20 ml) and trifluoromethanesulfonic acid (5 ml) and stirred at room temperature for 2 hours. The volatiles were removed under reduced pressure, the residue was taken up in THF and evaporated again to yield 182 mg of a residue that was used directly in the next step.

Step C: (E)-N-[2-[(6-Amino-2-methylsulfanyl-pyrimidin-4-yl)amino]ethyl]-4,4,4-trifluoro-but-2-enamide (E)-4,4,4-Trifluorobut-2-enoic acid (21 mg, 0.15 mmol) was dissolved in DCM (1 ml containing one drop of DMF), oxalyl chloride was added (13 μl, 0.15 mmol) and the solution was stirred at room temperature for 15 minutes. This solution was added to a solution of N6-(2-Aminoethyl)-2-methylsulfanyl-pyrimidine-4,6-diamine trifluoromethanesulfonate (20 mg, 0.057 mmol) and diisopropylethylamine (51 μl, 0.3 mmol) dissolved in dimethylformamide (1 ml) and the resulting mixture was stirred at room temperature for 2 hours. The mixture was diluted with ethyl acetate, washed with water and saturated sodium bicarbonate solution, dried over magnesium sulfate, the solvent was removed under reduced pressure. The residue was purified by preparative HPLC (gradient of water containing 0.1% NH$_3$ and acetonitrile) to yield 3.3 mg of a white solid (0.001 mmol, 18%).

Example 17

Synthesis of (E)-N-[2-[(5-ethyl-6-methyl-pyrimidin-4-yl)amino]butyl]-4,4,4-trifluoro-but-2-enamide (A-347)

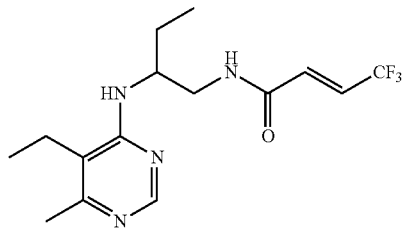 [SMILES: CCc1c(C)ncnc1NC(CC)CNC(=O)/C=C/C(F)(F)F]

Step A: N2-(5-Ethyl-6-methyl-pyrimidin-4-yl)-N1,N2-bis[(4-methoxyphenyl)methyl]butane-1,2-diamine N1,N1-Bis(4-methoxybenzyl)butane-1,2-diamine dihydrochloride (552 mg, 1.375 mmol), 4-chloro-5-ethyl-6-methylpyrimidine (331 mg, 2.113 mmol) and N,N-diisopropylethylamine (824 μl, 4.81 mmol) were mixed with acetonitrile (1.5 ml) and heated in a closed vial at 150° C. in an argon atmosphere for two days. The mixture was concentrated under reduced pressure and purified by column chromatography (silica, gradient from DCM to DCM containing 5% methanol) to yield 353 mg of a yellow oil (0.787 mmol, 57%). MS (ESI) m/z=449.2 [M+1]$^+$.

Step B: N2-(5-Ethyl-6-methyl-pyrimidin-4-yl)butane-1,2-diamine

N2-(5-Ethyl-6-methyl-pyrimidin-4-yl)-N1,N2-bis[(4-methoxyphenyl)methyl]butane-1,2-diamine (353 mg, 0.787 mmol) was dissolved in acetic acid (2 ml), the vial was flushed with argon, palladium (10% on activated carbon, 109 mg, 0.102 mmol) was added, and the mixture was stirred in an atmosphere of hydrogen at room temperature overnight. The mixture was filtered, the filter residue was washed with acetic acid, the combined filtrates were concentrated under reduced pressure to yield 472 mg of a brown oil. The residue was dissolved in DCM, washed with a saturated solution of sodium bicarbonate, the combined aqueous solutions were extracted three times with DCM. The organic phases were combined and concentrated under reduced pressure, the residue was purified by column chromatography (silica, gradient from DCM to a 9 to 1 mixture of DCM and 7N NH$_3$ in methanol) to yield 94.6 mg of a yellow oil. The oil was dissolved in a mixture of diethylether and DCM, 1M HCl in diethylether was added until the product precipitated. The precipitate was isolated by decantation, washed with diethylether and dried in stream of nitrogen and under reduced pressure to give 127 mg of a white solid (0.498 mmol, 63%). MS (ESI) m/z=209.2 [M+1]$^+$.

Step C: (E)-N-[2-[(5-Ethyl-6-methyl-pyrimidin-4-yl)amino]butyl]-4,4,4-trifluoro-but-2-enamide (E)-4,4,4-Trifluorobut-2-enoic acid (15 mg, 0.11 mmol) was dissolved in DCM (1 ml containing one drop of dimethyl formamide), oxalyl chloride was added (9.5 μl, 0.11 mmol) and the solution was stirred at room temperature for 15 minutes. This solution was added to a solution of N2-(5-Ethyl-6-methyl-pyrimidin-4-yl)butane-1,2-diamine (24.5 mg, 0.1 mmol) and diisopropylethylamine (44 μl, 0.25 mmol) dissolved in DMF (1 ml) and the resulting mixture was stirred at room temperature overnight. The volatiles were removed under reduced pressure and the residue was purified by preparative HPLC (gradient of water containing 0.1% NH$_3$ and acetonitrile) to yield 12.7 mg (0.038 mmol, 38%).

Example 18

Synthesis of (E)-4-methyl-N-[2-[(2-methyl-4-quinolyl)amino]ethyl]pent-2-enethioamide (A-449)

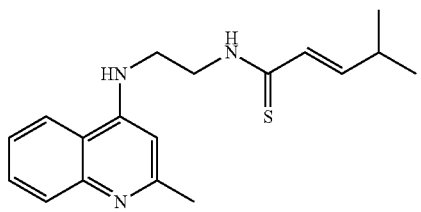 [SMILES: Cc1cc(NCCNC(=S)/C=C/C(C)C)c2ccccc2n1]

Step A: (E)-N-[2-[(2-Methyl-4-quinolyl)amino]ethyl]but-2-enamide (E)-4-Methylpent-2-enoic acid (190 mg, 1.3 mmol) was mixed together with HBTU (470 mg, 1.3 mmol) and N-(2-methyl-4-quinolyl)ethane-1,2-diamine (250 mg, 1.2 mmol) in acetonitrile (5 ml). Triethylamine (1 mll) was added with stirring at 0° C. over 15 minutes and the resulting mixture was stirred at room temperature overnight. The volatiles were removed under reduced pressure, the residue was dissolved in DCM and washed with a saturated solution of sodium bicarbonate. The combined aqueous solutions were extracted three times with DCM. The organic layers were combined, dried over sodium sulfate, the solvent was removed under reduced pressure to give 245 mg of a yellow solid (0.82 mmol, 66%). MS (APCI) m/z=298.2 [M+1]$^+$.

Step B: (E)-4-Methyl-N-[2-[(2-methyl-4-quinolyl)amino]ethyl]pent-2-enethioamide (E)-4-Methyl-N-[2-[(2-methyl-4-quinolyl)amino]ethyl]pent-2-enamide (50 mg, 0.15 mmol) was dissolved in dioxane (2 ml), Lawesson's reagent (75 mg, 0.18 mmol) was added in one portion and the resulting mixture was stirred at 130° C. under microwave heating for 0.5 hrs. The volatiles were removed under reduced pressure and the residue was purified by preparative HPLC (gradient of water containing 0.1% ammonia and acetonitrile) to yield 15 mg (0.047 mmol, 28.5%).

C. Analytics: HPLC Methods

Method 1
HPLC-MS System:
Agilent LC/MSD Trap 1100 series composed of:
Binary pump G 1312A included degasser G1379A, well plate sampler G1367A, column oven G1316A, diode array detector G1315B, and mass detector G2445D with APCI-source.
Chromatographic System:
Column: Waters Xbridge C-18, 4.6*50 mm, 2.5μ
Oven: 40° C.
Injection: 2.0 μl
Eluents:
Solvent A: water/ammonia: 99.9/0.1 vol./vol.
Solvent B: acetonitrile/ammonia: 99.9/0.1 vol./vol.
Flow: 1.0 ml/min
Gradient:

| Time [min] | Solvent A [%] | Solvent B [%] |
|---|---|---|
| 0.0 | 95 | 5 |
| 5 | 0 | 100 |
| 7 | 0 | 100 |

Run time: 10 min (equilibration included)
Detection Methods:
UV at 254 nm, 210 nm
APCI/MS (100-1500 m/z), positive ions
Comment: Samples diluted in a 1 to 1 mixture of solvents A and B prior to analysis
Method 2
HPLC-MS System:
Agilent LC/MSD Trap 1100 series composed of:
Binary pump G 1312A included degasser G1379A, well plate sampler G1367A, column oven G1316A, diode array detector G1315B, and mass detector G2445D with APCI-source.
Chromatographic System:
Column: Waters Xbridge C-18, 4.6*50 mm, 2.5μ
Oven: 40° C.
Injection: 2.0 μl
Eluents:
Solvent A: water/ammonia: 99.9/0.1 vol./vol.
Solvent B: acetonitrile/ammonia: 99.9/0.1 vol./vol.
Flow: 1.0 ml/min
Gradient:

| Time [min] | Solvent A [%] | Solvent B [%] |
|---|---|---|
| 0.0 | 90 | 10 |
| 4 | 0 | 100 |
| 5 | 0 | 100 |

Run time: 7 min (equilibration included)
Detection Methods:
UV at 254 nm, 210 nm
APCI/MS (80-1000 m/z), positive ions
Comment: Samples diluted in a 1 to 1 mixture of solvents A and B prior to analysis
Method 3
HPLC-MS System:
Agilent HPLC/MSD 1100 series composed of:
Binary pump G 1312A included degasser G1379A, well plate sampler G1367A, column oven G1316A, diode array detector G1315B, mass detector G1946D SL with ESI-source and evaporative light scattering detector Sedex 75.
Chromatographic System:
Column: Chromolith FastGradient RP-18e from Merck, 2*50 mm
Oven: 30° C.
Injection: 1.0 μl
Eluents:
Solvent A: water/formic acid: 99.9/0.1 vol./vol.
Solvent B: acetonitrile/formic acid: 99.9/0.1 vol./vol.
Flow: 1.2 ml/min Gradient:

| Time [min] | Solvent A [%] | Solvent B [%] |
|---|---|---|
| 0.0 | 98 | 2 |
| 0.2 | 98 | 2 |
| 2.2 | 2 | 98 |
| 2.7 | 2 | 98 |

Run time: 3.5 min (equilibration included)
Detection Methods:
 UV at 210 nm and 254 nm
 ESI/MS (100-1000 m/z), positive ions
 ELSD (Sedex 75)
Comment: Samples diluted in a 1 to 1 mixture of solvents A and B prior to analysis
Method 4
HPLC-MS System:
Agilent HPLC/MSD 1100 series composed of:
Binary pump G 1312A included degasser G1379A, well plate sampler G1367A, column oven G1316A, diode array detector G1315B, mass detector G1946D SL with ESI-source and evaporative light scattering detector Sedex 75.
Chromatographic System:
Column: Chromolith FastGradient RP-18e from Merck, 2*50 mm
Oven: 30° C.
Injection: 1.0 µl
Eluents:
Solvent A: water/formic acid: 99.9/0.1 vol./vol.
Solvent B: acetonitrile/formic acid: 99.9/0.1 vol./vol.
Flow: 1.2 ml/min
Gradient:

| Time [min] | Solvent A [%] | Solvent B [%] |
|---|---|---|
| 0.0 | 90 | 10 |
| 2 | 0 | 100 |
| 2.7 | 0 | 100 |

Run time: 3.5 min (equilibration included)
Detection Methods:
 UV at 210 nm and 254 nm
 ESI/MS (105-1000 m/z), positive ions
 ELSD (Sedex 75)
Comment: Samples diluted in a 1 to 1 mixture of solvents A and B prior to analysis
Method 5
HPLC-MS System:
Agilent LC/MSD Trap 1100 series composed of:
Binary pump G 1312A included degasser G1379A, well plate sampler G1367A, column oven G1316A, diode array detector G1315B, and mass detector G2445D with APCI-source.
Chromatographic System:
Column: Waters Sunfire C-18, 4.6*50 mm, 3.5µ
Oven: 40° C.
Injection: 2.0 µl
Eluents:
Solvent A: water/formic acid: 99.9/0.1 vol./vol.
Solvent B: acetonitrile/formic acid: 99.9/0.1 vol./vol.
Flow: 1.0 ml/min
Gradient:

| Time [min] | Solvent A [%] | Solvent B [%] |
|---|---|---|
| 0.0 | 90 | 10 |
| 4 | 0 | 100 |
| 5 | 0 | 100 |

Run time: 7.5 min (equilibration included)
Detection Methods:
UV at 254 nm, 210 nm
APCI/MS (80-1000 m/z), positive ions
Comment: Samples diluted in a 1 to 1 mixture of solvents A and B prior to analysis D. Specific Compounds Table A below provides for each of the exemplified compounds of the formula (A') the structure, the calculated molecular weight (MVV) (gram/mol), the observed MS signal (m/z), the HPLC retention time (Rt) in minutes, and the number of the HPLC-method as described in paragraph C above ("Analytics: HPLC-Methods") used for analysis. From compound A-451 until the end of Table A the methods by which the compounds are synthesized are identified by referring to the synthetic steps described in the synthesis examples of paragraph B above ("Synthesis Examples"). If a compound contains a chiral center, mentioning of such compound is indicating the racemate.

In Table A—in case of a) a ring formation between $Y^1$ and $Y^2$ by the substituents $R^{12}$ and $R^{13}$ or b) a ring formation between $Y^3$ and $Y^4$ by the substituents $R^{14}$ and $R^{15}$— in the columns for $R^{12}$ and $R^{13}$ or in the columns for $R^{14}$ and $R^{15}$, as the case may be, the symbols Y1, Y2, Y3 and Y4 indicate the ring atoms $Y^1$, $Y^2$, $Y^3$ and $Y^4$ in formula (A') to which the group joining them is bound.

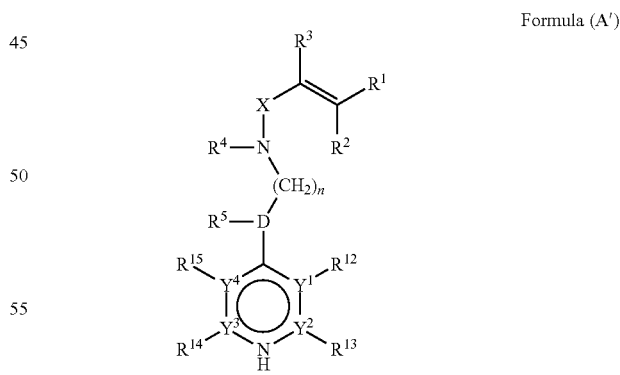

Formula (A')

TABLE A

| No | R¹ | R² | R³ | X | Y¹ | Y² | Y³ | Y⁴ | R¹² | R¹³ | R¹⁴ | R¹⁵ | n | R⁴ | R⁵ | D | HPLC | Rt | m/z | MW |
|---|---|---|---|---|---|---|---|---|---|---|---|---|---|---|---|---|---|---|---|---|
| A-1 | CF₃ | H | H | CO | N | C | C | C | — | CH₃ | CH₂CH₃ | H | 2 | H | H | N | 2 | 3.09 | 303.2 | 302.3 |
| A-2 | CF₂CHF₂ | H | H | CO | N | C | C | C | — | CH₃ | CH₂CH₃ | H | 2 | H | H | N | 2 | 3.13 | 335.2 | 334.3 |
| A-3 | C₂F₅ | H | H | CO | N | C | C | C | — | CH₃ | CH₂CH₃ | H | 2 | H | H | N | 2 | 3.43 | 353.2 | 352.3 |
| A-4 | (CF₂)₂CF₃ | H | H | CO | N | C | C | C | — | CH₃ | CH₂CH₃ | H | 2 | H | H | N | 2 | 3.69 | 403.2 | 402.3 |
| A-5 | (CF₂)₂CF₃ | H | H | CO | N | C | C | C | H | CH₃ | CH₃ | H | 3 | H | H | N | 4 | 1.29 | 401.9 | 401.3 |
| A-6 | (CF₂)₂CF₃ | H | H | CO | C | C | C | C | H | CH₃ | CH₃ | H | 2 | H | H | N | 4 | 1.23 | 387.9 | 387.3 |
| A-7 | CF₃ | H | H | CO | N | C | C | C | — | H | CH₃ | CH₂CH₃ | 2 | H | H | N | 3 | 1.34 | 303.0 | 302.3 |
| A-8 | CF₂CHF₂ | H | H | CO | N | C | C | C | — | H | CH₃ | CH₂CH₃ | 2 | H | H | N | 3 | 1.36 | 335.0 | 334.3 |
| A-9 | C₂F₅ | H | H | CO | N | C | C | C | — | H | CH₃ | CH₂CH₃ | 2 | H | H | N | 3 | 1.48 | 353.0 | 352.3 |
| A-10 | CF(CF₃)₂ | H | H | CO | N | C | C | C | — | H | CH₃ | CH₂CH₃ | 2 | H | H | N | 3 | 1.58 | 402.9 | 402.3 |
| A-11 | CF₃ | H | H | CO | N | C | C | C | — | H | CH₃ | CH₃ | 2 | H | H | N | 2 | 3.89 | 289.1 | 288.3 |
| A-12 | CF₂CHF₂ | H | H | CO | N | C | C | C | — | H | CH₃ | CH₃ | 2 | H | H | N | 2 | 2.95 | 321.2 | 320.3 |
| A-13 | C₂F₅ | H | H | CO | N | C | C | C | — | H | CH₃ | CH₃ | 2 | H | H | N | 2 | 3.25 | 339.2 | 338.3 |
| A-14 | CF(CF₃)₂ | H | H | CO | N | C | C | C | — | H | CH₃ | CH₃ | 2 | H | H | N | 2 | 3.52 | 389.2 | 388.3 |
| A-15 | CH₂CH₃ | H | H | CO | N | C | C | C | — | H | CH₃ | CH₃ | 2 | H | H | N | 2 | 2.66 | 249.2 | 248.3 |
| A-16 | CH(CH₃)₂ | H | H | CO | N | C | C | C | — | H | CH₃ | CH₃ | 2 | H | H | N | 2 | 2.90 | 263.2 | 262.4 |
| A-17 | CH(CH₃)CH₂CH₃ | H | H | CO | N | C | C | C | — | H | CH₃ | CH₃ | 2 | H | H | N | 2 | 3.13 | 277.2 | 276.4 |
| A-18 | cyclopropyl | H | H | CO | N | C | C | C | — | H | CH₃ | CH₃ | 2 | H | H | N | 2 | 2.69 | 261.2 | 260.3 |
| A-19 | (CH₂)₂CH₃ | H | H | CO | N | C | C | C | — | H | CH₃ | CH₃ | 2 | H | H | N | 2 | 2.93 | 263.2 | 262.4 |
| A-20 | CH(CH₃)₂ | H | H | CO | N | C | C | C | — | H | CH₃ | CH₂CH₃ | 2 | H | H | N | 2 | 2.98 | 277.2 | 276.4 |
| A-21 | CH(CH₃)CH₂CH₃ | H | H | CO | N | C | C | C | — | H | CH₃ | CH₂CH₃ | 2 | H | H | N | 2 | 3.21 | 291.2 | 290.4 |
| A-22 | (CH₂)₂CH₃ | H | H | CO | N | C | C | C | — | H | CH₃ | CH₂CH₃ | 2 | H | H | N | 2 | 3.01 | 277.2 | 276.4 |
| A-23 | CF₃ | H | H | CO | N | C | C | C | H | CH₃ | CH₃ | H | 3 | H | H | N | 2 | 3.59 | 275.9 | 275.4 |
| A-24 | C₂F₅ | H | H | CO | N | C | C | C | H | CH₃ | CH₃ | H | 2 | H | H | N | 2 | 3.41 | 261.9 | 261.4 |
| A-25 | CF₃ | H | H | CO | N | C | C | C | H | CH₃ | CH₃ | H | 2 | H | H | N | 2 | 3.41 | 288.2 | 287.3 |
| A-26 | CF₂CHF₂ | H | H | CO | N | C | C | C | H | CH₃ | CH₃ | H | 2 | H | H | N | 2 | 3.49 | 320.2 | 319.3 |
| A-27 | C₂F₅ | H | H | CO | N | C | C | C | H | CH₃ | CH₃ | H | 2 | H | H | N | 2 | 3.90 | 338.2 | 337.3 |
| A-28 | CF(CF₃)₂ | H | H | CO | N | C | C | C | H | CH₃ | CH₃ | H | 2 | H | H | N | 2 | 4.37 | 388.2 | 387.3 |
| A-29 | CH₂CH₃ | H | H | CO | N | C | C | C | H | CH₃ | CH₃ | H | 2 | H | H | N | 2 | 3.09 | 248.2 | 247.3 |
| A-30 | CH(CH₃)₂ | H | H | CO | N | C | C | C | H | CH₃ | CH₃ | H | 2 | H | H | N | 2 | 3.39 | 262.2 | 261.4 |
| A-31 | CF₃ | H | H | CO | N | C | C | C | — | CH₃ | CH₃ | H | 3 | H | H | N | 2 | 3.73 | 276.3 | 275.4 |
| A-32 | C₂F₅ | H | H | CO | N | C | C | C | — | CH₃ | CH₃ | H | 3 | H | H | N | 2 | 3.09 | 260.2 | 259.4 |
| A-33 | CF(CF₃)₂ | H | H | CO | N | C | C | C | — | CH₃ | CH₃ | H | 3 | H | H | N | 2 | 3.58 | 302.2 | 301.3 |
| A-34 | CF₃ | H | H | CO | N | C | C | C | — | CH₃ | CH₃ | H | 3 | H | H | N | 2 | 3.69 | 334.2 | 333.3 |
| A-35 | C₂F₅ | H | H | CO | N | C | C | C | — | CH₃ | CH₃ | H | 3 | H | H | N | 2 | 4.21 | 352.2 | 351.3 |
| A-36 | CF(CF₃)₂ | H | H | CO | N | C | C | C | — | CH₃ | CH₃ | H | 3 | H | H | N | 2 | 4.69 | 402.1 | 401.3 |
| A-37 | CH₂CH₃ | H | H | CO | N | C | C | C | — | CH₃ | CH₃ | H | 3 | H | H | N | 2 | 3.29 | 262.2 | 261.4 |
| A-38 | CH(CH₃)₂ | H | H | CO | N | C | C | C | — | CH₃ | CH₃ | H | 3 | H | H | N | 2 | 3.68 | 276.2 | 275.4 |
| A-39 | CH(CH₃)CH₂CH₃ | H | H | CO | N | C | C | C | — | CH₃ | CH₃ | H | 3 | H | H | N | 2 | 4.04 | 290.3 | 289.4 |
| A-40 | cyclopropyl | H | H | CO | N | C | C | C | — | CH₃ | CH₃ | H | 3 | H | H | N | 2 | 3.35 | 274.2 | 273.4 |
| A-41 | CF₃ | H | H | CO | N | C | C | C | — | H | CH₃ | CH₂CH₃ | 3 | H | H | N | 2 | 2.98 | 299.2 | 298.3 |
| A-42 | CF₂CHF₂ | H | H | CO | N | C | C | C | — | H | CH₃ | CH₂CH₃ | 2 | H | H | N | 2 | 2.79 | 285.2 | 284.3 |
| A-43 | CF₂OCH₃ | H | H | CO | N | C | C | C | — | H | CH₃ | CH₂CH₃ | 2 | H | H | N | 2 | 2.53 | 279.2 | 278.4 |
| A-44 | CF₃ | H | CH₃ | CO | N | C | C | C | — | H | CH₃ | CH₂CH₃ | 2 | H | H | N | 2 | 3.26 | 317.2 | 316.3 |
| A-45 | CF₃ | CH₃ | H | CO | N | C | C | C | H | CH₃ | CH₃ | H | 2 | H | H | N | 2 | 3.28 | 317.2 | 316.3 |
| A-46 | CF₂CH₃ | H | H | CO | N | C | C | C | H | CH₃ | CH₃ | H | 2 | H | H | N | 2 | 3.40 | 284.2 | 283.3 |
| A-47 | CF₂CH₃ | H | H | CO | C | C | C | C | H | CH₃ | CH₃ | H | 2 | H | H | N | 2 | 3.32 | 284.2 | 283.3 |
| A-48 | CHF₂ | H | H | CO | C | C | C | C | H | H | CH₃ | H | 2 | H | H | N | 2 | 2.90 | 270.1 | 269.3 |
| A-49 | CHF₂ | H | H | CO | C | C | C | C | H | H | CH₃ | CH₃ | 2 | H | H | N | 2 | 2.95 | 270.2 | 269.3 |

TABLE A-continued

| | | | | | | | | | | | | |
|---|---|---|---|---|---|---|---|---|---|---|---|---|
| A-50 | CHF$_2$ | H | H | CO | C | C | H | CH$_3$ | CH$_3$ | H | 3 | H | N | 2 | 3.12 | 284.2 | 283.3 |
| A-51 | CH$_2$OCH$_3$ | H | H | CO | C | C | H | CH$_3$ | CH$_3$ | H | 2 | H | N | 2 | 2.63 | 264.2 | 263.3 |
| A-52 | CH$_2$OCH$_3$ | H | H | CO | C | C | H | CH$_3$ | H | H | 3 | H | N | 2 | 2.72 | 264.2 | 263.3 |
| A-53 | CH$_2$OCH$_3$ | CH$_3$ | H | CO | C | C | H | CH$_3$ | CH$_3$ | H | 2 | H | N | 2 | 2.84 | 278.2 | 277.4 |
| A-54 | CF$_3$ | CH$_3$ | H | CO | C | C | H | CH$_3$ | CH$_3$ | H | 2 | H | N | 2 | 3.57 | 302.2 | 301.3 |
| A-55 | CF$_3$ | H | CH$_3$ | CO | C | C | H | CH$_3$ | CH$_3$ | H | 2 | H | N | 2 | 3.58 | 302.2 | 301.3 |
| A-56 | CF$_3$ | H | CH$_3$ | CO | C | C | H | CH$_3$ | H | H | 3 | H | N | 2 | 3.79 | 316.2 | 315.3 |
| A-57 | CF$_3$ | H | CH$_3$ | CO | C | C | H | CH$_3$ | CH$_3$ | H | 2 | H | N | 2 | 3.63 | 302.2 | 301.3 |
| A-58 | CF$_3$ | CH$_3$ | H | CO | C | C | H | CH$_3$ | CH$_3$ | H | 2 | H | N | 2 | 3.62 | 302.2 | 301.3 |
| A-59 | CF$_3$ | CH$_3$ | H | CO | C | C | H | CH$_3$ | H | H | 3 | H | N | 2 | 3.85 | 316.2 | 315.3 |
| A-60 | CF$_3$ | H | H | CO | C | C | — | CH$_3$ | H | H | 2 | H | N | 2 | 3.39 | 305.1 | 304.3 |
| A-61 | CF$_3$ | H | H | CO | N | C | — | OCH$_3$ | H | H | 2 | H | N | 2 | 3.82 | 319.2 | 318.3 |
| A-62 | CF$_3$ | H | H | CO | N | C | — | OCH$_3$ | CH$_3$ | H | 2 | H | N | 2 | 3.62 | 319.2 | 318.3 |
| A-63 | CF$_3$ | H | H | CO | N | C | — | OCH$_2$CH$_3$ | CH$_3$ | H | 2 | H | N | 2 | 4.05 | 333.2 | 332.3 |
| A-64 | CF$_2$CHF$_2$ | H | H | CO | N | C | — | OCH$_3$ | H | H | 2 | H | N | 2 | 3.43 | 337.2 | 336.3 |
| A-65 | CF$_2$CHF$_2$ | H | H | CO | N | C | — | OCH$_2$CH$_3$ | H | H | 2 | H | N | 2 | 3.82 | 351.2 | 350.3 |
| A-66 | CF$_2$CHF$_2$ | H | H | CO | N | C | — | OCH$_3$ | CH$_3$ | H | 2 | H | N | 2 | 3.65 | 351.2 | 350.3 |
| A-67 | CF$_2$CHF$_2$ | H | H | CO | N | C | — | OCH$_2$CH$_3$ | CH$_3$ | H | 2 | H | N | 2 | 4.03 | 365.2 | 364.3 |
| A-68 | CF$_2$CF$_3$ | H | H | CO | N | C | — | OCH$_3$ | H | H | 2 | H | N | 2 | 3.72 | 355.2 | 354.3 |
| A-69 | CF$_2$CF$_3$ | H | H | CO | N | C | — | OCH$_3$ | CH$_3$ | H | 2 | H | N | 2 | 4.12 | 369.2 | 368.3 |
| A-70 | CF$_2$CF$_3$ | H | H | CO | N | C | — | OCH$_2$CH$_3$ | CH$_3$ | H | 2 | H | N | 2 | 3.92 | 369.2 | 368.3 |
| A-71 | CF$_2$CF$_3$ | H | H | CO | N | C | — | OCH$_2$CH$_3$ | CH$_3$ | H | 2 | H | N | 2 | 4.32 | 383.2 | 382.3 |
| A-72 | CF$_2$CF$_3$ | H | H | CO | N | C | — | OCH$_3$ | H | H | 3 | H | N | 2 | 3.29 | 301.2 | 300.3 |
| A-73 | CF$_2$CH$_3$ | H | H | CO | N | C | — | OCH$_3$ | H | H | 2 | H | N | 2 | 3.69 | 315.2 | 314.3 |
| A-74 | CF$_2$CH$_3$ | H | H | CO | N | C | — | OCH$_3$ | CH$_3$ | H | 2 | H | N | 2 | 3.51 | 315.2 | 314.3 |
| A-75 | CF$_2$CH$_3$ | H | H | CO | N | C | H | OCH$_3$ | CH$_3$ | H | 2 | H | N | 2 | 3.92 | 329.2 | 328.4 |
| A-76 | cyclopropyl | H | H | CO | N | C | CH$_3$ | OCH$_3$ | H | H | 2 | H | N | 2 | 3.19 | 277.2 | 276.3 |
| A-77 | cyclopropyl | H | H | CO | N | C | CH$_3$ | OCH$_3$ | CH$_3$ | H | 2 | H | N | 2 | 3.60 | 291.2 | 290.4 |
| A-78 | CF$_3$ | H | H | CO | N | C | H | OCH$_3$ | CH$_3$ | H | 2 | H | N | 2 | 3.43 | 318.2 | 317.3 |
| A-79 | CF$_2$CHF$_2$ | H | H | CO | N | C | H | OCH$_3$ | CH$_3$ | H | 2 | H | N | 2 | 3.47 | 350.2 | 349.3 |
| A-80 | CF$_2$CF$_3$ | H | H | CO | N | C | CH$_3$ | OCH$_3$ | CH$_3$ | H | 2 | H | N | 2 | 3.77 | 368.2 | 367.3 |
| A-81 | CF$_2$CF$_3$ | H | H | CO | N | C | H | OCH$_3$ | CH$_3$ | H | 2 | H | N | 2 | 3.30 | 314.2 | 313.3 |
| A-82 | (CF$_2$)$_2$CF$_3$ | H | H | CO | C | C | H | CH$_3$ | H | H | 3 | H | N | 4 | 1.24 | 387.9 | 387.3 |
| A-83 | (CF$_2$)$_2$CF$_3$ | H | H | CO | C | C | CH$_3$ | CH$_3$ | H | H | 3 | H | N | 4 | 1.30 | 401.9 | 401.3 |
| A-84 | (CF$_2$)$_2$CF$_3$ | H | H | CO | C | C | H | CH$_3$ | H | H | 2 | H | N | 4 | 1.26 | 387.9 | 387.3 |
| A-85 | (CF$_2$)$_2$CF$_3$ | H | H | CO | C | C | CH$_3$ | CH$_3$ | H | H | 2 | H | N | 4 | 1.16 | 373.9 | 373.3 |
| A-86 | CF$_3$ | H | H | CO | C | C | H | CH$_3$ | H | H | 3 | H | N | 3 | 1.28 | 274.0 | 273.3 |
| A-87 | CF$_2$CHF$_2$ | H | H | CO | C | C | H | CH$_3$ | H | H | 2 | H | N | 3 | 1.30 | 306.0 | 305.3 |
| A-88 | C$_2$F$_5$ | H | H | CO | C | C | H | CH$_3$ | H | H | 3 | H | N | 3 | 1.44 | 323.9 | 323.3 |
| A-89 | (CH$_2$)$_2$CH$_3$ | H | H | CO | C | C | H | CH$_3$ | H | H | 2 | H | N | 2 | 3.29 | 261.9 | 261.4 |
| A-90 | (CH$_2$)$_2$CH$_3$ | H | H | CO | C | C | CH$_3$ | CH$_3$ | H | H | 3 | H | N | 2 | 3.65 | 275.9 | 275.4 |
| A-91 | CH(CF$_3$)$_2$ | H | H | CO | C | C | H | CH(CH$_3$)$_2$ | H | H | 2 | H | N | 2 | 3.49 | 275.9 | 275.4 |
| A-92 | CH$_2$CH$_3$ | H | H | CO | C | C | H | CH$_3$ | H | H | 3 | H | N | 2 | 3.78 | 373.9 | 373.3 |
| A-93 | CH(CH$_3$)$_2$ | H | H | CO | C | C | H | CH$_3$ | H | H | 2 | H | N | 2 | 2.77 | 233.9 | 233.3 |
| A-94 | CH(CH$_3$)$_2$ | H | H | CO | C | C | H | CH$_3$ | H | H | 2 | H | N | 2 | 3.06 | 247.9 | 247.3 |
| A-95 | CH(CH$_3$)CH$_2$CH$_3$ | H | H | CO | C | C | H | CH$_3$ | H | H | 2 | H | N | 2 | 3.35 | 261.9 | 261.4 |
| A-96 | cyclopropyl | H | H | CO | C | C | H | CH$_3$ | H | H | 3 | H | N | 2 | 2.79 | 245.9 | 245.3 |
| A-97 | CF$_3$ | H | H | CO | C | C | H | CH$_3$ | H | H | 3 | H | N | 2 | 3.26 | 288.2 | 287.3 |
| A-98 | CF$_2$CHF$_2$ | H | H | CO | C | C | H | CH$_3$ | H | H | 2 | H | N | 2 | 3.31 | 320.2 | 319.3 |
| A-99 | C$_2$F$_5$ | H | H | CO | C | C | H | CH$_3$ | H | H | 3 | H | N | 2 | 3.66 | 338.2 | 337.3 |
| A-100 | CF(CF$_3$)$_2$ | H | H | CO | C | C | H | CH$_3$ | H | H | 3 | H | N | 2 | 4.02 | 388.2 | 387.3 |
| A-101 | CH$_2$CH$_3$ | H | H | CO | C | C | H | CH$_3$ | H | H | 3 | H | N | 2 | 3.93 | 248.2 | 247.3 |
| A-102 | CH(CH$_3$)$_2$ | H | H | CO | C | C | H | CH$_3$ | H | H | 3 | H | N | 2 | 3.24 | 262.2 | 261.4 |

TABLE A-continued

| No. | R | | | | | | | | | | | | | | | |
|---|---|---|---|---|---|---|---|---|---|---|---|---|---|---|---|---|
| A-103 | CH(CH₃)CH₂CH₃ | H | CO | C | C | C | H | CH₃ | | H | 3 | H | N | 2 | 3.55 | 276.2 | 275.4 |
| A-104 | cyclopropyl | H | CO | C | C | C | CH₃ | CH₃ | | H | 3 | H | N | 2 | 3.02 | 260.2 | 259.4 |
| A-105 | CF₃ | H | CO | C | C | C | CH₃ | CH₃ | | H | 2 | H | N | 2 | 3.37 | 288.2 | 287.3 |
| A-106 | CF₂CHF₂ | H | CO | C | C | C | CH₃ | CH₃ | | H | 2 | H | N | 2 | 3.43 | 320.2 | 319.3 |
| A-107 | C₂F₅ | H | CO | C | C | C | CH₃ | CH₃ | | H | 2 | H | N | 2 | 3.82 | 338.1 | 337.3 |
| A-108 | CF(CF₃)₂ | H | CO | C | C | C | CH₃ | CH₃ | | H | 2 | H | N | 2 | 4.21 | 388.2 | 387.3 |
| A-109 | CH₂CH₃ | H | CO | C | C | C | CH₃ | CH₃ | | H | 2 | H | N | 2 | 3.14 | 248.2 | 247.3 |
| A-110 | CH(CH₃)₂ | H | CO | C | C | C | CH₃ | CH₃ | | H | 2 | H | N | 2 | 3.45 | 262.2 | 261.4 |
| A-111 | CH(CH₃)CH₂CH₃ | H | CO | C | C | C | CH₃ | CH₃ | | H | 2 | H | N | 2 | 3.82 | 276.2 | 275.4 |
| A-112 | cyclopropyl | H | CO | C | C | C | CH₃ | CH₃ | | H | 2 | H | N | 2 | 3.16 | 260.2 | 259.4 |
| A-113 | CF₃ | H | CO | C | C | C | CH₃ | CH₃ | | H | 3 | H | N | 2 | 3.60 | 302.2 | 301.3 |
| A-114 | CF₂CHF₂ | H | CO | C | C | C | CH₃ | CH₃ | | H | 3 | H | N | 2 | 3.64 | 334.2 | 333.3 |
| A-115 | C₂F₅ | H | CO | C | C | C | CH₃ | CH₃ | | H | 3 | H | N | 2 | 4.04 | 352.2 | 351.3 |
| A-116 | CF(CF₃)₂ | H | CO | C | C | C | CH₃ | CH₃ | | H | 3 | H | N | 2 | 4.47 | 402.2 | 401.3 |
| A-117 | CH₂CH₃ | H | CO | C | C | C | CH₃ | CH₃ | | H | 3 | H | N | 2 | 3.29 | 262.2 | 261.4 |
| A-118 | CH(CH₃)₂ | H | CO | C | C | C | CH₃ | CH₃ | | H | 3 | H | N | 2 | 3.62 | 276.2 | 275.4 |
| A-119 | CH(CH₃)CH₂CH₃ | H | CO | C | C | C | CH₃ | CH₃ | | H | 3 | H | N | 2 | 3.97 | 290.3 | 289.4 |
| A-120 | cyclopropyl | H | CO | C | C | C | CH₃ | CH₃ | | H | 3 | H | N | 2 | 3.34 | 274.2 | 273.4 |
| A-121 | CF₃ | H | CO | C | C | C | H | CH(CH₃)₂ | | H | 2 | H | N | 2 | 3.46 | 302.2 | 301.3 |
| A-122 | CF₂CHF₂ | H | CO | C | C | C | H | CH(CH₃)₂ | | H | 2 | H | N | 2 | 3.51 | 334.3 | 333.3 |
| A-123 | C₂F₅ | H | CO | C | C | C | H | CH(CH₃)₂ | | H | 2 | H | N | 2 | 3.86 | 352.2 | 351.3 |
| A-124 | CH₂CH₃ | H | CO | C | C | C | H | CH(CH₃)₂ | | H | 2 | H | N | 2 | 4.14 | 402.2 | 401.3 |
| A-125 | CH(CH₃)₂ | H | CO | C | C | C | H | CH(CH₃)₂ | | H | 2 | H | N | 2 | 3.22 | 262.2 | 261.4 |
| A-126 | CH(CH₃)CH₂CH₃ | H | CO | C | C | C | H | CH(CH₃)₂ | | H | 2 | H | N | 2 | 3.49 | 276.2 | 275.4 |
| A-127 | cyclopropyl | H | CO | C | C | C | H | CH(CH₃)₂ | | H | 2 | H | N | 2 | 3.76 | 290.3 | 289.4 |
| A-128 | (CH₂)₂CH₃ | H | CO | C | C | C | H | CH(CH₃)₂ | | H | 2 | H | N | 2 | 3.24 | 274.2 | 273.4 |
| A-129 | (CH₂)₂CH₃ | H | CO | C | C | C | H | CH₃ | | H | 2 | H | N | 2 | 3.13 | 247.9 | 247.3 |
| A-130 | CF₃ | H | CO | C | C | C | CH₃ | CH₃ | | H | 2 | H | N | 2 | 3.52 | 261.9 | 261.4 |
| A-131 | CF₃ | H | CO | C | C | C | H | 2-methyl-1,3-dioxolan-2-yl | | H | 2 | H | N | 2 | 2.95 | 346.2 | 345.3 |
| A-132 | CF₂CHF₂ | H | CO | C | C | C | H | 2-methyl-1,3-dioxolan-2-yl | | H | 2 | H | N | 2 | 2.99 | 378.2 | 377.3 |
| A-133 | C₂F₅ | H | CO | C | C | C | H | 2-methyl-1,3-dioxolan-2-yl | | H | 2 | H | N | 2 | 3.30 | 396.2 | 395.3 |
| A-134 | C₂F₅ | H | CO | C | C | C | H | COCH₃ | | H | 2 | H | N | 2 | 3.37 | 352.2 | 351.3 |
| A-135 | CF₂CHF₂ | H | CO | C | C | C | H | COCH₃ | | H | 2 | H | N | 2 | 3.05 | 334.2 | 333.3 |
| A-136 | CF₃ | H | CO | C | C | C | H | COCH₃ | | H | 2 | H | N | 2 | 2.98 | 302.1 | 301.3 |
| A-137 | (CH₂)₂CH₃ | H | CO | C | C | C | H | OCH₃ | | H | 2 | H | N | 2 | 3.30 | 277.9 | 277.4 |
| A-138 | CF₃ | H | CO | C | C | C | H | OCH₂CH₃ | | H | 2 | H | N | 2 | 3.30 | 304.2 | 303.3 |
| A-139 | CF₂CHF₂ | H | CO | C | C | C | H | OCH₂CH₃ | | H | 2 | H | N | 2 | 3.34 | 336.2 | 335.3 |
| A-140 | C₂F₅ | H | CO | C | C | C | H | OCH₂CH₃ | | H | 2 | H | N | 2 | 3.64 | 354.2 | 353.3 |
| A-141 | CF(CF₃)₂ | H | CO | C | C | C | H | OCH₂CH₃ | | H | 2 | H | N | 2 | 3.89 | 404.2 | 403.3 |
| A-142 | CH₂CH₃ | H | CO | C | C | C | H | OCH₂CH₃ | | H | 2 | H | N | 2 | 3.04 | 264.2 | 263.3 |
| A-143 | CH(CH₃)₂ | H | CO | C | C | C | H | OCH₂CH₃ | | H | 2 | H | N | 2 | 3.29 | 278.2 | 277.4 |
| A-144 | CH(CH₃)CH₂CH₃ | H | CO | C | C | C | H | OCH₂CH₃ | | H | 2 | H | N | 2 | 3.52 | 292.3 | 291.4 |
| A-145 | cyclopropyl | H | CO | C | C | C | H | OCH₂CH₃ | | H | 2 | H | N | 2 | 3.06 | 276.2 | 275.3 |
| A-146 | CF₂CH₃ | H | CO | C | C | C | H | CH₃ | | H | 2 | H | N | 2 | 2.97 | 270.1 | 269.3 |
| A-147 | CHF₂ | H | CO | C | C | C | H | CH₃ | | H | 2 | H | N | 2 | 2.64 | 256.1 | 255.3 |
| A-148 | CF₂CH₃ | H | CO | C | C | C | H | OCH₂CH₃ | | H | 2 | H | N | 2 | 3.16 | 300.2 | 299.3 |
| A-149 | CHF₂ | H | CO | C | C | C | H | OCH₂CH₃ | | H | 2 | H | N | 2 | 2.96 | 286.2 | 285.3 |
| A-150 | CH₂OCH₃ | H | CO | C | C | C | H | OCH₂CH₃ | | H | 2 | H | N | 2 | 2.67 | 280.2 | 279.3 |
| A-151 | CF₃ | H | CO | N | C | C | — | CH₃ | OCH₂CH₃ | H | 2 | CH₃ | N | 2 | 3.64 | 333.2 | 332.3 |
| A-152 | CF₂CHF₂ | H | CO | N | C | C | — | CH₃ | OCH₂CH₃ | H | 2 | H | N | 2 | 3.31 | 351.2 | 350.3 |

TABLE A-continued

| | | | | | | | | | | | |
|---|---|---|---|---|---|---|---|---|---|---|---|
| A-153 | CF$_2$CHF$_2$ | H | H | CO | N | C | — | CH$_3$ | OCH$_2$CH$_3$ | H | 2 | H | N | 2 | 3.65 | 365.2 | 364.3 |
| A-154 | CF$_2$CF$_3$ | H | H | CO | N | C | — | CH$_3$ | OCH$_2$CH$_3$ | H | 2 | H | N | 2 | 3.61 | 369.2 | 368.3 |
| A-155 | CF$_2$CH$_3$ | H | H | CO | N | C | — | CH$_3$ | OCH$_2$CH$_3$ | H | 2 | H | N | 2 | 3.96 | 383.2 | 382.3 |
| A-156 | CF$_2$CH$_3$ | H | H | CO | N | C | — | CH$_3$ | OCH$_2$CH$_3$ | H | 2 | H | N | 2 | 3.15 | 315.2 | 314.3 |
| A-157 | CF$_2$CH$_3$ | H | H | CO | N | C | — | CH$_3$ | OCH$_3$ | H | 2 | H | N | 2 | 3.49 | 329.2 | 328.4 |
| A-158 | CF$_3$ | H | H | CO | N | C | — | CH$_3$ | OCH$_3$ | H | 2 | H | N | 2 | 3.36 | 319.2 | 318.3 |
| A-159 | CF$_2$CHF$_2$ | H | H | CO | N | C | — | CH$_3$ | OCH$_3$ | H | 2 | H | N | 2 | 3.08 | 337.2 | 336.3 |
| A-160 | CF$_2$CF$_3$ | H | H | CO | N | C | — | CH$_3$ | OCH$_3$ | H | 2 | H | N | 2 | 3.40 | 351.2 | 350.3 |
| A-161 | CF$_2$CF$_3$ | H | H | CO | N | C | — | CH$_3$ | OCH$_3$ | H | 2 | H | N | 2 | 3.39 | 355.2 | 354.3 |
| A-162 | CF$_2$CH$_3$ | H | H | CO | N | C | — | CH$_3$ | OCH$_3$ | H | 2 | H | N | 2 | 3.72 | 369.2 | 368.3 |
| A-163 | CF$_2$CH$_3$ | H | H | CO | N | C | — | CH$_3$ | OCH$_3$ | H | 2 | H | N | 2 | 2.90 | 301.2 | 300.3 |
| A-164 | CF$_2$CH$_3$ | H | H | CO | N | C | — | CH$_3$ | OCH$_3$ | H | 2 | H | N | 2 | 3.22 | 315.0 | 314.3 |
| A-165 | cyclopropyl | H | H | CO | N | C | — | CH$_3$ | OCH$_3$ | H | 2 | H | N | 2 | 3.10 | 291.2 | 290.4 |
| A-166 | (CF$_2$)$_2$CF$_3$ | H | H | CO | N | C | — | H | H | Y3—CH=CH—CH=CH—Y4 | 4 | H | N | 4 | 1.36 | 409.9 | 409.3 |
| A-167 | (CF$_2$)$_2$CF$_3$ | H | H | CO | N | C | — | CH$_3$ | H | Y3—CH=CH—CH=CH—Y4 | 2 | H | N | 4 | 1.40 | 423.9 | 423.3 |
| A-168 | CH(CH$_3$)$_2$ | H | H | CO | N | C | — | CH$_3$ | H | Y3—CH=CH—CH=CH—Y4 | 2 | H | N | 3 | 1.47 | 284.2 | 283.4 |
| A-169 | CH$_2$CH$_3$ | H | H | CO | N | C | — | H | H | Y3—CH=CH—CH=CH—Y4 | 2 | H | N | 3 | 1.40 | 270.2 | 269.3 |
| A-170 | CF$_3$ | H | H | CO | N | C | — | H | H | Y3—CH=CH—CH=CH—Y4 | 2 | H | N | 3 | 1.45 | 310.1 | 309.3 |
| A-171 | CH(CH$_3$)$_2$ | H | H | CO | N | C | — | CH$_3$ | CH3 | Y3—CH=CH—CH=CH—Y4 | 2 | CH3 | N | 3 | 1.48 | 326.2 | 325.5 |
| A-172 | CH$_2$CH$_3$ | H | H | CO | N | C | — | CH$_3$ | CH3 | Y3—CH=CH—CH=CH—Y4 | 2 | CH3 | N | 3 | 1.38 | 312.2 | 311.4 |
| A-173 | (CH$_2$)$_2$CH$_3$ | H | H | CO | N | C | — | CH$_3$ | CH3 | Y3—CH=CH—CH=CH—Y4 | 2 | CH3 | N | 3 | 1.50 | 326.1 | 325.5 |
| A-174 | CH(CH$_3$)$_2$ | H | H | CO | N | C | — | OCH$_3$ | H | Y3—CH=CH—CH=CH—Y4 | 2 | H | N | 3 | 1.44 | 352.2 | 351.4 |
| A-175 | CH$_2$CH$_3$ | H | H | CO | N | C | — | OCH$_3$ | H | Y3—CH=CH—CH=CH—Y4 | 2 | H | N | 3 | 1.67 | 314.2 | 313.4 |
| A-176 | (CH$_2$)$_2$CH$_3$ | H | H | CO | N | C | — | OCH$_3$ | H | Y3—CH=CH—CH=CH—Y4 | 2 | H | N | 3 | 1.61 | 300.2 | 299.4 |
| A-177 | CF$_3$ | H | H | CO | N | C | — | OCH$_3$ | H | Y3—CH=CH—CH=CH—Y4 | 2 | H | N | 3 | 1.67 | 314.2 | 313.4 |
| A-178 | CH(CH$_3$)$_2$ | H | H | CO | N | C | — | H | CH3 | Y3—CH=CH—CH=CH—Y4 | 2 | CH3 | N | 3 | 1.63 | 340.1 | 339.3 |
| A-179 | CH$_2$CH$_3$ | H | H | CO | N | C | — | H | CH3 | Y3—CH=CH—CH=CH—Y4 | 2 | CH3 | N | 3 | 1.49 | 284.2 | 283.4 |
| A-180 | CH(CH$_3$)$_2$ | H | H | CO | N | C | — | H | CH3 | Y3—CH=CH—CH=CH—Y4 | 2 | CH3 | N | 3 | 1.42 | 312.2 | 311.4 |
| A-181 | CF$_3$ | H | H | CO | N | C | — | H | CH3 | Y3—CH=CH—CH=CH—Y4 | 2 | CH3 | N | 3 | 1.39 | 338.2 | 337.3 |
| A-182 | CH(CH$_3$)$_2$ | H | H | CO | N | C | — | CH$_3$ | H | Y3—CH=CH—CH=CH—Y4 | 2 | CH3 | N | 3 | 1.44 | 312.2 | 311.4 |
| A-183 | CH$_2$CH$_3$ | H | H | CO | N | C | — | CH$_3$ | H | Y3—CH=CH—CH=CH—Y4 | 2 | CH3 | N | 3 | 1.38 | 298.2 | 297.4 |
| A-184 | CH(CH$_3$)$_2$ | H | H | CO | N | C | — | H | H | Y3—CH=CH—CH=CH—Y4 | 2 | CH3 | N | 3 | 1.52 | 284.2 | 283.4 |
| A-185 | CH$_2$CH$_3$ | H | H | CO | N | C | — | CH$_3$ | CH3 | Y3—CH=CH—CH=CH—Y4 | 2 | H | N | 2 | 1.45 | 298.2 | 297.4 |
| A-186 | (CF$_2$)$_2$CF$_3$ | H | H | CO | N | C | — | CH$_3$ | H | Y3—CH=CH—CH=CH—Y4 | 2 | H | N | 2 | 1.52 | 324.1 | 323.3 |
| A-187 | CF$_2$CHF$_2$ | H | H | CO | N | C | — | CH$_3$ | H | Y3—CH=CH—CH=CH—Y4 | 2 | H | N | 2 | 1.46 | 372.2 | 371.3 |
| A-188 | C$_2$F$_5$ | H | H | CO | N | C | — | CH$_3$ | H | Y3—CH=CH—CH=CH—Y4 | 2 | H | N | 2 | 3.77 | 390.2 | 389.3 |
| A-189 | CH(CF$_3$)$_2$ | H | H | CO | N | C | — | CH$_3$ | H | Y3—CH=CH—CH=CH—Y4 | 2 | H | N | 2 | 4.06 | 440.2 | 439.3 |
| A-190 | CH(CH$_3$)CH$_2$CH$_3$ | H | H | CO | N | C | — | CH$_3$ | H | Y3—CH=CH—CH=CH—Y4 | 2 | H | N | 2 | 4.27 | 328.3 | 327.4 |
| A-191 | cyclopropyl | H | H | CO | N | C | — | CH$_3$ | CH3 | Y3—CH=CH—CH=CH—Y4 | 2 | CH3 | N | 2 | 3.99 | 312.2 | 311.4 |
| A-192 | CF$_2$CHF$_2$ | H | H | CO | N | C | — | CH$_3$ | CH3 | Y3—CH=CH—CH=CH—Y4 | 2 | CH3 | N | 2 | 3.56 | 384.2 | 383.4 |
| A-193 | C$_2$F$_5$ | H | H | CO | N | C | — | CH$_3$ | CH3 | Y3—CH=CH—CH=CH—Y4 | 2 | CH3 | N | 2 | 3.63 | 402.2 | 401.4 |
| A-194 | CH(CF$_3$)$_2$ | H | H | CO | N | C | — | CH$_3$ | CH3 | Y3—CH=CH—CH=CH—Y4 | 2 | CH3 | N | 2 | 3.93 | 452.2 | 451.4 |
| A-195 | CH(CH$_3$)CH$_2$CH$_3$ | H | H | CO | N | C | — | CH$_3$ | CH3 | Y3—CH=CH—CH=CH—Y4 | 2 | CH3 | N | 2 | 4.18 | 340.3 | 339.5 |
| A-196 | cyclopropyl | H | H | CO | N | C | — | CH$_3$ | H | Y3—CH=CH—CH=CH—Y4 | 2 | CH3 | N | 2 | 3.88 | 324.3 | 323.4 |
| A-197 | CF$_2$CHF$_2$ | H | H | CO | N | C | — | CH$_3$ | H | Y3—CH=CH—CH=CH—Y4 | 2 | CH3 | N | 2 | 3.43 | 342.2 | 341.3 |
| A-198 | C$_2$F$_5$ | H | H | CO | N | C | — | CH$_3$ | H | Y3—CH=CH—CH=CH—Y4 | 2 | CH3 | N | 2 | 3.32 | 360.2 | 359.3 |
| A-199 | CF$_2$CF$_3$ | H | H | CO | N | C | — | CH$_3$ | H | Y3—CH=CH—CH=CH—Y4 | 2 | CH3 | N | 2 | 3.87 | 410.2 | 409.3 |
| A-200 | CH(CH$_3$)CH$_2$CH$_3$ | H | H | CO | N | C | — | CH$_3$ | H | Y3—CH=CH—CH=CH—Y4 | 2 | CH3 | N | 2 | 3.62 | 360.2 | 359.3 |
| A-201 | cyclopropyl | H | H | CO | N | C | — | H | CH3 | Y3—CH=CH—CH=CH—Y4 | 2 | CH3 | N | 2 | 3.56 | 298.2 | 297.4 |
| A-202 | CF$_2$CHF$_2$ | H | H | CO | N | C | — | H | CH3 | Y3—CH=CH—CH=CH—Y4 | 2 | CH3 | N | 2 | 3.09 | 282.2 | 281.4 |
| A-203 | C$_2$F$_5$ | H | H | CO | N | C | — | H | CH3 | Y3—CH=CH—CH=CH—Y4 | 2 | CH3 | N | 2 | 3.52 | 370.2 | 369.4 |
| A-204 | CH(CH$_3$)CH$_2$CH$_3$ | H | H | CO | N | C | — | H | CH3 | Y3—CH=CH—CH=CH—Y4 | 2 | CH3 | N | 2 | 4.05 | 438.2 | 437.4 |
| A-205 | C$_2$F$_5$ | H | H | CO | N | C | — | H | H | Y3—CH=CH—CH=CH—Y4 | 2 | CH3 | N | 2 | 3.81 | 388.2 | 387.4 |

TABLE A-continued

| | | | | | | | | | | | |
|---|---|---|---|---|---|---|---|---|---|---|---|
| A-206 | CH(CH₃)CH₂CH₃ | H | H | CO | C | H | CH₃ | Y3—CH═CH—CH═Y4 | 2 | H | N | 2 | 3.76 | 326.3 | 325.5 |
| A-207 | cyclopropyl | H | H | CO | C | H | CH3 | Y3—CH═CH—CH═Y4 | 2 | CH3 | N | 2 | 3.32 | 310.2 | 309.4 |
| A-208 | (CH₂)₂CH₃ | H | H | CO | C | H | CH3 | Y3—CH═CH—CH═Y4 | 3 | H | N | 2 | 3.68 | 311.9 | 311.4 |
| A-209 | (CH₂)₂CH₃ | H | H | CO | C | H | CH₃ | Y3—CH═CH—CH═Y4 | 4 | H | N | 2 | 3.74 | 325.9 | 325.5 |
| A-210 | CF₂CHF₂ | H | H | CO | C | H | CH₃ | Y3—CH═CH—CH═Y4 | 2 | H | N | 2 | 3.47 | 355.8 | 355.3 |
| A-211 | C₂F₅ | H | H | CO | C | H | CH₃ | Y3—CH═CH—CH═Y4 | 2 | H | N | 2 | 3.79 | 373.8 | 373.3 |
| A-212 | CF(CF₃)₂ | H | H | CO | C | H | CH₃ | Y3—CH═CH—CH═Y4 | 2 | H | N | 2 | 4.06 | 423.7 | 423.3 |
| A-213 | CH(CH₃)CH₂CH₃ | H | H | CO | C | H | CH₃ | Y3—CH═CH—CH═Y4 | 2 | H | N | 2 | 3.74 | 311.9 | 311.4 |
| A-214 | cyclopropyl | H | H | CO | C | H | CH₃ | Y3—CH═CH—CH═Y4 | 2 | H | N | 2 | 3.26 | 295.9 | 295.4 |
| A-215 | CF₃ | H | H | CO | C | H | CH₃ | Y3—CH═CH—CH═Y4 | 3 | H | N | 2 | 3.56 | 337.8 | 337.3 |
| A-216 | CF₂CHF₂ | H | H | CO | C | H | CH₃ | Y3—CH═CH—CH═Y4 | 3 | H | N | 2 | 3.61 | 369.8 | 369.4 |
| A-217 | C₂F₅ | H | H | CO | C | H | CH₃ | Y3—CH═CH—CH═Y4 | 3 | H | N | 2 | 3.95 | 387.8 | 387.4 |
| A-218 | CF(CF₃)₂ | H | H | CO | C | H | CH₃ | Y3—CH═CH—CH═Y4 | 3 | H | N | 2 | 4.20 | 437.7 | 437.4 |
| A-219 | CH₂CH₃ | H | H | CO | C | H | CH₃ | Y3—CH═CH—CH═Y4 | 3 | H | N | 2 | 3.36 | 297.9 | 297.4 |
| A-220 | CH(CH₃)₂ | H | H | CO | C | H | CH₃ | Y3—CH═CH—CH═Y4 | 3 | H | N | 2 | 3.63 | 311.9 | 311.4 |
| A-221 | CH(CH₃)CH₂CH₃ | H | H | CO | C | H | CH₃ | Y3—CH═CH—CH═Y4 | 3 | H | N | 2 | 3.90 | 325.9 | 325.5 |
| A-222 | cyclopropyl | H | H | CO | C | H | CH₃ | Y3—CH═CH—CH═Y4 | 3 | H | N | 2 | 3.37 | 309.9 | 309.4 |
| A-223 | CF₃ | H | H | CO | C | H | CH₃ | Y3—CH═CH—CH═Y4 | 4 | H | N | 2 | 3.70 | 351.8 | 351.4 |
| A-224 | CF₂CHF₂ | H | H | CO | C | H | CH₃ | Y3—CH═CH—CH═Y4 | 4 | H | N | 2 | 3.71 | 383.8 | 383.4 |
| A-225 | C₂F₅ | H | H | CO | C | H | CH₃ | Y3—CH═CH—CH═Y4 | 4 | H | N | 2 | 4.03 | 401.8 | 401.4 |
| A-226 | CF(CF₃)₂ | H | H | CO | C | H | CH₃ | Y3—CH═CH—CH═Y4 | 4 | H | N | 2 | 4.33 | 451.7 | 451.4 |
| A-227 | CH₂CH₃ | H | H | CO | C | H | CH₃ | Y3—CH═CH—CH═Y4 | 4 | H | N | 2 | 3.44 | 311.9 | 311.4 |
| A-228 | CH(CH₃)₂ | H | H | CO | C | H | CH₃ | Y3—CH═CH—CH═Y4 | 4 | H | N | 2 | 3.69 | 325.9 | 325.5 |
| A-229 | CH(CH₃)CH₂CH₃ | H | H | CO | C | H | CH₃ | Y3—CH═CH—CH═Y4 | 4 | H | N | 2 | 3.96 | 339.9 | 339.5 |
| A-230 | cyclopropyl | H | H | CO | C | H | CH₃ | Y3—CH═CH—CH═Y4 | 4 | H | N | 2 | 3.47 | 323.9 | 323.4 |
| A-231 | CF₂CH₃ | H | H | CO | C | H | CH₃ | Y3—CH═CH—CH═Y4 | 2 | H | N | 2 | 3.36 | 320.2 | 319.4 |
| A-232 | CHF₂ | H | H | CO | C | H | CH₃ | Y3—CH═CH—CH═Y4 | 2 | H | N | 2 | 3.10 | 306.2 | 305.3 |
| A-233 | CH₂OCH₃ | H | H | CO | C | H | CH₃ | Y3—CH═CH—CH═Y4 | 2 | H | N | 2 | 2.86 | 300.2 | 299.4 |
| A-234 | CF₃ | H | CH₃ | CO | C | H | CH₃ | Y3—CH═CH—CH═Y4 | 2 | H | N | 2 | 3.60 | 338.2 | 337.3 |
| A-235 | CF₃ | CH₃ | H | CO | C | H | CH₃ | Y3—CH═CH—CH═Y4 | 2 | H | N | 2 | 3.65 | 338.2 | 337.3 |
| A-236 | CH(CH₃)₂ | H | H | CO | C | H | H | Y3—S—CH═CH—Y4 | 2 | CH₃ | N | 1 | 3.59 | 304.9 | 304.4 |
| A-237 | (CH₂)₂CH₃ | H | H | CO | C | H | H | Y3—S—CH═CH—Y4 | 2 | CH₃ | N | 1 | 3.63 | 304.9 | 304.4 |
| A-238 | CH₂CH₃ | H | H | CO | C | H | H | Y3—S—CH═CH—Y4 | 2 | CH₃ | N | 1 | 3.32 | 290.9 | 290.4 |
| A-239 | CF₃ | H | H | CO | N | — | H | N-pyrrolidinyl | 2 | H | N | 2 | 3.11 | 329.8 | 329.3 |
| A-240 | CF₃ | H | H | CO | N | — | H | N-piperidinyl | 2 | H | N | 2 | 3.44 | 343.8 | 343.4 |
| A-241 | CF₃ | H | H | CO | N | — | H | N-morpholinyl | 2 | H | N | 2 | 2.84 | 345.8 | 345.3 |
| A-242 | CF₃ | H | H | CO | C | — | CH₃ | CH₃ | 2 | H | N | 2 | 3.31 | 316.8 | 316.3 |
| A-243 | CF₃ | H | H | CO | N | — | CH₂CH₃ | CH₃ | 2 | H | N | 2 | 3.31 | 301.8 | 301.3 |
| A-244 | CF₃ | H | H | CO | N | — | CH₂CH₃ | CH₃ | 2 | H | N | 2 | 3.00 | 302.8 | 302.3 |
| A-245 | CF₃ | H | H | CO | N | — | CH(CH₃)₂ | CH₃ | 2 | H | N | 2 | 3.31 | 316.8 | 316.3 |
| A-246 | CF₃ | H | H | CO | C | — | CH₃ | (CH₂)₂CH₃ | 2 | H | N | 2 | 3.65 | 330.8 | 330.4 |
| A-247 | C₂F₅ | H | H | CO | C | — | H | H | 2 | CH₃ | N | 2 | 3.38 | 352.8 | 352.3 |
| A-248 | C₂F₅ | H | H | CO | N | — | CH₂CH₃ | H | 2 | CH₃ | N | 2 | 3.57 | 379.7 | 379.4 |
| A-249 | C₂F₅ | H | H | CO | N | — | CH₂CH₃ | Y3—CH═CH—S—Y4 | 2 | H | N | 2 | 3.76 | 393.7 | 393.4 |
| A-250 | C₂F₅ | H | H | CO | N | — | CH(CH₃)₂ | N-piperidinyl | 2 | H | N | 2 | 3.22 | 395.7 | 395.3 |
| A-251 | CF₃ | H | H | CO | C | — | CH₃ | N-morpholinyl | 2 | H | N | 2 | 3.45 | 365.7 | 365.3 |
| A-252 | C₂F₅ | H | H | CO | C | — | H | Y3—CH═CH—S—Y4 | 2 | CH₃ | N | 2 | 3.64 | 351.8 | 351.3 |
| A-253 | CF₃ | H | H | CO | C | — | CH₃ | OCH₂CH₃ | 2 | H | N | 2 | 3.62 | 351.8 | 351.3 |
| A-254 | C₂F₅ | H | H | CO | C | — | H | CH₃ | 2 | CH₃ | N | 2 | 3.26 | 318.8 | 318.3 |
| A-255 | CF₃ | H | H | CO | C | — | CH₂CH₃ | OCH₃ | 2 | CH₃ | N | 2 | 3.38 | 352.8 | 352.3 |
| A-256 | cyclopropyl | H | H | CO | C | — | H | CH₃ | 2 | H | N | 2 | 2.73 | 276.8 | 276.3 |
| A-257 | C₂F₅ | H | H | CO | C | — | CH₂CH₃ | H | 2 | H | N | 2 | 3.70 | 366.8 | 366.3 |
| A-258 | C₂F₅ | H | H | CO | N | — | CH(CH₃)CH₂CH₃ | CH₃ | 2 | CH₃ | N | 2 | 3.66 | 366.8 | 366.3 |

TABLE A-continued

| No. | | | | | | | | | | | | | | | | | | |
|---|---|---|---|---|---|---|---|---|---|---|---|---|---|---|---|---|---|---|
| A-259 | C$_2$F$_5$ | H | H | CO | N | C | — | CH(CH$_3$)$_2$ | — | — | H | CH$_3$ | 2 | H | CH$_3$ | 2 | 3.97 | 380.8 | 380.4 |
| A-260 | CF$_2$CH$_3$ | H | H | CO | N | C | — | CH$_3$ | — | — | H | CH$_3$ | 2 | H | CH$_3$ | 2 | 2.87 | 298.8 | 298.3 |
| A-261 | CF$_2$CH$_3$ | H | H | CO | N | C | — | H | — | — | Y3—CH=CH—S—Y4 | 2 | H | H | 2 | 3.10 | 325.8 | 325.4 |
| A-262 | CF$_2$CH$_3$ | H | H | CO | C | C | H | CH$_3$ | — | — | H | CH$_3$ | 2 | H | CH$_3$ | 2 | 3.26 | 297.8 | 297.3 |
| A-263 | CF$_2$CH$_3$ | H | H | CO | C | C | H | CH$_3$ | — | — | CH$_3$ | CH$_3$ | 2 | H | CH$_3$ | 2 | 3.17 | 297.8 | 297.3 |
| A-264 | CF$_2$CH$_3$ | H | H | CO | N | C | — | CH$_2$CH$_3$ | — | — | H | CH$_3$ | 2 | H | CH$_3$ | 2 | 3.17 | 312.8 | 312.4 |
| A-265 | CF$_2$CH$_3$ | H | H | CO | N | C | — | CH(CH$_3$)$_2$ | — | — | H | CH$_3$ | 2 | H | CH$_3$ | 2 | 3.50 | 326.8 | 326.4 |
| A-266 | CF$_2$CHF$_2$ | H | H | CO | C | C | H | CH$_3$ | — | — | H | CH$_3$ | 2 | H | CH$_3$ | 2 | 3.50 | 334.8 | 334.3 |
| A-267 | CF$_2$CHF$_2$ | H | H | CO | N | C | — | H | — | — | N-morpholinyl | 2 | H | CH$_3$ | 2 | 3.05 | 361.7 | 361.4 |
| A-268 | CF$_2$CHF$_2$ | H | H | CO | N | C | — | H | — | — | Y3—CH=CH—S—Y4 | 2 | H | H | 2 | 3.27 | 377.7 | 377.3 |
| A-269 | CF$_2$CHF$_2$ | H | H | CO | C | C | H | CH$_3$ | — | — | H | CH$_3$ | 2 | H | H | 2 | 2.91 | 320.8 | 320.3 |
| A-270 | CF$_2$CHF$_2$ | H | H | CO | C | C | H | CH$_3$ | — | — | H | CH$_3$ | 2 | H | CH$_3$ | 2 | 2.82 | 347.7 | 347.3 |
| A-271 | CF$_2$CHF$_2$ | H | H | CO | N | C | — | H | — | — | Y3—CH=CH—S—Y4 | 2 | H | CH$_3$ | 2 | 3.15 | 333.8 | 333.3 |
| A-272 | CF$_2$CHF$_2$ | H | H | CO | C | C | H | CH$_3$ | — | — | CH$_3$ | CH$_3$ | 2 | H | CH$_3$ | 2 | 3.63 | 333.8 | 333.3 |
| A-273 | CF$_2$CHF$_2$ | H | H | CO | N | C | — | CH(CH$_3$)$_2$ | — | — | H | CH$_3$ | 2 | H | CH$_3$ | 2 | 3.31 | 333.8 | 333.3 |
| A-274 | CF$_2$CHF$_2$ | H | H | CO | N | C | — | CH$_2$CH$_3$ | — | — | H | CH$_3$ | 2 | H | CH$_3$ | 2 | 3.39 | 348.8 | 348.3 |
| A-275 | CF$_2$CHF$_2$ | H | H | CO | N | C | — | CH(CH$_3$)$_2$ | — | — | H | CH$_3$ | 2 | H | CH$_3$ | 2 | 3.34 | 348.8 | 348.3 |
| A-276 | (CH$_2$)$_2$CCH | H | H | CO | N | C | — | H | — | — | CH$_3$ | CH$_2$CH$_3$ | 2 | H | CH$_3$ | 2 | 3.66 | 362.8 | 362.4 |
| A-277 | (CO)CH$_3$ | H | H | CO | N | C | — | CH$_3$ | — | — | Y3—CH=CH—CH=Y4 | 2 | H | CH$_3$ | 2 | 2.85 | 286.8 | 286.4 |
| A-278 | (CO)OC$_2$H$_5$ | H | H | CO | N | C | — | CH$_3$ | — | — | Y3—CH=CH—CH=Y4 | 2 | H | CH$_3$ | 2 | 2.71 | 298.2 | 297.4 |
| A-279 | C$_2$F$_5$ | H | H | CO | C | C | H | OCH$_2$CH$_3$ | — | — | H | CH$_3$ | 2 | H | CH$_3$ | 2 | 3.27 | 328.2 | 327.4 |
| A-280 | C$_2$F$_5$ | H | H | CO | C | C | H | OCH$_2$CH$_3$ | — | — | H | H | 2 | H | CO$_2$C$_2$H$_5$ | 2 | 4.43 | 381.7 | 381.3 |
| A-281 | C$_2$F$_5$ | H | H | CO | C | C | H | OCH$_2$CH$_3$ | — | — | H | H | 2 | H | CO$_2$C$_2$H$_5$ | 2 | 4.08 | 426.2 | 425.4 |
| A-282 | C$_2$F$_5$ | H | H | CO | C | C | H | OCH$_3$ | — | — | H | H | 2 | H | COCH$_3$ | 2 | 3.69 | 396.1 | 395.3 |
| A-283 | C$_2$F$_5$ | H | H | CO | C | C | H | CH$_3$ | — | — | H | H | 2 | H | COCH$_3$ | 2 | 3.44 | 340.2 | 339.3 |
| A-284 | C$_2$F$_5$ | H | H | CO | C | C | H | OCH$_2$CH$_3$ | — | — | H | CH$_3$ | 2 | H | CH$_3$ | 2 | 3.23 | 380.2 | 379.3 |
| A-285 | C$_2$F$_5$ | H | H | CO | C | C | H | OCH(CH$_3$)$_2$ | — | — | H | H | 2 | H | H | 2 | 3.80 | 368.2 | 367.3 |
| A-286 | C$_2$F$_5$ | H | H | CO | N | C | — | O(CH$_2$)$_2$CH$_3$ | — | — | H | CH$_3$ | 2 | H | H | 2 | 4.07 | 382.2 | 381.3 |
| A-287 | C$_2$F$_5$ | H | H | CO | C | C | H | OCH$_2$CH$_3$ | — | — | H | CH$_2$CH$_3$ | 2 | CH$_3$ | H | 2 | 3.85 | 368.2 | 367.3 |
| A-288 | C$_2$F$_5$ | H | H | CO | C | C | H | OCH$_3$ | — | — | H | CH$_3$ | 2 | H | H | 2 | 3.67 | 367.7 | 367.3 |
| A-289 | C$_2$F$_5$ | H | H | CO | C | C | H | OCH$_2$—cyclopropyl | — | — | H | CH$_3$ | 2 | H | H | 2 | 3.59 | 353.7 | 353.3 |
| A-290 | C$_2$F$_5$ | H | H | CO | C | C | H | OCH$_2$CH(CH$_3$)C$_2$H$_5$ | — | — | H | CH$_3$ | 2 | H | H | 2 | 4.08 | 394.2 | 393.4 |
| A-291 | C$_2$F$_5$ | H | H | CO | C | C | H | (CO)NHCH$_3$ | — | — | H | CH$_3$ | 2 | H | H | 2 | 4.44 | 410.2 | 409.4 |
| A-292 | C$_2$F$_5$ | H | H | CO | C | C | H | CN | — | — | H | CH$_3$ | 2 | H | H | 2 | 3.24 | 367.1 | 366.3 |
| A-293 | C$_2$F$_5$ | H | H | CO | C | C | H | OCH(CH$_3$)$_2$ | — | — | H | CH$_3$ | 2 | H | H | 2 | 3.52 | 349.1 | 348.3 |
| A-294 | C$_2$F$_5$ | H | H | CO | N | C | — | (CH$_2$)$_3$CH$_3$ | — | — | H | CH$_3$ | 2 | H | H | 2 | 3.83 | 368.2 | 367.3 |
| A-295 | C$_2$F$_5$ | H | H | CO | C | C | H | (CH$_2$)$_2$CH$_3$ | — | — | H | CH$_3$ | 2 | H | H | 2 | 3.81 | 381.2 | 380.4 |
| A-296 | C$_2$F$_5$ | H | H | CO | C | C | H | OCHF$_2$ | — | — | H | CH$_3$ | 2 | H | H | 2 | 4.05 | 367.2 | 366.3 |
| A-297 | C$_2$F$_5$ | H | H | CO | C | C | H | CO$_2$CH$_3$ | — | — | H | H | 4 | H | H | 2 | 3.89 | 376.1 | 375.2 |
| A-298 | C$_2$F$_5$ | H | H | CO | C | C | H | Cl | — | — | H | CH$_3$ | 2 | H | H | 2 | 3.23 | 368.1 | 367.3 |
| A-299 | C$_2$F$_5$ | H | H | CO | C | C | H | H | — | — | H | CH$_3$ | 2 | H | H | 2 | 3.59 | 358.1 | 357.7 |
| A-300 | C$_2$F$_5$ | H | H | CO | C | C | H | H | — | — | Y3—N(CH$_3$)—CH=N—Y4 | 2 | H | H | 2 | 3.42 | 363.1 | 362.3 |
| A-301 | C$_2$F$_5$ | H | H | CO | C | C | CONH$_2$ | CONH$_2$ | — | — | Y3—N(CH$_3$)—N=C(CH$_3$)—Y4 | 2 | H | H | 2 | 3.82 | 450.1 | 449.4 |
| A-302 | C$_2$F$_5$ | H | H | CO | N | C | — | H | — | — | H | CH$_3$ | 2 | H | H | 2 | 3.11 | 353.1 | 352.3 |
| A-303 | C$_2$F$_5$ | H | H | CO | C | C | CONH$_2$ | H | — | — | Y3—N=CH—NH—Y4 | 2 | H | H | 2 | 2.43 | 351.1 | 350.2 |
| A-304 | C$_2$F$_5$ | H | H | CO | N | C | CO$_2$H | H | — | — | Y3—N(CH$_3$)—N=C(CH$_3$)—Y4 | 2 | H | H | 2 | 2.97 | 421.1 | 420.3 |
| A-305 | CF$_2$CH$_3$ | H | H | CO | N | C | — | H | — | — | Y3—N(CH$_3$)—N=C(CH$_3$)—Y4 | 2 | H | H | 2 | 3.08 | 422.1 | 421.3 |
| A-306 | CF$_2$CH$_3$ | H | H | CO | C | C | H | OCH$_2$CH$_3$ | — | — | H | CH$_3$ | 2 | H | CO$_2$C$_2$H$_5$ | 2 | 3.39 | 314.2 | 313.3 |
| A-307 | CF$_2$CH$_3$ | H | H | CO | C | C | H | OCH$_2$CH$_3$ | — | — | H | CH$_3$ | 2 | H | H | 2 | 3.64 | 372.2 | 371.4 |
| A-308 | CF$_2$CH$_3$ | H | H | CO | C | C | H | OCH$_3$ | — | — | H | CH$_3$ | 2 | H | H | 2 | 2.93 | 286.1 | 285.3 |
| A-309 | CF$_2$CH$_3$ | H | H | CO | C | C | H | OCH$_3$ | — | — | H | CH$_3$ | 2 | H | CO$_2$C$_2$H$_5$ | 2 | 3.34 | 314.2 | 313.3 |
| A-310 | CF$_2$CH$_3$ | H | H | CO | C | C | H | CN | — | — | H | CH$_3$ | 2 | H | H | 2 | 3.09 | 299.8 | 299.3 |
| A-311 | CF$_2$CH$_3$ | H | H | CO | N | C | — | CH$_2$CH$_3$ | — | — | H | CH$_3$ | 2 | H | H | 2 | 3.02 | 294.7 | 294.3 |

TABLE A-continued

| No. | | | | | | | | | | | | | | | | | |
|---|---|---|---|---|---|---|---|---|---|---|---|---|---|---|---|---|---|
| A-312 | CF$_2$CHF$_2$ | H | CO | C | C | H | OCH$_2$CH$_3$ | | CH$_3$ | 2 | H | H | N | 2 | 3.55 | 350.2 | 349.3 |
| A-313 | CF$_2$CHF$_2$ | H | CO | C | C | H | OCH$_2$CH$_3$ | | CH$_3$ | 2 | H | CO$_2$C$_2$H$_5$ | N | 2 | 3.79 | 408.2 | 407.4 |
| A-314 | CF$_2$CHF$_2$ | H | CO | C | C | H | OCH$_3$ | | H | 2 | H | H | N | 2 | 3.12 | 322.2 | 321.3 |
| A-315 | CF$_2$CHF$_2$ | H | CO | C | C | H | OCH$_2$CH$_3$ | | H | 2 | H | CH$_3$ | N | 2 | 3.50 | 350.2 | 349.3 |
| A-316 | CF$_2$CHF$_2$ | H | CO | C | C | H | OCH$_2$CH$_3$ | | H | 2 | H | CH$_2$CH$_3$ | N | 2 | 4.12 | 363.7 | 363.4 |
| A-317 | CF$_2$CHF$_2$ | H | CO | C | C | H | OCH(CH$_3$)$_2$ | | CH$_3$ | 2 | H | H | N | 2 | 3.55 | 350.2 | 349.3 |
| A-318 | CF$_2$CHF$_2$ | H | CO | C | C | H | OCH(CH$_3$)$_2$ | | H | 2 | H | H | N | 2 | 3.77 | 364.2 | 363.4 |
| A-319 | CF$_2$CHF$_2$ | H | CO | C | C | H | O(CH$_2$)$_2$CH$_3$ | | H | 2 | H | H | N | 2 | 3.57 | 350.2 | 349.3 |
| A-320 | CF$_2$CHF$_2$ | H | CO | C | C | H | OCH$_2$CH$_3$ | | CH$_3$ | 2 | CH$_3$ | H | N | 2 | 3.38 | 349.7 | 349.3 |
| A-321 | CF$_2$CHF$_2$ | H | CO | C | C | H | OCH$_3$ | | CH$_3$ | 2 | H | H | N | 2 | 3.28 | 335.7 | 335.3 |
| A-322 | CF$_2$CHF$_2$ | H | CO | C | C | H | OCH$_2$-cyclopropyl | | CH$_3$ | 2 | H | H | N | 2 | 3.80 | 376.2 | 375.4 |
| A-323 | CF$_2$CHF$_2$ | H | CO | C | C | H | OCH$_2$CH(CH$_3$)C$_2$H$_5$ | | CH$_3$ | 2 | H | H | N | 2 | 4.19 | 392.2 | 391.4 |
| A-324 | CF$_2$CHF$_2$ | H | CO | C | C | H | (CO)NHCH$_3$ | | H | 2 | H | H | N | 2 | 2.94 | 349.2 | 348.3 |
| A-325 | CF$_2$CHF$_2$ | H | CO | C | N | — | CN | | CH$_3$ | 2 | H | H | N | 2 | 3.21 | 331.1 | 330.3 |
| A-326 | CF$_2$CHF$_2$ | H | CO | C | N | — | CH$_2$CH$_3$ | | CH$_3$ | 2 | H | H | N | 2 | 3.08 | 335.2 | 334.3 |
| A-327 | CF$_2$CHF$_2$ | H | CO | C | N | — | (CH$_2$)$_3$CH$_3$ | | CH$_3$ | 2 | H | H | N | 2 | 3.52 | 363.2 | 362.4 |
| A-328 | CF$_2$CHF$_2$ | H | CO | C | N | — | (CH$_2$)$_2$CH$_3$ | | CH$_3$ | 2 | H | H | N | 2 | 3.69 | 349.2 | 348.3 |
| A-329 | CF$_2$CHF$_2$ | H | CO | N | C | H | OCHF$_2$ | | H | 2 | H | H | N | 2 | 3.63 | 358.1 | 357.3 |
| A-330 | CF$_2$CHF$_2$ | H | CO | N | C | H | CO$_2$CH$_3$ | | CH$_3$ | 2 | H | H | N | 2 | 2.93 | 350.1 | 349.3 |
| A-331 | CF$_2$CHF$_2$ | H | CO | N | C | H | Cl | | H | 2 | H | H | N | 2 | 3.30 | 340.1 | 339.7 |
| A-332 | CF$_2$CHF$_2$ | H | CO | C | C | H | CONH$_2$ | | CH$_3$ | 2 | H | H | N | 2 | 2.79 | 335.1 | 334.3 |
| A-333 | CF$_2$Cl | H | CO | C | C | H | OCH$_2$CH$_3$ | | CH$_3$ | 2 | H | H | N | 2 | 3.42 | 320.1 | 319.7 |
| A-334 | CF$_2$Cl | H | CO | C | N | — | CH$_2$CH$_3$ | | CH$_3$ | 2 | H | H | N | 2 | 3.10 | 319.1 | 318.8 |
| A-335 | CF$_2$Cl | H | CO | C | C | H | CH(CH$_3$)$_2$ | | CH$_3$ | 2 | H | H | N | 2 | 3.43 | 333.2 | 332.8 |
| A-336 | CF$_3$ | H | CO | C | C | H | OCH$_2$CH$_3$ | | CH$_3$ | 2 | H | H | N | 2 | 3.52 | 318.2 | 317.3 |
| A-337 | CF$_3$ | H | CO | C | C | H | OCH$_2$CH$_3$ | | H | 2 | H | COCH$_3$ | N | 2 | 3.31 | 345.32 | 345.3 |
| A-338 | CF$_3$ | H | CO | C | C | H | OCH$_3$ | | H | 2 | H | H | N | 2 | 3.06 | 290.1 | 289.3 |
| A-339 | CF$_3$ | H | CO | C | C | H | OCH$_2$CH$_3$ | | H | 2 | H | H | N | 2 | 3.47 | 318.1 | 317.3 |
| A-340 | CF$_3$ | H | CO | C | C | H | OCH(CH$_3$)$_2$ | | H | 2 | CH$_3$ | CH$_3$ | N | 2 | 3.80 | 376.2 | 375.3 |
| A-341 | CF$_3$ | H | CO | C | C | H | OCH(CH$_3$)$_2$ | | H | 2 | H | CO$_2$C$_2$H$_5$ | N | 2 | 3.53 | 318.2 | 317.3 |
| A-342 | CF$_3$ | H | CO | C | C | H | O(CH$_2$)$_2$CH$_3$ | | H | 2 | H | H | N | 2 | 3.76 | 322.2 | 321.3 |
| A-343 | CF$_3$ | H | CO | C | C | H | OCH$_2$CH$_3$ | | H | 2 | H | H | N | 2 | 3.55 | 318.2 | 317.3 |
| A-344 | CF$_3$ | H | CO | C | C | H | OCH$_2$CH$_3$ | | CH$_3$ | 2 | H | CH$_2$CH$_3$ | N | 2 | 4.14 | 331.7 | 331.3 |
| A-345 | CF$_3$ | H | CO | C | C | H | CH$_3$ | CH$_2$CH$_3$ | CH$_3$ | 2 | CH$_3$ | H | N | 2 | 3.32 | 317.8 | 317.3 |
| A-346 | CF$_3$ | H | CO | C | C | H | H | Y3—CH═CH—CH═CH—Y4 | CH$_3$ | 2 | CH$_3$ | H | N | 2 | 3.77 | 301.8 | 301.3 |
| A-347 | CF$_3$ | H | CO | C | N | — | OCH$_3$ | Y3—CH═CH—CCl═CH—Y4 | H | 2 | CH$_3$ | H | N | 2 | 3.05 | 316.8 | 316.3 |
| A-348 | CF$_3$ | H | CO | C | C | H | OCH$_2$-cyclopropyl | Y3—N(CH$_3$)—N═CH—CH—Y4 | H | 2 | H | H | N | 2 | 3.23 | 303.7 | 303.3 |
| A-349 | CF$_3$ | H | CO | C | C | H | OCH$_2$CH(CH$_3$)C$_2$H$_5$ | Y3—N(CH$_3$)—N═C(CH$_3$)—Y4 | H | 2 | CH$_3$ | H | N | 2 | 3.79 | 344.2 | 343.3 |
| A-350 | CF$_3$ | H | CO | C | C | H | CH$_3$ | Y3—N(CH$_3$)—N═C(CH$_3$)—Y4 | H | 2 | CH$_3$ | H | N | 2 | 4.20 | 360.2 | 359.4 |
| A-351 | CF$_3$ | H | CO | C | C | H | (CO)NHCH$_3$ | Y3—CH═CH—S—Y4 | H | 2 | CH$_3$ | H | N | 2 | 3.50 | 338.2 | 337.3 |
| A-352 | CF$_3$ | H | CO | C | C | CO$_2$C$_2$H$_5$ | SCH$_3$ | | H | 2 | H | H | N | 2 | 2.86 | 317.2 | 316.3 |
| A-353 | CF$_3$ | H | CO | C | C | H | CH$_3$ | | CH$_3$ | 2 | CH$_3$ | CH$_3$ | N | 2 | 4.71 | 462.2 | 461.9 |
| A-354 | CF$_3$ | H | CO | C | N | — | H | | CH$_3$ | 2 | CH$_3$ | H | N | 2 | 2.90 | 325.2 | 324.3 |
| A-355 | CF$_3$ | H | CO | C | C | CO$_2$CH$_3$ | OCH$_3$ | | CH$_3$ | 2 | CH$_3$ | H | N | 2 | 3.32 | 386.2 | 385.3 |
| A-356 | CF$_3$ | H | CO | C | C | H | OCH$_2$-cyclopropyl | | CH$_3$ | 2 | CH$_3$ | H | N | 2 | 2.86 | 329.1 | 328.3 |
| A-357 | CF$_3$ | H | CO | C | C | H | OCH$_2$CH(CH$_3$)C$_2$H$_5$ | | H | 2 | CH$_3$ | H | N | 2 | 2.93 | 317.1 | 316.3 |
| A-358 | CF$_3$ | H | CO | N | C | — | CH$_3$ | | CH$_3$ | 2 | H | H | N | 2 | 3.15 | 299.1 | 298.3 |
| A-359 | CF$_3$ | H | CO | C | N | — | CN | | CH$_3$ | 2 | H | H | N | 2 | 3.37 | 317.2 | 316.3 |
| A-360 | CF$_3$ | H | CO | C | N | — | CH(CH$_3$)$_2$ | | CH$_3$ | 2 | H | H | N | 2 | 3.49 | 331.2 | 330.4 |
| A-361 | CF$_3$ | H | CO | C | N | — | (CH$_2$)$_3$CH$_3$ | | CH$_3$ | 2 | H | H | N | 2 | 3.68 | 317.2 | 316.3 |
| A-362 | CF$_3$ | H | CO | C | N | — | (CH$_2$)$_2$CH$_3$ | | CH$_3$ | 2 | H | H | N | 2 | 4.14 | 332.2 | 331.3 |
| A-363 | CF$_3$ | H | CO | C | N | — | N(CH$_3$)$_2$ | | CH$_3$ | 2 | H | H | N | 2 | 4.02 | 344.2 | 343.4 |
| A-364 | CF$_3$ | H | CO | C | C | H | N-pyrrolidinyl | | CH$_3$ | 2 | H | H | N | 2 | 3.86 | 326.1 | 325.2 |

TABLE A-continued

| | | | | | | | | | | | | | |
|---|---|---|---|---|---|---|---|---|---|---|---|---|---|
| A-365 | CF₃ | H | CO | C | C | H | CF₃ | H | 2 | H | H | N | 2 | 328.1 327.2 |
| A-366 | CF₃ | H | CO | C | N | — | H | Y3=CH—CH=CH—CH=Y4 | 2 | H | H | N | 2 | 311.1 310.3 |
| A-367 | CF₃ | H | CO | C | C | Cl | H | Y3=CH=C(OCH₃)—CH=CH—Y4 | 2 | H | H | N | 2 | 374.1 373.8 |
| A-368 | CF₃ | H | CO | C | C | NO₂ | H | Y3=CH—CH=C(CH₃)—CH=CH—Y4 | 2 | H | H | N | 2 | 355.1 354.3 |
| A-369 | CF₃ | H | CO | C | C | H | Cl | Y3=CH=C(CF₃)—CH=CH—Y4 | 2 | H | H | N | 2 | 378.1 377.3 |
| A-370 | CF₃ | H | CO | C | C | H | OCH₂CH₃ | H | 3 | CH₃ | H | N | 2 | 308.1 307.7 |
| A-371 | CF₃ | H | CO | C | C | H | OCH₃ | H | 2 | H | H | N | 2 | 318.1 317.3 |
| A-372 | CF₃ | H | CO | C | N | CH₃ | OCH₃ | H | 2 | H | H | N | 2 | 304.1 303.3 |
| A-373 | CF₃ | H | CO | C | C | H | H | H | 2 | H | H | N | 3 | 274.1 273.3 |
| A-374 | CF₃ | H | CO | C | C | — | SCH₃ | NH₂ | 2 | H | H | N | 2 | 322.1 321.3 |
| A-375 | CF₃ | H | CO | N | C | CF₃ | H | Y3—O—CH=CH—Y4 | 2 | H | H | N | 2 | 301.1 300.2 |
| A-376 | CF₃ | H | CO | C | C | H | H | H | 2 | H | H | N | 2 | 328.1 327.2 |
| A-377 | CF₃ | H | CO | C | C | H | CO₂CH₃ | H | 2 | H | H | N | 2 | 318.1 317.3 |
| A-378 | CF₃ | H | CO | N | C | H | CH₃ | H | 2 | H | H | N | 2 | 315.1 314.3 |
| A-379 | CF₃ | H | CO | C | C | CONH₂ | H | Y3=N—CH=N—Y4 | 2 | H | H | N | 2 | 371.1 370.3 |
| A-380 | CF₃ | H | CO | C | C | CO₂C₂H₅ | H | H | 2 | H | H | N | 2 | 313.1 312.3 |
| A-381 | CF₃ | H | CO | C | C | H | H | Y3—N(CH₃)—N=C(CH₃)—CH=CH—Y4 | 2 | H | H | N | 2 | 400.1 399.4 |
| A-382 | CF₃ | H | CO | C | C | H | N(CH₃)₂ | H | 2 | H | H | N | 2 | 318.1 317.3 |
| A-383 | CF₃ | H | CO | C | C | H | S(CH₃)₂ | H | 2 | H | H | N | 2 | 303.1 302.3 |
| A-384 | CF₃ | H | CO | C | C | H | CONH₂ | Y3—N(CH₃)—N=C(CH₃)—CH=CH—Y4 | 2 | H | H | N | 2 | 306.1 305.3 |
| A-385 | CF₃ | H | CS | C | C | H | OCH₂CH₃ | H | 2 | H | H | N | 2 | 303.1 302.3 |
| A-386 | CF₃ | H | CO | C | C | H | H | Y3—O—(CH₂)₂—O—Y4 | 2 | H | H | N | 2 | 320.1 319.3 |
| A-387 | CF₃ | H | CO | C | N | H | H | H | 2 | H | H | N | 3 | 394 393.3 |
| A-388 | CF₃ | H | CO | C | C | H | — | H | 2 | H | H | N | 2 | 311.1 310.3 |
| A-389 | CH(CH₃)₂ | H | CO | C | C | H | CH₃ | Y3=CH—CH=CH—CH=Y4 | 2 | H | H | N | 2 | 275.2 274.3 |
| A-390 | CH(CH₃)₂ | H | CO | N | C | H | OCH₃ | H | 2 | H | H | N | 3 | 289.2 288.4 |
| A-391 | CH₂Cl | H | CO | C | C | — | OCH₂CH₃ | H | 2 | H | H | N | 2 | 283.7 283.8 |
| A-392 | CH₂N(CH₃)₂ | H | CO | C | C | H | OCH₂CH₃ | H | 2 | H | CO₂C₂H₅ | N | 2 | 365.3 364.4 |
| A-393 | CH₃ | CH₃ | CO | C | C | H | CH₃ | H | 2 | CH₃ | H | N | 2 | 283.8 283.4 |
| A-394 | CHClCH₃ | H | CO | C | C | H | OCH₂CH₃ | H | 2 | H | H | N | 2 | 296.2 295.4 |
| A-395 | CHF₂ | H | CO | C | C | H | OCH₂CH₃ | Y3=CH—CH=CH—CH=Y4 | 2 | H | CO₂C₂H₅ | N | 2 | 300.2 299.3 |
| A-396 | CHF₂ | H | CO | C | C | H | OCH₃ | Y3=CH—CH=CH—CH=Y4 | 2 | H | COCH₃ | N | 2 | 358.2 357.4 |
| A-397 | CHF₂ | H | CO | C | C | H | OCH₂CH₃ | H | 2 | H | CH₃ | N | 2 | 328.2 327.3 |
| A-398 | CHF₂ | H | CO | C | C | H | OCH₂CH₃ | H | 2 | H | H | N | 2 | 272.1 271.3 |
| A-399 | CHF₂ | H | CO | C | C | H | OCH(CH₃)₂ | H | 2 | H | H | N | 2 | 300.2 299.3 |
| A-400 | CHF₂ | H | CO | C | C | H | OCH₃ | H | 2 | H | H | N | 2 | 300.2 299.3 |
| A-401 | CHF₂ | H | CO | C | C | H | OCH₃ | H | 2 | H | H | N | 2 | 314.2 313.3 |
| A-402 | CHF₂ | H | CO | C | C | H | OCH(CH₃)₂ | H | 2 | H | H | N | 2 | 300.2 299.3 |
| A-403 | CHF₂ | H | CO | C | C | H | O(CH₂)₂CH₃ | H | 2 | CH₃ | H | N | 2 | 299.8 299.3 |
| A-404 | CHF₂ | H | CO | C | N | H | OCH₂CH₃ | H | 3 | H | H | N | 2 | 285.8 285.3 |
| A-405 | CHF₂ | H | CO | C | C | H | OCH₃ | H | 2 | H | H | N | 2 | 299.1 298.3 |
| A-406 | CHF₂ | H | CO | C | C | H | (CO)NHCH₃ | H | 2 | H | H | N | 2 | 299.2 298.3 |
| A-407 | CHF₂ | H | CO | C | C | H | CH(CH₃)₂ | H | 2 | H | H | N | 2 | 280.7 280.3 |
| A-408 | CHF₂ | H | CO | C | N | H | CN | H | 2 | H | H | N | 2 | 285.2 284.3 |
| A-409 | CHF₂ | H | CO | C | C | — | CH₂CH₃ | H | 2 | H | H | N | 2 | 313.2 312.4 |
| A-410 | CHF₂ | H | CO | C | C | — | (CH₂)₃CH₃ | H | 2 | H | H | N | 2 | 299.2 298.3 |
| A-411 | CHF₂ | H | CO | C | C | — | (CH₂)₂CH₃ | H | 2 | H | H | N | 2 | 308.1 307.2 |
| A-412 | CHF₂ | H | CO | C | C | H | OCHF₂ | H | 3 | H | H | N | 2 | 300.2 299.3 |
| A-413 | CHF₂ | H | CO | C | C | H | OCH₂CH₃ | H | 2 | H | H | N | 2 | 286.1 285.3 |
| A-414 | CHF₂ | H | CO | C | C | H | OCH₃ | Y3=N—CH=N—Y4 | 2 | H | H | N | 2 | 296.7 296.3 |
| A-415 | CHF₂ | H | CO | C | C | H | H | H | 2 | H | H | N | 2 | 300.1 299.3 |
| A-416 | CHF₂ | H | CO | C | C | H | N(CH₃)₂ | Y3—O—(CH₂)₂—O—Y4 | 2 | H | H | N | 2 | 285.1 284.3 |
| A-417 | CHF₂ | H | CO | C | C | H | S(CH₃)₂ | H | 2 | H | H | N | 2 | 288.1 287.3 |

TABLE A-continued

| No | R¹ | R² | R³ | X | Y¹ | Y² | Y³ | Y⁴ | R¹² | R¹³ | R¹⁴ | R¹⁵ | R⁴ | R⁵ | n | | | Synth. Methods |
|---|---|---|---|---|---|---|---|---|---|---|---|---|---|---|---|---|---|---|
| A-418 | CHF₂ | H | H | CO | C | C | C | C | CONH₂ | | H | H | 2 | H | N | 2.38 | 285.1 | 284.3 |
| A-419 | Cl | H | H | CO | C | C | C | C | OCH₃ | | CH₃ | H | 2 | H | N | 2.88 | 269.8 | 269.7 |
| A-420 | Cl | H | H | CO | C | C | C | C | OCH₃ | | H | H | 2 | H | N | 2.69 | 256.1 | 255.7 |
| A-421 | Cl | H | H | CO | C | C | C | C | CH₃ | | Y3—CH=CH—CH=CH—Y4 | H | 2 | H | N | 3.28 | 290.1 | 289.8 |
| A-422 | furan-2-yl | Cl | H | CO | C | C | C | C | OCH₃ | | Y3—CH=CH—CH=CH—Y4 | H | 2 | H | N | 3.41 | 322.2 | 321.4 |
| A-423 | H | N(CH₃)₂ | H | CO | C | C | C | C | CH₃ | | H | H | 2 | H | N | 2.44 | 256.0 | 255.7 |
| A-424 | H | Cl | H | CO | C | C | C | C | OCH₃ | | Y3—CH=CH—CH=CH—Y4 | H | 2 | H | N | 2.49 | 265.1 | 264.3 |
| A-425 | H | Cl | H | CO | C | C | C | C | CH₃ | | H | H | 2 | H | N | 3.01 | 290.1 | 289.8 |
| A-426 | CH₂N(CH₃)₂ | H | H | CO | C | C | C | C | OCH₃ | | CH₃ | H | 2 | H | N | 2.60 | 293.2 | 292.4 |
| A-427 | OC₂H₅ | H | H | CO | C | C | C | C | CH₃ | | Y3—CH=CH—CH=CH—Y4 | H | 2 | H | N | 3.28 | 300.2 | 299.4 |
| A-428 | phenyl | H | H | CO | C | C | C | C | CH₃ | | Y3—CH=CH—CH=CH—Y4 | H | 2 | H | N | 3.83 | 332.2 | 331.4 |
| A-429 | SCH₃ | H | H | CO | C | C | C | C | CH₃ | | Y3—CH=CH—CH=CH—Y4 | H | 2 | H | N | 3.24 | 302.1 | 301.4 |
| A-430 | thiophen-2-yl | H | H | CO | C | C | C | C | SC2H5 | | Y3—CH=CH—CH=CH—Y4 | H | 2 | H | N | 3.69 | 338.2 | 337.4 |
| A-431 | CF₃ | H | H | CO | C | C | C | C | CF₃ | | H | H | 2 | H | N | 3.43 | 320.1 | 319.3 |
| A-432 | CF₃ | H | H | CO | C | C | C | C | H | | H | H | 1 | H | N | 2.87 | 245.1 | 244.2 |
| A-433 | CF₂CHF₂ | H | H | CO | C | C | C | C | H | | H | H | 1 | H | N | 2.95 | 277.1 | 276.2 |
| A-434 | C₂F₅ | H | H | CO | C | C | C | C | H | | H | H | 2 | H | N | 3.29 | 295.1 | 294.2 |
| A-435 | CF₃ | H | H | CO | C | C | C | C | H | | H | H | 2 | H | C | 3.05 | 259.1 | 258.2 |
| A-436 | CF₂CHF₂ | H | H | CO | C | C | C | C | H | | H | H | 2 | H | C | 3.11 | 291.1 | 290.3 |
| A-437 | C₂F₅ | H | H | CO | C | C | C | C | H | | H | H | 2 | H | C | 3.44 | 309.1 | 308.2 |
| A-438 | CH(CH₃)₂ | H | H | SO₂ | C | C | C | C | OCH₂CH₃ | | H | H | 2 | H | N | 3.38 | 314.2 | 313.4 |
| A-439 | CH(CH₃)₂ | H | H | SO₂ | C | C | C | C | OCH₃ | | Y3—CH=CH—CH=CH—Y4 | H | 2 | H | N | 3.23 | 300.2 | 299.4 |
| A-440 | SCH₃ | H | H | CO | C | C | C | C | OCH₂CH₃ | | H | H | 2 | H | N | 1.65 | 282.1 | 281.4 |
| A-441 | SF₅ | H | H | CO | C | C | C | C | OCH₃ | | H | H | 5 | H | N | 3.52 | 332.0 | 331.3 |
| A-442 | SF₅ | H | H | CO | C | C | C | C | OCH₂CH₃ | | H | H | 2 | H | N | 3.51 | 362.0 | 361.3 |
| A-443 | SO₂CH₃ | H | H | CO | C | C | C | C | OCH₃ | | H | H | 2 | H | N | 2.82 | 334.1 | 333.4 |
| A-444 | SCH₃ | H | H | CO | C | C | C | C | OCH₃ | | H | H | 2 | H | N | 2.71 | 268.1 | 267.4 |
| A-445 | SF₅ | H | H | CO | C | C | C | C | CH₃ | | Y3—CH=CH—CH=CH—Y4 | H | 2 | H | N | 3.33 | 348.0 | 347.3 |
| A-446 | CF₃ | H | H | SO₂ | C | N | C | C | CH₃ | | Y3—CH=CH—CH=CH—Y4 | H | 2 | H | N | 3.82 | 382.1 | 381.4 |
| A-447 | CH₂N(CH₃)₂ | H | H | CO | N | C | C | C | CH₃ | | CH₂CH₃ | H | 2 | H | N | 3.63 | 334.3 | 333.5 |
| A-448 | CF₃ | H | H | CO | C | C | — | C | OCH₃ | | — | — | 2 | H | N | 3.14 | 320.1 | 319.3 |
| A-449 | CH(CH₃)₂ | H | H | CS | C | C | H | C | CH₃ | | Y3—CH=CH—CH=CH—Y4 | H | 3 | H | N | 1.62 | 314.1 | 313.5 |
| A-450 | CH(CH₃)₂ | H | H | SO₂ | C | C | C | C | CH₃ | | CH₃ | H | 2 | H | N | 4.38 | 298.2 | 297.4 |

(X = CO, n = 2, D = N):

| No | R¹ | R¹² | R¹³ | R¹⁴ | R¹⁵ | Synth. Methods |
|---|---|---|---|---|---|---|
| A-451 | CH₂OCH₃ | H | CH₃ | H | H | 4A; 2H |
| A-452 | CH₂OCH₃ | H | CH₃ | CH₃ | H | 4A; 2H |
| A-453 | CH₂OCH₃ | CH₃ | CH(CH₃)₂ | H | H | 4A; 2H |
| A-454 | CH₂OCH₃ | H | CH₃ | CH₃ | H | 4A; 2H |
| A-455 | CH₂OCH₃ | — | CH₂CH₃ | CH₃ | H | 4A; 2H |
| A-456 | CH₂OCH₃ | H | OCH₂CH₃ | CH₃ | H | 4A; 2H |
| A-457 | CH₂OCH₃ | — | OCH₂CH₃ | CH₃ | H | 9A; 4A; 2H |
| A-458 | CH₂OCH₃ | H | OCH₃ | CH₃ | H | 9A; 4A; 2H |
| A-459 | CH₂OCH₃ | — | OCH₃ | CH₃ | H | 9A; 4A; 2H |
| A-460 | CH₂OCH₃ | H | H | H | CH₂CH₃ | 4A; 2H |
| A-461 | CH₂N(CH₃)₂ | H | CH₃ | CH₃ | H | 4A; 2H |
| A-462 | CH₂N(CH₃)₂ | CH₃ | CH₃ | H | H | 4A; 2H |
| A-463 | CH₂N(CH₃)₂ | H | CH(CH₃)₂ | H | H | 4A; 2H |
| A-464 | CH(CH₃)₂ | H | CH₃ | H | H | 4A; 2H |
| A-465 | CH(CH₃)₂ | H | CH₃ | CH₃ | H | 4A; 2H |

TABLE A-continued

| | | | | | | | | | |
|---|---|---|---|---|---|---|---|---|---|
| A-466 | CH$_2$N(CH$_3$)$_2$ | H | N | C | — | CH$_2$CH$_3$ | CH$_3$ | H | H | 4A; 2H |
| A-467 | CH$_2$N(CH$_3$)$_2$ | H | C | C | H | OCH$_3$ | H | H | H | 9A; 4A; 2H |
| A-468 | CH$_2$N(CH$_3$)$_2$ | H | C | C | H | OCH$_2$CH$_3$ | H | CH$_2$CH$_3$ | H | 4A; 2H |
| A-469 | N(CH$_3$)$_2$ | H | N | C | CH$_3$ | H | CH$_3$ | H | H | 4A; 2H |
| A-470 | N(CH$_3$)$_2$ | H | C | C | H | CH$_3$ | CH$_3$ | H | H | 4A; 2H |
| A-471 | N(CH$_3$)$_2$ | H | C | C | H | CH$_3$ | H | H | H | 4A; 2H |
| A-472 | N(CH$_3$)$_2$ | H | C | C | CH$_3$ | CH$_3$ | CH$_3$ | H | H | 4A; 2H |
| A-473 | N(CH$_3$)$_2$ | H | N | C | H | CH(CH$_3$)$_2$ | CH$_3$ | H | H | 4A; 2H |
| A-474 | N(CH$_3$)$_2$ | H | C | C | — | CH$_3$ | H | H | H | 4A; 2H |
| A-475 | N(CH$_3$)$_2$ | H | N | C | H | CH$_2$CH$_3$ | CH$_3$ | H | H | 9A; 4A; 2H |
| A-476 | N(CH$_3$)$_2$ | H | C | C | H | OCH$_3$ | H | H | H | 9A; 4A; 2H |
| A-477 | N(CH$_3$)$_2$ | H | N | C | H | OCH$_2$CH$_3$ | CH$_3$ | CH$_2$CH$_3$ | H | 4A; 2H |
| A-478 | N(CH$_3$)$_2$ | H | C | C | — | H | H | H | H | 4A; 2H |
| A-479 | CH$_2$NHCH$_3$ | H | C | C | H | CH$_3$ | CH$_3$ | H | H | 4A; 2H |
| A-480 | CH$_2$NHCH$_3$ | H | N | C | CH$_3$ | CH$_3$ | H | H | H | 4A; 2H |
| A-481 | CH$_2$NHCH$_3$ | H | C | C | H | CH$_3$ | CH$_3$ | H | H | 4A; 2H |
| A-482 | CH$_2$NHCH$_3$ | H | C | C | H | CH(CH$_3$)$_2$ | CH$_3$ | H | H | 4A; 2H |
| A-483 | CH$_2$NHCH$_3$ | H | N | C | H | CH$_3$ | H | H | H | 4A; 2H |
| A-484 | CH$_2$NHCH$_3$ | H | C | C | H | CH$_2$CH$_3$ | CH$_3$ | H | H | 4A; 2H |
| A-485 | CH$_2$NHCH$_3$ | H | C | C | — | OCH$_3$ | H | H | H | 9A; 4A; 2H |
| A-486 | CH$_2$NHCH$_3$ | H | C | C | H | OCH$_2$CH$_3$ | CH$_3$ | CH$_2$CH$_3$ | H | 9A; 4A; 2H |
| A-487 | CH$_2$NHCH$_3$ | H | N | C | H | OCH$_3$ | CH$_3$ | H | H | 9A; 4A; 2H |
| A-488 | CH$_2$NHCH$_3$ | H | C | C | H | H | CH$_3$ | H | H | 4A; 2H |
| A-489 | CH$_2$OCH$_3$ | H | C | C | H | COCH$_3$ | CH$_3$ | H | H | 6A-C; 7 |
| A-490 | CH$_2$N(CH$_3$)$_2$ | H | C | C | OCH$_3$ | COCH$_3$ | CH$_3$ | H | H | 6A-C; 7 |
| A-491 | CH$_2$NHCH$_3$ | H | C | C | H | COCH$_3$ | CH$_3$ | H | H | 6A-C; 7 |
| A-492 | CF$_3$ | H | C | C | H | CH$_3$ | CH$_3$ | H | H | 2A-E; 4A; 2H |
| A-493 | CHF$_2$ | H | C | C | H | CH(CH$_3$)$_2$ | H | H | H | 2A-E; 6A-C; 7 |
| A-494 | CHF$_2$ | H | C | C | H | COCH$_3$ | CH$_3$ | H | H | 2A-E; 4A; 2H |
| A-495 | CF$_2$CH$_3$ | H | C | C | H | CH(CH$_3$)$_2$ | CH$_3$ | H | H | 2A-E; 6A-C; 7 |
| A-496 | CF$_2$CF$_3$ | H | C | C | H | COCH$_3$ | H | H | H | 2A-E; 4A; 2H |
| A-497 | CH$_2$OCH$_3$ | H | C | C | H | CH$_3$ | CH$_3$ | H | H | 9A; 4A; 2H |
| A-498 | CH$_2$OCH$_2$ | H | C | C | H | OCH$_2$CH$_3$ | CH$_3$ | H | H | 9A; 4A; 2H |
| A-499 | CH$_2$N(CH$_3$)$_2$ | H | C | C | H | OCH$_2$CH$_3$ | CH$_3$ | H | H | 9A; 4A; 2H |
| A-500 | CH$_2$NHCH$_3$ | H | C | C | H | OCH$_2$CH$_3$ | CH$_3$ | H | H | 9A; 4A; 2H |
| A-501 | CF$_3$ | H | C | C | H | OCH(CH$_3$)$_2$ | CH$_3$ | H | H | 9A; 4A; 2A-E; 2H |
| A-502 | CH$_2$OCH$_3$ | H | C | C | H | OCH$_2$CH$_3$ | CH$_3$ | H | H | 9A; 4A; 2H |
| A-503 | CH$_2$N(CH$_3$)$_2$ | H | C | C | H | OCH$_2$CH$_3$ | CH$_3$ | H | H | 9A; 4A; 2H |
| A-504 | CH$_2$NHCH$_3$ | H | C | C | H | OCH$_2$CH$_3$ | CH$_3$ | H | H | 9A; 4A; 2H |
| A-505 | CF$_3$ | H | C | C | H | OCH(CH$_3$)$_2$ | CH$_3$ | H | H | 9A; 4A; 2A-E; 2H |
| A-506 | CHF$_2$ | H | C | C | H | OCH$_2$CH$_3$ | CH$_3$ | H | H | 9A; 4A; 2A-E; 2H |
| A-507 | CF$_2$CH$_3$ | H | C | C | H | OCH$_2$CH$_3$ | CH$_3$ | H | H | 9A; 4A; 2A-E; 2H |
| A-508 | CF$_2$CHF$_2$ | H | C | C | H | OCH$_2$CH$_3$ | CH$_3$ | H | H | 9A; 4A; 2A-E; 2H |
| A-509 | CF$_2$CF$_3$ | H | C | C | H | OCH$_2$CH$_3$ | CH$_3$ | H | H | 9A; 4A; 2A-E; 2H |
| A-510 | CH$_2$OCH$_3$ | H | C | C | H | OCH$_2$CH$_3$ | CH$_3$ | H | H | 9A; 4A; 2H |
| A-511 | CH$_2$N(CH$_3$)$_2$ | H | C | C | H | OCH$_2$CH$_3$ | CH$_3$ | H | H | 9A; 4A; 2H |
| A-512 | CH$_2$NHCH$_3$ | H | C | C | H | OCH$_2$CH$_3$ | CH$_3$ | H | H | 9A; 4A; 2H |
| A-513 | CF$_3$ | H | C | C | H | OCH$_2$CH$_3$ | CH$_3$ | H | H | 9A; 4A; 2A-E; 2H |
| A-514 | CHF$_2$ | H | C | C | H | OCH$_2$CH$_3$ | CH$_3$ | H | H | 9A; 4A; 2A-E; 2H |
| A-515 | CH$_2$OCH$_3$ | H | C | C | H | OCH$_2$CH$_3$ | CH$_3$ | H | H | 9A; 4A; 2H |
| A-516 | CH$_2$N(CH$_3$)$_2$ | H | C | C | H | OCH$_2$CH$_3$ | CH$_3$ | H | H | 9A; 4A; 2H |
| A-517 | CF$_2$CH$_3$ | H | C | C | H | OCH(CH$_3$)$_2$ | CH$_3$ | H | H | 9A; 4A; 2A-E; 2H |
| A-518 | CH$_2$OCH$_2$ | H | C | C | H | OCH(CH$_3$)$_2$ | CH$_3$ | H | H | 9A; 4A; 2A-E; 2H |

TABLE A-continued

| | | | | | | | | | |
|---|---|---|---|---|---|---|---|---|---|
| A-519 | CH$_2$N(CH$_3$)$_2$ | H | C | C | C | H | OCH(CH$_3$)$_2$ | H | H | H | 9A; 4A; 2H |
| A-520 | CH$_2$NHCH$_3$ | H | C | C | C | H | OCH(CH$_3$)$_2$ | H | H | H | 9A; 4A; 2H |
| A-521 | CF$_3$ | H | C | C | C | H | OCH$_3$ | CH$_2$CH$_3$ | H | H | 9A; 4A; 2A-E; 2H |
| A-522 | CHF$_2$ | H | C | C | C | H | OCH$_3$ | CH$_2$CH$_3$ | H | H | 9A; 4A; 2A-E; 2H |
| A-523 | CF$_2$CH$_3$ | H | C | C | C | H | OCH$_3$ | CH$_2$CH$_3$ | H | H | 9A; 4A; 2A-E; 2H |
| A-524 | CF$_2$CHF$_2$ | H | C | C | C | H | OCH$_3$ | CH$_2$CH$_3$ | H | H | 9A; 4A; 2A-E; 2H |
| A-525 | CF$_2$CF$_3$ | H | C | C | C | H | OCH$_3$ | CH$_2$CH$_3$ | H | H | 9A; 4A; 2A-E; 2H |
| A-526 | CH$_2$OCH$_2$ | H | C | C | C | H | OCH$_3$ | CH$_2$CH$_3$ | H | H | 9A; 4A; 2A-E; 2H |
| A-527 | CH$_2$N(CH$_3$)$_2$ | H | C | C | C | H | OCH$_3$ | CH$_2$CH$_3$ | H | H | 9A; 4A; 2H |
| A-528 | CH$_2$NHCH$_3$ | H | C | C | C | H | OCH$_3$ | CH$_2$CH$_3$ | H | H | 9A; 4A; 2H |
| A-529 | CF$_3$ | H | C | C | C | H | OCH$_2$CH$_3$ | CH$_2$CH$_3$ | H | H | 9A; 4A; 2A-E; 2H |
| A-530 | CHF$_2$ | H | C | C | C | H | OCH$_2$CH$_3$ | CH$_2$CH$_3$ | H | H | 9A; 4A; 2A-E; 2H |
| A-531 | CF$_2$CH$_3$ | H | C | C | C | H | OCH$_2$CH$_3$ | CH$_2$CH$_3$ | H | H | 9A; 4A; 2A-E; 2H |
| A-532 | CF$_2$CHF$_2$ | H | C | C | C | H | OCH$_2$CH$_3$ | CH$_2$CH$_3$ | H | H | 9A; 4A; 2A-E; 2H |
| A-533 | CF$_2$CF$_3$ | H | C | C | C | H | OCH$_2$CH$_3$ | CH$_2$CH$_3$ | H | H | 9A; 4A; 2A-E; 2H |
| A-534 | CH$_2$OCH$_2$ | H | C | C | C | H | OCH$_2$CH$_3$ | CH$_2$CH$_3$ | H | H | 9A; 4A; 2A-E; 2H |
| A-535 | CH$_2$N(CH$_3$)$_2$ | H | C | C | C | H | OCH$_2$CH$_3$ | CH$_2$CH$_3$ | H | H | 9A; 4A; 2H |
| A-536 | CH$_2$NHCH$_3$ | H | C | C | C | H | OCH$_2$CH$_3$ | CH$_2$CH$_3$ | H | H | 9A; 4A; 2H |
| A-537 | CF$_3$ | H | C | C | C | H | OCH$_3$ | CH(CH$_3$)$_2$ | H | H | 9A; 4A; 2A-E; 2H |
| A-538 | CHF$_2$ | H | C | C | C | H | OCH$_3$ | CH(CH$_3$)$_2$ | H | H | 9A; 4A; 2A-E; 2H |
| A-539 | CF$_2$CH$_3$ | H | C | C | C | H | OCH$_3$ | CH(CH$_3$)$_2$ | H | H | 9A; 4A; 2A-E; 2H |
| A-540 | CF$_2$CHF$_2$ | H | C | C | C | H | OCH$_3$ | CH(CH$_3$)$_2$ | H | H | 9A; 4A; 2A-E; 2H |
| A-541 | CF$_2$CF$_3$ | H | C | C | C | H | OCH$_3$ | CH(CH$_3$)$_2$ | H | H | 9A; 4A; 2A-E; 2H |
| A-542 | CH$_2$OCH$_2$ | H | C | C | C | H | OCH$_3$ | CH(CH$_3$)$_2$ | H | H | 9A; 4A; 2A-E; 2H |
| A-543 | CH$_2$N(CH$_3$)$_2$ | H | C | C | C | H | OCH$_3$ | CH(CH$_3$)$_2$ | H | H | 9A; 4A; 2H |
| A-544 | CH$_2$NHCH$_3$ | H | C | C | C | H | OCH$_3$ | CH(CH$_3$)$_2$ | H | H | 9A; 4A; 2H |
| A-545 | CF$_3$ | H | C | C | C | H | OCH$_2$CH$_3$ | CH(CH$_3$)$_2$ | H | H | 9A; 4A; 2A-E; 2H |
| A-546 | CHF$_2$ | H | C | C | C | H | OCH$_2$CH$_3$ | CH(CH$_3$)$_2$ | H | H | 9A; 4A; 2A-E; 2H |
| A-547 | CF$_2$CH$_3$ | H | C | C | C | H | OCH$_2$CH$_3$ | CH(CH$_3$)$_2$ | H | H | 9A; 4A; 2A-E; 2H |
| A-548 | CF$_2$CHF$_2$ | H | C | C | C | H | OCH$_2$CH$_3$ | CH(CH$_3$)$_2$ | H | H | 9A; 4A; 2A-E; 2H |
| A-549 | CF$_2$CF$_3$ | H | C | C | C | H | OCH$_2$CH$_3$ | CH(CH$_3$)$_2$ | H | H | 9A; 4A; 2A-E; 2H |
| A-550 | CH$_2$OCH$_2$ | H | C | C | C | H | OCH$_2$CH$_3$ | CH(CH$_3$)$_2$ | H | H | 9A; 4A; 2A-E; 2H |
| A-551 | CH$_2$N(CH$_3$)$_2$ | H | C | C | C | H | OCH$_2$CH$_3$ | CH(CH$_3$)$_2$ | H | H | 9A; 4A; 2H |
| A-552 | CH$_2$NHCH$_3$ | H | C | C | C | H | OCH$_2$CH$_3$ | CH(CH$_3$)$_2$ | H | H | 9A; 4A; 2H |
| A-553 | CF$_3$ | H | C | C | C | H | CH$_2$CH$_3$ | H | H | H | 9A; 4A; 2A-E; 2H |
| A-554 | CHF$_2$ | H | C | C | C | H | CH$_2$CH$_3$ | H | H | H | 9A; 4A; 2A-E; 2H |
| A-555 | CF$_2$CH$_3$ | H | C | C | C | H | CH$_2$CH$_3$ | H | H | H | 9A; 4A; 2A-E; 2H |
| A-556 | CF$_2$CHF$_2$ | H | C | C | C | H | CH$_2$CH$_3$ | H | H | H | 9A; 4A; 2A-E; 2H |
| A-557 | CF$_2$CF$_3$ | H | C | C | C | H | CH$_2$CH$_3$ | H | H | H | 9A; 4A; 2A-E; 2H |
| A-558 | CH$_2$OCH$_2$ | H | C | C | C | H | CH$_2$CH$_3$ | H | H | H | 9A; 4A; 2A-E; 2H |
| A-559 | CH$_2$N(CH$_3$)$_2$ | H | C | C | C | H | CH$_2$CH$_3$ | H | H | H | 9A; 4A; 2H |
| A-560 | CH$_2$NHCH$_3$ | H | C | C | C | H | CH$_2$CH$_3$ | H | H | H | 9A; 4A; 2H |
| A-561 | CF$_3$ | H | C | C | C | H | CH$_2$CH$_2$CH$_3$ | H | H | H | 9A; 4A; 2A-E; 2H |
| A-562 | CHF$_2$ | H | C | C | C | H | CH$_2$CH$_2$CH$_3$ | H | H | H | 9A; 4A; 2A-E; 2H |
| A-563 | CF$_2$CH$_3$ | H | C | C | C | H | CH$_2$CH$_2$CH$_3$ | H | H | H | 9A; 4A; 2A-E; 2H |
| A-564 | CF$_2$CHF$_2$ | H | C | C | C | H | CH$_2$CH$_2$CH$_3$ | H | H | H | 9A; 4A; 2A-E; 2H |
| A-565 | CF$_2$CF$_3$ | H | C | C | C | H | CH$_2$CH$_2$CH$_3$ | H | H | H | 9A; 4A; 2A-E; 2H |
| A-566 | CH$_2$OCH$_2$ | H | C | C | C | H | CH$_2$CH$_2$CH$_3$ | H | H | H | 9A; 4A; 2A-E; 2H |
| A-567 | CH$_2$N(CH$_3$)$_2$ | H | C | C | C | H | CH$_2$CH$_2$CH$_3$ | H | H | H | 9A; 4A; 2H |
| A-568 | CH$_2$NHCH$_3$ | H | C | C | C | H | CH$_2$CH$_2$CH$_3$ | H | H | H | 9A; 4A; 2H |
| A-569 | CF$_3$ | H | C | C | C | H | COCH$_3$ | CH$_3$ | H | H | 2A-E; 6A-C; 7 |
| A-570 | CHF$_2$ | H | C | C | C | H | COCH$_3$ | CH$_3$ | H | H | 2A-E; 6A-C; 7 |
| A-571 | CF$_2$CH$_3$ | H | C | C | C | H | COCH$_3$ | CH$_3$ | H | H | 2A-E; 6A-C; 7 |

TABLE A-continued

| | | | | | | | | | |
|---|---|---|---|---|---|---|---|---|---|
| A-572 | CF₂CHF₂ | H | H | C | C | H | COCH₃ | CH₃ | H | 2A-E; 6A-C; 7 |
| A-573 | CF₂CF₃ | H | H | C | C | H | COCH₃ | CH₃ | H | 2A-E; 6A-C; 7 |
| A-574 | CH₂OCH₃ | H | H | C | C | H | COCH₃ | CH₃ | H | 6A-C; 7 |
| A-575 | CH₂N(CH₃)₂ | H | H | C | C | H | COCH₃ | CH₃ | H | 6A-C; 7 |
| A-576 | CH₂NHCH₃ | H | H | C | C | H | COCH₃ | CH₃ | H | 6A-C; 7 |
| A-577 | CF₃ | H | H | C | C | H | COCH₂CH₃ | H | H | 2A-E; 6A-C; 7 |
| A-578 | CHF₂ | H | H | C | C | H | COCH₂CH₃ | H | H | 2A-E; 6A-C; 7 |
| A-579 | CF₂CH₃ | H | H | C | C | H | COCH₂CH₃ | H | H | 2A-E; 6A-C; 7 |
| A-580 | CF₂CHF₂ | H | H | C | C | H | COCH₂CH₃ | H | H | 2A-E; 6A-C; 7 |
| A-581 | CF₂CF₃ | H | H | C | N | H | COCH₂CH₃ | H | H | 2A-E; 6A-C; 7 |
| A-582 | CH₂OCH₃ | H | H | C | C | H | COCH₂CH₃ | H | H | 6A-C; 7 |
| A-583 | CH₂N(CH₃)₂ | H | H | C | C | H | COCH₂CH₃ | H | H | 6A-C; 7 |
| A-584 | CH₂NHCH₃ | H | H | C | C | H | COCH₂CH₃ | H | H | 6A-C; 7 |
| A-585 | CF₃ | H | H | C | C | H | | Y3—CH=CH—S—Y4 | H | 2A-E; 3B, 4B |
| A-586 | CF₃ | H | H | C | C | H | H | Y3—CH—CH—CH=N—Y4 | H | 2A-E; 3B, 4B |
| A-587 | CF₃ | H | H | N | C | H | CH₃ | Y3—CH=CH—N—Y4 | H | 2A-E; 4A, B |
| A-588 | CF₃ | H | H | C | C | H | CH₃ | Y3—N(CH₃)—N=C(CH₃)—Y4 | H | 2A-E; 3B, 4B |
| A-589 | CF₃ | H | H | C | C | H | — | H | H | 2A-E; 3B, 4B |
| A-590 | CF₃ | H | H | C | C | H | H | Y3—CH=CH—O—Y4 | H | 2A-E; 3B, 4B |
| A-591 | CF₃ | H | H | C | C | H | H | Y3—O—CH=CH—Y4 | H | 2A-E; 3B, 4B |
| A-592 | CF₃ | H | H | C | C | H | H | Y3—O—CH₂—CH₂—Y4 | H | 2A-E; 8A-C |
| A-593 | CF₂CF₃ | H | H | C | C | CH₃ | OCH₃ | H | H | 3A-B; 10F-I; 16C |
| A-594 | CF₂CF₃ | H | H | C | C | CH₃ | OCH₂CH₃ | H | H | 3A-B; 10F-I; 16C |
| A-595 | CF₂CF₃ | H | H | C | C | H | OCH₂CH₃ | CH₃ | H | 3A-B; 10F-I; 16C |
| A-596 | CF₂CF₃ | H | H | C | C | H | OCH₂CH₃ | CH₃ | H | 3A-B; 10F-I; 16C |
| A-597 | CF₂CF₃ | H | H | C | C | H | OCH₂-cyclopropyl | H | H | 10A-I; 16C |
| A-598 | CF₂CF₃ | H | H | C | C | H | SCH₃ | H | H | 10A-J |
| A-599 | CF₂CF₃ | H | H | C | C | H | SCH₂CH₃ | H | H | 10A-J |
| A-600 | CF₂CF₃ | H | H | C | C | H | S(CH₂)₂CH₃ | H | H | 10A-J |
| A-601 | CF₂CF₃ | H | H | C | C | H | SCH(CH₃)₂ | H | H | 10A-J |
| A-602 | CF₂CF₃ | H | H | C | C | H | SCH₃ | CH₃ | H | 10A-J |
| A-603 | CF₂CF₃ | H | H | C | C | H | SCH₂CH₃ | CH₃ | H | 10A-J |
| A-604 | CF₂CH₃ | H | H | C | C | CH₃ | OCH₃ | H | H | 3A-B; 10F-I; 16C |
| A-605 | CF₂CH₃ | H | H | C | C | CH₃ | OCH₂CH₃ | H | H | 3A-B; 10F-I; 16C |
| A-606 | CF₂CH₃ | H | H | C | C | H | OCH₂CH₃ | CH₃ | H | 3A-B; 10F-I; 16C |
| A-607 | CF₂CH₃ | H | H | C | C | H | OCH₃ | CH₃ | H | 3A-B; 10F-I; 16C |
| A-608 | CF₂CH₃ | H | H | C | C | H | OCH₂-cyclopropyl | H | H | 10A-I; 16C |
| A-609 | CF₂CH₃ | H | H | C | C | H | SCH₃ | H | H | 10A-J |
| A-610 | CF₂CH₃ | H | H | C | C | H | SCH₂CH₃ | H | H | 10A-J |
| A-611 | CF₂CH₃ | H | H | C | C | H | S(CH₂)₂CH₃ | H | H | 10A-J |
| A-612 | CF₂CH₃ | H | H | C | C | H | SCH(CH₃)₂ | H | H | 10A-J |
| A-613 | CF₂CH₃ | H | H | C | C | H | SCH₃ | CH₃ | H | 10A-J |
| A-614 | CF₂CH₃ | H | H | C | C | H | SCH₂CH₃ | CH₃ | H | 10A-J |
| A-615 | CF₂CHF₂ | H | H | C | C | CH₃ | OCH₃ | H | H | 3A-B; 10F-I; 16C |
| A-616 | CF₂CHF₂ | H | H | C | C | CH₃ | OCH₂CH₃ | H | H | 3A-B; 10F-I; 16C |
| A-617 | CF₂CHF₂ | H | H | C | C | H | OCH₂CH₃ | CH₃ | H | 3A-B; 10F-I; 16C |
| A-618 | CF₂CHF₂ | H | H | C | C | H | OCH₃ | CH₃ | H | 3A-B; 10F-I; 16C |
| A-619 | CF₂CHF₂ | H | H | C | C | H | OCH₂-cyclopropyl | H | H | 10A-I; 16C |
| A-620 | CF₂CHF₂ | H | H | C | C | H | SCH₃ | H | H | 10A-J |
| A-621 | CF₂CHF₂ | H | H | C | C | H | SCH₂CH₃ | H | H | 10A-J |
| A-622 | CF₂CHF₂ | H | H | C | C | H | S(CH₂)₂CH₃ | H | H | 10A-J |
| A-623 | CF₂CHF₂ | H | H | C | C | H | SCH(CH₃)₂ | H | H | 10A-J |
| A-624 | CF₂CHF₂ | H | H | C | C | H | SCH₃ | CH₃ | H | 10A-J |

TABLE A-continued

| | | | | | | | | | | | |
|---|---|---|---|---|---|---|---|---|---|---|---|
| A-625 | CF₂CHF₂ | H | H | C | C | C | H | SCH₂CH₃ | CH₃ | H | 10A-J |
| A-626 | CF₂Cl | H | H | C | C | C | H | CH(CH₃)₂ | H | H | 10F-I; 4A; 2H |
| A-627 | CF₂Cl | H | H | C | C | C | H | CH₂CH₂CH₃ | H | H | 9A; 4A; 2H |
| A-628 | CF₂Cl | H | H | C | C | C | H | CH₂CH₃ | H | H | 9A; 4A; 2H |
| A-629 | CF₂Cl | H | H | C | C | C | H | CH₃ | CH₃ | H | 4A; 2H |
| A-630 | CF₂Cl | H | H | C | C | C | H | COCH₃ | H | H | 10F-I; 6A-C; 7 |
| A-631 | CF₂Cl | H | H | C | C | C | H | OCH(CH₃)₂ | CH₃ | H | 10A-E; 2H |
| A-632 | CF₂Cl | H | H | C | C | C | H | OCH(CH₃)₂ | H | H | 9A; 4A; 2H |
| A-633 | CF₂Cl | H | H | C | C | C | H | OCH₂CH₂CH₃ | CH₃ | H | 10A-E; 2H |
| A-634 | CF₂Cl | H | H | C | C | C | H | OCH₂CH₂CH₃ | H | H | 9A; 4A; 2H |
| A-635 | CF₂Cl | H | H | C | C | C | H | OCH₂CH₃ | CH(CH₃)₂ | H | 10A-E; 2H |
| A-636 | CF₂Cl | H | H | C | C | C | H | OCH₂CH₃ | CH₂CH₃ | H | 10A-E; 2H |
| A-637 | CF₂Cl | H | H | C | C | C | H | OCH₃ | CH(CH₃)₂ | H | 10A-E; 2H |
| A-638 | CF₂Cl | H | H | C | C | C | H | OCH₂CH₃ | CH₃ | H | 10A-I; 2H |
| A-639 | CF₂Cl | H | H | C | C | C | H | OCH₂CH₃ | H | H | 10A-I; 16C |
| A-640 | CF₂Cl | H | H | C | C | C | CH₃ | OCH₂CH₃ | CH₃ | H | 3A-B; 10F-I; 16C |
| A-641 | CF₂Cl | H | H | C | C | C | H | OCH₂CH₃ | H | H | 3A-B; 10F-I; 16C |
| A-642 | CF₂Cl | H | H | C | C | C | H | OCH₂-cyclopropyl | H | H | 10A-I; 16C |
| A-643 | CF₂Cl | H | H | C | C | C | H | OCH₃ | CH₂CH₃ | H | 10A-I; 16C |
| A-644 | CF₂Cl | H | H | C | C | C | H | OCH₃ | CH₃ | H | 10A-I; 16C |
| A-645 | CF₂Cl | H | H | C | C | C | H | OCH₃ | H | H | 3A-B; 10F-I; 16C |
| A-646 | CF₂Cl | H | H | C | C | C | H | S(CH₂)₂CH₃ | H | H | 10A-J |
| A-647 | CF₂Cl | H | H | C | C | C | H | SCH(CH₃)₂ | CH₃ | H | 10A-J |
| A-648 | CF₂Cl | H | H | C | C | C | H | SCH₂CH₃ | H | H | 10A-J |
| A-649 | CF₂Cl | H | H | C | C | C | H | SCH₂CH₃ | CH₃ | H | 10A-J |
| A-650 | CF₂Cl | H | H | C | C | C | H | SCH₃ | H | H | 10A-J |
| A-651 | CF₂Cl | H | H | C | C | C | H | SCH₃ | CH₃ | H | 10A-J |
| A-652 | CF₃ | H | H | C | C | C | CH₃ | OCH₃ | CH₃ | H | 3A-B; 10F-I; 16C |
| A-653 | CF₃ | H | H | C | C | C | CH₃ | OCH₂CH₃ | CH₃ | H | 3A-B; 10F-I; 16C |
| A-654 | CF₃ | H | H | C | C | C | H | OCH₃ | H | H | 3A-B; 10F-I; 16C |
| A-655 | CF₃ | H | H | C | C | C | H | OCH₂CH₃ | H | H | 3A-B; 10F-I; 16C |
| A-656 | CF₃ | H | H | C | C | C | H | OCH₂-cyclopropyl | H | H | 3A-B; 10F-I; 16C |
| A-657 | CF₃ | H | H | C | C | C | H | S(CH₂)₂CH₃ | H | H | 10A-I; 16C |
| A-658 | CF₃ | H | H | C | C | C | H | SCH(CH₃)₂ | H | H | 10A-J |
| A-659 | CF₃ | H | H | C | C | C | H | SCH₃ | CH₃ | H | 10A-J |
| A-660 | CF₃ | H | H | C | C | C | H | SCH₂CH₃ | CH₃ | H | 10A-J |
| A-661 | CH₂OCH₂ | H | H | C | C | C | CH₃ | OCH₃ | H | H | 3A-B; 10F-I; 16C |
| A-662 | CH₂OCH₂ | H | H | C | C | C | CH₃ | OCH₂CH₃ | H | H | 3A-B; 10F-I; 16C |
| A-663 | CH₂OCH₂ | H | H | C | C | C | H | OCH₃ | CH₃ | H | 3A-B; 10F-I; 16C |
| A-664 | CH₂OCH₂ | H | H | C | C | C | H | OCH₂CH₃ | CH₃ | H | 3A-B; 10F-I; 16C |
| A-665 | CH₂OCH₂ | H | H | C | C | C | H | OCH₂-cyclopropyl | H | H | 10A-I; 16C |
| A-666 | CH₂OCH₂ | H | H | C | C | C | H | SCH₂CH₃ | H | H | 10A-J |
| A-667 | CH₂OCH₂ | H | H | C | C | C | H | SCH₂CH₃ | CH₃ | H | 10A-J |
| A-668 | CH₂OCH₂ | H | H | C | C | C | H | S(CH₂)₂CH₃ | H | H | 10A-J |
| A-669 | CH₂OCH₂ | H | H | C | C | C | H | SCH(CH₃)₂ | H | H | 10A-J |
| A-670 | CH₂OCH₂ | H | H | C | C | C | H | SCH₃ | CH₃ | H | 3A-B; 10F-I; 16C |
| A-671 | CH₂OCH₂ | H | H | C | C | C | CH₃ | SCH₂CH₃ | CH₃ | H | 3A-B; 10F-I; 16C |
| A-672 | CHF₂ | H | H | C | C | C | H | OCH₂CH₃ | CH₃ | H | 10A-J |
| A-673 | CHF₂ | H | H | C | C | C | H | OCH₂CH₃ | H | H | 3A-B; 10F-I; 16C |
| A-674 | CHF₂ | H | H | C | C | C | H | OCH₃ | CH₃ | H | 10A-J |
| A-675 | CHF₂ | H | H | C | C | C | CH₃ | OCH₃ | CH₃ | H | 3A-B; 10F-I; 16C |
| A-676 | CHF₂ | H | H | C | C | C | H | OCH₂-cyclopropyl | H | H | 10A-J |
| A-677 | CHF₂ | H | H | C | C | C | H | SCH₃ | H | H | 10A-J |

TABLE A-continued

| | | | | | | |
|---|---|---|---|---|---|---|
| A-678 | CHF₂ | H | C | C | H | SCH₂CH₃ | H | H | 10A-J |
| A-679 | CHF₂ | H | C | C | H | S(CH₂)₂CH₃ | H | H | 10A-J |
| A-680 | CHF₂ | H | C | C | H | SCH(CH₃)₂ | H | H | 10A-J |
| A-681 | CHF₂ | H | C | C | H | SCH₃ | CH₃ | H | 10A-J |
| A-682 | CHF₂ | H | C | C | H | SCH₂CH₃ | CH₃ | H | 10A-J |
| A-683 | SF₅ | H | C | C | H | OCH₃ | CH₃ | H | 10A-I; 16C |
| A-684 | SF₅ | H | C | C | H | OCH₂CH₃ | CH₃ | H | 10A-I; 16C |
| A-685 | SF₅ | H | C | C | H | OCH₂-cyclopropyl | H | H | 10A-I; 16C |
| A-686 | SF₅ | H | C | C | H | OCH₃ | CH₂CH₃ | H | 10A-I; 16C |
| A-687 | SF₅ | H | C | C | H | SCH₃ | H | H | 10A-J |
| A-688 | SF₅ | H | C | C | H | SCH₂CH₃ | H | H | 10A-J |
| A-689 | SF₅ | H | C | C | H | S(CH₂)₂CH₃ | H | H | 10A-J |
| A-690 | SF₅ | H | C | C | H | SCH(CH₃)₂ | H | H | 10A-J |
| A-691 | SF₅ | H | C | C | H | SCH₃ | CH₃ | H | 10A-J |
| A-692 | SF₅ | H | C | C | H | SCH₂CH₃ | CH₃ | H | 10A-J |
| A-693 | SF₅ | H | C | N | — | CH(CH₃)₂ | CH₃ | H | 10F-I; 4A; 2H |
| A-694 | SF₅ | H | C | N | — | CH₂CH₃ | CH₃ | H | 10F-I; 4A; 2H |
| A-695 | SF₅ | H | C | N | — | CH₃ | CH₃ | H | 10F-I; 4A; 2H |
| A-696 | SF₅ | H | C | C | H | H | CH₂CH₃ | H | 10F-I; 4A; 2H |
| A-697 | SF₅ | H | C | C | H | OCH₃ | CH₃ | H | 3A-B; 10F-I; 16C |

Further examples of specific compounds of the present invention include each of the compounds of table A above wherein X=SO$_2$ instead of CO and each of the compounds of table A wherein X=CS instead of CO if not already contained in table A and wherein n is equal to 2 or wherein n is equal to 3.

Further examples of specific compounds of the present invention include each of the compounds in table A and analogues wherein X=SO$_2$ or wherein X=CS and wherein n is equal to 2 or wherein n is equal to 3 in form of its pyridine-N-oxide such as the N-oxides shown in the table below:

| No | Structure | HPLC | Rt | m/z | MW |
|---|---|---|---|---|---|
| Aa-1 | 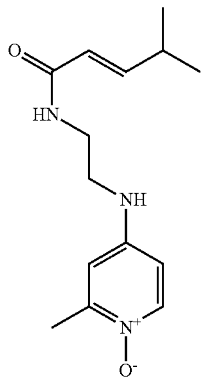 [SMILES: Cc1cc(NCCNC(=O)/C=C/C(C)C)cc[n+]1[O-]] | 2 | 2.48 | 264.2 | 263.3 |
| Aa-2 | 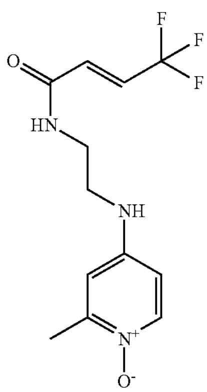 [SMILES: Cc1cc(NCCNC(=O)/C=C/C(F)(F)F)cc[n+]1[O-]] | 2 | 2.40 | 290.1 | 289.3 |
| Aa-3 | 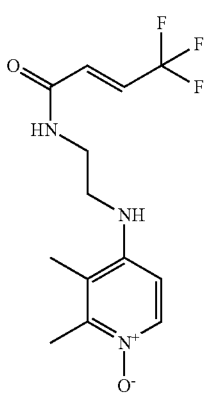 [SMILES: Cc1c(NCCNC(=O)/C=C/C(F)(F)F)cc[n+]([O-])c1C] | 2 | 2.62 | 304.2 | 303.3 |
| Aa-4 | 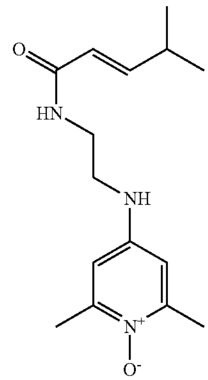 [SMILES: Cc1cc(NCCNC(=O)/C=C/C(C)C)cc(C)[n+]1[O-]] | 2 | 2.53 | 278.2 | 277.4 |
| Aa-5 | 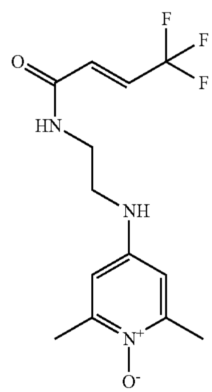 [SMILES: Cc1cc(NCCNC(=O)/C=C/C(F)(F)F)cc(C)[n+]1[O-]] | 2 | 2.57 | 304.2 | 303.3 |

Table B below provides for each of the exemplified compounds of the formula (B) the structure, the calculated molecular weight (MVV) (gram/mol), the observed MS signal (m/z), the HPLC retention time (Rt) in minutes, and the number of the HPLC-method as described in paragraph C above ("Analytics: HPLC-Methods") used for analysis. From compound B-51 until the end of the table the methods by which the compounds are synthesized are identified by referring to the synthetic steps described in the synthesis examples of paragraph B above ("Synthesis Examples"). If a compound contains one or more chiral centers, the mentioning of such compound is indicating the racemate.

In Table B—in case of a) a ring formation between Y$^1$ and Y$^2$ by the substituents R$^{12}$ and R$^{13}$ or b) a ring formation between Y$^3$ and Y$^4$ by the substituents R$^{14}$ and R$^{15}$— in the columns for R$^{12}$ and R$^{13}$ or in the columns for R$^{14}$ and R$^{15}$, as the case may be, the symbols Y1, Y2, Y3 and Y4 indicate the ring atoms Y$^1$, Y$^2$, Y$^3$ and Y$^4$ in formula (B) to which the group joining them is bound.

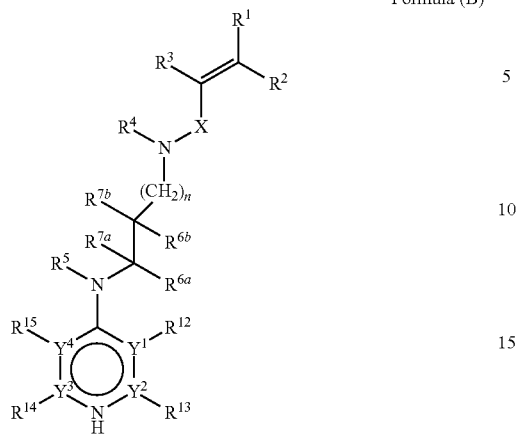
Formula (B)

TABLE B (X = CO; R² = H; R³ = H; Y², Y³, Y⁴ = C)

| No | R¹ | Y¹ | R¹² | R¹³ | R¹⁴ | R¹⁵ | R⁶ᵃ | R⁴ | R⁷ᵃ | R⁶ᵇ | R⁷ᵇ | R⁵ | n | HPLC | Rt | m/z | MW |
|---|---|---|---|---|---|---|---|---|---|---|---|---|---|---|---|---|---|
| B-1 | CF₃ | C | H | CH₃ | CH₃ | H | CH₃ | H | H | H | H | H | 0 | 2 | 3.91 | 302.2 | 301.3 |
| B-2 | CF₃ | C | H | H | Y3—CH=CH—CH=CH—Y4 | | CH(CH₃)₂ | H | H | H | H | H | 0 | 2 | 3.77 | 352.3 | 351.4 |
| B-3 | CF₂CHF₂ | C | H | H | Y3—CH=CH—CH=CH—Y4 | | CH(CH₃)₂ | H | H | H | H | H | 0 | 2 | 3.79 | 384.3 | 383.4 |
| B-4 | C₂F₅ | C | H | H | Y3—CH=CH—CH=CH—Y4 | | CH(CH₃)₂ | H | H | H | H | H | 0 | 2 | 4.04 | 402.3 | 401.4 |
| B-5 | CF₃ | C | H | OCH₂CH₃ | H | H | CH₂CH₃ | H | H | H | H | H | 0 | 2 | 3.61 | 332.2 | 331.3 |
| B-6 | CF₃ | C | H | OCH₂CH₃ | H | H | H | H | H | CH₂CH₃ | H | H | 0 | 2 | 3.62 | 332.2 | 331.3 |
| B-7 | CF₃ | C | H | OCH₂CH₃ | H | H | CH₃ | H | H | H | H | H | 0 | 2 | 3.45 | 318.2 | 317.3 |
| B-8 | CF₃ | C | H | OCH₂CH₃ | H | H | H | H | H | CH₃ | H | H | 0 | 2 | 3.43 | 317.8 | 317.3 |
| B-9 | CF₃ | C | H | OCH₂CH₃ | H | H | CH₃ | H | H | CH₃ | H | H | 0 | 2 | 3.73 | 331.8 | 331.3 |
| B-10 | CF₃ | C | H | CH₃ | H | H | CO₂CH₃ | H | H | H | H | H | 0 | 2 | 3.33 | 361.1 | 360.3 |
| B-11 | CF₃ | C | H | CH₃ | CH₃ | H | CH₂CH₃ | H | H | H | H | H | 0 | 2 | 5.04 | 316.2 | 315.3 |
| B-12 | CF₃ | C | H | CH₃ | CH₃ | H | H | H | H | CH₂CH₃ | H | H | 0 | 2 | 4.59 | 316.2 | 315.3 |
| B-13 | CF₃ | C | H | CH₃ | CH₃ | H | CH₃ | H | H | CH₃ | CH₃ | H | 0 | 2 | 3.91 | 301.8 | 301.3 |
| B-14 | CF₃ | C | H | CH₃ | CH₃ | H | CH₃ | H | H | CH₃ | H | H | 0 | 2 | 4.81 | 315.8 | 315.3 |
| B-15 | CF₃ | N | — | OCH₂CH₃ | H | CH₂CH₃ | CH₂CH₃ | H | H | H | H | H | 0 | 2 | 3.42 | 331.2 | 330.4 |
| B-16 | CF₃ | N | — | OCH₂CH₃ | H | CH₂CH₃ | H | H | H | CH₂CH₃ | H | H | 0 | 2 | 3.38 | 331.2 | 330.4 |
| B-17 | CF₃ | N | — | OCH₂CH₃ | H | CH₂CH₃ | CH₃ | H | H | H | H | H | 0 | 2 | 3.27 | 317.2 | 316.3 |
| B-18 | CF₃ | N | — | OCH₂CH₃ | H | CH₂CH₃ | H | H | H | CH₃ | H | H | 0 | 2 | 3.22 | 317.2 | 316.3 |
| B-19 | CF₃ | N | — | OCH₂CH₃ | H | CH₂CH₃ | CH₃ | H | H | CH₃ | H | H | 0 | 2 | 3.65 | 330.8 | 330.4 |
| B-20 | CF₃ | C | H | CH₃ | Y3—CH=CH—CH=CH—Y4 | | CO₂CH₃ | H | H | H | H | H | 0 | 2 | 3.43 | 362.1 | 361.3 |
| B-21 | CF₃ | C | H | CH₃ | Y3—CH=CH—CH=CH—Y4 | | CH₂CH₃ | H | H | H | H | H | 0 | 2 | 3.99 | 352.2 | 351.4 |
| B-22 | CF₃ | C | H | CH₃ | Y3—CH=CH—CH=CH—Y4 | | H | H | H | CH₂CH₃ | H | H | 0 | 2 | 4.02 | 352.2 | 351.4 |
| B-23 | CF₃ | C | H | CH₃ | Y3—CH=CH—CH=CH—Y4 | | CH₃ | H | H | H | H | H | 0 | 2 | 3.80 | 338.2 | 337.3 |
| B-24 | CF₃ | C | H | CH₃ | Y3—CH=CH—CH=CH—Y4 | | H | H | H | CH₃ | H | H | 0 | 2 | 3.85 | 338.2 | 337.3 |
| B-25 | CF₃ | C | H | OCH₂CH₃ | H | CH₂CH₃ | CH₂CH₃ | H | H | H | H | H | 0 | 2 | 4.24 | 352.2 | 351.4 |
| B-26 | CHF₂ | C | H | OCH₂CH₃ | H | H | CH₂CH₃ | H | H | H | H | H | 0 | 2 | 3.33 | 313.8 | 313.3 |
| B-27 | CHF₂ | C | H | OCH₂CH₃ | H | H | H | H | H | CH₂CH₃ | H | H | 0 | 2 | 3.33 | 313.8 | 313.3 |
| B-28 | CHF₂ | C | H | OCH₂CH₃ | H | H | CH₃ | H | H | H | H | H | 0 | 2 | 3.13 | 299.8 | 299.3 |
| B-29 | CHF₂ | C | H | OCH₂CH₃ | H | H | H | H | H | CH₃ | H | H | 0 | 2 | 3.13 | 299.8 | 299.3 |
| B-30 | CHF₂ | C | H | OCH₂CH₃ | H | H | CH₃ | H | H | CH₃ | H | H | 0 | 2 | 3.42 | 313.8 | 313.3 |
| B-31 | CHF₂ | C | H | OCH₂CH₃ | H | H | CH₂CH₃ | H | H | CH₂CH₃ | H | H | 0 | 2 | 3.13 | 343.7 | 343.3 |
| B-32 | CF₂CHF₂ | C | H | OCH₂CH₃ | H | H | CO₂CH₃ | H | H | H | H | H | 0 | 2 | 3.93 | 381.7 | 381.3 |
| B-33 | CF₂CHF₂ | C | H | OCH₂CH₃ | H | H | CH₂CH₃ | H | H | H | H | H | 0 | 2 | 3.93 | 381.7 | 381.3 |
| B-34 | CF₂CHF₂ | C | H | OCH₂CH₃ | H | H | H | H | H | CH₂CH₃ | H | H | 0 | 2 | 3.77 | 367.7 | 367.3 |
| B-35 | CF₂CHF₂ | C | H | OCH₂CH₃ | H | H | CH₃ | H | H | H | H | H | 0 | 2 | 3.77 | 367.7 | 367.3 |
| B-36 | CF₂CHF₂ | C | H | OCH₂CH₃ | H | H | H | H | H | CH₃ | H | H | 0 | 2 | 4.03 | 381.7 | 381.3 |
| B-37 | CF₂CHF₂ | C | H | OCH₂CH₃ | H | H | CH₂CH₃ | H | H | CH₂CH₃ | H | H | 0 | 2 | 3.75 | 411.7 | 411.3 |
| B-38 | CF₂CHF₂ | C | H | OCH₂CH₃ | H | H | H | H | H | CH₃ | H | H | 0 | 2 | 3.64 | 363.8 | 363.4 |
| B-39 | CF₂CHF₂ | C | H | OCH₂CH₃ | H | H | CH₃ | H | H | H | H | H | 0 | 2 | 3.64 | 363.8 | 363.4 |
| B-40 | CF₂CHF₂ | C | H | OCH₂CH₃ | H | H | CH₃ | H | H | CH₃ | H | H | 0 | 2 | 3.47 | 349.8 | 349.3 |
| B-41 | CF₂CHF₂ | C | H | OCH₂CH₃ | H | H | H | H | H | CH₃ | H | H | 0 | 2 | 3.48 | 349.8 | 349.3 |
| B-42 | CF₂CHF₂ | C | H | CH₃ | H | H | CH₃ | H | H | CH₃ | H | H | 0 | 2 | 3.73 | 363.7 | 363.4 |
| B-43 | CF₃ | C | H | CH₃ | Y3—CH=CH—CH=CH—Y4 | | COOH | H | H | H | H | H | 0 | 2 | 2.16 | 368.1 | 367.3 |
| B-44 | CF₃ | C | H | H | Y3—CH=CH—O—Y4 | | =O | | | | | H | 0 | 2 | 2.83 | 314.1 | 313.2 |
| B-45 | C₂F5 | C | H | H | Y3—CH=CH—O—Y4 | | =O | | | | | H | 0 | 2 | 3.25 | 364.1 | 363.2 |
| B-46 | CF₂CHF₂ | C | H | H | Y3—CH=CH—O—Y4 | | =O | | | | | H | 0 | 2 | 2.93 | 346.1 | 345.3 |
| B-47 | CHF₂ | C | H | H | Y3—CH=CH—O—Y4 | | =O | | | | | H | 0 | 2 | 2.49 | 296.1 | 295.2 |

TABLE B-continued (X = CO; R² = H; R³ = H; Y² , Y³ , Y⁴ = C)

| No | R¹ | Y¹ | R¹² | R¹³ | R¹⁴ | R¹⁵ | R⁴ | R⁵ | R⁶ᵃ | R⁷ᵃ | R⁶ᵇ | R⁷ᵇ | | | | Synth. Method |
|---|---|---|---|---|---|---|---|---|---|---|---|---|---|---|---|---|
| B-48 | CF₃ | C | H | H | Y3—CH=CH—CH=CH—Y4 | H | H | H | H | phenyl | H | 0 | 2 | 4.01 | 400.2 | 2A-E; 12A-B; 2H |
| B-49 | CF₃ | C | H | H | Y3—CH=CH—CH=CH—Y4 | H | H | H | H | benzyl | H | 0 | 2 | 4.19 | 414.2 | 2A-E; 8A, 12A-B; 2H |
| B-50 | CH3 | C | H | CH3 | H | H | H | H | H | —CH₂— | —CH₂— | 1 | 2 | 2.96 | 258.2 | 2A-E; 12A-B; 2H |
| B-51 | CF₃ | C | H | OCH₂CH₃ | H | H | H | H | CH₃ | CH₃ | H | H | | | | 2A-E; 12A-B; 2H |
| B-52 | CF₃ | C | H | OCH₂CH₃ | H | H | CH₃ | H | H | H | H | H | | | | 2A-E; 8A; 12A-B; 2H |
| B-53 | CF₃ | C | H | CH₃ | CH₃ | H | H | H | CH₃ | CH₃ | H | H | | | | 2A-E; 12A-B; 2H |
| B-54 | CF₃ | C | H | CH₃ | CH₃ | H | CH₃ | H | CH₃ | H | H | H | | | | 2A-E; 12A-B; 2H |
| B-55 | CF₃ | C | H | CH₃ | CH₃ | H | H | H | CH₃ | CH₃ | H | H | | | | 2A-E; 8A,12B; 2H |
| B-56 | CF₃ | C | H | CH₃ | CH₃ | H | CH₃ | H | CO₂CH₃ | H | H | H | | | | 2A-E; 12B; 2H |
| B-57 | CF₃ | N | — | H | CH₃ | CH₂CH₃ | H | H | CH₃ | CH₃ | H | H | | | | 2A-E; 17A, 12B; 2H |
| B-58 | CF₃ | N | — | H | CH₃ | CH₂CH₃ | CH₃ | H | H | H | H | H | | | | 2A-E; 17A, 12B; 2H |
| B-59 | CF₃ | C | H | CH₃ | Y3—CH=CH—CH=CH—Y4 | H | H | H | CH₃ | CH₃ | H | H | | | | 2A-E; 8A, 12B; 2H |
| B-60 | CF₃ | C | H | CH₃ | Y3—CH=CH—CH=CH—Y4 | H | CH₃ | H | H | H | H | H | | | | 2A-E; 8A, 12B; 2H |
| B-61 | CF₃ | C | H | CH₃ | Y3—CH=CH—CH=CH—Y4 | H | H | H | CO₂CH₃ | H | H | H | | | | 2A-E; 8A, 12B; 2H |
| B-62 | CHF₂ | C | H | OCH₂CH₃ | H | H | H | H | CH₃ | CH₃ | H | H | | | | 2A-E; 12A-B; 2H |
| B-63 | CHF₂ | C | H | OCH₂CH₃ | H | H | CH₃ | H | H | H | H | H | | | | 10F-I; 12A-B; 2H |
| B-64 | CHF₂ | C | H | CH₃ | H | H | H | H | CH₂CH₃ | H | H | H | | | | 10F-I; 8A, 12A-B; 2H |
| B-65 | CHF₂ | C | H | CH₃ | CH₃ | H | H | H | H | H | CH₂CH₃ | H | | | | 10F-I; 12A-B; 2H |
| B-66 | CHF₂ | C | H | CH₃ | CH₃ | H | H | H | CH₃ | CH₃ | H | H | | | | 10F-I; 12A-B; 2H |
| B-67 | CHF₂ | C | H | CH₃ | CH₃ | H | CH₃ | H | CH₃ | H | CH₃ | H | | | | 10F-I; 8A, 12A-B; 2H |
| B-68 | CHF₂ | C | H | CH₃ | CH₃ | H | H | H | CH₂CH₃ | H | CH₃ | CH₃ | | | | 10F-I; 12A-B; 2H |
| B-69 | CHF₂ | C | H | CH₃ | CH₃ | H | CH₃ | H | H | H | CH₃ | H | | | | 10F-I; 12A-B; 2H |
| B-70 | CHF₂ | C | H | CH₃ | CH₃ | H | H | H | CH₃ | CH₃ | H | H | | | | 10F-I; 8A, 12A-B; 2H |
| B-71 | CHF₂ | C | H | CH₃ | CH₃ | CH₂CH₃ | H | H | CO₂CH₃ | H | H | H | | | | 10F-I; 12A-B; 2H |
| B-72 | CHF₂ | N | — | H | CH₃ | CH₂CH₃ | H | H | CH₂CH₃ | H | CH₂CH₃ | H | | | | 10F-I; 17A, 12B; 2H |
| B-73 | CHF₂ | N | — | H | CH₃ | CH₂CH₃ | H | H | H | H | H | CH₃ | | | | 10F-I; 17A, 12B; 2H |
| B-74 | CHF₂ | N | — | H | CH₃ | CH₂CH₃ | CH₃ | H | CH₃ | H | CH₃ | H | | | | 10F-I; 17A, 12B; 2H |
| B-75 | CHF₂ | N | — | H | CH₃ | CH₂CH₃ | H | H | CH₃ | H | CH₃ | H | | | | 10F-I; 17A, 12B; 2H |
| B-76 | CHF₂ | N | — | H | CH₃ | CH₂CH₃ | H | H | H | H | CH₃ | H | | | | 10F-I; 17A, 12B; 2H |
| B-77 | CHF₂ | N | — | H | CH₃ | CH₂CH₃ | CH₃ | H | CH₃ | H | CH₃ | CH₃ | | | | 10F-I; 17A, 12B; 2H |
| B-78 | CHF₂ | N | — | H | CH₃ | CH₂CH₃ | H | H | CO₂CH₃ | H | H | H | | | | 10F-I; 17A, 12B; 2H |
| B-79 | CHF₂ | C | H | CH₃ | Y3—CH=CH—CH=CH—Y4 | H | H | H | CH₂CH₃ | H | CH₂CH₃ | H | | | | 10F-I; 12A-B; 2H |
| B-80 | CHF₂ | C | H | CH₃ | Y3—CH=CH—CH=CH—Y4 | H | H | H | H | H | H | CH₃ | | | | 10F-I; 8A, 12B; 2H |
| B-81 | CHF₂ | C | H | CH₃ | Y3—CH=CH—CH=CH—Y4 | H | CH₃ | H | CH₃ | H | CH₃ | H | | | | 10F-I; 8A, 12B; 2H |
| B-82 | CHF₂ | C | H | CH₃ | Y3—CH=CH—CH=CH—Y4 | H | H | H | CH₃ | H | CH₃ | H | | | | 10F-I; 8A, 12B; 2H |
| B-83 | CHF₂ | C | H | CH₃ | Y3—CH=CH—CH=CH—Y4 | H | H | H | H | H | CH₃ | H | | | | 10F-I; 8A, 12B; 2H |
| B-84 | CHF₂ | C | H | CH₃ | Y3—CH=CH—CH=CH—Y4 | H | CH₃ | H | CH₃ | H | CH₃ | CH₃ | | | | 10F-I; 8A, 12B; 2H |
| B-85 | CHF₂ | C | H | CH₃ | Y3—CH=CH—CH=CH—Y4 | H | H | H | CO₂CH₃ | H | H | H | | | | 10F-I; 8A, 12B; 2H |
| B-86 | CHF₂ | C | H | CH₃ | H | CH₂CH₃ | H | H | CH₂CH₃ | H | CH₂CH₃ | H | | | | 10F-I; 12A-B; 2H |
| B-87 | CHF₂ | C | H | CH₃ | H | CH₂CH₃ | CH₃ | H | H | H | H | H | | | | 10F-I; 8A, 12B; 2H |
| B-88 | CF₂CF₃ | C | H | OCH₂CH₃ | H | H | H | H | CH₃ | CH₃ | H | H | | | | 2A-E; 12A-B; 2H |
| B-89 | CF₂CF₃ | C | H | OCH₂CH₃ | H | H | CH₃ | H | CH₃ | H | H | H | | | | 2A-E; 8A,12B; 2H |
| B-90 | CF₂CF₃ | C | H | CH₃ | CH₃ | H | H | H | H | H | CH₂CH₃ | H | | | | 2A-E; 12A-B; 2H |
| B-91 | CF₂CF₃ | C | H | CH₃ | CH₃ | H | H | H | CH₃ | CH₃ | H | H | | | | 2A-E; 12A-B; 2H |
| B-92 | CF₂CF₃ | C | H | CH₃ | CH₃ | H | CH₃ | H | H | H | H | H | | | | 2A-E; 12A-B; 2H |
| B-93 | CF₂CF₃ | C | H | CH₃ | CH₃ | H | H | H | CH₃ | H | CH₃ | H | | | | 2A-E; 8A, 12B; 2H |

TABLE B-continued (X = CO; R² = H; R³ = H; Y², Y³, Y⁴ = C)

| | | | | | | | | | |
|---|---|---|---|---|---|---|---|---|---|
| B-94 | CF₂CF₃ | C | H | CH₃ | CH₃ | H | H | CH₃ | 2A-E; 8A, 12B; 2H |
| B-95 | CF₂CF₃ | C | H | CH₃ | CH₃ | H | CH₃ | H | 2A-E; 12A-B; 2H |
| B-96 | CF₂CF₃ | C | H | CH₃ | CH₃ | CH₃ | H | H | 2A-E; 8A, 12B; 2H |
| B-97 | CF₂CF₃ | C | H | CH₃ | CH₃ | H | CO₂CH₃ | H | 2A-E; 12A-B; 2H |
| B-98 | CF₂CF₃ | N | — | CH₃ | H | H | CH₂CH₃ | H | 2A-E; 17A, 12B; 2H |
| B-99 | CF₂CF₃ | N | — | CH₃ | CH₂CH₃ | H | H | H | 2A-E; 17A, 12B; 2H |
| B-100 | CF₂CF₃ | N | — | CH₃ | CH₂CH₃ | H | CH₃ | H | 2A-E; 17A, 12B; 2H |
| B-101 | CF₂CF₃ | N | — | CH₃ | CH₂CH₃ | H | H | CH₃ | 2A-E; 17A, 12B; 2H |
| B-102 | CF₂CF₃ | N | — | CH₃ | CH₂CH₃ | H | CH₃ | H | 2A-E; 17A, 12B; 2H |
| B-103 | CF₂CF₃ | N | — | CH₃ | CH₂CH₃ | CH₃ | H | H | 2A-E; 17A, 12B; 2H |
| B-104 | CF₂CF₃ | N | — | CH₃ | CH₂CH₃ | H | CO₂CH₃ | H | 2A-E; 17A, 12B; 2H |
| B-105 | CF₂CF₃ | N | — | CH₃ | CH₂CH₃ | H | H | CH₃ | 2A-E; 12A-B; 2H |
| B-106 | CF₂CF₃ | C | H | CH₃ | Y3—CH=CH—CH=CH—Y4 | H | CO₂CH₃ | H | 2A-E; 8A, 12B; 2H |
| B-107 | CF₂CF₃ | C | H | OCH₂CH₃ | Y3—CH=CH—CH=CH—Y4 | H | CH₂CH₃ | H | 2A-E; 8A, 12B; 2H |
| B-108 | CF₂CF₃ | C | H | CH₃ | Y3—CH=CH—CH=CH—Y4 | H | H | H | 2A-E; 8A, 12B; 2H |
| B-109 | CF₂CF₃ | C | H | CH₃ | Y3—CH=CH—CH=CH—Y4 | H | CH₃ | H | 2A-E; 8A, 12B; 2H |
| B-110 | CF₂CF₃ | C | H | CH₃ | Y3—CH=CH—CH=CH—Y4 | H | H | CH₃ | 2A-E; 8A, 12B; 2H |
| B-111 | CF₂CF₃ | C | H | CH₃ | Y3—CH=CH—CH=CH—Y4 | H | CH₃ | H | 2A-E; 8A, 12B; 2H |
| B-112 | CF₂CF₃ | C | H | CH₃ | Y3—CH=CH—CH=CH—Y4 | CH₃ | H | H | 2A-E; 8A, 12B; 2H |
| B-113 | CF₂CF₃ | C | H | CH₃ | H | CH₃ | CH₃ | H | 2A-E; 12A-B; 2H |
| B-114 | CF₂CHF₂ | C | — | OCH₂CH₃ | CH₃ | H | H | H | 2A-E; 8A, 12B; 2H |
| B-115 | CF₂CHF₂ | C | — | OCH₂CH₃ | H | H | CH₂CH₃ | H | 2A-E; 8A, 12B; 2H |
| B-116 | CF₂CHF₂ | C | H | CH₃ | CH₃ | H | H | H | 2A-E; 8A, 12B; 2H |
| B-117 | CF₂CHF₂ | C | H | CH₃ | CH₃ | H | CH₃ | H | 2A-E; 12A-B; 2H |
| B-118 | CF₂CHF₂ | C | H | CH₃ | CH₃ | H | H | CH₃ | 2A-E; 8A, 12B; 2H |
| B-119 | CF₂CHF₂ | C | H | CH₃ | CH₃ | H | CH₃ | H | 2A-E; 12A-B; 2H |
| B-120 | CF₂CHF₂ | C | H | CH₃ | CH₃ | CH₃ | H | H | 2A-E; 8A, 12B; 2H |
| B-121 | CF₂CHF₂ | C | H | CH₃ | CH₃ | H | CO₂CH₃ | H | 2A-E; 8A, 12B; 2H |
| B-122 | CF₂CHF₂ | C | H | CH₃ | CH₃ | H | CH₂CH₃ | H | 2A-E; 8A, 12B; 2H |
| B-123 | CF₂CHF₂ | C | H | CH₃ | CH₃ | CH₃ | CH₃ | H | 2A-E; 12A-B; 2H |
| B-124 | CF₂CHF₂ | C | H | CH₃ | CH₃ | CH₃ | H | H | 2A-E; 8A, 12B; 2H |
| B-125 | CF₂CHF₂ | N | — | H | CH₃ | H | CH₂CH₃ | H | 2A-E; 17A, 12B; 2H |
| B-126 | CF₂CHF₂ | N | — | H | CH₃ | H | CH₃ | H | 2A-E; 17A, 12B; 2H |
| B-127 | CF₂CHF₂ | N | — | H | CH₃ | H | H | H | 2A-E; 17A, 12B; 2H |
| B-128 | CF₂CHF₂ | N | — | H | CH₃ | H | CH₃ | H | 2A-E; 17A, 12B; 2H |
| B-129 | CF₂CHF₂ | N | — | H | CH₃ | H | H | CH₃ | 2A-E; 17A, 12B; 2H |
| B-130 | CF₂CHF₂ | N | — | H | CH₃ | H | CH₃ | H | 2A-E; 17A, 12B; 2H |
| B-131 | CF₂CHF₂ | N | — | H | CH₃ | CH₃ | H | H | 2A-E; 17A, 12B; 2H |
| B-132 | CF₂CHF₂ | N | — | H | CH₃ | H | CO₂CH₃ | H | 2A-E; 17A, 12B; 2H |
| B-133 | CF₂CHF₂ | C | H | CH₃ | Y3—CH=CH—CH=CH—Y4 | H | CH₂CH₃ | H | 2A-E; 12A-B; 2H |
| B-134 | CF₂CHF₂ | C | H | CH₃ | Y3—CH=CH—CH=CH—Y4 | H | H | H | 2A-E; 8A, 12B; 2H |
| B-135 | CF₂CHF₂ | C | H | CH₃ | Y3—CH=CH—CH=CH—Y4 | H | CH₃ | H | 2A-E; 8A, 12B; 2H |
| B-136 | CF₂CHF₂ | C | H | CH₃ | Y3—CH=CH—CH=CH—Y4 | H | H | CH₃ | 2A-E; 8A, 12B; 2H |
| B-137 | CF₂CHF₂ | C | H | CH₃ | Y3—CH=CH—CH=CH—Y4 | H | CH₃ | H | 2A-E; 8A, 12B; 2H |
| B-138 | CF₂CHF₂ | C | H | CH₃ | Y3—CH=CH—CH=CH—Y4 | CH₃ | H | H | 2A-E; 8A, 12B; 2H |
| B-139 | CF₂CHF₂ | C | H | CH₃ | Y3—CH=CH—CH=CH—Y4 | H | CO₂CH₃ | H | 2A-E; 8A, 12B; 2H |
| B-140 | CF₂CHF₂ | C | H | CH₃ | H | CH₃ | CH₃ | H | 2A-E; 12A-B; 2H |
| B-141 | CF₂CH₃ | C | H | OCH₂CH₃ | H | H | CH₂CH₃ | H | 10F-I; 12A-B; 2H |
| B-142 | CF₂CH₃ | C | H | OCH₂CH₃ | H | H | CH₂CH₃ | H | 10F-I; 8A, 12B; 2H |

TABLE B-continued (X = CO; R² = H; R³ = H; Y², Y³, Y⁴ = C)

| | | | | | | | | | | | |
|---|---|---|---|---|---|---|---|---|---|---|---|
| B-143 | CF₂CH₃ | H | C | OCH₂CH₃ | CH₃ | | H | CH₃ | H | H | 10F-I; 12A-B; 2H |
| B-144 | CF₂CH₃ | H | C | OCH₂CH₃ | CH₃ | | H | H | H | H | 10F-I; 8A, 12A-B; 2H |
| B-145 | CF₂CH₃ | H | C | OCH₂CH₃ | CH₃ | | H | CH₃ | H | CH₃ | 10F-I; 12A-B; 2H |
| B-146 | CF₂CH₃ | H | C | OCH₂CH₃ | CH₃ | | CH₃ | CH₃ | H | H | 10F-I; 8A, 12A-B; 2H |
| B-147 | CF₂CH₃ | H | C | OCH₂CH₃ | CH₃ | | H | H | CH₃ | H | 10F-I; 12A-B; 2H |
| B-148 | CF₂CH₃ | H | C | CH₃ | CH₃ | | H | CO₂CH₃ | H | H | 10F-I; 12A-B; 2H |
| B-149 | CF₂CH₃ | H | C | CH₃ | CH₃ | | H | CH₂CH₃ | CH₂CH₃ | H | 10F-I; 12A-B; 2H |
| B-150 | CF₂CH₃ | H | C | CH₃ | CH₃ | | H | H | CH₃ | H | 10F-I; 12A-B; 2H |
| B-151 | CF₂CH₃ | H | C | CH₃ | CH₃ | | H | CH₃ | CH₃ | H | 10F-I; 8A, 12A-B; 2H |
| B-152 | CF₂CH₃ | H | C | CH₃ | CH₃ | | H | CH₃ | H | CH₃ | 10F-I; 12A-B; 2H |
| B-153 | CF₂CH₃ | H | C | CH₃ | CH₃ | | CH₃ | CH₃ | H | H | 10F-I; 8A, 12A-B; 2H |
| B-154 | CF₂CH₃ | H | C | CH₃ | CH₃ | | H | H | CH₃ | H | 10F-I; 12A-B; 2H |
| B-155 | CF₂CH₃ | H | C | CH₃ | CH₃ | | CH₃ | CO₂CH₃ | H | H | 10F-I; 12A-B; 2H |
| B-156 | CF₂CH₃ | H | C | CH₃ | CH₃ | | H | CH₂CH₃ | H | H | 10F-I; 12A-B; 2H |
| B-157 | CF₂CH₃ | — | N | H | CH₃ | | H | H | H | H | 10F-I; 17A, 12B; 2H |
| B-158 | CF₂CH₃ | — | N | H | CH₃ | | H | CH₃ | H | CH₃ | 10F-I; 17A, 12B; 2H |
| B-159 | CF₂CH₃ | — | N | H | CH₃ | | H | H | CH₃ | H | 10F-I; 17A, 12B; 2H |
| B-160 | CF₂CH₃ | — | N | H | CH₃ | | H | CH₃ | H | H | 10F-I; 17A, 12B; 2H |
| B-161 | CF₂CH₃ | — | N | H | CH₃ | | H | CH₃ | CH₃ | H | 10F-I; 17A, 12B; 2H |
| B-162 | CF₂CH₃ | — | N | H | CH₃ | | H | CO₂CH₃ | H | H | 10F-I; 17A, 12B; 2H |
| B-163 | CF₂CH₃ | — | N | H | CH₃ | | CH₃ | CH₂CH₃ | H | CH₃ | 10F-I; 17A, 12B; 2H |
| B-164 | CF₂CH₃ | — | N | H | CH₃ | | H | H | H | H | 10F-I; 12A-B; 2H |
| B-165 | CF₂CH₃ | H | C | CH₃ | Y3—CH=CH—CH=CH—Y4 | CH₂CH₃ | H | CH₃ | H | H | 10F-I; 8A, 12B; 2H |
| B-166 | CF₂CH₃ | H | C | CH₃ | Y3—CH=CH—CH=CH—Y4 | CH₂CH₃ | H | CH₂CH₃ | H | H | 10F-I; 8A, 12B; 2H |
| B-167 | CF₂CH₃ | H | C | CH₃ | Y3—CH=CH—CH=CH—Y4 | CH₂CH₃ | H | CH₃ | H | CH₃ | 10F-I; 8A, 12B; 2H |
| B-168 | CF₂CH₃ | H | C | CH₃ | Y3—CH=CH—CH=CH—Y4 | CH₂CH₃ | H | H | H | H | 10F-I; 8A, 12B; 2H |
| B-169 | CF₂CH₃ | H | C | CH₃ | Y3—CH=CH—CH=CH—Y4 | CH₂CH₃ | H | CH₃ | H | H | 10F-I; 8A, 12B; 2H |
| B-170 | CF₂CH₃ | H | C | CH₃ | Y3—CH=CH—CH=CH—Y4 | CH₂CH₃ | H | CH₂CH₃ | H | H | 10F-I; 8A, 12B; 2H |
| B-171 | CF₂CH₃ | H | C | CH₃ | Y3—CH=CH—CH=CH—Y4 | CH₂CH₃ | H | H | CH₃ | H | 10F-I; 8A, 12B; 2H |
| B-172 | CF₂CH₃ | H | C | CH₃ | Y3—CH=CH—CH=CH—Y4 | CH₂CH₃ | H | CH₃ | H | H | 10F-I; 12A-B; 2H |
| B-173 | CH₂OCH₃ | H | C | OCH₂CH₃ | CH₃ | | H | CH₃ | H | H | 12A-B; 2H |
| B-174 | CH₂OCH₃ | H | C | OCH₂CH₃ | CH₃ | | H | H | H | H | 8A, 12B; 2H |
| B-175 | CH₂OCH₃ | H | C | OCH₂CH₃ | CH₃ | | H | CH₃ | H | CH₃ | 8A, 12B; 2H |
| B-176 | CH₂OCH₃ | H | C | OCH₂CH₃ | CH₃ | | CH₃ | CH₃ | H | H | 8A, 12B; 2H |
| B-177 | CH₂OCH₃ | H | C | OCH₂CH₃ | CH₃ | | H | H | CH₃ | H | 12A-B; 2H |
| B-178 | CH₂OCH₃ | H | C | CH₃ | CH₃ | | H | CO₂CH₃ | H | H | 12A-B; 2H |
| B-179 | CH₂OCH₃ | H | C | CH₃ | CH₃ | | H | CH₂CH₃ | CH₂CH₃ | H | 8A, 12B; 2H |
| B-180 | CH₂OCH₃ | H | C | CH₃ | CH₃ | | H | H | CH₃ | H | 12A-B; 2H |
| B-181 | CH₂OCH₃ | H | C | CH₃ | CH₃ | | CH₃ | CH₃ | H | H | 8A, 12B; 2H |
| B-182 | CH₂OCH₃ | H | C | CH₃ | CH₃ | | H | CH₃ | H | CH₃ | 12A-B; 2H |
| B-183 | CH₂OCH₃ | H | C | CH₃ | CH₃ | | CH₃ | CH₃ | H | H | 8A, 12B; 2H |
| B-184 | CH₂OCH₃ | H | C | CH₃ | CH₃ | | H | H | CH₃ | H | 12A-B; 2H |
| B-185 | CH₂OCH₃ | H | C | CH₃ | CH₃ | | CH₃ | CO₂CH₃ | H | H | 8A, 12B; 2H |
| B-186 | CH₂OCH₃ | H | C | CH₃ | CH₃ | | H | CH₂CH₃ | H | H | 8A, 12B; 2H |
| B-187 | CH₂OCH₃ | H | C | H | CH₃ | | CH₃ | H | H | H | 12A-B; 2H |
| B-188 | CH₂OCH₃ | H | C | H | CH₃ | | H | CO₂CH₃ | H | H | 12A-B; 2H |
| B-189 | CH₂OCH₃ | — | N | H | CH₃ | CH₂CH₃ | H | CH₂CH₃ | H | H | 17A, 12B; 2H |
| B-190 | CH₂OCH₃ | — | N | H | CH₃ | CH₂CH₃ | H | H | H | CH₂CH₃ | 17A, 12B; 2H |

TABLE B-continued (X = CO; R² = H; R³ = H; Y², Y³, Y⁴ = C)

| No. | | | | | | | | | | | |
|---|---|---|---|---|---|---|---|---|---|---|---|
| B-191 | $CH_2OCH_3$ | N | — | $CH_3$ | $CH_2CH_3$ | H | H | H | H | H | 17A, 12B; 2H |
| B-192 | $CH_2OCH_3$ | N | — | $CH_3$ | $CH_2CH_3$ | H | H | $CH_3$ | $CH_3$ | H | 17A, 12B; 2H |
| B-193 | $CH_2OCH_3$ | N | — | $CH_3$ | $CH_2CH_3$ | H | H | $CH_3$ | $CH_3$ | $CH_3$ | 17A, 12B; 2H |
| B-194 | $CH_2OCH_3$ | N | — | $CH_3$ | $CH_2CH_3$ | $CH_3$ | $CH_3$ | H | H | H | 17A, 12B; 2H |
| B-195 | $CH_2OCH_3$ | N | — | $CH_3$ | $CH_2CH_3$ | H | H | H | H | H | 17A, 12B; 2H |
| B-196 | $CH_2OCH_3$ | N | — | $CH_3$ | $CH_2CH_3$ | H | $CO_2CH_3$ | H | H | H | 12A-B; 2H |
| B-197 | $CH_2OCH_3$ | C | H | Y3—CH=CH—CH=CH—Y4 | $CH_3$ | H | $CH_3$ | H | $CH_2CH_3$ | H | 8A, 12B; 2H |
| B-198 | $CH_2OCH_3$ | C | H | Y3—CH=CH—CH=CH—Y4 | $CH_3$ | H | H | H | H | H | 8A, 12B; 2H |
| B-199 | $CH_2OCH_3$ | C | H | Y3—CH=CH—CH=CH—Y4 | $CH_3$ | H | $CH_3$ | $CH_3$ | $CH_3$ | H | 8A, 12B; 2H |
| B-200 | $CH_2OCH_3$ | C | H | Y3—CH=CH—CH=CH—Y4 | $CH_3$ | H | H | $CH_3$ | $CH_3$ | $CH_3$ | 8A, 12B; 2H |
| B-201 | $CH_2OCH_3$ | C | H | Y3—CH=CH—CH=CH—Y4 | $CH_3$ | $CH_3$ | $CH_3$ | $CH_3$ | H | H | 8A, 12B; 2H |
| B-202 | $CH_2OCH_3$ | C | H | Y3—CH=CH—CH=CH—Y4 | $CH_3$ | H | H | H | H | H | 8A, 12B; 2H |
| B-203 | $CH_2OCH_3$ | C | H | Y3—CH=CH—CH=CH—Y4 | $CH_3$ | H | $CO_2CH_3$ | H | H | H | 8A, 12B; 2H |
| B-204 | $CH_2OCH_3$ | C | H | Y3—CH=CH—CH=CH—Y4 | $CH_3$ | H | H | H | H | H | 8A, 12B; 2H |

Further examples of specific compounds of the present invention include each of the compounds of table B above wherein X=SO$_2$ instead of CO and each of the compounds of table B wherein X=CS instead of CO.

Further examples of specific compounds of the present invention include each of the compounds in table B and analogues wherein X=SO$_2$ or wherein X=CS, in form of its pyridine-N-oxide.

E Biological Examples

Determining Activity Against *Ascaridia galli* and *Oesophagostomum dentatum*

Anthelmintic effects of compounds of this invention were tested in vitro using gut-welling larval stages of two parasitic nematode species: *Ascaridia galli* (intestinal roundworm of chicken), larval stage 3 ("L3"); and *Oesophagostumum dentatum* (nodular worm of swine), larval stages 3 and 4 (respectively "L3" and "L4"). When conducting these experiments, DMSO-solutions of various concentrations of compounds of this invention were prepared and incubated in 96-well microtiter plates. The parasites were then distributed at 20 larvae per well. The anthelmintic effects were classified by microscopic examination. The microscopic examination included assessing mortality, damage, motility, progression of development, and neutral red uptake by the larvae in comparison to a DMSO-control. The anthelmintic effects were defined by the minimum effective concentration ("MEC"), which is the concentration by which at least one of the larvae shows mortality, damage, change in motility, change in progression of development, or no neutral red uptake. The following compounds showed at least some activity against one or more of the nematodes at an MEC of 50 µM or less: A-1-A-5, A-7-A-9, A-11-A-14, A-17, A-19-A-22, A-25-A-27, A-29-A-31, A-33-A-35, A-41-A-44, A-46-A-52, A-55-A-56, A-60-A-75, A-78-A-81, A-83, A-86-A-89, A-91-A-92, A-95-A-100, A-102-A-103, A-105-A-107, A-111, A-113-A-119, A-121-A-123, A-125, A-129-A153, A-156-A-159, A-163, A-166-A-168, A-170-A-180, A-182-A-187, A-189-A-190, A-192-A-206, A-210-A-226, A-229, A-231-A-234, A-236-A-248, A-251-A-255, A-257-A-267, A-269-A-276, A-279-A-290, A-292-A-296, A-298-A-303, A-305-A-329, A-331, A-333-A-352, A-354-A-393, A-395-A-404, A-406-A-413, A-415-A-421, A-428-A-429, A-431-A-432, A-434-A-437, A-440-A-446, Aa2, Aa3, Aa5, B-1-B-9, B-11-B-19, B-21-B-49.

F Formulation Examples

Formulation A: 5% Suspension:
  4.5 g of compound A (a compound according to this invention, but which may be any compound in line with the invention) was dissolved in DMSO, the resulting solution was mixed with a 0.1% solution of methyl cellulose in isotonic NaCl to give a homogeneous suspension of compound A (5% by weight).

Formulation B: 0.5% Suspension:
  18.6 mg of compound B (a compound according to this invention, but which may be any compound in line with the invention) was dissolved in DMSO, the resulting solution was mixed with a 0.1% solution of methyl cellulose in isotonic NaCl to give a homogeneous suspension of compound B (0.5% by weight).

Formulation C: 5% Solution:
  0.25 g of Compound C (a compound according to this invention, but which may be any compound in line with the invention) was dissolved in 1-methyl-2-pyrrolidinone (3.25 ml). 1,2-Propanediol (0.75 ml) and water was added until a total volume of 5.0 ml was reached to give a homogeneous solution with a content by weight of 5% compound C.

The formulations can be used i.a. for parenteral and oral administration to animals, e.g. sheep or cattle.

DEFINITIONS

The term "acyl" (alone or in combination with (an)other term(s)) means a the radical derived from an oxo acid, preferably from a carboxylic acid, by removal of the OH-group. Preferred acyl groups have the formula R—CO, wherein R is H or an aromatic or heteroaromatic ring, preferably of 4 to 10 ring atoms, or an aliphatic hydrocarbon radical, preferably of 1 to 10 carbon atoms, more preferred are unsubstituted or substituted alkyl of 1 to 6 carbon atoms.

The term "alkyl" (alone or in combination with (an)other term(s)) means a straight-chain or branched-chain saturated hydrocarbyl substituent (i.e., a substituent containing only carbon and hydrogen) which unless otherwise specified typically contains from 1 to 6 carbon atoms, and even more typically from 1 to about 4 carbon atoms. Examples of such substituents include methyl, ethyl, n-propyl, isopropyl, n-butyl, iso-butyl, sec-butyl, tert-butyl, pentyl, iso-pentyl, hexyl, and octyl. For instance the term "$C_1$-$C_6$-alkyl" includes but is not limited to methyl, ethyl, n-propyl, isopropyl, n-butyl, iso-butyl, sec-butyl, tert-butyl, n-pentyl, iso-pentyl, neo-pentyl, n-hexyl, iso-hexyl.

The term "alkenyl" (alone or in combination with (an)other term(s)) means a straight- or branched-chain hydrocarbyl substituent containing one or more double bonds and unless otherwise specified typically contains from 2 to 6 carbon atoms, even more typically from 2 to 4 carbon atoms. Examples of such substituents include ethenyl (vinyl); 2-propenyl; 3-propenyl; 1,4-pentadienyl; 1,4-butadienyl; 1-butenyl; 2-butenyl; 3-butenyl; and 2-hexenyl.

The term "alkynyl" (alone or in combination with (an)other term(s)) means a straight- or branched-chain hydrocarbyl substituent containing one or more triple bonds and unless otherwise specified typically from 2 to 6 atoms, even more typically from 2 to 4 carbon atoms. Examples of such substituents include ethynyl, 2-propynyl, 3-propynyl, 1-butynyl, 2-butynyl, 3-butynyl, and 2-hexynyl.

The term "cycloalkyl" (alone or in combination with (an) other term(s)) means a cyclic saturated hydrocarbyl substituent (i.e., a substituent containing only carbon and hydrogen) which unless otherwise specified typically contains from 3 to 8 carbon atoms. The cycle or ring in the "cycloalkyl" substituent may be formed by all carbon atoms of the substituent, or may be formed by some, but not all of the carbon atoms of the substituent. In the latter case, the substituent may be connected at a carbon atom that is part of a cycle or that is not part of a cycle. Examples of such substituents include cyclopropyl, cyclobutyl, cyclopentyl, cyclohexyl, cycloheptyl, 2-methylcyclopropyl, cyclopropylmethyl, cyclohexylmethyl.

The term "halogen" (alone or in combination with (an) other term(s)) means a fluorine radical ("fluoro", which may be depicted as F), chlorine radical ("chloro", which may be depicted as Cl), bromine radical ("bromo", which may be depicted as Br), or iodine radical ("iodo", which may be depicted as I). Typically, fluoro or chloro is preferred.

When a chemical formula is used to describe a monovalent substituent, the dash on the left side of the formula indicates the portion of the substituent that has the free valence. To illustrate, benzene substituted with —C(O)—OH has the following structure:

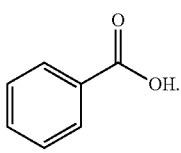

When a chemical formula is used to describe a di-valent (or "linking") component between two other components of a depicted chemical structure (the right and left components), the leftmost dash of the linking component indicates the portion of the linking component that is bound to the left component in the depicted structure. The rightmost dash, on the other hand, indicates the portion of the linking component that is bound to the right component in the depicted structure.

The term "pharmaceutically acceptable" is used adjectivally to mean that the modified noun is appropriate for use in a pharmaceutical product. When it is used, for example, to describe a salt, solvate, N-oxide, active compound or excipient, it characterizes the salt, solvate, N-oxide, active compound or excipient as being compatible with the other ingredients of the composition, and not deleterious to the intended recipient animal, e.g. to the extent that the benefit(s) outweigh(s) the deleterious effect(s).

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

The invention claimed is:

1. A compound of the formula (I) or pharmaceutically acceptable salts, or N-oxides thereof,

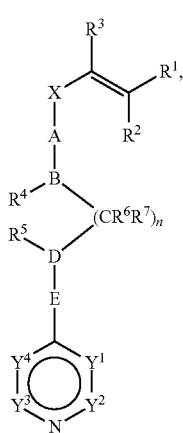

Formula (I)

wherein $R^1$ is halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_2$-$C_6$-alkenyl carbonyl, $SF_5$, $C_1$-$C_6$-alkyl sulfonyl, wherein each of the carbon-containing radicals optionally is substituted by one or more halogen atoms, $R^2$ is hydrogen, halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkyl, $C_1$-$C_6$-alkylthio $C_1$-$C_6$-alkyl, $C_1$-$C_6$-alkyl carbonyl, $C_2$-$C_6$-alkenyl carbonyl, wherein each of the carbon-containing radicals optionally is substituted by one or more halogen atoms, $R^3$ is hydrogen, $C_1$-$C_6$-alkyl or cycloalkyl, $R^4$ is hydrogen, $C_1$-$C_6$-alkyl or cycloalkyl, $R^5$ is hydrogen, $C_1$-$C_6$-alkyl, cycloalkyl, acyl, cycloalkyloxycarbony or $C_1$-$C_6$-alkyloxycarbonyl, $R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy, cycloalkyloxy or $C_1$-$C_6$-alkyloxy, $R^7$ is hydrogen, $C_1$-$C_6$-alkyl or cycloalkyl, or $R^6$ is joined together with $R^8$ to form a $C_1$-$C_3$-alkylene group and $R^7$ is joined together with $R^9$ to form a $C_1$-$C_3$-alkylene group, wherein one or both of said $C_1$-$C_3$-alkylene groups are optionally substituted by one or more $C_1$-$C_6$-alkyl or cycloalkyl radicals, n is an integer from 1 to 3, X is a carbonyl, thiocarbonyl or sulfonyl group, A is a bond or $NR^8$, wherein $R^8$ is hydrogen or $C_1$-$C_6$-alkyl, E is a bond or $NR^9$, wherein $R^9$ is hydrogen or $C_1$-$C_6$-alkyl, B is N or $CR^{10}$, wherein $R^{10}$ is hydrogen or $C_1$-$C_6$-alkyl, D is N or $CR^{11}$, wherein $R^{11}$ is hydrogen or $C_1$-$C_6$-alkyl, $Y^1$=C—$R^{12}$, wherein $R^{12}$ is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, C1-C6-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane, dioxane, or dioxepane, wherein each ring is unsubstituted or substituted by $C_1$-$C_6$-alkyl, $Y^2$ is $CR^{13}$, wherein $R^{13}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, C1-C6-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, dioxolane, dioxane, or dioxepane, wherein each ring is unsubstituted or substituted by $C_1$-$C_6$-alkyl, $Y^3$ is $CR^{14}$, wherein $R^{14}$ is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane, dioxane, or dioxepane, wherein each ring is unsubstituted or substituted by $C_1$-$C_6$-alkyl, $Y^4$ is $CR^{15}$, wherein $R^{15}$ is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, $C_1$-$C_6$-alkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane, dioxane, or dioxepane, wherein each ring is unsubstituted or substituted by $C_1$-$C_6$-alkyl, or $Y^1$ and $Y^2$ and/or $Y^3$ and $Y^4$ are joined together to form a ring system, and wherein at least one of B and D is a nitrogen atom.

2. A compound according to claim 1, wherein $R^1$ is halogen, $C_1$-$C_6$-alkyl, $C_1$-$C_6$-alkyloxy, $C_1$-$C_6$-alkylthio, $C_2$-$C_6$-alkenyl, $C_2$-$C_6$-alkynyl, $C_1$-$C_6$-alkyloxy $C_1$-$C_6$-alkylthio $C_1$-$C_6$-alkyl, $C_1$-$C_6$-alkyl carbonyl, $C_2$-$C_6$-alkenyl carbonyl, $SF_5$, $C_1$-$C_6$-alkyl sulfonyl, wherein each of the carbon-containing radicals optionally is substituted by one or more halogen atoms, $R^2$ is hydrogen, $R^3$ is hydrogen, $R^4$ is hydrogen or $C_1$-$C_6$-alkyl, $R^5$ is hydrogen, $C_1$-$C_6$-alkyl, acyl or $C_1$-$C_6$-alkyloxycarbonyl ($CR^6R^7$), is a $C_1$-$C_3$-alkylene group, which is optionally substituted by one or more $C_1$-$C_6$-alkyl radicals, A is a bond or $NR^8$, wherein $R^8$ is H or $C_1$-$C_6$-alkyl, E is a bond or $NR^9$, wherein $R^9$ is H or $C_1$-$C_6$-alkyl, B is N or $CR^{10}$, wherein $R^{10}$ is H or $C_1$-$C_6$-alkyl, D is N or $CR^{11}$, wherein $R^{11}$ is H or $C_1$-$C_6$-alkyl, X is a carbonyl, thiocarbonyl or sulfonyl group, $Y^1$=$CR^{12}$, wherein $R^{12}$ is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane, dioxane, or dioxepane, wherein each ring is unsubstituted or substituted by $C_1$-$C_6$-alkyl, $Y^2$ is $CR^{13}$, wherein $R^{13}$ which is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, dioxolane, dioxane, or dioxepane, wherein each ring is unsubstituted or substituted by $C_1$-$C_6$-alkyl, $Y^3$ is $CR^{14}$, wherein $R^{14}$ is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, thiol, hydroxy, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane, dioxane, or dioxepane, wherein each ring is unsubstituted or substituted by $C_1$-$C_6$-alkyl, $Y^4$ is $CR^{15}$, wherein $R^{15}$ is hydrogen, halogen, $C_1$-$C_6$-alkyl, $C_1$-$C_6$-alkenyl, Cycloalkyl, Cycloalkyloxy, $C_1$-$C_6$-haloalkyl, $C_1$-$C_6$-alkoxy, $C_1$-$C_6$-haloalkoxy, nitrilo, nitro, amino, $C_1$-$C_6$-alkylamino, Cycloalkylamino, di($C_1$-$C_6$-alkyl)amino, ($C_1$-$C_6$-alkyl)-(Cycloalkyl)amino, N-pyrrolidinyl, N-piperidinyl, N-morpholinyl, $C_1$-$C_6$-alkylthio, Cycloalkylthio, $C_1$-$C_6$-haloalkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, phenyl, dioxolane, dioxane, or dioxepane, wherein each ring is unsubstituted or substituted by $C_1$-$C_6$-alkyl, or $Y^1$ and $Y^2$ and/or $Y^3$ and $Y^4$ are joined together to form a ring system, and wherein at least one of B and D is a nitrogen atom.

3. A compound of the formula (II) according to claim 1,

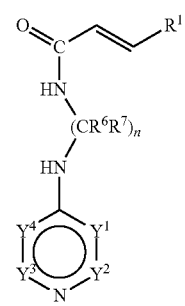

Formula (II)

wherein $R^1$ is $C_1$-$C_6$-alkyl, $C_1$-$C_6$-alkyloxy $C_1$-$C_6$-alkyl, or $C_1$-$C_6$-alkylthio $C_1$-$C_6$-alkyl, wherein each of the carbon-containing radicals is unsubstituted or substituted by one or more halogen atoms, $R^6$ is hydrogen, $C_1$-$C_6$-alkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkyl, $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl)aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxy or $C_1$-$C_6$-alkyloxy, $R^7$ is hydrogen or $C_1$-$C_6$-alkyl, n is 2 or 3, $Y^1 = CR^{12}$, wherein $R^{12}$ is hydrogen, halogen, $C_1$-$C_6$-alkyl, $C_1$-$C_6$-haloalkyl, $C_1$-$C_6$-alkoxy, $C_1$-$C_6$-haloalkoxy, Cycloalkyl, Cycloalkyloxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, C1-C6-alkylaminocarbonyl, di($C_1$-$C_6$-alkyl)aminocarbonyl, $Y^2 = CR^{13}$, wherein $R^{13}$ is hydrogen, halogen, $C_1$-$C_6$-alkyl, $C_1$-$C_6$-haloalkyl, $C_1$-$C_6$-alkoxy, $C_1$-$C_6$-haloalkoxy, Cycloalkyl, Cycloalkyloxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane, dioxane, or dioxepane, wherein each ring is unsubstituted or substituted by $C_1$-$C_6$-alkyl, $Y^3 = CR^{14}$, wherein $R^{14}$ is hydrogen, halogen, $C_1$-$C_6$-alkyl, $C_1$-$C_6$-haloalkyl, $C_1$-$C_6$-alkoxy, $C_1$-$C_6$-haloalkoxy, Cycloalkyl, Cycloalkyloxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane, dioxane, or dioxepane, wherein each ring is unsubstituted or substituted by $C_1$-$C_6$-alkyl, $Y^4 = CR^{15}$, wherein $R^{15}$ is hydrogen, halogen, $C_1$-$C_6$-alkyl, C1-C6-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, or $Y^1$ and $Y^2$ and/or $Y^3$ and $Y^4$ are joined together to form a 5- or 6-membered ring system.

4. A compound according to claim 3, wherein
$R^1$ is $C_1$-$C_6$-alkyl, $C_1$-$C_6$-alkyloxy $C_1$-$C_6$-alkyl, or $C_1$-$C_6$-alkylthio $C_1$-$C_6$-alkyl,
wherein each of the carbon-containing radicals is unsubstituted or substituted by one or more halogen atoms,
$Y^1 = C-R^{12}$, where $R^{12}$ is H or $C_1$-$C_6$-alkyl,
$Y^2$ is C, wherein C is substituted by $R^{13}$ is H, $C_1$-$C_6$-alkyl, $C_1$-$C_6$-alkoxy, $C_1$-$C_6$-alkyl carbonyl, Cycloalkyl, Cycloalkyloxy, $C_1$-$C_6$-alkylthio
$Y^3$ is C, wherein C is substituted by $R^{14}$ is H, $C_1$-$C_6$-alkyl, $C_1$-$C_6$-alkoxy, $C_1$-$C_6$-alkyl carbonyl, Cycloalkyl, Cycloalkyloxy, $C_1$-$C_6$-alkylthio
$Y^4$ is C, wherein C is substituted by $R^{15}$ is H, $C_1$-$C_6$-alkyl, $C_1$-$C_6$-alkoxy, $C_1$-$C_6$-alkylthio
or $Y^1$ and $Y^2$ or $Y^3$ and $Y^4$ are joined together to form a 5- or 6-membered ring system.

5. A compound according to claim 1, wherein the group of the formula (A)

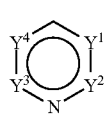

Formula (A)

represents a pyridine, thienopyridine, pyridopyridine, pyrrolopyridine, pyrazolopyridine, furopyridine, 2,3-dihydrofuropyridine, 2,3-dihydro-1,4-dioxinopyridine, or cinnoline group, wherein each group is optionally substituted by one or more radicals, selected from the group of $C_1$-$C_6$-alkyl, Cycloalkyl, Cycloalkyloxy, $C_1$-$C_6$-haloalkyl, $C_1$-$C_6$-alkoxy, $C_1$-$C_6$-haloalkoxy, halogen, nitrilo, nitro, amino, $C_1$-$C_6$-alkylamino, di($C_1$-$C_6$-alkyl) amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, dioxolane, dioxane, or dioxepane, wherein each ring is unsubstituted or substituted by $C_1$-$C_6$-alkyl.

6. A compound according to claim 1, wherein
$R^2$ is hydrogen,
$R^3$ is hydrogen,
$R^4$ is hydrogen or $C_1$-$C_6$-alkyl,
$R^5$ is hydrogen or $C_1$-$C_6$-alkyl,
$R^6$ is hydrogen or $C_1$-$C_6$-alkyl,
$R^7$ is hydrogen,
X is a carbonyl group,
n is 2,
the group of formula (A) represents a pyridine or quinoline group,
wherein each group is optionally substituted by one or more radicals, selected
from the group of $C_1$-$C_6$-alkyl, $C_1$-$C_6$-haloalkyl, $C_1$-$C_6$-alkoxy, Cycloalkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thio, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl, dioxolane, dioxane, or dioxepane, wherein each ring is unsubstituted or substituted by $C_1$-$C_6$-alkyl, and
one of A and B and one of D and E contains a nitrogen atom.

7. A pharmaceutical composition, wherein the composition comprises:
a) one or more compounds as defined in claim 1; and
b) one or more pharmaceutically acceptable excipients and optionally one or more pharmaceutically acceptable active ingredients which differ in structure from component a).

8. A compound of formula (1-IV),

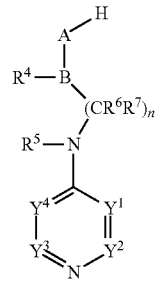

Formula 1-IV wherein $Y^1$, $Y^2$, $Y^3$ and $Y^4$ are C, substituted by $R^{12}$, $R^{13}$, $R^{14}$ and $R^{15}$ respectively and which are selected from the group of hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, $C_1$-$C_6$-alkylthio, $C_1$-$C_6$-alkyl carbonyl, aminocarbonyl, $C_1$-$C_6$-alkylaminocarbonyl, di($C_1$-$C_6$-alkyl)aminocarbonyl and phenyl, and wherein at least one of $R^{12}$ and $R^{13}$ is $C_1$-$C_6$-alkoxy or
$C_1$-$C_6$-haloalkoxy, and B is N, A is $NR^8$ or a bond, n is 2, $R^6$, $R^7$, and $R^8$ are H, and $R^4$ and $R^5$ are defined as in claim 1.

9. A kit, wherein the kit comprises:
a) one or more compounds as defined in claim 1, and
b) one or more other components selected from the group consisting of an excipient, an active ingredient, an apparatus for combining the compound of component a) with an excipient and/or active ingredient, an apparatus for administering the compound of component a) to an animal, and a diagnostic tool.

10. A method of treating a parasitic infection, wherein the method comprises administering to an the pharmaceutical composition as defined in claim 7.

11. A method as claimed in claim 10, wherein the animal is a non-human animal.

12. A compound of the formula (I a) or pharmaceutically acceptable N-oxides or salts thereof,

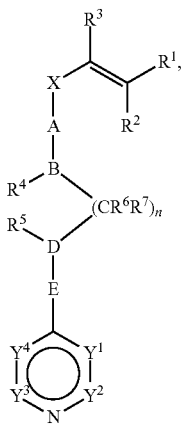

Formula (Ia)

wherein
$R^1$ is hydrogen, halogen, $C_1$-$C_6$-alkyl, cycloalkyl, $C_1$-$C_6$-alkyloxy, cycloalkyloxy, $C_1$-$C_6$-alkylthio, cycloalkylthio, $C_2$-$C_6$-alkenyl, $C_2$-$C_6$-alkynyl, $C_1$-$C_6$-alkyloxy $C_1$-$C_6$-alkyl, cycloalkyloxy $C_1$-$C_6$-alkyl, $C_1$-$C_6$-alkyloxy cycloalkyl, cycloalkyloxy cycloalkyl, $C_1$-$C_6$-alkylthio $C_1$-$C_6$-alkyl, cycloalkylthio $C_1$-$C_6$-alkyl, $C_1$-$C_6$-alkylthio cycloalkyl, cycloalkylthio cycloalkyl, amino, $C_1$-$C_6$-alkylamino, cycloalkylamino, di-($C_1$-$C_6$-alkyl)amino, di-(cycloalkyl)amino, $C_1$-$C_6$-alkyl-cycloalkylamino, $C_1$-$C_6$-alkylamino-$C_1$-$C_6$-alkyl, cycloalkylamino-$C_1$-$C_6$-alkyl, $C_1$-$C_6$-alkylamino-cycloalkyl, cycloalkylamino-cycloalkyl, di-($C_1$-$C_6$-alkyl)amino-$C_1$-$C_6$-alkyl, di-($C_1$-$C_6$-alkyl)amino-cycloalkyl, di-(cycloalkyl)amino-$C_1$-$C_6$-alkyl, di-(cycloalkyl)amino-cycloalkyl, $C_1$-$C_6$-alkyl-cycloalkylamino-$C_1$-$C_6$-alkyl, $C_1$-$C_6$-alkyl-cycloalkylamino-cycloalkyl, $C_1$-$C_6$-alkyl carbonyl, cycloalkylcarbonyl, $C_1$-$C_6$-alkyloxy carbonyl, cycloalkoxy carbonyl, $C_2$-$C_6$-alkenyl carbonyl, wherein each of the carbon-containing radicals optionally is substituted by one or more halogen atoms, or $R^1$ is phenyl, furanyl, imidazolinyl, or thiophenyl, wherein each of the rings optionally is substituted by one or more radicals from the group of $C_1$-$C_6$-alkyl, cycloalkyl and halogen, $R^2$ is hydrogen, halogen, $C_1$-$C_6$-alkyl, cycloalkyl, $C_1$-$C_6$-alkyloxy, cycloalkyloxy, $C_1$-$C_6$-alkylthio, cycloalkylthio, $C_2$-$C_6$-alkenyl, $C_2$-$C_6$-alkynyl, $C_1$-$C_6$-alkyloxy $C_1$-$C_6$-alkyl, cycloalkyloxy $C_1$-$C_6$-alkyl, $C_1$-$C_6$-alkyloxy cycloalkyl, cycloalkyloxy cycloalkyl, $C_1$-$C_6$-alkylthio $C_1$-$C_6$-alkyl, cycloalkylthio $C_1$-$C_6$-alkyl, $C_1$-$C_6$-alkylthio cycloalkyl, cycloalkylthio cycloalkyl, amino, $C_1$-$C_6$-alkylamino, cycloalkylamino, di-($C_1$-$C_6$-alkyl)amino, di-(cycloalkyl)amino, $C_1$-$C_6$-alkyl-cycloalkylamino, $C_1$-$C_6$-alkylamino-$C_1$-$C_6$-alkyl, cycloalkylamino-$C_1$-$C_6$-alkyl, $C_1$-$C_6$-alkylamino-cycloalkyl, cycloalkylamino-cycloalkyl, di-($C_1$-$C_6$-alkyl)amino-$C_1$-$C_6$-alkyl, di-($C_1$-$C_6$-alkyl)amino-cycloalkyl, di-(cycloalkyl)amino-$C_1$-$C_6$-alkyl, di-(cycloalkyl)amino-cycloalkyl, $C_1$-$C_6$-alkyl-cycloalkylamino-$C_1$-$C_6$-alkyl, $C_1$-$C_6$-alkyl-cycloalkylamino-cycloalkyl, $C_1$-$C_6$-alkyl carbonyl, cycloalkylcarbonyl, $C_1$-$C_6$-alkyloxy carbonyl, cycloalkoxy carbonyl, $C_2$-$C_6$-alkenyl carbonyl, wherein each of the carbon-containing radicals optionally is substituted by one or more halogen atoms, or $R^2$ is phenyl, furanyl, imidazolinyl, or thiophenyl, wherein each of the rings optionally is substituted by one or more radicals from the group of $C_1$-$C_6$-alkyl, cycloalkyl and halogen, $R^3$ is hydrogen, $C_1$-$C_6$-alkyl or cycloalkyl $R^4$ is hydrogen, $C_1$-$C_6$-alkyl or cycloalkyl $R^5$ is hydrogen, $C_1$-$C_6$-alkyl, cycloalkyl or acyl, $R^6$ is hydrogen, $C_1$-$C_6$-alkyl, cycloalkyl, hydroxy, $C_1$-$C_6$-alkyloxy, phenyl $C_1$-$C_6$-alkyloxy, hydroxy $C_1$-$C_6$-alkyl, $C_1$-$C_6$-alkyloxy $C_1$-$C_6$-alkyl, phenyl $C_1$-$C_6$-alkyloxy $C_1$-$C_6$-alkyl, thiol $C_1$-$C_6$-alkylthio $C_1$-$C_6$-alkyl, phenyl $C_1$-$C_6$-alkylthio $C_1$-$C_6$-alkyl, hydroxycarbonyl, hydroxycarbonyl $C_1$-$C_6$-alkyl, $C_1$-$C_6$-alkyloxycarbonyl, $C_1$-$C_6$-alkyloxycarbonyl $C_1$-$C_6$-alkyl, aminocarbonyl, aminocarbonyl $C_1$-$C_6$-alkyl, $C_1$-$C_6$-alkylaminocarbonyl, $C_1$-$C_6$-alkylaminocarbonyl ($C_1$-$C_6$-alkyl), di($C_1$-$C_6$-alkyl)aminocarbonyl, di($C_1$-$C_6$-alkyl) aminocarbonyl ($C_1$-$C_6$-alkyl), $C_1$-$C_6$-alkylamino $C_1$-$C_6$-alkyl, di($C_1$-$C_6$-alkyl)amino $C_1$-$C_6$-alkyl, phenyl, phenyl $C_1$-$C_6$-alkyl, wherein each phenyl group is optionally substituted by hydroxyl, $C_1$-$C_6$-alkyloxy or cycloalkyloxy, $R^7$ is hydrogen, $C_1$-$C_6$-alkyl or cycloalkyl, or $R^6$ and $R^7$ together represent an oxo-group or a thioxo-group, or $R^6$ is joined together with $R^8$ to form a $C_1$-$C_3$-alkylene group and $R^7$ is joined together with $R^9$ to form a $C_1$-$C_3$-alkylene group, wherein one or both of said $C_1$-$C_3$-alkylene groups are optionally substituted by one or more $C_1$-$C_6$-alkyl or cycloalkyl radicals, n is an integer from 1 to 3, X is a carbonyl or sulfonyl group, A is a bond or $NR^8$, wherein $R^8$ is hydrogen or $C_1$-$C_6$-alkyl, E is a bond or $NR^9$, wherein $R^9$ is hydrogen or $C_1$-$C_6$-alkyl, B is N or $CR^{10}$, wherein $R^{10}$ is hydrogen or $C_1$-$C_6$-alkyl, D is N or $CR^{11}$, wherein $R^{11}$ is hydrogen or $C_1$-$C_6$-alkyl, $Y^1$ is $CR^{12}$, wherein $R^{12}$ is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, C1-C6-alkoxycarbonyl, cycloalkyl, cycloalkyloxy, cycloalkylamino, ($C_1$-$C_6$-alkyl)-(cycloalkyl)amino, cycloalkylthio, phenyl, dioxolane, dioxane, or dioxepane, wherein each ring is unsubstituted or substituted by $C_1$-$C_6$-alkyl or cycloalkyl, $Y^2$ is $CR^{13}$ wherein $R^{13}$ is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, aminocarbonyl, $C_1$-$C_6$-alkylaminocarbonyl, di($C_1$-$C_6$-alkyl)aminocarbonyl, $C_1$-$C_6$-alkylcarbonylamino, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, dioxolane, dioxane, or dioxepane, wherein each ring is unsubstituted or substituted by $C_1$-$C_6$-alkyl or cycloalkyl, $Y^3$ is $CR^{14}$, wherein $R^{14}$ is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, thiol, hydroxy, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, $C_1$-$C_6$-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, dioxolane, dioxane, or dioxepane, wherein each ring is unsubstituted or substituted by $C_1$-$C_6$-alkyl or cycloalkyl, $Y^4$ is $CR^{15}$, wherein $R^{15}$ is hydrogen, halogen, $C_1$-$C_6$-alkyl, $C_1$-$C_6$-haloalkyl, $C_1$-$C_6$-alkoxy, $C_1$-$C_6$-haloalkoxy, nitrilo, nitro, amino, $C_1$-$C_6$-alkylamino, di($C_1$-$C_6$-alkyl)amino, N-pyrrolidinyl, N-piperidinyl, N-morpholinyl, $C_1$-$C_6$-alkylthio, $C_1$-$C_6$-alkyl carbonyl, $C_1$-$C_6$-haloalkyl carbonyl, $C_1$-$C_6$-alkylcarbonylamino, aminocarbonyl, C1-C6-alkylaminocarbonyl, di($C_1$-$C_6$-alkyl)aminocarbonyl, $C_1$-$C_6$-alkoxycarbonyl, cycloalkyl, cycloalkyloxy, cycloalkylamino, ($C_1$-$C_6$-alkyl)-(cycloalkyl)amino, cycloalkylthio, phenyl, dioxolane, dioxane, or dioxepane, wherein each ring is unsubstituted or substituted by $C_1$-$C_6$-alkyl or cycloalkyl, or $Y^1$ and $Y^2$ and/or $Y^3$ and $Y^4$ are joined together to form a ring system, and wherein at least one of B and D is a nitrogen atom, for treating a helminth infection.

13. An anthelmintic composition, wherein the composition comprises:

a) one or more compounds as defined in claim 12; and b) one or more pharmaceutically acceptable excipients and-optionally one or more pharmaceutically acceptable active ingredients which differ from the said one or more compounds as defined in claim 12.

14. The method of claim 11, wherein the parasitic infection is a helminth infection.

15. The method of claim 14, wherein the helminth infection is selected from the group consisting of a nematode infection, cestode infection and a trematode infection.

16. The compound of claim 1, wherein the compound is

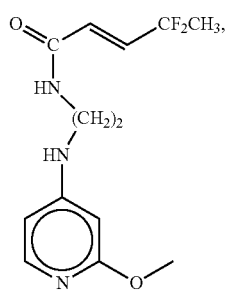

or pharmaceutically acceptable salts, or N-oxides thereof.

17. The compound of claim 1, wherein the compound is

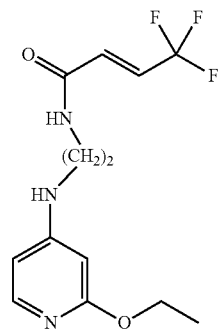

or the pharmaceutically acceptable salts or N-oxides thereof.

18. The compound of claim 1, wherein the compound is

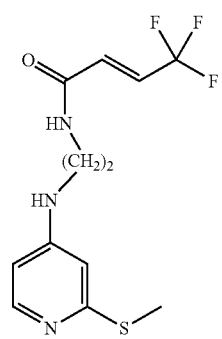

or the pharmaceutically acceptable salts or N-oxides thereof.

19. The compound of claim 1, wherein the compound is

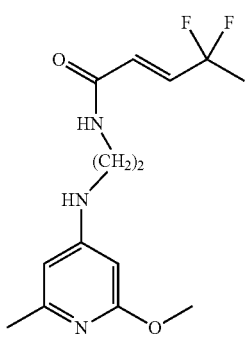

or the pharmaceutically acceptable salts or N-oxides thereof.

20. The compound of claim 1, wherein the compound is
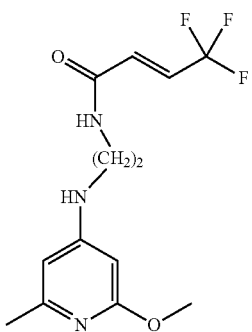
or the pharmaceutically acceptable salts or N-oxides thereof.
21. The compound of claim 1, wherein the compound is
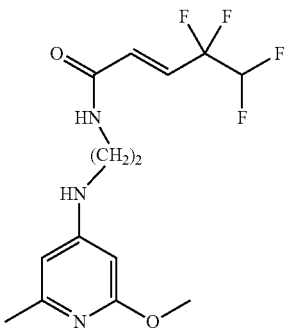
or the pharmaceutically acceptable salts or N-oxides thereof.
* * * * *